(12) United States Patent
Cristau et al.

(10) Patent No.: US 11,457,629 B2
(45) Date of Patent: Oct. 4, 2022

(54) HETEROARYLPHENYLAMINOQUINOLINES AND ANALOGUES

(71) Applicants: Bayer Aktiengesellschaft, Leverkusen (DE); Bayer CropScience Aktiengesellschaft, Monheim am Rhein (DE)

(72) Inventors: Pierre Cristau, Lyons (FR); Philippe Desbordes, Lyons (FR); Jérémy Dufour, Lyons (FR); Christophe Dubost, La tour de Salvagny (FR); Anthony Millet, Décines-Charpieu (FR); Sebastien Naud, Lyons (FR); Mathieu Gourgues, Lyons (FR); Valérie Toquin, Saint-Romain-au-Mont-d'Or (FR); Virginie Lempereur, Lyons (FR); Francois Villalba, Albigny-sur-Saone (FR); Philippe Rinolfi, Chatillon D Azergues (FR); Dominique Loque, Vernie (CH); Ulrike Wachendorff-Neumann, Neuwied (DE)

(73) Assignees: Bayer Aktiengesellschaft, Leverkusen (DE); Bayer CropScience Aktiengesellschaft, Monheim am Rhein (DE)

( * ) Notice: Subject to any disclaimer, the term of this patent is extended or adjusted under 35 U.S.C. 154(b) by 0 days.

(21) Appl. No.: 16/607,871

(22) PCT Filed: Apr. 27, 2018

(86) PCT No.: PCT/EP2018/060928
§ 371 (c)(1),
(2) Date: Oct. 24, 2019

(87) PCT Pub. No.: WO2018/197692
PCT Pub. Date: Nov. 1, 2010

(65) Prior Publication Data
US 2020/0196602 A1    Jun. 25, 2020

(30) Foreign Application Priority Data
Apr. 27, 2017   (EP) .................................... 17290056

(51) Int. Cl.
| *A01N 43/56* | (2006.01) |
| *A01N 43/60* | (2006.01) |
| *A01N 43/80* | (2006.01) |
| *A01N 43/86* | (2006.01) |
| *A01N 43/90* | (2006.01) |
| *C07D 401/12* | (2006.01) |

(Continued)

(52) U.S. Cl.
CPC .............. *A01N 43/56* (2013.01); *A01N 43/60* (2013.01); *A01N 43/80* (2013.01); *A01N 43/86* (2013.01); *A01N 43/90* (2013.01); *C07D 401/12* (2013.01); *C07D 403/12* (2013.01); *C07D 413/12* (2013.01); *C07D 417/12* (2013.01); *C07D 487/04* (2013.01)

(58) Field of Classification Search
CPC ........ A01N 43/56; A01N 43/60; A01N 43/80; A01N 43/86; A01N 43/90; C07D 231/12; C07D 401/10; C07D 401/12; C07D 403/12; C07D 413/12; C07D 417/12; C07D 487/04
See application file for complete search history.

(56) References Cited

U.S. PATENT DOCUMENTS

| 7,417,063 B2 | 8/2008 | Smallheer et al. |
| 11,103,139 B2 | 8/2021 | Frank et al. |

FOREIGN PATENT DOCUMENTS

| EP | 2522658 A1 | 11/2012 |
| JP | 2007/532657 A1 | 11/2007 |

(Continued)

OTHER PUBLICATIONS

Wermuth, C.G. (The Practice of Medicinal Chemistry. Chapter 13 Molecular Variations Based on Isoteric Replacements. Academic Press, 2003. "B. Interchange of divalent atoms"; p. 204-210).*
Patani (Chem. Rev. 1996, 96, 3147-3176).*
Wikipedia "Bioisostere" (https://en.wikipedia.org/wiki/Bioisostere-available online as of Sep. 27, 2015).*

(Continued)

*Primary Examiner* — Valerie Rodriguez-Garcia
(74) *Attorney, Agent, or Firm* — McBee Moore & Vanik IP, LLC; Susan McBee; Brett Stauffer

(57) ABSTRACT

The present disclosure relates to fungicidal active compounds, more specifically to heteroarylphenylaminoquinolines according to formula (I):

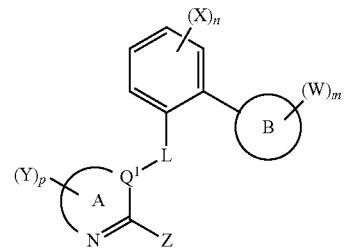

and analogues thereof, processes and, intermediates for their preparation and use thereof as fungicidal active compound, particularly in the form of fungicide compositions. The present disclosure also relates to methods for the control of phytopathogenic fungi of plants using these compounds or compositions comprising thereof.

12 Claims, No Drawings

(51) Int. Cl.
  *C07D 403/12* (2006.01)
  *C07D 413/12* (2006.01)
  *C07D 417/12* (2006.01)
  *C07D 487/04* (2006.01)

(56) References Cited

FOREIGN PATENT DOCUMENTS

| JP | 2522658 | * | 11/2012 |
| JP | WO 2013/002205 | * | 1/2013 |
| JP | WO 2013/058256 | * | 4/2013 |
| WO | 2005/099709 A2 | | 10/2005 |
| WO | 2013002205 A1 | | 1/2013 |
| WO | 2013058256 A1 | | 4/2013 |

OTHER PUBLICATIONS

Xiantao, Lei, et al., "Approach to N-aryl pyrroles via diphenyl phosphate-catalyzed [1,5]—Hydride shift/isomerization reaction with indoles," Tetrahedron, (2015), vol. 71: pp. 4098-4101.

Xiantao, Lei, et al., "Dearomatization of Indole Derivatives via Palladium-Catalyzed C-H Bond Functionalization of Pyrroles: Convenient Construction of Spiroindolenines," Adv. Synth. Catal., (2016), vol. 358: pp. 1892-1896.

PCT International Search Report for PCT/EP2018/060928, dated Jun. 25, 2018.

Tohru Koyanagi et al., "Bioisosterism in Agrochemicals", Chapter 2, 1995 American Chemical Society, pp. 1-10.

* cited by examiner

HETEROARYLPHENYLAMINOQUINOLINES AND ANALOGUES

CROSS-REFERENCE TO RELATED APPLICATIONS

This application is the National Stage entry of International Application No. PCT/EP2018/060928, filed 27 Apr. 2018, which claims priority to European Patent Application No. 17290056.5, filed 27 Apr. 2017.

BACKGROUND

Technical Field

The present disclosure relates to fungicidal active compounds, more specifically to heteroarylphenylaminoquinolines and analogues thereof, processes and intermediates for their preparation and use thereof as fungicidal active compounds, particularly in the form of fungicide compositions. The present disclosure also relates to methods for the control of phytopathogenic fungi of plants using these compounds or compositions comprising thereof.

Description of Related Art

EP 2 522 658 discloses nitrogen-containing heterocyle compounds suitable for use as fungicides.

WO 2013/058256 discloses further nitrogen-containing heterocyle compounds suitable for use as fungicides.

However, since the ecological and economic demands made on fungicide active compounds are increasing constantly, for example with respect to activity spectrum, toxicity, selectivity, application rate, formation of residues and favourable manufacture, and since there can also be problems associated with resistances, there is a constant need to develop novel fungicidal compounds and compositions which have advantages over the known compounds and compositions in at least some of these aspects.

SUMMARY

Active Ingredients

The present invention provides compounds of formula (I)

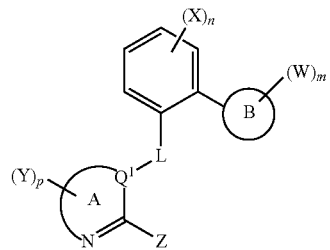

(I)

wherein
A is a partially saturated or unsaturated fused bicyclic 8-, 9-, 10- or 11-membered heterocyclyl ring comprising at least 1 nitrogen atom and from 0 to 4 more heteroatoms independently selected in the list consisting of N, O and S;
B is a partially saturated or unsaturated 5-membered heterocyclyl ring comprising 1, 2, 3 or 4 heteroatoms independently selected in the list consisting of N, O and S;
$Q^1$ is C;
Z is selected from the group consisting of hydrogen atom, halogen atom, hydroxyl, $C_1$-$C_8$-alkyl, $C_2$-$C_8$-alkenyl, $C_2$-$C_8$-alkynyl, $C_2$-$C_8$-halogenoalkynyl comprising up to 9 halogen atoms that can be the same or different, $C_1$-$C_8$-alkoxy, $C_1$-$C_8$-halogenoalkyl comprising up to 9 halogen atoms that can be the same or different, $C_2$-$C_8$-halogenoalkenyl comprising up to 9 halogen atoms that can be the same or different, $C_1$-$C_8$-halogenoalkoxy comprising up to 9 halogen atoms that can be the same or different, $C_3$-$C_7$-cycloalkyl, $C_4$-$C_7$-cycloalkenyl, aryl, heterocyclyl, formyl, $C_1$-$C_8$-alkylcarbonyl, (hydroxyimino)$C_1$-$C_8$-alkyl, ($C_1$-$C_8$-alkoxyimino)$C_1$-$C_8$-alkyl, carboxyl, $C_1$-$C_8$-alkoxycarbonyl, $C_1$-$C_8$-alkylcarbamoyl, di-$C_1$-$C_8$-alkylcarbamoyl, $C_1$-$C_8$-alkylamino, di-$C_1$-$C_8$-alkylamino, sulfanyl, $C_1$-$C_8$-alkylsulfanyl, $C_1$-$C_8$-alkylsulfinyl, $C_1$-$C_8$-alkylsulfonyl, $C_1$-$C_8$-trialkylsilyl, cyano and nitro,
wherein said $C_3$-$C_7$-cycloalkyl, $C_4$-$C_7$-cycloalkenyl, aryl and heterocyclyl may be substituted with one or more $Z^a$ substituents that may be the same or different;
m is 0, 1, 2, 3 or 4;
n is 0, 1, 2, 3 or 4;
p is 0, 1, 2, 3, 4 or 5;
L is $CR^1R^2$ or $NR^3$ wherein
$R^1$ and $R^2$ are independently selected from the group consisting of hydrogen atom, halogen atom, $C_1$-$C_8$-alkoxy and $C_1$-$C_8$ alkyl;
$R^3$ is selected from the group consisting of hydrogen atom, $C_1$-$C_8$-alkyl, $C_1$-$C_8$-halogenoalkyl comprising up to 9 halogen atoms that can be the same or different, $C_2$-$C_8$-alkenyl, $C_2$-$C_8$-halogenoalkenyl comprising up to 9 halogen atoms that can be the same or different, $C_3$-$C_8$-alkynyl, $C_3$-$C_8$-halogenoalkynyl comprising up to 9 halogen atoms that can be the same or different, $C_3$-$C_7$-cycloalkyl, $C_3$-$C_7$-halogenocycloalkyl comprising up to 9 halogen atoms that can be the same or different, $C_3$-$C_7$-cycloalkyl-$C_1$-$C_8$-alkyl, $C_1$-$C_8$-alkylcarbonyl, $C_1$-$C_8$-halogenoalkylcarbonyl comprising up to 9 halogen atoms that can be the same or different, $C_1$-$C_8$-alkoxycarbonyl, $C_1$-$C_8$-halogenoalkoxycarbonyl comprising up to 9 halogen atoms that can be the same or different, $C_1$-$C_8$-alkylsulfonyl, $C_1$-$C_8$-halogenoalkylsulfonyl comprising up to 9 halogen atoms that can be the same or different, aryl-$C_1$-$C_8$-alkyl and phenylsulfonyl,
wherein said $C_3$-$C_7$-cycloalkyl, $C_3$-$C_7$-cycloalkyl-$C_1$-$C_8$-alkyl, aryl-$C_1$-$C_8$-alkyl and phenylsulfonyl may be substituted with one or more $R^{3a}$ substituents that may be the same or different;
W is independently selected from the group consisting of halogen atom, hydroxyl, $C_1$-$C_8$-alkyl, $C_1$-$C_8$-halogenoalkyl comprising up to 9 halogen atoms that can be the same or different, $C_1$-$C_8$-alkoxy, $C_1$-$C_8$-halogenoalkoxy comprising up to 9 halogen atoms that can be the same or different, hydroxy-$C_1$-$C_8$-alkyl, $C_1$-$C_8$-alkoxy-$C_1$-$C_8$-alkyl, $C_2$-$C_8$-alkenyl, $C_2$-$C_8$-halogenoalkenyl comprising up to 9 halogen atoms that can be the same or different, $C_2$-$C_8$-alkynyl, $C_2$-$C_8$-halogenoalkynyl comprising up to 9 halogen atoms that can be the same or different, $C_3$-$C_7$-cycloalkyl, $C_4$-$C_8$-cycloalkenyl, aryl, aryl-$C_1$-$C_8$-alkyl, heterocyclyl, heterocyclyl-$C_1$-$C_8$-alkyl, aryloxy, heteroaryloxy, arylsulfanyl, arylsulfinyl, arylsulfonyl, heteroarylsulfanyl, heteroarylsulfinyl, heteroarylsulfonyl, arylamino, heteroarylamino, aryloxy-$C_1$-$C_8$-alkyl, heteroaryloxy-$C_1$-$C_8$-alkyl, arylsulfanyl-$C_1$-$C_8$-alkyl, arylsulfinyl-$C_1$-$C_8$-alkyl, arylsulfonyl-$C_1$-$C_8$-alkyl, heteroarylsulfanyl-$C_1$-$C_8$-alkyl, heteroarylsulfinyl-$C_1$-$C_8$-alkyl, heteroarylsulfonyl-$C_1$-$C_8$-alkyl, arylamino-$C_1$-$C_8$-alkyl, heteroarylamino-$C_1$-$C_8$-alkyl, aryl-$C_1$-$C_8$-alkoxy, heteroaryl-$C_1$-$C_8$-alkoxy, aryl-$C_1$-$C_8$-alkylsulfanyl, aryl-$C_1$-$C_8$-alkylsulfinyl, aryl-$C_1$-$C_8$-alkylsulfonyl, heteroaryl-$C_1$-$C_8$alkylsulfanyl, heteroaryl-$C_1$-$C_8$-alkylsulfinyl, heteroaryl-$C_1$-$C_8$-alkylsulfonyl, aryl-$C_1$-$C_8$-alkylamino, heteroaryl-$C_1$-$C_8$-alkylamino, formyl, $C_1$-$C_8$-alkylcarbonyl, (hydroxyimino)$C_1$-$C_8$-alkyl, ($C_1$-$C_8$-alkoxyimino)$C_1$-$C_8$-alkyl, carboxyl, $C_1$-$C_8$-alkoxycarbonyl, carbamoyl, $C_1$-$C_8$-alkylcarbamoyl, di-$C_1$-$C_8$-alkylcarbamoyl, amino, $C_1$-$C_8$-alkylamino, di-$C_1$-$C_8$-alkylamino, sulfanyl, $C_1$-$C_8$-alkylsulfanyl, $C_1$-$C_8$-alkylsulfinyl, $C_1$-$C_8$-alkylsulfonyl, $C_1$-$C_6$-trialkylsilyl, tri($C_1$-$C_8$alkyl)silyloxy, tri($C_1$-$C_8$-alkyl)silyloxy-$C_1$-$C_8$-alkyl, cyano and nitro, wherein said $C_3$-$C_7$-cycloalkyl, $C_4$-$C_8$-cycloalkenyl, heterocyclyl, aryl and the aryl, heterocyclyl and heteroaryl moieties of the aryl-$C_1$-$C_8$-alkyl, heterocyclyl-$C_1$-$C_8$-alkyl, aryloxy, heteroaryloxy, arylsulfanyl, arylsulfinyl, arylsulfonyl, heteroarylsulfanyl, heteroarylsulfinyl, heteroarylsulfonyl, arylamino, heteroarylamino, aryloxy-$C_1$-$C_8$-alkyl, heteroaryloxy-$C_1$-$C_8$-alkyl, arylsulfanyl-$C_1$-$C_8$-alkyl, arylsulfinyl-$C_1$-$C_8$-alkyl, arylsulfonyl-$C_1$-$C_8$-alkyl, heteroarylsulfanyl-$C_1$-$C_8$-alkyl, heteroarylsulfinyl-$C_1$-$C_8$-alkyl, heteroarylsulfonyl-$C_1$-$C_8$-alkyl, arylamino-$C_1$-$C_8$-alkyl, heteroarylamino-$C_1$-$C_8$-alkyl, aryl-$C_1$-$C_8$-alkoxy, heteroaryl-$C_1$-$C_8$-alkoxy, aryl-$C_1$-$C_8$-alkylsulfanyl, aryl-$C_1$-$C_8$-alkylsulfinyl, aryl-$C_1$-$C_8$-alkylsulfonyl, heteroaryl-$C_1$-$C_8$-alkylsulfanyl, heteroaryl-$C_1$-$C_8$-alkylsulfinyl, heteroaryl-$C_1$-$C_8$-alkylsulfonyl, aryl-$C_1$-$C_8$-alkylamino, heteroaryl-$C_1$-$C_8$-alkylamino groups may be substituted with one or more $W^a$ substituents that may be the same or different;

X is independently selected from the group consisting of halogen atom, hydroxyl, $C_1$-$C_8$-alkyl, $C_1$-$C_8$-halogenoalkyl comprising up to 9 halogen atoms that can be the same or different, $C_1$-$C_8$-alkoxy, $C_1$-$C_8$-halogenoalkoxy comprising up to 9 halogen atoms that can be the same or different, $C_2$-$C_8$-alkenyl, $C_2$-$C_8$-halogenoalkenyl comprising up to 9 halogen atoms that can be the same or different, $C_2$-$C_8$-alkynyl, $C_2$-$C_8$-halogenoalkynyl comprising up to 9 halogen atoms that can be the same or different, $C_3$-$C_7$-cycloalkyl, $C_4$-$C_7$-cycloalkenyl, aryl, heterocyclyl, formyl, $C_1$-$C_8$-alkylcarbonyl, (hydroxyimino)$C_1$-$C_8$-alkyl, ($C_1$-$C_8$-alkoxyimino)$C_1$-$C_8$-alkyl, carboxyl, $C_1$-$C_8$-alkoxycarbonyl, carbamoyl, $C_1$-$C_8$-alkylcarbamoyl, di-$C_1$-$C_8$-alkylcarbamoyl, amino, $C_1$-$C_8$-alkylamino, di-$C_1$-$C_8$-alkylamino, sulfanyl, $C_1$-$C_8$-alkylsulfanyl, $C_1$-$C_8$-alkylsulfinyl, $C_1$-$C_8$-alkylsulfonyl, $C_1$-$C_8$-trialkylsilyl, cyano, nitro and hydroxyl-$C_1$-$C_8$-alkyl, wherein said $C_3$-$C_7$-cycloalkyl, $C_4$-$C_7$-cycloalkenyl, aryl and heterocyclyl may be substituted with one or more $X^a$ substituents that may be the same or different;

Y is independently selected from the group consisting of halogen atom, hydroxyl, $C_1$-$C_8$-alkyl, $C_1$-$C_8$-halogenoalkyl comprising up to 9 halogen atoms that can be the same or different, $C_1$-$C_8$-alkoxy, $C_1$-$C_8$-halogenoalkoxy comprising up to 9 halogen atoms that can be the same or different, $C_2$-$C_8$-alkenyl, $C_2$-$C_8$-halogenoalkenyl comprising up to 9 halogen atoms that can be the same or different, $C_2$-$C_8$-alkynyl, $C_2$-$C_8$-halogenoalkynyl comprising up to 9 halogen atoms that can be the same or different, $C_3$-$C_7$-cycloalkyl, $C_4$-$C_7$-cycloalkenyl, aryl, heterocyclyl, formyl, $C_1$-$C_8$-alkylcarbonyl, (hydroxyimino)$C_1$-$C_8$-alkyl, ($C_1$-$C_8$-alkoxyimino)$C_1$-$C_8$-alkyl, carboxyl, $C_1$-$C_8$-alkoxycarbonyl, carbamoyl, $C_1$-$C_8$-alkylcarbamoyl, di-$C_1$-$C_8$-alkylcarbamoyl, amino, $C_1$-$C_8$-alkylamino, di-$C_1$-$C_8$-alkylamino, sulfanyl, $C_1$-$C_8$-alkylsulfanyl, $C_1$-$C_8$-alkylsulfinyl, $C_1$-$C_8$-alkylsulfonyl, $C_1$-$C_6$-trialkylsilyl, cyano and nitro, wherein said $C_3$-$C_7$-cycloalkyl, $C_4$-$C_7$-cycloalkenyl, aryl and heterocyclyl may be substituted with one or more $Y^a$ substituents that may be the same or different;

$Z^a$, $R^{3a}$, $W^a$, $X^a$ and $Y^a$ are independently selected from the group consisting of halogen atom, nitro, hydroxyl, cyano, carboxyl, amino, sulfanyl, pentafluoro-$\lambda^6$-sulfanyl, formyl, carbamoyl, carbamate, $C_1$-$C_8$-alkyl, $C_3$-$C_7$-cycloalkyl, $C_1$-$C_8$-halogenoalkyl having 1 to 5 halogen atoms, $C_3$-$C_8$-halogenocycloalkyl having 1 to 5 halogen atoms, $C_2$-$C_8$-alkenyl, $C_2$-$C_8$-alkynyl, $C_1$-$C_8$-alkylamino, di-$C_1$-$C_8$-alkylamino, $C_1$-$C_8$-alkoxy, $C_1$-$C_8$-halogenoalkoxy having 1 to 5 halogen atoms, $C_1$-$C_8$-alkylsulfanyl, $C_1$-$C_8$-halogenoalkylsulfanyl having 1 to 5 halogen atoms, $C_1$-$C_8$-alkylcarbonyl, $C_1$-$C_8$-halogenoalkylcarbonyl having 1 to 5 halogen atoms, $C_1$-$C_8$-alkylcarbamoyl, di-$C_1$-$C_8$-alkylcarbamoyl, $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, $C_1$-$C_8$-alkylsulfanyl, $C_1$-$C_8$-halogenoalkylsulfanyl having 1 to 5 halogen atoms, $C_1$-$C_8$-alkylsulfinyl, $C_1$-$C_8$-halogenoalkylsulfinyl having 1 to 5 halogen atoms, $C_1$-$C_8$-alkylsulfonyl and $C_1$-$C_8$-halogeno-alkyl-sulfonyl having 1 to 5 halogen atoms;

as well as their salts, N-oxides, metal complexes, metalloid complexes and optically active isomers or geometric isomers.

DETAILED DESCRIPTION OF A PREFERRED EMBODIMENT

As used herein, the expression "one or more substituents" refers to a number of substituents that ranges from one to the maximum number of substituents possible based on the number of available bonding sites, provided that the conditions of stability and chemical feasibility are met.

As used herein, halogen means fluorine, chlorine, bromine or iodine; formyl means —CH(=O); carboxy means —C(=O)OH; carbonyl means —C(=O)—; carbamoyl means —C(=O)NH$_2$; N-hydroxycarbamoyl means —C(=O)NHOH; SO represents a sulfoxide group; SO$_2$ represents a sulfone group; heteroatom means sulfur, nitrogen or oxygen; methylene means the diradical —CH$_2$—; aryl means an organic radical derived from an aromatic hydrocarbon by removal of one hydrogen, such as phenyl or naphthyl; unless provided differently, heterocyclyl means an unsaturated, saturated or partially saturated 5- to 7-membered ring, preferably a 5- to 6-membered ring, comprising from 1 to 4 heteroatoms independently selected in the list consisting of N, O and S. The term "heterocyclyl" as used herein encompasses heteroaryl.

The term "membered" as used herein in the expression "8-, 9-, 10- or 11-membered heterocyclyl ring" or "5- to 6-membered ring" designates the number of skeletal atoms that constitutes the ring.

As used herein, the expression "partially saturated or unsaturated fused bicyclic 8-, 9-, 10- or 11-membered heterocyclyl ring" designates fused bicyclic ring systems comprising a saturated ring fused with an unsaturated ring or two fused unsaturated rings, the bicyclic ring system being constituted from 8 to 11 skeletal atoms.

As used herein, an alkyl group, an alkenyl group and an alkynyl group as well as moieties containing these terms, can be linear or branched.

The expression "1 or 2" positioned as indicia with respect to a substituent, such as used for instance in the definition of groups $B^5$ and $B^6$ with respect to the W substituent (e.g. $(W^2)_{1 \text{ or } 2}$), indicates that one or two substituents may be attached to the substituted atom (e.g. the carbon atom may bear one or two $W^2$ substituent). The two substituents may be identical or different.

When an amino group or the amino moiety of any other amino-containing group is substituted by two substituents that can be the same or different, the two substituents together with the nitrogen atom to which they are linked can form a heterocyclyl group, preferably a 5- to 7-membered heterocyclyl group, that can be substituted or that can include other hetero atoms, for example a morpholino group or piperidinyl group.

Any of the compounds of the present invention can exist in one or more optical or chiral isomer forms depending on the number of asymmetric centres in the compound. The invention thus relates equally to all optical isomers and racemic or scalemic mixtures thereof (the term "scalemic" denotes a mixture of enantiomers in different proportions) and to mixtures of all possible stereoisomers, in all proportions. The diastereoisomers and/or the optical isomers can be separated according to methods which are known per se by the man ordinary skilled in the art.

Any of the compounds of the present invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

Any of the compounds of the present invention can also exist in one or more geometric isomer forms depending on the relative position (syn/anti or cis/trans) of the substituents of the chain or ring. The invention thus relates equally to all syn/anti (or cis/trans) isomers and to all possible syn/anti (or cis/trans) mixtures, in all proportions. The syn/anti (or cis/trans) isomers can be separated according to general methods, which are known per se by the man ordinary skilled in the art.

When a compound of the invention can be present in tautomeric form, the invention also encompasses any tautomeric forms of such compound, even when this is not expressly mentioned.

Compounds of formula (I) are herein referred to as "active ingredient(s)".

In the above formula (I) wherein $Q^1$ is said to be a carbon atom, it is to be understood that said carbon atom may bear a hydrogen atom or Y substituent ($Q^1$ is then bonded to 4 adjacent atoms) or may be a $sp^2$ carbon atom ($Q^1$ does not bear further substituents), preferably $Q^1$ is a $sp^2$ carbon atom ($Q^1$ is bonded to 3 adjacent atoms).

In the above formula (I), B may be selected from the group consisting of pyrrolyl, thiazolyl, imidazolyl, dihydroisoxazolyl, isoxazolyl, pyrazolyl, triazolyl and tetrazolyl.

In some embodiments, in the above formula (I), B is a partially saturated or unsaturated 5-membered heterocyclyl ring comprising 1, 2, 3 or 4 heteroatoms independently selected in the list consisting of N, O and S and m is 1, 2, 3 or 4, preferably m is 1. In these embodiments, W is as disclosed herein above, preferably W is selected from the group consisting of halogen atom, $C_1$-$C_6$-alkyl, $C_1$-$C_6$-halogenoalkyl comprising up to 9 halogen atoms that can be the same or different, hydroxy-$C_1$-$C_6$-alkyl, $C_2$-$C_6$-alkenyl, $C_1$-$C_6$-alkoxycarbonyl, $C_3$-$C_7$-cycloalkyl, aryl, aryl-$C_1$-$C_6$-alkyl (wherein said aryl may be substituted with one or more halogen atoms), heterocyclyl, carboxyl, tri($C_1$-$C_6$-alkyl)silyloxy-$C_1$-$C_6$-alkyl, heteroaryl-$C_1$-$C_6$-alkyl and $C_1$-$C_6$-alkoxy-$C_1$-$C_6$-alkyl, more preferably W is halogen (e.g. chlorine, bromine), $C_1$-$C_6$-alkyl, $C_1$-$C_6$-halogenoalkyl comprising up to 9 halogen atoms that can be the same or different, hydroxy-$C_1$-$C_6$-alkyl, tri($C_1$-$C_6$-alkyl)silyloxy-$C_1$-$C_6$-alkyl, $C_3$-$C_7$-cycloalkyl (e.g. cyclopropyl) or aryl-$C_1$-$C_6$-alkyl (wherein said aryl may be substituted with one or more halogen atoms).

In some other embodiments, in the above formula (I), B is a partially saturated or unsaturated 5-membered heterocyclyl ring comprising a nitrogen atom and 1, 2 or 3 heteroatoms independently selected in the list consisting of N, O and S.

In the above formula (I), B is preferably selected from the group consisting of pyrazolyl, dihydroisoxazolyl, thiazolyl, isoxazolyl, triazolyl and imidazolyl, more preferably B is selected from the group consisting of pyrazol-1-yl, pyrazol-3-yl, pyrazol-4-yl, pyrazol-5-yl, dihydroisoxazol-3-yl, dihydroisoxazol-5-yl, thiazol-5-yl, thiazol-2-yl, 1,2,4-triazol-5-yl, imidazol-5-yl and imidazol-2-yl.

In the above formula (I), B is even more preferably selected from the group consisting of

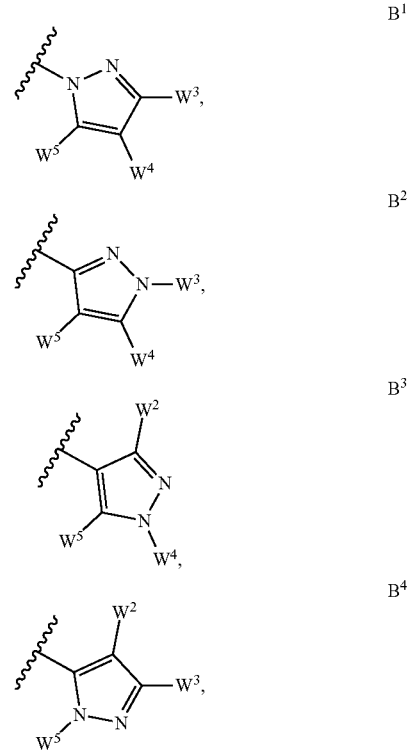

-continued

B⁵ 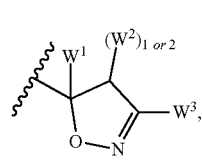

B⁶ 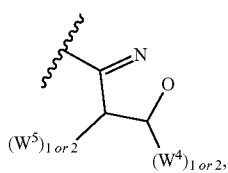

B⁷ 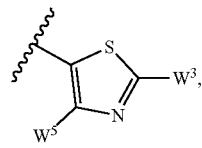

B⁸ 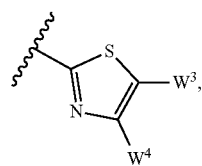

B⁹ 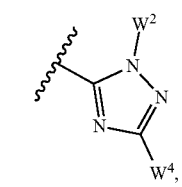

B¹⁰ 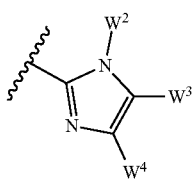

and

B¹¹ 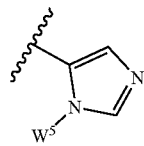

wherein $W^1$, $W^2$, $W^3$, $W^4$ and $W^5$ are independently a hydrogen atom or W as disclosed above, preferably $W^1$, $W^2$, $W^3$, $W^4$ and $W^5$ are independently selected from the group consisting of hydrogen atom, halogen atom, $C_1$-$C_6$-alkyl, $C_1$-$C_6$-halogenoalkyl comprising up to 9 halogen atoms that can be the same or different, hydroxy-$C_1$-$C_6$-alkyl, $C_2$-$C_6$-alkenyl, $C_1$-$C_6$-alkoxycarbonyl, $C_3$-$C_7$-cycloalkyl, aryl, aryl-$C_1$-$C_6$-alkyl (wherein said aryl may be substituted with one or more halogen atoms), heterocyclyl, carboxyl, tri($C_1$-$C_6$-alkyl)silyloxy-$C_1$-$C_6$-alkyl, heteroaryl-$C_1$-$C_6$-alkyl and $C_1$-$C_6$-alkoxy-$C_1$-$C_6$-alkyl, more preferably $W^1$, $W^2$, $W^3$, $W^4$ and $W^5$ are independently selected from the group consisting of hydrogen atom, halogen (e.g. chlorine, bromine), $C_1$-$C_6$-alkyl, $C_1$-$C_6$-halogenoalkyl comprising up to 9 halogen atoms that can be the same or different, hydroxy-$C_1$-$C_6$-alkyl, tri($C_1$-$C_6$-alkyl)silyloxy-$C_1$-$C_6$-alkyl, $C_3$-$C_7$-cycloalkyl (e.g. cyclopropyl) or aryl-$C_1$-$C_6$-alkyl (wherein said aryl may be substituted with one or more halogen atoms). More preferably B is selected from the group consisting of $B^1$, $B^4$, $B^5$ and $B^6$ wherein $W^1$, $W^2$, $W^3$, $W^4$ and $W^5$ are as disclosed herein.

In the above formula (I), Z is preferably selected from the group consisting of hydrogen atom, halogen atom, $C_1$-$C_6$-alkyl, $C_1$-$C_6$-halogenoalkyl comprising up to 9 halogen atoms that can be the same or different, $C_1$-$C_6$-alkoxy, $C_1$-$C_6$-halogenoalkoxy comprising up to 9 halogen atoms that can be the same or different and cyano. More preferably Z is a hydrogen atom, a halogen atom, a $C_1$-$C_6$-alkyl or a $C_1$-$C_6$-halogenoalkyl comprising up to 9 halogen atoms that can be the same or different, even more preferably Z is a hydrogen atom, a chlorine atom, a methyl or a difluoromethyl group.

In the above formula (I), X is preferably independently selected from the group consisting of halogen atom, $C_1$-$C_6$-alkyl, $C_1$-$C_6$-halogenoalkyl comprising up to 9 halogen atoms that can be the same or different, hydroxyl, $C_1$-$C_6$-alkoxy and $C_1$-$C_6$-halogenoalkoxy comprising up to 9 halogen atoms that can be the same or different, more preferably X is a halogen atom, $C_1$-$C_6$-alkyl, $C_1$-$C_6$-halogenoalkyl comprising up to 9 halogen atoms that can be the same or different or $C_1$-$C_6$-halogenoalkoxy comprising up to 9 halogen atoms that can be the same or different, even more preferably X is a chlorine atom, a fluorine atom, a methyl group or a trifluoromethoxy group.

In the above formula (I), n is preferably 0, 1, 2 or 3, more preferably 0 or 1.

In the above formula (I), n is preferably 0, 1, 2 or 3, more preferably 0 or 1, with X being preferably a halogen atom, a $C_1$-$C_6$-alkyl, a $C_1$-$C_6$-halogenoalkyl comprising up to 9 halogen atoms that can be the same or different, a hydroxyl, a $C_1$-$C_6$-alkoxy or a $C_1$-$C_6$-halogenoalkoxy comprising up to 9 halogen atoms that can be the same or different, more preferably with X being a halogen atom (e.g. fluorine or chlorine), $C_1$-$C_6$-alkyl (e.g. methyl), $C_1$-$C_6$-halogenoalkyl comprising up to 9 halogen atoms that can be the same or different or $C_1$-$C_6$-halogenoalkoxy comprising up to 9 halogen atoms that can be the same or different (e.g. trifluoromethoxy).

In the above formula (I), Y is preferably independently selected from the group consisting of halogen atom, hydroxyl, $C_1$-$C_6$-alkyl and $C_1$-$C_6$-halogenoalkyl comprising up to 9 halogen atoms that can be the same or different, more preferably Y is independently a hydroxyl, a fluorine atom, a chlorine atom, a methyl group, a difluoromethyl group or a trifluoromethyl group.

In the above formula (I), p is preferably 0, 1, 2 or 3, more preferably 0, 1 or 2.

In the above formula (I), p is preferably 0, 1, 2 or 3, more preferably 0, 1 or 2 with Y being preferably independently selected from the group consisting of halogen atom, hydroxyl, substituted or unsubstituted $C_1$-$C_6$-alkyl and $C_1$-$C_6$-halogenoalkyl comprising up to 9 halogen atoms that can be the same or different, more preferably with Y being independently a hydroxyl, a fluorine atom, a chlorine atom, a methyl group, a difluoromethyl group or a trifluoromethyl group.

In the above formula (I), W is preferably independently selected from the group consisting of halogen atom, $C_1$-$C_6$-alkyl, $C_1$-$C_6$-halogenoalkyl comprising up to 9 halogen atoms that can be the same or different, hydroxy-$C_1$-$C_6$-alkyl, $C_2$-$C_6$-alkenyl, $C_1$-$C_6$-alkoxycarbonyl, $C_3$-$C_7$-cycloalkyl, aryl, aryl-$C_1$-$C_6$-alkyl (wherein said aryl may be substituted with one or more halogen atoms), heterocyclyl, carboxyl, tri($C_1$-$C_6$-alkyl)silyloxy-$C_1$-$C_6$-alkyl, heteroaryl-$C_1$-$C_6$-alkyl and $C_1$-$C_6$-alkoxy-$C_1$-$C_6$-alkyl, more preferably W is halogen (e.g. chlorine, bromine, fluorine), $C_1$-$C_6$-alkyl, $C_1$-$C_6$-halogenoalkyl comprising up to 9 halogen atoms that can be the same or different, hydroxy-$C_1$-$C_6$-alkyl, tri($C_1$-$C_6$-alkyl)silyloxy-$C_1$-$C_6$-alkyl, $C_3$-$C_7$-cycloalkyl (e.g. cyclopropyl) or aryl-$C_1$-$C_6$-alkyl (wherein said aryl may be substituted with one or more halogen atoms).

In the above formula (I), m is preferably 0, 1, 2 or 3, more preferably m is 1, 2 or 3, even more preferably 1 or 2.

In the above formula (I), m is preferably 1, 2 or 3, more preferably m is 1 or 2, and W is independently selected from the group consisting of halogen atom, $C_1$-$C_6$-alkyl, $C_1$-$C_6$-halogenoalkyl comprising up to 9 halogen atoms that can be the same or different, hydroxy-$C_1$-$C_6$-alkyl, $C_2$-$C_6$-alkenyl, $C_1$-$C_6$-alkoxycarbonyl, $C_3$-$C_7$-cycloalkyl, aryl, aryl-$C_1$-$C_6$-alkyl (wherein said aryl may be substituted with one or more halogen atoms), heterocyclyl, carboxyl, heteroaryl-$C_1$-$C_6$-alkyl, tri($C_1$-$C_6$-alkyl)silyloxy-$C_1$-$C_6$-alkyl and $C_1$-$C_6$-alkoxy-$C_1$-$C_6$-alkyl, more preferably W is halogen (e.g. chlorine, bromine), $C_1$-$C_6$-alkyl, $C_1$-$C_6$-halogenoalkyl comprising up to 9 halogen atoms that can be the same or different, hydroxy-$C_1$-$C_6$-alkyl, tri($C_1$-$C_6$-alkyl)silyloxy-$C_1$-$C_6$-alkyl, $C_3$-$C_7$-cycloalkyl (e.g. cyclopropyl) or aryl-$C_1$-$C_6$-alkyl (wherein said aryl may be substituted with one or more halogen atoms).

In the above formula (I), $R^1$ is preferably a hydrogen atom or a halogen atom, more preferably $R^1$ is a hydrogen atom.

In the above formula (I), $R^2$ is preferably a hydrogen atom or a halogen atom, more preferably $R^2$ is a hydrogen atom.

In the above formula (I), $R^3$ is preferably a hydrogen atom or a substituted or non-substituted $C_1$-$C_6$-alkyl, preferably $R^3$ is a hydrogen atom or a methyl group, even more preferably $R^3$ is a hydrogen atom.

In the above formula (I), A is preferably selected from the group consisting of:

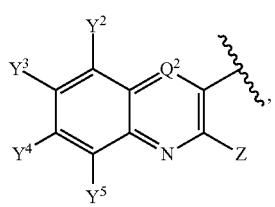
(A$^1$)

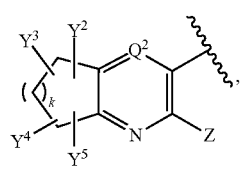
(A$^2$)

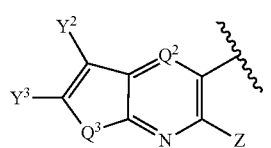
(A$^3$)

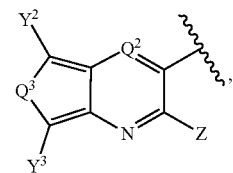
(A$^4$)

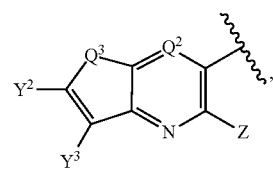
(A$^5$)

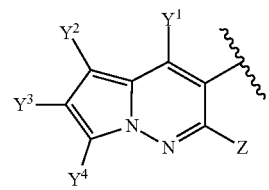
(A$^6$)

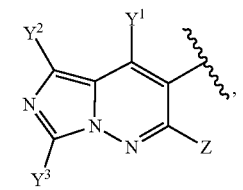
(A$^7$)

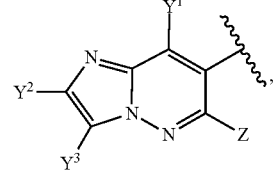
(A$^8$)

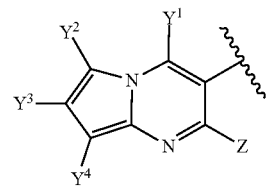
(A$^9$)

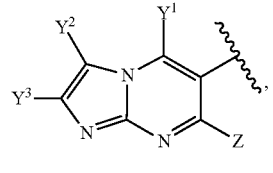
(A$^{10}$)

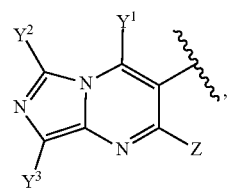
(A$^{11}$)

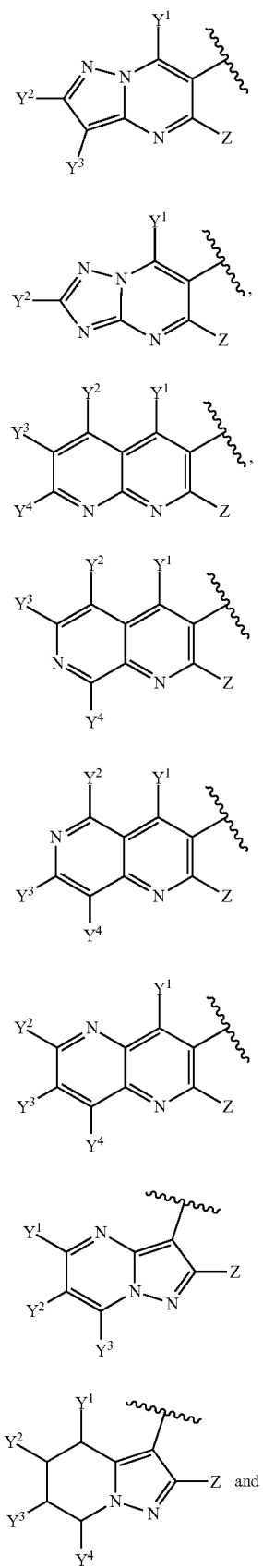

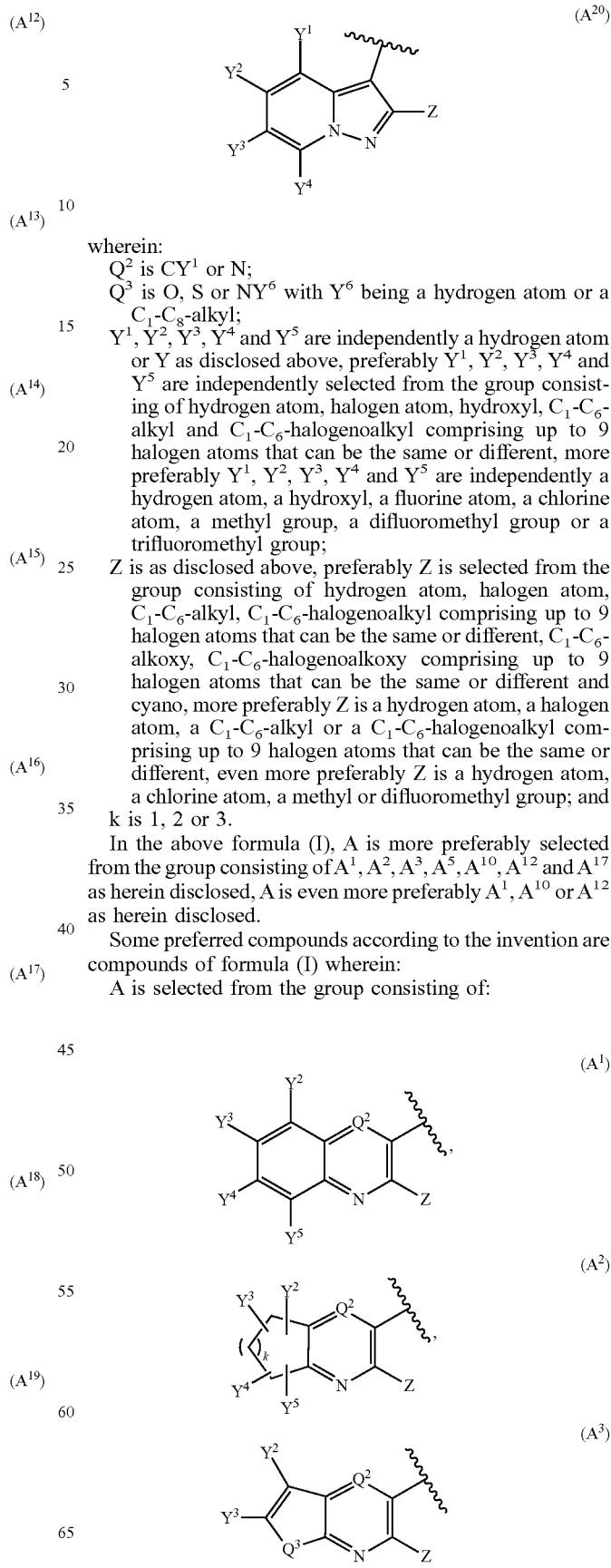

wherein:
$Q^2$ is $CY^1$ or N;
$Q^3$ is O, S or $NY^6$ with $Y^6$ being a hydrogen atom or a $C_1$-$C_8$-alkyl;
$Y^1$, $Y^2$, $Y^3$, $Y^4$ and $Y^5$ are independently a hydrogen atom or Y as disclosed above, preferably $Y^1$, $Y^2$, $Y^3$, $Y^4$ and $Y^5$ are independently selected from the group consisting of hydrogen atom, halogen atom, hydroxyl, $C_1$-$C_6$-alkyl and $C_1$-$C_6$-halogenoalkyl comprising up to 9 halogen atoms that can be the same or different, more preferably $Y^1$, $Y^2$, $Y^3$, $Y^4$ and $Y^5$ are independently a hydrogen atom, a hydroxyl, a fluorine atom, a chlorine atom, a methyl group, a difluoromethyl group or a trifluoromethyl group;
Z is as disclosed above, preferably Z is selected from the group consisting of hydrogen atom, halogen atom, $C_1$-$C_6$-alkyl, $C_1$-$C_6$-halogenoalkyl comprising up to 9 halogen atoms that can be the same or different, $C_1$-$C_6$-alkoxy, $C_1$-$C_6$-halogenoalkoxy comprising up to 9 halogen atoms that can be the same or different and cyano, more preferably Z is a hydrogen atom, a halogen atom, a $C_1$-$C_6$-alkyl or a $C_1$-$C_6$-halogenoalkyl comprising up to 9 halogen atoms that can be the same or different, even more preferably Z is a hydrogen atom, a chlorine atom, a methyl or difluoromethyl group; and
k is 1, 2 or 3.

In the above formula (I), A is more preferably selected from the group consisting of $A^1$, $A^2$, $A^3$, $A^5$, $A^{10}$, $A^{12}$ and $A^{17}$ as herein disclosed, A is even more preferably $A^1$, $A^{10}$ or $A^{12}$ as herein disclosed.

Some preferred compounds according to the invention are compounds of formula (I) wherein:
A is selected from the group consisting of:

-continued

-continued

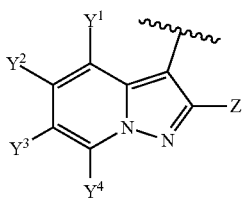
(A²⁰)

wherein:

- Q² is CY¹ or N;
- Q³ is O, S or NY⁶ with Y⁶ being a hydrogen atom or a $C_1$-$C_8$-alkyl;
- $Y^1$, $Y^2$, $Y^3$, $Y^4$ and $Y^5$ are independently a hydrogen atom or Y as disclosed above, preferably $Y^1$, $Y^2$, $Y^3$, $Y^4$ and $Y^5$ are independently selected from the group consisting of hydrogen atom, halogen atom, hydroxyl, $C_1$-$C_6$-alkyl and $C_1$-$C_6$-halogenoalkyl comprising up to 9 halogen atoms that can be the same or different, more preferably $Y^1$, $Y^2$, $Y^3$, $Y^4$ and $Y^5$ are independently a hydrogen atom, a hydroxyl, a fluorine atom, a chlorine atom, a methyl group, a difluoromethyl group or a trifluoromethyl group;
- Z is as disclosed above, preferably Z is selected from the group consisting of hydrogen atom, halogen atom, $C_1$-$C_6$-alkyl, $C_1$-$C_6$-halogenoalkyl comprising up to 9 halogen atoms that can be the same or different, $C_1$-$C_6$-alkoxy, $C_1$-$C_6$-halogenoalkoxy comprising up to 9 halogen atoms that can be the same or different and cyano, more preferably Z is a hydrogen atom, a halogen atom, a $C_1$-$C_6$-alkyl or a $C_1$-$C_6$-halogenoalkyl comprising up to 9 halogen atoms that can be the same or different, even more preferably Z is a hydrogen atom, a chloro atom, a methyl or difluoromethyl group; and
- k is 1, 2 or 3;
- preferably A is selected from the group consisting of $A^1$, $A^2$, $A^3$, $A^5$, $A^{10}$, $A^{12}$ and $A^{17}$ as herein disclosed, more preferably A is $A^1$, $A^{10}$ or $A^{12}$ as herein disclosed;
- B is selected from the group consisting of pyrrolyl, thiazolyl, imidazolyl, dihydroisoxazolyl, isoxazolyl, pyrazolyl, triazolyl and tetrazolyl or from the group consisting of pyrazolyl, dihydroisoxazolyl, thiazolyl, isoxazolyl, triazolyl and imidazolyl;
- preferably B is selected from the group consisting of:

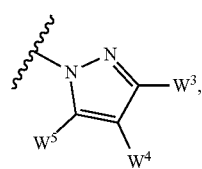
B¹

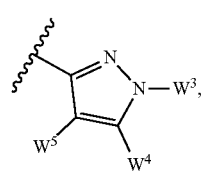
B²

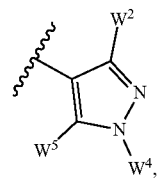
B³

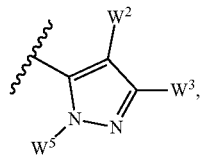
B⁴

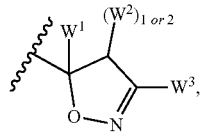
B⁵

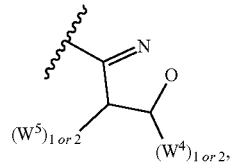
B⁶

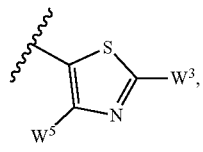
B⁷

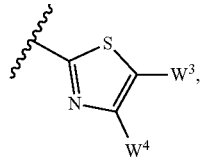
B⁸

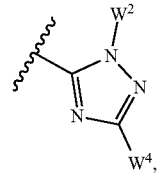
B⁹

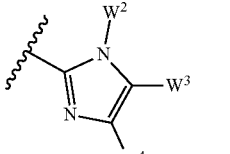
B¹⁰
and

B¹¹ wherein $W^1$, $W^2$, $W^3$, $W^4$ and $W^5$ are independently a hydrogen atom or W as disclosed above, preferably $W^1$, $W^2$, $W^3$, $W^4$ and $W^5$ are independently selected from the group consisting of hydrogen atom, halogen atom, $C_1$-$C_6$-alkyl, $C_1$-$C_6$-halogenoalkyl comprising up to 9 halogen atoms that can be the same or different, hydroxy-$C_1$-$C_6$-alkyl, $C_2$-$C_6$-alkenyl, $C_1$-$C_6$-alkoxycarbonyl, $C_3$-$C_7$-cycloalkyl, aryl, aryl-$C_1$-$C_6$-alkyl (wherein said aryl may be substituted with one or more halogen atoms), heterocyclyl, carboxyl, tri($C_1$-$C_6$-alkyl)silyloxy-$C_1$-$C_6$-alkyl, heteroaryl-$C_1$-$C_6$-alkyl and $C_1$-$C_6$-alkoxy-$C_1$-$C_6$-alkyl, more preferably $W^1$, $W^2$, $W^3$, $W^4$ and $W^5$ are independently selected from the group consisting of hydrogen atom, halogen (e.g. chlorine, bromine), $C_1$-$C_6$-alkyl, $C_1$-$C_6$-halogenoalkyl comprising up to 9 halogen atoms that can be the same or different, hydroxy-$C_1$-$C_6$-alkyl, tri($C_1$-$C_6$-alkyl)silyloxy-$C_1$-$C_6$-alkyl, $C_3$-$C_7$-cycloalkyl (e.g. cyclopropyl) or aryl-$C_1$-$C_6$-alkyl (wherein said aryl may be substituted with one or more halogen atoms), more preferably B is selected from the group consisting of $B^1$, $B^4$, $B^5$ and $B^6$ wherein $W^1$, $W^2$, $W^3$, $W^4$ and $W^5$ are as disclosed herein;

W is as disclosed herein, preferably W is independently selected from the group consisting of halogen atom, $C_1$-$C_6$-alkyl, $C_1$-$C_6$-halogenoalkyl comprising up to 9 halogen atoms that can be the same or different, hydroxy-$C_1$-$C_6$-alkyl, $C_2$-$C_6$-alkenyl, $C_1$-$C_6$-alkoxycarbonyl, $C_3$-$C_7$-cycloalkyl, aryl, aryl-$C_1$-$C_6$-alkyl (wherein said aryl may be substituted with one or more halogen atoms), heterocyclyl, carboxyl, tri($C_1$-$C_6$-alkyl)silyloxy-$C_1$-$C_6$-alkyl, heteroaryl-$C_1$-$C_6$-alkyl and $C_1$-$C_6$-alkoxy-$C_1$-$C_6$-alkyl, more preferably W is halogen (e.g. chlorine, bromine), $C_1$-$C_6$-alkyl, $C_1$-$C_6$-halogenoalkyl comprising up to 9 halogen atoms that can be the same or different, hydroxy-$C_1$-$C_6$-alkyl, tri($C_1$-$C_6$-alkyl)silyloxy-$C_1$-$C_6$-alkyl, $C_3$-$C_7$-cycloalkyl (e.g. cyclopropyl) or aryl-$C_1$-$C_6$-alkyl (wherein said aryl may be substituted with one or more halogen atoms), m is as disclosed herein, preferably m is 0, 1, 2 or 3, more preferably m is 1, 2 or 3, even more preferably m is 1 or 2;

L is as disclosed herein, more preferably L is $CR^1R^2$ or $NR^3$ wherein
  $R^1$ and $R^2$ are independently a hydrogen atom or a halogen atom, preferably $R^1$ and $R^2$ are hydrogen;
  $R^3$ is a hydrogen atom or a $C_1$-$C_6$-alkyl, preferably $R^3$ is hydrogen or methyl;

X is as disclosed herein, preferably X is selected from the group consisting of halogen atom, $C_1$-$C_6$-alkyl, $C_1$-$C_6$-halogenoalkyl comprising up to 9 halogen atoms that can be the same or different, hydroxyl, $C_1$-$C_6$-alkoxy and $C_1$-$C_6$-halogenoalkoxy comprising up to 9 halogen atoms that can be the same or different, more preferably X is a halogen atom, $C_1$-$C_6$-alkyl, $C_1$-$C_6$-halogenoalkyl comprising up to 9 halogen atoms that can be the same or different or $C_1$-$C_6$-halogenoalkoxy comprising up to 9 halogen atoms that can be the same or different, even more preferably X is a chlorine atom, a fluorine atom, a methyl group or a trifluoromethoxy group;

n is as disclosed herein, preferably n is 0, 1, 2 or 3, more preferably n is 0 or 1.

In the above embodiments, wherein B is selected from the group consisting of $B^1$ to $B^{11}$, or when B is selected from the group consisting of $B^1$, $B^4$, $B^5$ and $B^6$, it may be preferred to have $W^1$, $W^3$ and $W^4$ being a hydrogen atom and $W^2$ and $W^5$ being independently a hydrogen atom or W as disclosed above, preferably $W^2$ and $W^5$ being independently a hydrogen atom, a $C_1$-$C_6$-alkyl, a $C_2$-$C_6$-alkenyl, a $C_1$-$C_6$-alkoxycarbonyl, an aryl-$C_1$-$C_6$-alkyl, a heteroaryl-$C_1$-$C_6$-alkyl (preferably benzyl), a tri($C_1$-$C_6$-alkyl)silyloxy-$C_1$-$C_6$-alkyl or a $C_1$-$C_6$-alkoxy-$C_1$-$C_6$-alkyl, more preferably $W^2$ and $W^5$ are independently a hydrogen atom, a $C_1$-$C_6$-alkyl, a tri($C_1$-$C_6$-alkyl)silyloxy-$C_1$-$C_6$-alkyl or an aryl-$C_1$-$C_6$-alkyl.

The above mentioned preferences with regard to the substituents of the compounds according to the invention can be combined in various manners. These combinations of preferred features thus provide sub-classes of compounds according to the invention. Examples of such sub-classes of preferred compounds according to the invention are:

preferred features of A with one or more preferred features of B, Z, m, n, p, $R^1$, $R^2$, $R^3$, W, X and Y;

preferred features of B with one or more preferred features of A, Z, m, n, p, $R^1$, $R^2$, $R^3$, W, X and Y;

preferred features of Z with one or more preferred features of A, B, m, n, p, $R^1$, $R^2$, $R^3$, W, X and Y;

preferred features of m with one or more preferred features of A, B, Z, n, p, $R^1$, $R^2$, $R^3$, W, X and Y;

preferred features of n with one or more preferred features of A, B, Z, m, p, $R^1$, $R^2$, $R^3$, W, X and Y;

preferred features of p with one or more preferred features of A, B, Z, m, n, $R^1$, $R^2$, $R^3$, W, X and Y;

preferred features of $R^1$ with one or more preferred features of A, B, Z, m, n, p, $R^2$, $R^3$, W, X and Y;

preferred features of $R^2$ with one or more preferred features of A, B, Z, m, n, p, $R^1$, $R^3$, W, X and Y;

preferred features of $R^3$ with one or more preferred features of A, B, Z, m, n, p, $R^1$, $R^2$, W, X and Y;

preferred features of W with one or more preferred features of A, B, Z, m, n, p, $R^1$, $R^2$, $R^3$, X and Y;

preferred features of X with one or more preferred features of A, B, Z, m, n, p, $R^1$, $R^2$, $R^3$, W and Y;

preferred features of Y with one or more preferred features of A, B, Z, m, n, p, $R^1$, $R^2$, $R^3$, W and X.

In these combinations of preferred features of the substituents of the compounds according to the invention, the said preferred features can also be selected among the more preferred features of each of A, B, Z, m, n, p, $R^1$, $R^2$, $R^3$, W, X and Y so as to form most preferred subclasses of compounds according to the invention.

As shown herein below in the examples section, the compounds of formula (I) were shown to exhibit better efficacy than the structurally related compounds disclosed in WO 2013/058256.

Processes for the Preparation of the Active Ingredients

The present invention also relates to processes for the preparation of compounds of formula (I). Unless indicated otherwise, the radicals A, B, L, m, n, p, $Q^1$, W, X, Y and Z have the meanings given above for the compounds of formula (I). These definitions apply not only to the end products of the formula (I) but likewise to all intermediates.

Compounds of formula (I) as herein-defined can be prepared by a process P1 which comprises the step of reacting a compound of formula (II) with a compound of formula (III):

Process P1:

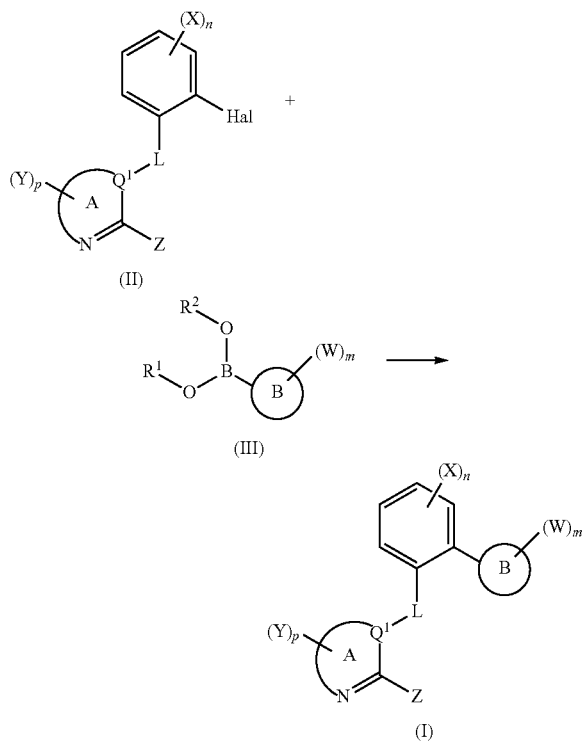

Hal=Cl, Br, I, preferably Br or I;

$R^1$ and $R^2$=are independently H or substituted or non-substituted $C_1$-$C_8$-alkyl, or $R^1$ and $R^2$ groups may form together with the oxygen atom to which they are respectively attached a 5- or 6-membered ring; preferably both $R^1$ and $R^2$ are H or $R^1$ and $R^2$ form together with the oxygen atom to which they are respectively attached a pinacolboranyl.

Process P1 can be performed in the presence of a transition metal catalyst such as palladium and if appropriate in the presence of a phosphine ligand or a N-heterocyclic carbene ligand, if appropriate in the presence of a base and if appropriate in the presence of a solvent according to known processes.

Halogenoaryl derivatives of formula (II) can be prepared by diazotation of an aniline of formula (IV) or one of its salts according to known processes (Patai's Chemistry of Functional Groups—Amino, Nitroso, Nitro and Related Groups—1996).

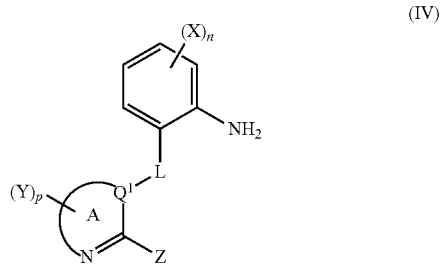

Halogenoaryl derivatives of formula (II) can also be prepared by aromatic nucleophilic substitution according to known processes (Journal of Heterocyclic Chemistry (2008), 45, 1199 and Synthetic Communications (1999), 29, 1393).

Anilines of formula (IV) can be prepared by reduction of a nitro group of formula (V) or one of its salts according to known processes (Patai's Chemistry of Functional Groups—Amino, Nitroso, Nitro and Related Groups—1996).

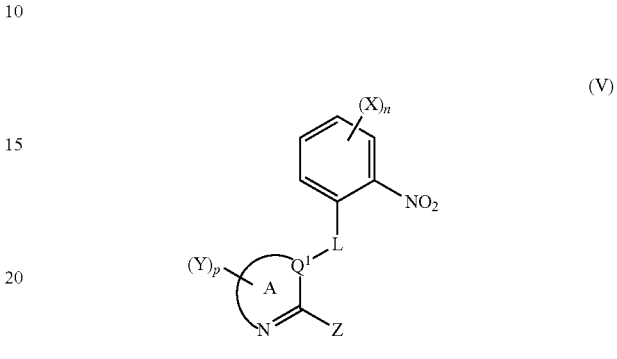

Boronic acid or boronic ester derivatives of formula (III) are commercially available or can be prepared by known processes.

Process P1 can be carried out in the presence of a catalyst, such as a metal salt or complex. Suitable metal derivatives for this purpose are transition metal catalysts such as palladium. Suitable metal salts or complexes for this purpose are for example, palladium chloride, palladium acetate, tetrakis(triphenylphosphine)palladium(0), bis(dibenzylideneacetone)palladium(0), tris(dibenzylideneacetone)dipalladium(0), bis(triphenylphosphine)palladium(II) dichloride, [1,1'-bis(diphenylphosphino)ferrocene]dichloropalladium (II), bis(cinnamyl)dichlorodipalladium(II), bis(allyl)dichlorodipalladium(II) or [1,1'-Bis(di-tert-butylphosphino)ferrocene]dichloropalladium(II).

It is also possible to generate a palladium complex in the reaction mixture by separate addition to the reaction of a palladium salt and a ligand or salt, such as triethylphosphine, tri-tert-butylphosphine, tri-tert-butylphosphonium tetrafluoroborate, tricyclohexylphosphine, 2-(dicyclohexylphosphino)biphenyl, 2-(di-tert-butylphosphino)biphenyl, 2-(dicyclohexylphosphino)-2'-(N,N-dimethylamino)biphenyl, 2-(tert-butylphosphino)-2'-(N,N-dimethylamino)biphenyl, 2-di-tert-butylphosphino-2',4',6'-triisopropylbiphenyl 2-dicyclohexylphosphino-2',4',6'-triisopropylbiphenyl, 2-dicyclohexylphosphino-2,6'-dimethoxybiphenyl, 2-dicyclohexylphosphino-2',6'-diisopropoxybiphenyl, triphenylphosphine, tris-(o-tolyl)phosphine, sodium 3-(diphenylphosphino)benzenesulfonate, tris-2-(methoxyphenyl)phosphine, 2,2'-bis(diphenylphosphino)-1,1'-binaphthyl, 1,4-bis(diphenylphosphino)butane, 1,2-bis(diphenylphosphino) ethane, 1,4-bis(dicyclohexylphosphino) butane, 1,2-bis(dicyclohexylphosphino)-ethane, 2-(dicyclohexylphosphino)-2'-(N,N-dimethylamino)-biphenyl, 1,1'-bis(diphenylphosphino)-ferrocene, (R)-(-)-1-[(S)-2-diphenyl-phosphino)ferrocenyl]ethyldicyclohexylphosphine, tris-(2,4-tert-butyl-phenyl)phosphite, di(1-adamantyl)-2-morpholinophenylphosphine or 1,3-bis(2,4,6-trimethylphenyl)imidazolium chloride.

It is also advantageous to choose the appropriate catalyst and/or ligand from commercial catalogues such as "Metal Catalysts for Organic Synthesis" by Strem Chemicals or "Phosphorous Ligands and Compounds" by Strem Chemicals.

Suitable bases for carrying out Process P1 can be inorganic and organic bases which are customary for such reactions. Preference is given to using alkaline earth metal or alkali metal hydroxides, such as sodium hydroxide, calcium hydroxide, potassium hydroxide or other ammonium hydroxide derivatives; alkaline earth metal, alkali metal or ammonium fluorides such as potassium fluoride, caesium fluoride or tetrabutylammonium fluoride; alkaline earth metal or alkali metal carbonates, such as sodium carbonate, potassium carbonate, potassium bicarbonate, sodium bicarbonate or caesium carbonate; alkali metal or alkaline earth metal acetates, such as sodium acetate, lithium acetate, potassium acetate or calcium acetate; alkali metal or alkaline earth metal phosphate, such as tripotassium phosphate alkali; alkali metal alcoholates, such as potassium tert-butoxide or sodium tert-butoxide; tertiary amines, such as trimethylamine, triethylamine, tributylamine, N,N-dimethylaniline, N,N-dicyclohexylmethylamine, N,N-diisopropylethylamine, N-methylpiperidine, N,N-dimethylaminopyridine, diazabicyclooctane (DABCO), diazabicyclononene (DBN) or diazabicycloundecene (DBU); and also aromatic bases, such as pyridine, picolines, lutidines or collidines.

Suitable solvents for carrying out process P1 can be customary inert organic solvents. Preference is given to using optionally halogenated, aliphatic, alicyclic or aromatic hydrocarbons, such as petroleum ether, pentane, hexane, heptane, cyclohexane, methylcyclohexane, benzene, toluene, xylene or decalin; chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 2-methyltetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; ureas, such as 1,3-dimethyl-3,4,5,6-tetrahydro-2(1H)-pyrimidinone; esters, such as methyl acetate or ethyl acetate, sulfoxides, such as dimethyl sulfoxide, or sulfones, such as sulfolane; and a mixture thereof.

It can also be advantageous to carry out process P1 with a co-solvent such as water or an alcohol such as methanol, ethanol, propanol, isopropanol or tert-butanol.

Process P1 may be performed in an inert atmosphere such as argon or nitrogen atmosphere. When carrying out process P1, 1 mole or an excess of compound of formula (III) and from 1 to 5 moles of base and from 0.01 to 20 mole percent of a palladium complex can be employed per mole of compound of formula (II). It is also possible to employ the reaction components in other ratios. Work-up is carried out by known methods.

Compounds of formula (I) as herein-defined can be prepared by a process P2 which comprises the step of reacting a compound of formula (VI) with a compound of formula (VII):

Process P2:

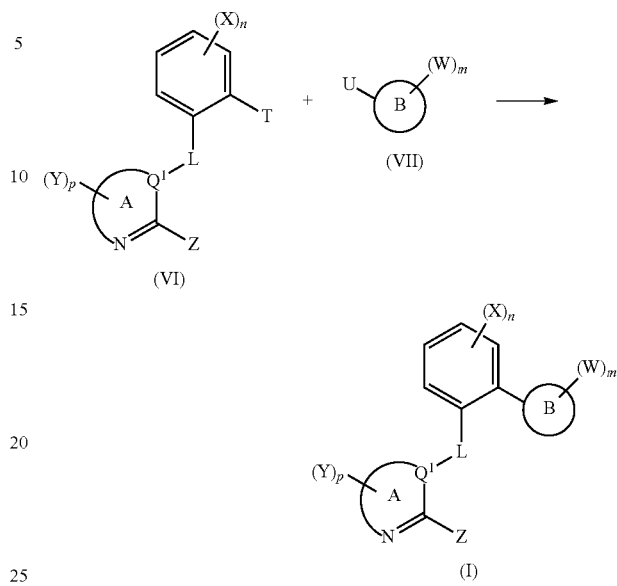

T represents a boron derivative such as a boronic acid, a boronic ester or a potassium trifluoroborate derivative;

U represents chloro, bromo, iodo, a mesyl group, a tosyl group or a triflyl group; preferably bromo or iodo;

Process P2 can be performed in the presence of a transition metal catalyst such as palladium and if appropriate in the presence of a phosphine ligand or a N-heterocyclic carbene ligand, if appropriate in the presence of a base and if appropriate in the presence of a solvent according to known processes.

Boronic acid or boronic ester derivatives of formula (VI) can be prepared from halogenoaryl derivatives (III) using a reagent such as bis(pinacolato)diboron in presence of a transition metal catalyst such as palladium and if appropriate in presence of a phosphine ligand or a N-heterocyclic carbene ligand, if appropriate in presence of a base and if appropriate in presence of a solvent according to known processes.

Suitable catalysts, bases and solvents for carrying out process P2 and for the synthesis of intermediates of formula (VI) can be as disclosed in connection with process P1.

Alternatively, boronic acid or boronic ester derivatives of formula (VI) can be prepared from halogenoaryl derivatives (III) by halogen metal exchange using the appropriate organometallic reagent such as n-butyllithium and the appropriate boron derivative such as trimethyl borate in the appropriate organic solvent such as an ether, preferably tetrahydrofuran or diethyether.

Halide derivatives of formula (VII) are commercially available or can be prepared by processes known by the person skilled in the art.

Compounds of formula (Ia) as herein-defined, i.e. compounds of formula (I) wherein L is NH and $Q^1$ is C, can be prepared by a process P3 which comprises the step of reacting a compound of formula (VIII) with a compound of formula (IX):

Process P3:

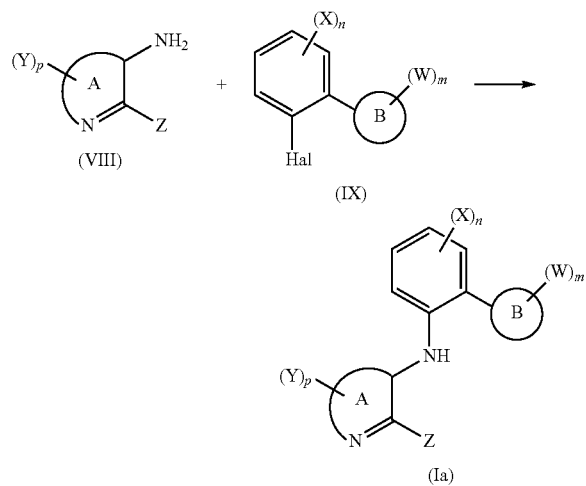

Hal=Cl, Br, I, preferably Br or I;

Process P3 can be performed in the presence of a transition metal catalyst such as palladium and if appropriate in the presence of a phosphine ligand or a N-heterocyclic carbene ligand, if appropriate in the presence of a base and if appropriate in the presence of a solvent according to known processes.

Amines of formula (VIII) and halogenoaryl of formula (IX) are commercially available or can be made according to methods known by the person skilled in the art.

Suitable catalysts, bases and solvents for carrying out process P3 can be as disclosed in connection with process P1.

Alternatively, compounds of formula (Ia) as herein-defined can be prepared by a process P4 which comprises the step of reacting a compound of formula (X) with a compound of formula (XI):

Process P4:

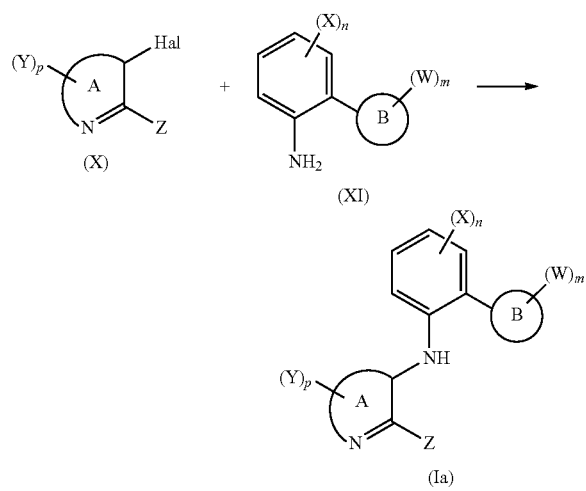

Hal=Cl, Br, I, preferably Br or I;

Process P4 can be performed in the presence of a transition metal catalyst such as palladium and if appropriate in the presence of a phosphine ligand or a N-heterocyclic carbene ligand, if appropriate in the presence of a base and if appropriate in the presence of a solvent according to known processes.

Halogenoaryl of formula (X) and amines of formula (XI) are commercially available or can be made according to methods known by the person skilled in the art.

Suitable catalysts, bases and solvents for carrying out process P4 can be as disclosed in connection with process P1.

Compounds of formula (Ib) as herein-defined, i.e. compounds of formula (I) wherein L is $CH_2$ and $Q^1$ is C, can be prepared by a process P5 which comprises the step of reacting a compound of formula (XII) with a compound of formula (XIII):

Process P5:

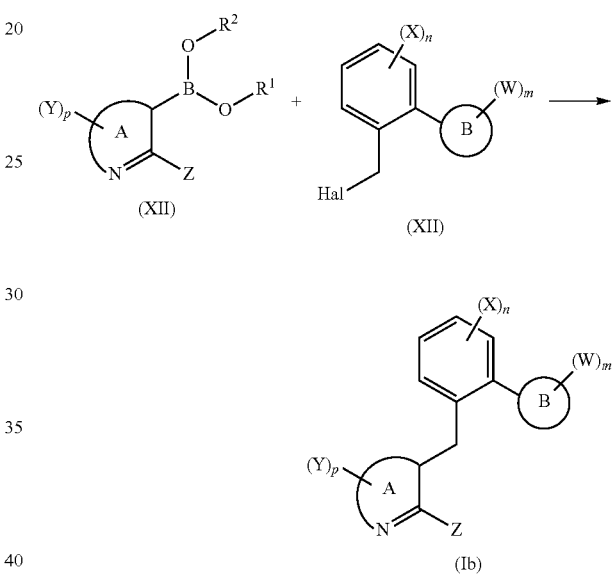

Hal=Cl, Br, I, preferably Cl, or Br;

$R^1$ and $R^2$= are independently H or substituted or non-substituted $C_1$-$C_8$-alkyl or $R^1$ and $R^2$ may form together with the oxygen atom to which they are respectively attached a 5- or 6-membered ring; preferably both $R^1$ and $R^2$ are H or $R^1$ and $R^2$ form together with the oxygen atom to which they are respectively attached a pinacolboranyl.

Process P5 can be performed in the presence of a transition metal catalyst such as palladium and if appropriate in the presence of a phosphine ligand or a N-heterocyclic carbene ligand, if appropriate in the presence of a base and if appropriate in the presence of a solvent according to known processes.

Intermediates of formula (XII) and halides of formula (XIII) are commercially available or can be made according to methods known by the person skilled in the art.

Suitable catalysts, bases and solvents for carrying out process P5 can be as disclosed in connection with process P1.

Alternatively, compounds of formula (Ib) as herein-defined can be prepared by a process P6 which comprises the step of reacting a compound of formula (XIV) with a compound of formula (XV):

Process P6:

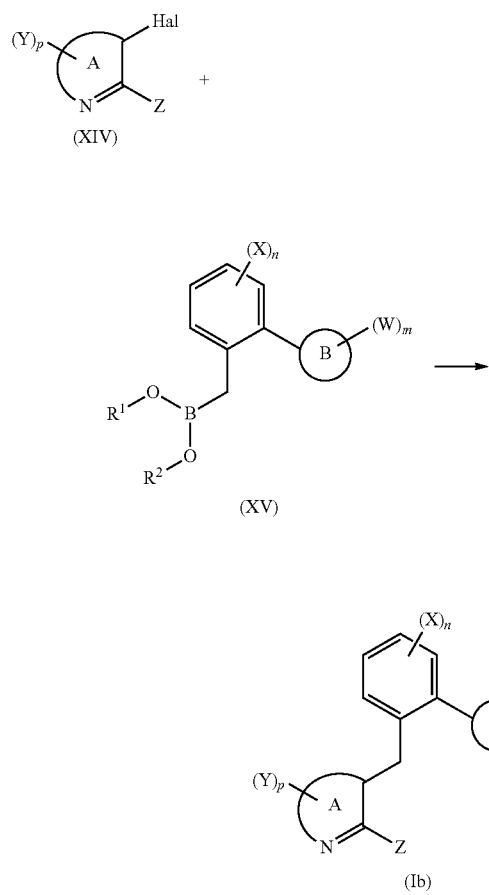

Process P8:

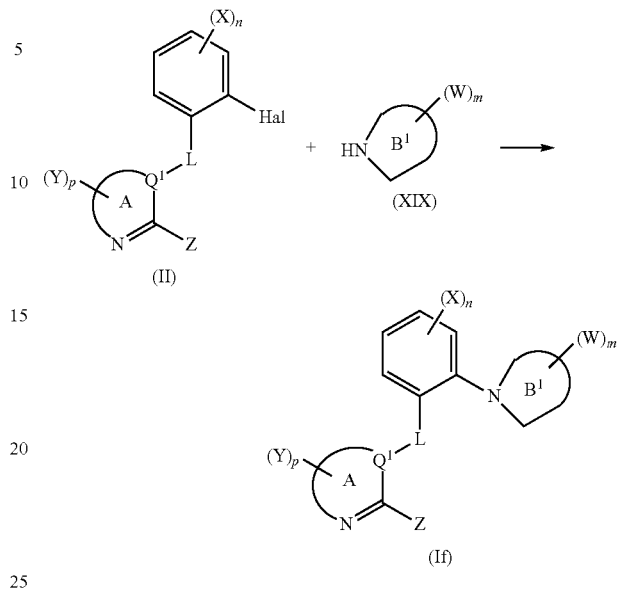

Hal=Cl, Br, I, preferably Br or I;

$R^1$ and $R^2$=are independently H or substituted or non-substituted $C_1$-$C_8$-alkyl or $R^1$ and $R^2$ may form together with the oxygen atom to which they are respectively attached a 5- or 6-membered ring; preferably both $R^1$ and $R^2$ are H or $R^1$ and $R^2$ form together with the oxygen atom to which they are respectively attached a pinacolboranyl.

Process P6 can be performed in the presence of a transition metal catalyst such as palladium and if appropriate in the presence of a phosphine ligand or a N-heterocyclic carbene ligand, if appropriate in the presence of a base and if appropriate in the presence of a solvent according to known processes.

Halides of formula (XIV) and intermediates of formula (XV) are commercially available or can be made according to methods known by the person skilled in the art.

Suitable catalysts, bases and solvents for carrying out process P6 can be as disclosed in connection with process P1.

Compounds of formula (If) as herein-defined, i.e. compounds of formula (I) wherein B is an heterocycle $B^1$ selected from the group consisting of pyrrole, imidazole, pyrazole, 1,2,3-triazole, 1,2,4-triazole and tetrazole, can be prepared following process P8 which comprises the step of reacting a compound of formula (II) with a compound of formula (XIX):

$B^1$ represents one of the following heterocycles: pyrrole, imidazole, pyrazole, 1,2,3-triazole, 1,2,4-triazole, tetrazole;

Compound of formula (If), where the heterocycle $B^1$ is linked to the phenyl ring via its nitrogen atom, can be made by reaction of a halide of formula (II) with a heterocycle of formula (XIX). This reaction may be carried out in presence of a catalyst such as copper iodide and a ligand such as a diamine, an amino alcohol, an amino acid or a phosphine may also be used. The reaction is usually carried out in presence of a base such as potassium phosphate, potassium carbonate or sodium carbonate. As for the solvent, polar aprotic solvents such as N,N-dimethylformamide or dimethylsulfoxide may be used. Intermediates of formula (II) can be made from an aniline of formula (IV) (process 1). Heterocycles of formula (XIX) are commercially available or can be made by methods known by the person skilled in the art.

Compounds of formula (Ig) as herein-defined may be used for the preparation of intermediates of formula (XXa) which may be used in multiple steps processes to provide compounds of formula (Ih) as herein-defined, for instance via the formation of intermediates of formula (XXb).

Compounds of formula (Ig) as herein-defined may be used for the preparation of intermediates of formula (XXa) according to process P9:

Process P9:

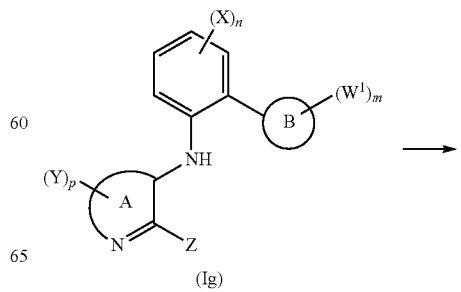

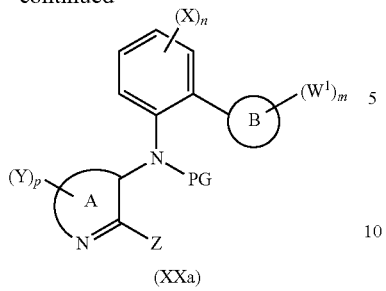

(XXa)

$W^1$=trialkylsilyl substituted alkoxyalkyl, preferably tert-butyldimethylsilyloxymethyl;

PG=alkyloxycarbonyl, preferably t-butyloxycarbonyl;

Compounds of formula (Ig) can be made from processes P1, P2, P3, P4 or P8. Compounds of formula (Ig) can be used to make intermediates of formula (XXa). Typical reagents for such a transformation are for example di-tert-butyl dicarbonate, dimethylaminopyridine. Dichloromethane may be a suitable solvent for this reaction.

Classical functional group interconversion methods known by the person skilled in the art can allow the transformation of the $W^1$ group in intermediates of formula (XXa) into a new group called $W^2$ in compounds of formula (XXb). This transformation may be achieved in one or several chemical steps. Examples of $W^2$ include: hydroxyl-substituted-$C_1$-$C_8$-alkyl, $C_1$-$C_8$-alkoxy-substituted $C_1$-$C_8$-alkyl, formyl, carboxy, $C_1$-$C_8$-alkoxycarbonyl, $C_1$-$C_8$-alkyl-substituted $C_2$-$C_8$-alkenyl and $C_1$-$C_8$-alkyl;

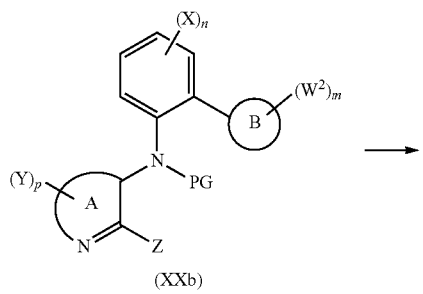

(XXb)

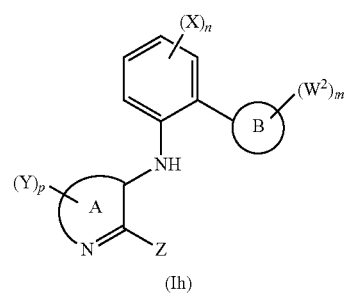

(Ih)

The protecting group in intermediates of formula (XXb) can then be cleaved to obtain compounds of formula (Ih) using methods known by the person skilled in the art. Such methods include the use of acids such as hydrogen chloride or trifluoroacetic acid in a solvent such as dichloromethane or methanol.

Compounds of formula (Ia) may be used for the preparation of compounds (If) according to process P10:

Process P10:

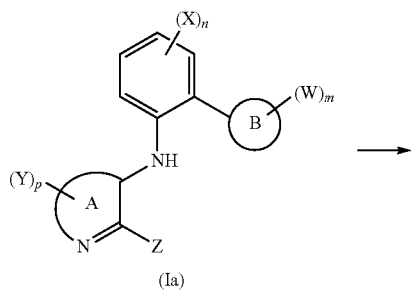

(Ia)

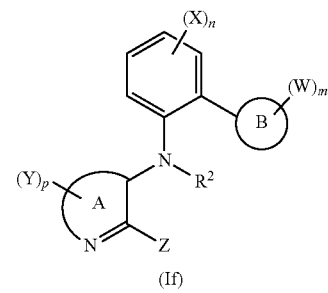

(If)

$R^2$=C1-C8-alkyl;

Compounds of formula (Ia) made according to processes P1, P2, P3, P4, P8 or P9 can be used to make compounds of formula (If). Typically, compounds of formula (Ia) are treated with a base such as sodium hydride and an alkyl halide, preferentially an iodoalkyl such as iodomethane. The reaction is usually carried out in polar aprotic solvents such as dimethylformamide.

Processes P1, P2, P3, P4, P5, P6, P7, P8, P9 and P10 are generally carried out under atmospheric pressure. It is also possible to operate under elevated or reduced pressure.

When carrying out processes P1, P2, P3, P4, P5, P6, P7, P8, P9 and P10, the reaction temperatures can be varied within a relatively wide range. In general, these processes are carried out at temperatures from −78° C. to 200° C., preferably from −78° C. to 150° C. A way to control the temperature for the processes is to use microwave technology.

In general, the reaction mixture is concentrated under reduced pressure. The residue that remains can be freed by known methods, such as chromatography or crystallization, from any impurities that can still be present.

Work-up is carried out by customary methods. Generally, the reaction mixture is treated with water and the organic phase is separated off and, after drying, concentrated under reduced pressure. If appropriate, the remaining residue can, be freed by customary methods, such as chromatography, crystallization or distillation, from any impurities that may still be present.

The compounds of formula (I) can be prepared according to the general processes of preparation described above. It will nevertheless be understood that, on the basis of his general knowledge and of available publications, the skilled worker will be able to adapt the methods according to the specifics of each compound, which it is desired to synthesize.

Intermediates for the Preparation of the Active Ingredients

The present invention also relates to intermediates for the preparation of compounds of formula (I).

As mentioned above, the radicals A, B, L, m, n, p, $Q^1$, W, X, Y and Z have the meanings given above for the compounds of formula (I).

Thus, the present invention relates to compounds of formula (VI) as well as their acceptable salts:

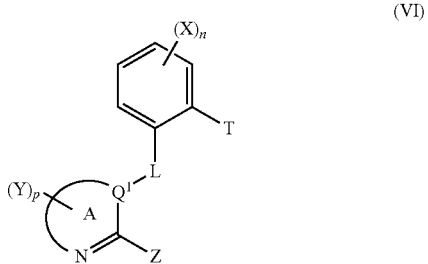

(VI)

wherein:
T represents a boron derivative such as a boronic acid, a boronic ester or a potassium trifluoroborate derivative;
provided that the compound of formula (VI) does not represent:
[2-[(5,6-dichloro-2-methyl-4-nitro-1H-benzimidazol-1-yl)methyl]phenyl]-boronic acid [1862212-46-1],
[2-[(6-amino-9H-purin-9-yl)methyl]phenyl]-boronic acid [902755-97-9], and
[2-(1H-benzimidazol-1-ylmethyl)phenyl]-boronic acid [1312793-78-4].

The following compounds of formula (VI) are also mentioned in chemical databases and/or suppliers' databases but without any references or information which enable these to be prepared and separated:
[5-fluoro-2-[(2-methyl-1H-benzimidazol-1-yl)methyl]phenyl]-boronic acid [1334334-16-5],
[2-[(2-methyl-1H-benzimidazol-1-yl)methyl]phenyl]-boronic acid [1333997-61-7],
[2-[(5,6-dimethyl-1H-benzimidazol-1-yl)methyl]phenyl]-boronic acid [1333997-56-0], and
[2-(1H-benzimidazol-1-ylmethyl)-5-fluorophenyl]-boronic acid [1332718-43-0].

Preferred compounds of formula (VI) according to the invention are:
N-[2-(4,4,5,5-tetramethyl-1,3,2-dioxaborolan-2-yl)phenyl]quinolin-3-amine,
8-fluoro-N-[2-(4,4,5,5-tetramethyl-1,3,2-dioxaborolan-2-yl)phenyl]quinolin-3-amine, and
3-[2-(4,4,5,5-tetramethyl-1,3,2-dioxaborolan-2-yl)benzyl]quinoline.

The present invention also relates to compounds of formula (XX) as well as their acceptable salts:

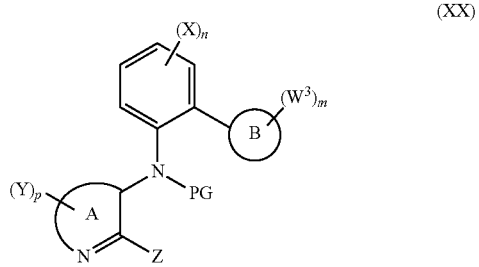

(XX)

wherein:
PG represents alkyloxycarbonyl, preferably t-butyloxycarbonyl; and
$W^3$ represents trialkylsilyl substituted alkoxyalkyl, hydroxyl-substituted-$C_1$-$C_8$-alkyl, $C_1$-$C_8$-alkoxy-substituted $C_1$-$C_8$-alkyl, formyl, carboxy, $C_1$-$C_8$-alkoxycarbonyl, $C_1$-$C_8$-alkyl-substituted $C_2$-$C_8$-alkenyl and $C_1$-$C_8$-alkyl.

Compounds of formula (XX) include compounds of formula (XXa) and (XXb).

Preferred compounds of formula (XX) according to the invention are:
tert-butyl {2-[5-(hydroxymethyl)-1H-pyrazol-1-yl]phenyl}quinolin-3-ylcarbamate,
1-{2-[(tert-butoxycarbonyl)(quinolin-3-yl)amino]phenyl}-1H-pyrazole-5-carboxylic acid,
tert-butyl [2-(5-formyl-1H-pyrazol-1-yl)phenyl]quinolin-3-ylcarbamate,
tert-butyl {2-[5-({[tert-butyl(dimethyl)silyl]oxy}methyl)-1H-pyrazol-1-yl]phenyl}quinolin-3-ylcarbamate,
methyl 1-{2-[(tert-butoxycarbonyl)(quinolin-3-yl)amino]phenyl}-1H-pyrazole-5-carboxylate,
tert-butyl {2-[5-(prop-1-en-2-yl)-1H-pyrazol-1-yl]phenyl}quinolin-3-ylcarbamate,
tert-butyl {2-[5-({[tert-butyl(dimethyl)silyl]oxy}methyl)-1H-pyrazol-1-yl]-3-fluorophenyl}quinolin-3-ylcarbamate,
tert-butyl {3-fluoro-2-[5-(hydroxymethyl)-1H-pyrazol-1-yl]phenyl}quinolin-3-ylcarbamate,
tert-butyl [3-fluoro-2-(5-formyl-1H-pyrazol-1-yl)phenyl]quinolin-3-ylcarbamate,
1-{2-[(tert-butoxycarbonyl)(quinolin-3-yl)amino]-6-fluorophenyl}-1H-pyrazole-5-carboxylic acid,
methyl 1-{2-[(tert-butoxycarbonyl)(quinolin-3-yl)amino]-6-fluorophenyl}-1H-pyrazole-5-carboxylate, and
tert-butyl {3-fluoro-2-[5-(2-hydroxypropan-2-yl)-1H-pyrazol-1-yl]phenyl}quinolin-3-ylcarbamate.

The present invention also relates to compounds of formula (IXa) as well as their acceptable salts:

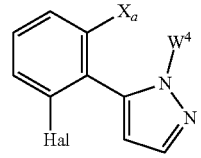

(IXa)

wherein:
$W^4$ represents a $C_1$-$C_8$-alkyl, a $C_1$-$C_8$-halogenoalkyl comprising up to 9 halogen atoms that can be the same or different, a $C_2$-$C_8$-alkenyl, a $C_2$-$C_8$-halogenoalkenyl comprising up to 9 halogen atoms that can be the same or different, a $C_2$-$C_8$-alkynyl, a $C_2$-$C_8$-halogenoalkynyl comprising up to 9 halogen atoms that can be the same or different, a $C_3$-$C_8$-cycloalkyl, a $C_4$-$C_8$-cycloalkenyl, an aryl, a heterocyclyl, a formyl, a $C_1$-$C_8$-alkylcarbonyl, a ($C_1$-$C_8$-alkoxyimino)$C_1$-$C_8$-alkyl, a $C_1$-$C_8$-alkoxycarbonyl, a carbamoyl, a $C_1$-$C_8$-alkylcarbamoyl, a di-$C_1$-$C_8$-alkylcarbamoyl, a $C_1$-$C_8$-alkylsulfinyl or a $C_1$-$C_8$-alkylsulfonyl;
Hal represents Br or I; and
$X_a$ represents F, Cl, Br or I, more preferably F or Cl.

Preferred compounds of formula (IXa) according to the invention are:
5-(2-bromo-6-fluorophenyl)-1-methyl-1H-pyrazole,
5-(2-bromo-6-fluorophenyl)-1-isopropyl-1H-pyrazole,
5-(2-bromo-6-fluorophenyl)-1-tert-butyl-1H-pyrazole,
5-(2-bromo-6-fluorophenyl)-1-ethyl-1H-pyrazole, and
5-(2-bromo-6-fluorophenyl)-1-(2-phenylethyl)-1H-pyrazole The present invention also relates to compounds of formula (IXb) as well as their acceptable salts:

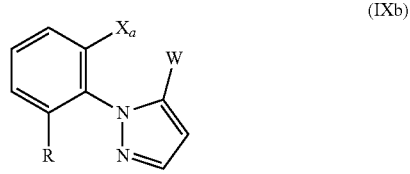

(IXb)

wherein:
R represents NH$_2$, Br or I; and
X$_a$ represents F, Cl, Br or I, more preferably F or Cl.
Preferred compounds of formula (IXb) according to the invention are:
methyl 1-(2-bromo-6-fluorophenyl)-1H-pyrazole-5-carboxylate,
[1-(2-bromo-6-fluorophenyl)-1H-pyrazol-5-yl]methanol,
1-(2-bromo-6-fluorophenyl)-5-({[tert-butyl(dimethyl)silyl]oxy}methyl)-1H-pyrazole, and
2-[5-({[tert-butyl(dimethyl)silyl]oxy}methyl)-1H-pyrazol-1-yl]-3-fluoroaniline.

Compositions and Formulations

The present invention further relates to a composition, in particular a composition for controlling unwanted microorganisms. The compositions may be applied to the microorganisms and/or in their habitat.

The composition typically comprises one or more compounds of formula (I) and at least one agriculturally suitable auxiliary, e.g. carrier(s) and/or surfactant(s).

A carrier is a solid or liquid, natural or synthetic, organic or inorganic substance that is generally inert. The carrier generally improves the application of the compounds, for instance, to plants, plants parts or seeds. Examples of suitable solid carriers include, but are not limited to, ammonium salts, natural rock flours, such as kaolins, clays, talc, chalk, quartz, attapulgite, montmorillonite and diatomaceous earth, and synthetic rock flours, such as finely divided silica, alumina and silicates. Examples of typically useful solid carriers for preparing granules include, but are not limited to crushed and fractionated natural rocks such as calcite, marble, pumice, sepiolite and dolomite, synthetic granules of inorganic and organic flours and granules of organic material such as paper, sawdust, coconut shells, maize cobs and tobacco stalks. Examples of suitable liquid carriers include, but are not limited to, water, organic solvents and combinations thereof. Examples of suitable solvents include polar and nonpolar organic chemical liquids, for example from the classes of aromatic and nonaromatic hydrocarbons (such as cyclohexane, paraffins, alkylbenzenes, xylene, toluene alkylnaphthalenes, chlorinated aromatics or chlorinated aliphatic hydrocarbons such as chlorobenzenes, chloroethylenes or methylene chloride), alcohols and polyols (which may optionally also be substituted, etherified and/or esterified, such as butanol or glycol), ketones (such as acetone, methyl ethyl ketone, methyl isobutyl ketone or cyclohexanone), esters (including fats and oils) and (poly)ethers, unsubstituted and substituted amines, amides (such as dimethylformamide), lactams (such as N-alkylpyrrolidones) and lactones, sulfones and sulfoxides (such as dimethyl sulfoxide). The carrier may also be a liquefied gaseous extender, i.e. liquid which is gaseous at standard temperature and under standard pressure, for example aerosol propellants such as halohydrocarbons, butane, propane, nitrogen and carbon dioxide. The amount of carrier typically ranges from 1 to 99.99%, preferably from 5 to 99.9%, more preferably from 10 to 99.5%, and most preferably from 20 to 99% by weight of the composition.

The surfactant can be an ionic (cationic or anionic) or non-ionic surfactant, such as ionic or non-ionic emulsifier(s), foam former(s), dispersant(s), wetting agent(s) and any mixtures thereof. Examples of suitable surfactants include, but are not limited to, salts of polyacrylic acid, salts of lignosulfonic acid, salts of phenolsulfonic acid or naphthalenesulfonic acid, polycondensates of ethylene and/or propylene oxide with fatty alcohols, fatty acids or fatty amines (polyoxyethylene fatty acid esters, polyoxyethylene fatty alcohol ethers, for example alkylaryl polyglycol ethers), substituted phenols (preferably alkylphenols or arylphenols), salts of sulfosuccinic esters, taurine derivatives (preferably alkyl taurates), phosphoric esters of polyethoxylated alcohols or phenols, fatty esters of polyols and derivatives of compounds containing sulfates, sulfonates, phosphates (for example, alkylsulfonates, alkyl sulfates, arylsulfonates) and protein hydrolysates, lignosulfite waste liquors and methylcellulose. A surfactant is typically used when the compound(s) of formula (I) and/or the carrier is insoluble in water and the application is made with water. Then, the amount of surfactants typically ranges from 5 to 40% by weight of the composition.

Further examples of suitable auxiliaries include water repellents, siccatives, binders (adhesive, tackifier, fixing agent, such as carboxymethylcellulose, natural and synthetic polymers in the form of powders, granules or lattices, such as gum arabic, polyvinyl alcohol and polyvinyl acetate, natural phospholipids such as cephalins and lecithins and synthetic phospholipids, polyvinylpyrrolidone and tylose), thickeners, stabilizers (e.g. cold stabilizers, preservatives, antioxidants, light stabilizers, or other agents which improve chemical and/or physical stability), dyes or pigments (such as inorganic pigments, e.g. iron oxide, titanium oxide and Prussian Blue; organic dyes, e.g. alizarin, azo and metal phthalocyanine dyes), antifoams (e.g. silicone antifoams and magnesium stearate), preservatives (e.g. dichlorophene and benzyl alcohol hemiformal), secondary thickeners (cellulose derivatives, acrylic acid derivatives, xanthan, modified clays and finely divided silica), stickers, gibberellins and processing auxiliaries, mineral and vegetable oils, perfumes, waxes, nutrients (including trace nutrients, such as salts of iron, manganese, boron, copper, cobalt, molybdenum and zinc), protective colloids, thixotropic substances, penetrants, sequestering agents and complex formers.

The choice of the auxiliaries is related to the intended mode of application of the compound(s) of the invention and/or to its physical properties. Furthermore, the auxiliaries may be chosen to impart particular properties (technical, physical and/or biological properties) to the compositions or use forms prepared therefrom. The choice of auxiliaries may allow customizing the compositions to specific needs.

The composition may be in any customary form, such as solutions (e.g aqueous solutions), emulsions, wettable powders, water- and oil-based suspensions, powders, dusts, pastes, soluble powders, soluble granules, granules for broadcasting, suspoemulsion concentrates, natural or synthetic products impregnated with one or more compounds of formula (I), fertilizers and also microencapsulations in polymeric substances. The compound(s) of formula (I) may be present in a suspended, emulsified or dissolved form.

The composition may be provided to the end user as ready-for-use formulation, i.e. the compositions may be directly applied to the plants or seeds by a suitable device, such as a spraying or dusting device. Alternatively, the compositions may be provided to the end user in the form of concentrates which have to be diluted, preferably with water, prior to use.

The composition can be prepared in conventional manners, for example by mixing the compound(s) of formula (I) with one or more suitable auxiliaries, such as disclosed herein above.

The composition contains generally from 0.01 to 99% by weight, from 0.05 to 98% by weight, preferably from 0.1 to 95% by weight, more preferably from 0.5 to 90% by weight, most preferably from 1 to 80% by weight of the compound of formula (I). It is possible that a composition comprises two or more compounds of formula (I). In such case the outlined ranges refer to the total amount of compounds of formula (I).

Mixtures/Combinations

The compound(s) of formula (I) and compositions comprising thereof can be mixed with other active ingredients like fungicides, bactericides, acaricides, nematicides, insecticides, herbicides, fertilizers, growth regulators, safeners or semiochemicals. This may allow to broaden the activity spectrum or to prevent development of resistance. Examples of known fungicides, insecticides, acaricides, nematicides and bactericides are disclosed in the Pesticide Manual, 17th Edition.

Examples of especially preferred fungicides which could be mixed with the compounds of formula (I) are:

1) Inhibitors of the ergosterol biosynthesis, for example (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazol, (1.016) prochloraz, (1.017) propiconazole, (1.018) prothioconazole, (1.019) Pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol, (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-difluorophenyl)-1,2-oxazol-4-yl](pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[[rel(2R,3R)-3-(2-chlorophenyl)-2-(2,4-difluorophenyl)oxiran-2-yl]methyl}-1H-1,2,4-triazol-5-yl thiocyanate, (1.041) 1-{[rel(2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) Mefentrifluconazole, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl]methyl}-1H-1,2,4-triazole, (1.062) 5-(allylsulfanyl)-1-{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3-tetrafluoropropoxy)phenyl]sulfanyl}phenyl)-N-ethyl-N-methylimidoformamide, (1.066) N'-(2,5-dimethyl-4-{[3-(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl)sulfanyl]phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimidoformamide, (1.069) N'-(2,5-dimethyl-4-{3-[(2, 2,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-[(1S)-1-(3,5-difluorophenyl)ethoxy]-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide, (1.081) Ipfentrifluconazole.

2) Inhibitors of the respiratory chain at complex I or II, for example (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) Isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of syn-epimeric racemate 1RS,4SR,9RS and anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) Pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3S)-1,1,3-trimethyl-2,3-dihydro-1H-inden-4-yl]-1H-pyrazole-4-carboxamide, (2.030) Fluindapyr, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-([4-(trifluoromethyl)pyridin-2-yl]oxy)-phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) isoflucypram, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, (2.056) N-cyclopropyl-N-(2-cyclopropylbenzyl)-3-(difluoromethyl)-5-fluoro-1-methyl-1H-pyrazole-4-carboxamide, (2.057) pyrapropoyne.

3) Inhibitors of the respiratory chain at complex III, for example (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadone, (3.010) fenamidone, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin, (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-{2-[(2,5-dimethylphenoxy)methyl]phenyl}-2-methoxy-N-methylacetamide, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) mandestrobin, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide, (3.029) methyl {5-[3-(2,4-dimethylphenyl)-1H-pyrazol-1-yl]-2-methylbenzyl}carbamate, (3.030) metyltetraprole, (3.031) florylpicoxamid.

4) Inhibitors of the mitosis and cell division, for example (4.001) carbendazim, (4.002) diethofencarb, (4.003) ethaboxam, (4.004) fluopicolide, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine.

5) Compounds capable to have a multisite action, for example (5.001) bordeaux mixture, (5.002) captafol, (5.003) captan, (5.004) chlorothalonil, (5.005) copper hydroxide, (5.006) copper naphthenate, (5.007) copper oxide, (5.008) copper oxychloride, (5.009) copper(2+) sulfate, (5.010) dithianon, (5.011) dodine, (5.012) folpet, (5.013) mancozeb, (5.014) maneb, (5.015) metiram, (5.016) metiram zinc, (5.017) oxine-copper, (5.018) propineb, (5.019) sulfur and sulfur preparations including calcium polysulfide, (5.020) thiram, (5.021) zineb, (5.022) ziram, (5.023) 6-ethyl-5,7-dioxo-6,7-dihydro-5H-pyrrolo[3',4':5,6][1,4]dithiino[2,3-c][1,2]thiazole-3-carbonitrile.

6) Compounds capable to induce a host defence, for example (6.001) acibenzolar-S-methyl, (6.002) isotianil, (6.003) probenazole, (6.004) tiadinil.

7) Inhibitors of the amino acid and/or protein biosynthesis, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinoline.

8) Inhibitors of the ATP production, for example (8.001) silthiofam.

9) Inhibitors of the cell wall synthesis, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, (9.009) (2Z)-3-(4-tert-butylphenyl)-3-(2-chloropyridin-4-yl)-1-(morpholin-4-yl)prop-2-en-1-one.

10) Inhibitors of the lipid and membrane synthesis, for example (10.001) propamocarb, (10.002) propamocarb hydrochloride, (10.003) tolclofos-methyl.

11) Inhibitors of the melanin biosynthesis, for example (11.001) tricyclazole, (11.002) 2,2,2-trifluoroethyl {3-methyl-1-[(4-methylbenzoyl)amino]butan-2-yl}carbamate.

12) Inhibitors of the nucleic acid synthesis, for example (12.001) benalaxyl, (12.002) benalaxyl-M (kiralaxyl), (12.003) metalaxyl, (12.004) metalaxyl-M (mefenoxam).

13) Inhibitors of the signal transduction, for example (13.001) fludioxonil, (13.002) iprodione, (13.003) procymidone, (13.004) proquinazid, (13.005) quinoxyfen, (13.006) vinclozolin.

14) Compounds capable to act as an uncoupler, for example (14.001) fluazinam, (14.002) meptyldinocap.

15) Further compounds, for example (15.001) Abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenone, (15.017) mildiomycin, (15.018) natamycin, (15.019) nickel dimethyldithiocarbamate, (15.020) nitrothal-isopropyl, (15.021) oxamocarb, (15.022) oxathiapiprolin, (15.023) oxyfenthiin, (15.024) pentachlorophenol and salts, (15.025) phosphorous acid and its salts, (15.026) propamocarb-fosetylate, (15.027) pyriofenone (chlazafenone), (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.033) 2-(6-benzylpyridin-2-yl)quinazoline, (15.034) dipymetitrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl]quinazoline, (15.039) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.041) Ipflufenoquin, (15.042) 2-{2-fluoro-6-[(8-fluoro-2-methylquinolin-3-yl)oxy]phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.044) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.045) 2-phenylphenol and salts, (15.046) 3-(4,4,5-trifluoro-3,3-dimethyl-3,4-dihydroisoquinolin-1-yl)quinoline, (15.047) quinofumelin, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butanoic acid, (15.050) 5-amino-1,3,4- thiadiazole-2-thiol, (15.051) 5-chloro-N'-phenyl-N'-(prop-2-yn-1-yl)thiophene-2-sulfonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl {6-[({[(1-methyl-1H-tetrazol-5-yl)(phenyl)methylene]amino}oxy)methyl]pyridin-2-yl}carbamate, (15.062) 5-fluoro-4-imino-3-methyl-1-[(4-methylphenyl)sulfonyl]-3,4-dihydropyrimidin-2(1H)-one, (15.063) aminopyrifen.

All named mixing partners of the classes (1) to (15) as described here above can be present in the form of the free compound and/or, if their functional groups enable this, an agriculturally acceptable salt thereof.

The compounds of formula (I) and compositions comprising thereof may also be combined with one or more biological control agents.

Examples of biological control agents which may be combined with the compound of formula (I) and composition comprising thereof are:

(A) Antibacterial agents selected from the group of:

(A1) bacteria, such as (A1.1) *Bacillus subtilis*, in particular strain QST713/AQ713 (available as SERENADE OPTI or SERENADE ASO from Bayer CropScience LP, US, having NRRL Accession No. B21661 and described in U.S. Pat. No. 6,060,051); (A1.2) *Bacillus amyloliquefaciens*, in particular strain D747 (available as Double Nickel™ from Certis, US, having accession number FERM BP-8234 and disclosed in U.S. Pat. No. 7,094,592); (A1.3) *Bacillus pumilus*, in particular strain BU F-33 (having NRRL Accession No. 50185); (A1.4) *Bacillus subtilis* var. *amyloliquefaciens* strain FZB24 (available as Taegro® from Novozymes, US); (A1.5) a *Paenibacillus* sp. strain having Accession No. NRRL B-50972 or Accession No. NRRL B-67129 and described in International Patent Publication No. WO 2016/154297; and (A2) fungi, such as (A2.1) *Aureobasidium pullulans*, in particular blastospores of strain DSM14940; (A2.2) *Aureobasidium pullulans* blastospores of strain DSM 14941; (A2.3) *Aureobasidium pullulans*, in particular mixtures of blastospores of strains DSM14940 and DSM14941;

(B) Fungicides selected from the group of:

(B1) bacteria, for example (B1.1) *Bacillus subtilis*, in particular strain QST713/AQ713 (available as SERENADE OPTI or SERENADE ASO from Bayer CropScience LP, US, having NRRL Accession No. B21661 and described in U.S. Pat. No. 6,060,051); (B1.2) *Bacillus pumilus*, in particular strain QST2808 (available as SONATA® from Bayer CropScience LP, US, having Accession No. NRRL B-30087 and described in U.S. Pat. No. 6,245,551); (B1.3) *Bacillus pumilus*, in particular strain GB34 (available as Yield Shield® from Bayer AG, DE); (B1.4) *Bacillus pumilus*, in particular strain BU F-33 (having NRRL Accession No. 50185); (B1.5) *Bacillus amyloliquefaciens*, in particular strain D747 (available as Double Nickel™ from Certis, US, having accession number FERM BP-8234 and disclosed in U.S. Pat. No. 7,094,592); (B1.6) *Bacillus subtilis* Y1336 (available as BIOBAC® WP from Bion-Tech, Taiwan, registered as a biological fungicide in Taiwan under Registration Nos. 4764, 5454, 5096 and 5277); (B1.7) *Bacillus amyloliquefaciens* strain MBI 600 (available as SUBTILEX from BASF SE); (B1.8) *Bacillus subtilis* strain GB03 (available as Kodiak® from Bayer AG, DE); (B1.9) *Bacillus subtilis* var. *amyloliquefaciens* strain FZB24 (available from Novozymes Biologicals Inc., Salem, Va. or Syngenta Crop Protection, LLC, Greensboro, N.C. as the fungicide TAEGRO® or TAEGRO® ECO (EPA Registration No. 70127-5); (B1.10) *Bacillus mycoides*, isolate J (available as BmJ TGAI or WG from Certis USA); (B1.11) *Bacillus licheniformis*, in particular strain SB3086 (available as EcoGuard™ Biofungicide and Green Releaf from Novozymes); (B1.12) a *Paenibacillus* sp. strain having Accession No. NRRL B-50972 or Accession No. NRRL B-67129 and described in International Patent Publication No. WO 2016/154297.

In some embodiments, the biological control agent is a *Bacillus subtilis* or *Bacillus amyloliquefaciens* strain that produces a fengycin or plipastatin-type compound, an iturin-type compound, and/or a surfactin-type compound. For background, see the following review article: Ongena, M., et al., "*Bacillus* Lipopeptides: Versatile Weapons for Plant Disease Biocontrol," Trends in Microbiology, Vol 16, No. 3, March 2008, pp. 115-125. *Bacillus* strains capable of producing lipopeptides include *Bacillus subtilis* QST713 (available as SERENADE OPTI or SERENADE ASO from Bayer CropScience LP, US, having NRRL Accession No. B21661 and described in U.S. Pat. No. 6,060,051), *Bacillus amyloliquefaciens* strain D747 (available as Double Nickel™ from Certis, US, having accession number FERM BP-8234 and disclosed in U.S. Pat. No. 7,094,592); *Bacillus subtilis* MBI600 (available as SUBTILEX® from Becker Underwood, US EPA Reg. No. 71840-8); *Bacillus subtilis* Y1336 (available as BIOBAC® WP from Bion-Tech, Taiwan, registered as a biological fungicide in Taiwan under Registration Nos. 4764, 5454, 5096 and 5277); *Bacillus amyloliquefaciens*, in particular strain FZB42 (available as RHIZOVITAL® from ABiTEP, DE); and *Bacillus subtilis* var. *amyloliquefaciens* FZB24 (available from Novozymes Biologicals Inc., Salem, Va. or Syngenta Crop Protection, LLC, Greensboro, N.C. as the fungicide TAEGRO® or TAEGRO® ECO (EPA Registration No. 70127-5); and (B2) fungi, for example: (B2.1) *Coniothyrium minitans*, in particular strain CON/M/91-8 (Accession No. DSM-9660; e.g. Contans® from Bayer); (B2.2) *Metschnikowia fructicola*, in particular strain NRRL Y-30752 (e.g. Shemer®); (B2.3) *Microsphaeropsis ochracea* (e.g. Microx® from Prophyta); (B2.5) *Trichoderma* spp., including *Trichoderma atroviride*, strain SC1 described in International Application No. PCT/IT2008/000196); (B2.6) *Trichoderma harzianum rifai* strain KRL-AG2 (also known as strain T-22, /ATCC 208479, e.g. PLANTSHIELD T-22G, Rootshield®, and TurfShield from BioWorks, US); (B2.14) *Gliocladium roseum*, strain 321U from W.F. Stoneman Company LLC; (B2.35) *Talaromyces flavus*, strain V117b; (B2.36) *Trichoderma asperellum*, strain ICC 012 from Isagro; (B2.37) *Trichoderma asperellum*, strain SKT-1 (e.g. ECO-HOPE® from Kumiai Chemical Industry); (B2.38) *Trichoderma atroviride*, strain CNCM 1-1237 (e.g. Esquive® WP from Agrauxine, FR); (B2.39) *Trichoderma atroviride*, strain no. V08/002387; (B2.40) *Trichoderma atroviride*, strain NMI no. V08/002388; (B2.41) *Trichoderma atroviride*, strain NMI no. V08/002389; (B2.42) *Trichoderma atroviride*, strain NMI no. V08/002390; (B2.43) *Trichoderma atroviride*, strain $LC_{52}$ (e.g. Tenet by Agrimm Technologies Limited); (B2.44) *Trichoderma atroviride*, strain ATCC 20476 (IMI 206040); (B2.45) *Trichoderma atroviride*, strain T11 (IMI352941/CECT20498); (B2.46) *Trichoderma harmatum*; (B2.47) *Trichoderma har-*

*zianum*; (B2.48) *Trichoderma harzianum rifai* T39 (e.g. Trichodex® from Makhteshim, US); (B2.49) *Trichoderma harzianum*, in particular, strain KD (e.g. Trichoplus from Biological Control Products, SA (acquired by Becker Underwood)); (B2.50) *Trichoderma harzianum*, strain ITEM 908 (e.g. Trianum-P from Koppert); (B2.51) *Trichoderma harzianum*, strain TH35 (e.g. Root-Pro by Mycontrol); (B2.52) *Trichoderma virens* (also known as *Gliocladium virens*), in particular strain GL-21 (e.g. SoilGard 12G by Certis, US); (B2.53) *Trichoderma viride*, strain TV1 (e.g. Trianum-P by Koppert); (B2.54) *Ampelomyces quisqualis*, in particular strain AQ 10 (e.g. AQ 10® by IntrachemBio Italia); (B2.56) *Aureobasidium pullulans*, in particular blastospores of strain DSM14940; (B2.57) *Aureobasidium pullulans*, in particular blastospores of strain DSM 14941; (B2.58) *Aureobasidium pullulans*, in particular mixtures of blastospores of strains DSM14940 and DSM 14941 (e.g. Botector® by bio-ferm, CH); (B2.64) *Cladosporium cladosporioides*, strain H39 (by Stichting Dienst Landbouwkundig Onderzoek); (B2.69) *Gliocladium catenulatum* (Synonym: *Clonostachys rosea f. catenulate*) strain J1446 (e.g. Prestop® by AgBio Inc. and also e.g. Primastop® by Kemira Agro Oy); (B2.70) *Lecanicillium lecanii* (formerly known as *Verticillium lecanii*) *conidia* of strain KV01 (e.g. Vertalec® by Koppert/Arysta); (B2.71) *Penicillium vermiculatum*; (B2.72) *Pichia anomala*, strain WRL-076 (NRRL Y-30842); (B2.75) *Trichoderma atroviride*, strain SKT-1 (FERM P-16510); (B2.76) *Trichoderma atroviride*, strain SKT-2 (FERM P-16511); (B2.77) *Trichoderma atroviride*, strain SKT-3 (FERM P-17021); (B2.78) *Trichoderma gamsii* (formerly *T. viride*), strain ICC080 (IMI CC 392151 CABI, e.g. BioDerma by AGROBIOSOL DE MEXICO, S.A. DE C.V.); (B2.79) *Trichoderma harzianum*, strain DB 103 (e.g., T-Gro 7456 by Dagutat Biolab); (B2.80) *Trichoderma polysporum*, strain IMI 206039 (e.g. Binab TF WP by BINAB Bio-Innovation AB, Sweden); (B2.81) *Trichoderma stromaticum* (e.g. Tricovab by Ceplac, Brazil); (B2.83) *Ulocladium oudemansii*, in particular strain HRU3 (e.g. Botry-Zen® by Botry-Zen Ltd, NZ); (B2.84) *Verticillium albo-atrum* (formerly *V. dahliae*), strain WCS850 (CBS 276.92; e.g. Dutch Trig by Tree Care Innovations); (B2.86) *Verticillium chlamydosporium*; (B2.87) mixtures of *Trichoderma asperellum* strain ICC 012 and *Trichoderma gamsii* strain ICC 080 (product known as e.g. BIO-TAM™ from Bayer CropScience LP, US).

Further examples of biological control agents which may be combined with the compounds of formula (I) and compositions comprising thereof are:

bacteria selected from the group consisting of *Bacillus cereus*, in particular *B. cereus* strain CNCM 1562 and *Bacillus firmus*, strain I-1582 (Accession number CNCM I-1582), *Bacillus subtilis* strain OST 30002 (Accession No. NRRL B-50421), *Bacillus thuringiensis*, in particular *B. thuringiensis* subspecies *israelensis* (serotype H-14), strain AM65-52 (Accession No. ATCC 1276), *B. thuringiensis* subsp. *aizawai*, in particular strain ABTS-1857 (SD-1372), *B. thuringiensis* subsp. *kurstaki* strain HD-1, *B. thuringiensis* subsp. *tenebrionis* strain NB 176 (SD-5428), *Pasteuria penetrans, Pasteuria* spp. (*Rotylenchulus reniformis* nematode)-PR3 (Accession Number ATCC SD-5834), *Streptomyces microflavus* strain AQ6121 (=QRD 31.013, NRRL B-50550), and *Streptomyces galbus* strain AQ 6047 (Accession Number NRRL 30232);

fungi and yeasts selected from the group consisting of *Beauveria bassiana*, in particular strain ATCC 74040, *Lecanicillium* spp., in particular strain HRO LEC 12, *Metarhizium anisopliae*, in particular strain F52 (DSM3884 or ATCC 90448), *Paecilomyces fumosoroseus* (now: *Isaria fumosorosea*), in particular strain IFPC 200613, or strain Apopka 97 (Accesion No. ATCC 20874), and *Paecilomyces lilacinus*, in particular *P. lilacinus* strain 251 (AGAL 89/030550);

viruses selected from the group consisting of *Adoxophyes orana* (summer fruit tortrix) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, and *Spodoptera littoralis* (African cotton leafworm) NPV.

bacteria and fungi which can be added as 'inoculant' to plants or plant parts or plant organs and which, by virtue of their particular properties, promote plant growth and plant health. Examples are: *Agrobacterium* spp., *Azorhizobium caulinodans, Azospirillum* spp., *Azotobacter* spp., *Bradyrhizobium* spp., *Burkholderia* spp., in particular *Burkholderia cepacia* (formerly known as *Pseudomonas cepacia*), *Gigaspora* spp., or *Gigaspora monosporum, Glomus* spp., *Laccaria* spp., *Lactobacillus buchneri, Paraglomus* spp., *Pisolithus tinctorus, Pseudomonas* spp., *Rhizobium* spp., in particular *Rhizobium trifolii, Rhizopogon* spp., *Scleroderma* spp., *Suillus* spp., and *Streptomyces* spp.

plant extracts and products formed by microorganisms including proteins and secondary metabolites which can be used as biological control agents, such as *Allium sativum, Artemisia absinthium*, azadirachtin, Biokeeper WP, *Cassia nigricans, Celastrus angulatus, Chenopodium anthelminticum, chitin*, Armour-Zen, *Dryopteris filix-mas, Equisetum arvense*, Fortune Aza, Fungastop, Heads Up (*Chenopodium quinoa* saponin extract), *Pyrethrum/Pyrethrins, Quassia amara, Quercus, Quillaja*, Regalia, "Requiem™ Insecticide", rotenone, ryania/ryanodine, *Symphytum officinale, Tanacetum vulgare*, thymol, Triact 70, TriCon, *Tropaeulum majus, Urtica dioica*, Veratrin, *Viscum album*, Brassicaceae extract, in particular oilseed rape powder or mustard powder.

Examples of insecticides, acaricides and nematicides, respectively, which could be mixed with the compounds of formula (I) and compositions comprising thereof are:

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, such as, for example, cyclodiene-organochlorines, for example chlordane and endosulfan or phenylpyrazoles (fiproles), for example ethiprole and fipronil.

(3) Sodium channel modulators, such as, for example, pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin or DDT or methoxychlor.

(4) Nicotinic acetylcholine receptor (nAChR) competitive modulators, such as, for example, neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, such as, for example, spinosyns, e.g. spinetoram and spinosad.

(6) Glutamate-gated chloride channel (GluCl) allosteric modulators, such as, for example, avermectins/milbemycins, for example abamectin, emamectin benzoate, lepimectin and milbemectin.

(7) Juvenile hormone mimics, such as, for example, juvenile hormone analogues, e.g. hydroprene, kinoprene and methoprene or fenoxycarb or pyriproxyfen.

(8) Miscellaneous non-specific (multi-site) inhibitors, such as, for example, alkyl halides, e.g. methyl bromide and other alkyl halides; or chloropicrine or sulphuryl fluoride or borax or tartar emetic or methyl isocyanate generators, e.g. diazomet and metam.

(9) Modulators of Chordotonal Organs, such as, for example pymetrozine or flonicamid.

(10) Mite growth inhibitors, such as, for example clofentezine, hexythiazox and diflovidazin or etoxazole.

(11) Microbial disruptors of the insect gut membrane, such as, for example *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and B.t. plant proteins: Cry1Ab, Cry1Ac, Cry1Fa, Cry1A.105, Cry2Ab, Vip3A, mCry3A, Cry3Ab, Cry3Bb, Cry34Ab1/35Ab1.

(12) Inhibitors of mitochondrial ATP synthase, such as, ATP disruptors such as, for example, diafenthiuron or organotin compounds, for example azocyclotin, cyhexatin and fenbutatin oxide or propargite or tetradifon.

(13) Uncouplers of oxidative phosphorylation via disruption of the proton gradient, such as, for example, chlorfenapyr, DNOC and sulfluramid.

(14) Nicotinic acetylcholine receptor channel blockers, such as, for example, bensultap, cartap hydrochloride, thiocylam, and thiosultap-sodium.

(15) Inhibitors of chitin biosynthesis, type 0, such as, for example, bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting disruptor (in particular for Diptera, i.e. dipterans), such as, for example, cyromazine.

(18) Ecdysone receptor agonists, such as, for example, chromafenozide, halofenozide, methoxyfenozide and tebufenozide.

(19) Octopamine receptor agonists, such as, for example, amitraz.

(20) Mitochondrial complex III electron transport inhibitors, such as, for example, hydramethylnone or acequinocyl or fluacrypyrim.

(21) Mitochondrial complex I electron transport inhibitors, such as, for example from the group of the METI acaricides, e.g. fenazaquin, fenpyroximate, pyrimidifen, pyridaben, tebufenpyrad and tolfenpyrad or rotenone (Derris).

(22) Voltage-dependent sodium channel blockers, such as, for example indoxacarb or metaflumizone.

(23) Inhibitors of acetyl CoA carboxylase, such as, for example, tetronic and tetramic acid derivatives, e.g. spirodiclofen, spiromesifen and spirotetramat.

(24) Mitochondrial complex IV electron transport inhibitors, such as, for example, phosphines, e.g. aluminium phosphide, calcium phosphide, phosphine and zinc phosphide or cyanides, e.g. calcium cyanide, potassium cyanide and sodium cyanide.

(25) Mitochondrial complex II electron transport inhibitors, such as, for example, beta-ketonitrile derivatives, e.g. cyenopyrafen and cyflumetofen and carboxanilides, such as, for example, pyflubumide.

(28) Ryanodine receptor modulators, such as, for example, diamides, e.g. chlorantraniliprole, cyantraniliprole and flubendiamide,

(29) further active compounds such as, for example, Afidopyropen, Afoxolaner, Azadirachtin, Benclothiaz, Benzoximate, Bifenazate, Broflanilide, Bromopropylate, Chinomethionat, Chloroprallethrin, Cryolite, Cyclaniliprole, Cycloxaprid, Cyhalodiamide, Dicloromezotiaz, Dicofol, epsilon-Metofluthrin, epsilon-Momfluthrin, Flometoquin, Fluazaindolizine, Fluensulfone, Flufenerim, Flufenoxystrobin, Flufiprole, Fluhexafon, Fluopyram, Fluralaner, Fluxametamide, Fufenozide, Guadipyr, Heptafluthrin, Imidaclothiz, Iprodione, kappa-Bifenthrin, kappa-Tefluthrin, Lotilaner, Meperfluthrin, Paichongding, Pyridalyl, Pyrifluquinazon, Pyriminostrobin, Spirobudiclofen, Tetramethylfluthrin, Tetraniliprole, Tetrachlorantraniliprole, Tigolaner, Tioxazafen, Thiofluoximate, Triflumezopyrim and iodomethane; furthermore preparations based on *Bacillus firmus* (I-1582, BioNeem, Votivo), and also the following compounds: 1-{2-fluoro-4-methyl-5-[(2,2,2-trifluoroethyl) sulphinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro [indol-3,4'-piperidin]-1(2H)-yl}(2-chloropyridin-4-yl) methanone (known from WO2003/106457) (CAS 637360-23-7), 2-chloro-N-[2-{1-[(2E)-3-(4-chlorophenyl)prop-2-en-1-yl]piperidin-4-yl}-4-(trifluoromethyl)phenyl] isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethyl carbonate (known from EP2647626) (CAS 1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2- pyridylidene]-1,1,1-trifluoro-propan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)-benzamide, 4-[5-(3,5-dichlorophenyl)-4,5-dihydro-5-(trifluoromethyl)-3-isoxazolyl]-2-methyl-N-(trans-1-oxido-3-thietanyl)-benzamide and 4-[(5S)-5-(3,5-dichlorophenyl)-4,5-dihydro-5-(trifluoromethyl)-3-isoxazolyl]-2-methyl-N-(cis-1-oxido-3-thietanyl)benzamide (known from WO 2013/050317 A1) (CAS 1332628-83-7), N-[3-chloro-1-(3-pyridinyl)-1H-pyrazol-4-yl]-N-ethyl-3-[(3, 3,3-trifluoropropyl)sulfinyl]-propanamide, (+)-N-[3-chloro-1-(3-pyridinyl)-1H-pyrazol-4-yl]-N-ethyl-3-[(3, 3,3-trifluoropropyl)sulfinyl]-propanamide and (−)-N-[3-chloro-1-(3-pyridinyl)-1H-pyrazol-4-yl]-N-ethyl-3-[(3,3,3-trifluoropropyl)sulfinyl]-propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino)thioxomethyl] phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl)amino]carbonyl]-6-methylphenyl]-1-(3-chloro-2-pyridinyl)-3-(fluoromethoxy)-1H-Pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy] phenoxy]propoxy]-2-methoxy-6-(trifluoromethyl)-pyrimidine (known from CN 101337940 A) (CAS 1108184-52-6); (2E)- and 2(Z)-2-[2-(4-cyanophenyl)-1-[3-(trifluoromethyl)phenyl]ethylidene]-N-[4-(difluoromethoxy)phenyl]-hydrazinecarboxamide (known from CN 101715774 A) (CAS 1232543-85-9); 3-(2,2-dichloroethenyl)-2,2-dimethyl-4-(1H-benzimidazol-2-yl)phenyl-cyclopropanecarboxylic acid ester (known from CN 103524422 A) (CAS 1542271-46-4); (4aS)-7-chloro-2,5-dihydro-2-[[(methoxycarbonyl)[4-[(trifluoromethyl)thio]phenyl]amino]carbonyl]-indeno[1,2-e][1,3,4]oxadiazine-4a(3H)-carboxylic acid methyl ester (known from CN 102391261 A) (CAS 1370358-69-2); 6-deoxy-3-O-ethyl-2,4-di-O-methyl-, 1-[N-[4-[1-[4-(1,1,2,2,2-pentafluoroethoxy)phenyl]-1H-1,2,4-triazol-3-yl] phenyl]carbamate]-α-L-mannopyranose (known from US 2014/0275503 A1) (CAS 1181213-14-8); 8-(2-cyclopropylmethoxy-4-trifluoromethyl-phenoxy)-3-(6-trifluoromethyl-pyridazin-3-yl)-3-azabicyclo[3.2.1]octane (CAS 1253850-56-4), (8-anti)-8-(2-cyclopropylmethoxy-4-trifluoromethyl-phenoxy)-3-(6-trifluoromethyl-pyridazin-3-yl)-3-aza-bicyclo[3.2.1]octane (CAS 933798-27-7), (8-syn)-8-(2-cyclopropylmethoxy-4-trifluoromethyl-phenoxy)-3-(6-trifluoromethyl-pyridazin-3-yl)-3-aza-bicyclo[3.2.1]octane (known from WO 2007040280 A1, WO 2007040282 A1) (CAS 934001-66-8), N-[3-chloro-1-(3-pyridinyl)-1H-pyrazol-4-yl]-N-ethyl-3-[(3,3,3-trifluoropropyl)thio]-propanamide (known from WO 2015/058021 A1, WO 2015/058028 A1) (CAS 1477919-27-9) and N-[4-(aminothioxomethyl)-2-methyl-6-[(methylamino)carbonyl]phenyl]-3-bromo-1-(3-chloro-2-pyridinyl)-1H-pyrazole-5-carboxamide (known from CN 103265527 A) (CAS 1452877-50-7), 5-(1,3-dioxan-2-yl)-4-[[4-(trifluoromethyl)phenyl]methoxy]-pyrimidine (known from WO 2013/115391 A1) (CAS 1449021-97-9), 3-(4-chloro-2,6-dimethylphenyl)-4-hydroxy-8-methoxy-1-methyl-1,8-diazaspiro[4.5]dec-3-en-2-one (known from WO 2010/066780 A1, WO 2011/151146 A1) (CAS 1229023-34-0), 3-(4-chloro-2,6-dimethylphenyl)-8-methoxy-1-methyl-1,8-diazaspiro[4.5]decane-2,4-dione (known from WO 2014/187846 A1) (CAS 1638765-58-8), 3-(4-chloro-2,6-dimethylphenyl)-8-methoxy-1-methyl-2-oxo-1, 8-diazaspiro[4.5]dec-3-en-4-yl-carbonic acid ethyl ester (known from WO 2010/066780 A1, WO 2011151146 A1) (CAS 1229023-00-0), N-[1-[(6-chloro-3-pyridinyl)methyl]-2(1H)-pyridinylidene]-2,2,2-trifluoro-acetamide (known from DE 3639877 A1, WO 2012029672 A1) (CAS 1363400-41-2), [N(E)]-N-[1-[(6-chloro-3-pyridinyl)methyl]-2(1H)-pyridinylidene]-2,2,2-trifluoro-acetamide, (known from WO 2016005276 A1) (CAS 1689566-03-7), [N(Z)]-N-[1-[(6-chloro-3-pyridinyl)methyl]-2(1H)-pyridinylidene]-2,2,2-trifluoro-acetamide, (CAS 1702305-40-5), 3-endo-3-[2-propoxy-4-(trifluoromethyl)phenoxy]-9-[[5-(trifluoromethyl)-2-pyridinyl]oxy]-9-azabicyclo[3.3.1]nonane (known from WO 2011/105506 A1, WO 2016/133011 A1) (CAS 1332838-17-1).

Examples of safeners which could be mixed with the compounds of formula (I) and compositions comprising thereof are, for example, benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}-sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Examples of herbicides which could be mixed with the compounds of formula (I) and compositions comprising thereof are:

Acetochlor, acifluorfen, acifluorfen-sodium, aclonifen, alachlor, allidochlor, alloxydim, alloxydim-sodium, ametryn, amicarbazone, amidochlor, amidosulfuron, 4-amino-3-chloro-6-(4-chloro-2-fluoro-3-methylphenyl)-5-fluoropyridine-2-carboxylic acid, aminocyclopyrachlor, aminocyclopyrachlor-potassium, aminocyclopyrachlor-methyl, aminopyralid, amitrole, ammoniumsulfamate, anilofos, asulam, atrazine, azafenidin, azimsulfuron, beflubutamid, benazolin, benazolin-ethyl, benfluralin, benfuresate, bensulfuron, bensulfuron-methyl, bensulide, bentazone, benzobicyclon, benzofenap, bicyclopyron, bifenox, bilanafos, bilanafos-sodium, bispyribac, bispyribac-sodium, bromacil, bromobutide, bromofenoxim, bromoxynil, bromoxynil-butyrate, -potassium, -heptanoate, and -octanoate, busoxinone, butachlor, butafenacil, butamifos, butenachlor, butralin, butroxydim, butylate, cafenstrole, carbetamide, carfentrazone, carfentrazone-ethyl, chloramben, chlorbromuron, chlorfenac, chlorfenac-sodium, chlorfenprop, chlorflurenol, chlorflurenol-methyl, chloridazon, chlorimuron, chlorimuron-ethyl, chlorophthalim, chlorotoluron, chlorthal-dimethyl, chlorsulfuron, cinidon, cinidon-ethyl, cinmethylin, cinosulfuron, clacyfos, clethodim, clodinafop, clodinafop-propargyl, clomazone, clomeprop, clopyralid, cloransulam, cloransulam-methyl, cumyluron, cyanamide, cyanazine, cycloate, cyclopyrimorate, cyclosulfamuron, cycloxydim, cyhalofop, cyhalofop-butyl, cyprazine, 2,4-D, 2,4-D-butotyl, -butyl, -dimethylammonium, -diolamin, -ethyl, -2-ethylhexyl, -isobutyl, -isooctyl, -isopropylammonium, -potassium, -triisopropanolammonium, and -trolamine, 2,4-DB, 2,4-DB-butyl, -dimethylammonium, -isooctyl, -potassium, and -sodium, daimuron (dymron), dalapon, dazomet, n-decanol, desmedipham, detosyl-pyrazolate (DTP), dicamba, dichlobenil, 2-(2,4-dichlorobenzyl)-4,4-dimethyl-1,2-oxazolidin-3-one, 2-(2,5-dichlorobenzyl)-4,4-dimethyl-1,2-oxazolidin-3-one, dichlorprop, dichlorprop-P, diclofop, diclofop-methyl, diclofop-P-methyl, diclosulam, difenzoquat, diflufenican, diflufenzopyr, diflufenzopyr-sodium, dimefuron, dimepiperate, dimethachlor, dimethametryn, dimethenamid, dimethenamid-P, dimetrasulfuron, dinitramine, dinoterb, diphenamid, diquat, diquat-dibromid, dithiopyr, diuron, DNOC, endothal, EPIC, esprocarb, ethalfluralin, ethametsulfuron, etha-metsulfuron-methyl, ethiozin, ethofumesate, ethoxyfen, ethoxyfen-ethyl, ethoxysulfuron, etobenzanid, F-9600, F-5231, i.e. N-{2-chloro-4-fluoro-5-[4-(3-fluoropropyl)-5-oxo-4,5-dihydro-1H-tetrazol-1-yl]phenyl}ethanesulfonamide, F-7967, i. e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoxaprop, fenoxaprop-P, fenoxaprop-ethyl, fenoxaprop-P-ethyl, fenoxasulfone, fenquinotrione, fentrazamide, flamprop, flamprop-M-isopropyl, flamprop-M-methyl, flazasulfuron, florasulam, fluazifop, fluazifop-P, fluazifop-butyl, fluazifop-P-butyl, flucarbazone, flucarbazone-sodium, flucetosulfuron, fluchloralin, flufenacet, flufenpyr, flufenpyr-ethyl, flumetsulam, flumiclorac, flumiclorac-pentyl, flumioxazin, fluometuron, flurenol, flurenol-butyl, -dimethylammonium and -methyl, fluoroglycofen, fluoroglycofen-ethyl, flupropanate, flupyrsulfuron, flupyrsulfuron-methyl-sodium, fluridone, flurochloridone, fluroxypyr, fluroxypyr-meptyl, flurtamone, fluthiacet, fluthiacet-methyl, fomesafen, fomesafen-sodium, foramsulfuron, fosamine, glufosinate, glufosinate-ammonium, glufosinate-P-sodium, glufosinate-P-ammonium, glufosinate-P-sodium, glyphosate, glyphosate-ammonium, -isopropylammonium, -diammonium, -dimethylammonium, -potassium, -sodium, and -trimesium, H-9201, i.e. O-(2,4-dimethyl-6-nitrophenyl) O-ethyl isopropylphosphoramidothioate, halauxifen, halauxifen-methyl, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl) ethyl-(2,4-dichlorophenoxy)acetate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazethapyr, imazethapyr-immonium, imazosulfuron, indanofan, indaziflam, iodosulfuron, iodosulfuron-methyl-sodium, ioxynil, ioxynil-octanoate, -potassium and -sodium, ipfencarbazone, isoproturon, isouron, isoxaben, isoxaflutole, karbutilate, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, ketospiradox, lactofen, lenacil, linuron, MCPA, MCPA-butotyl, -dimethylammonium, -2-ethylhexyl, -isopropylammonium, -potassium, and -sodium, MCPB, MCPB-methyl, -ethyl, and -sodium, mecoprop, mecoprop-sodium, and -butotyl, mecoprop-P, mecoprop-P-butotyl, -dimethylammonium, -2-ethylhexyl, and -potassium, mefenacet, mefluidide, mesosulfuron, mesosulfuron-methyl, mesotrione, methabenzthiazuron, metam, metamifop, metamitron, metazachlor, metazosulfuron, methabenzthiazuron, methiopyrsulfuron, methiozolin, methyl isothiocyanate, metobromuron, metolachlor, S-metolachlor, metosulam, metoxuron, metribuzin, metsulfuron, metsulfuron-methyl, molinat, monolinuron, monosulfuron, monosulfuron-ester, MT-5950, i.e. N-(3-chloro-4-isopropylphenyl)-2-methylpentan amide, NGGC-011, napropamide, NC-310, i.e. [5-(benzyloxy)-1-methyl-1H-pyrazol-4-yl](2,4-dichlorophenyl)methanone, neburon, nicosulfuron, nonanoic acid (pelargonic acid), norflurazon, oleic acid (fatty acids), orbencarb, orthosulfamuron, oryzalin, oxadiargyl, oxadiazon, oxasulfuron, oxaziclomefon, oxyfluorfen, paraquat, paraquat dichloride, pebulate, pendimethalin, penoxsulam, pentachlorphenol, pentoxazone, pethoxamid, petroleum oils, phenmedipham, picloram, picolinafen, pinoxaden, piperophos, pretilachlor, primisulfuron, primisulfuron-methyl, prodiamine, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, sethoxydim, siduron, simazine, simetryn, SL-261, sulcotrion, sulfentrazone, sulfometuron, sulfometuron-methyl, sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, 2,3,6-TBA, TCA (trichloroacetic acid), TCA-sodium, tebuthiuron, tefuryltrione, tembotrione, tepraloxydim, terbacil, terbucarb, terbumeton, terbuthylazin, terbutryn, thenylchlor, thiazopyr, thiencarbazone, thien-carbazone-methyl, thifensulfuron, thifensulfuron-methyl, thiobencarb, tiafenacil, tolpyralate, topra-mezone, tralkoxydim, triafamone, tri-allate, triasulfuron, triaziflam, tribenuron, tribenuron-methyl, triclopyr, trietazine, trifloxysulfuron, trifloxysulfuron-sodium, trifludimoxazin, trifluralin, triflusulfuron, triflusulfuron-methyl, tritosulfuron, urea sulfate, vernolate, XDE-848, ZJ-0862, i.e. 3,4-dichloro-N-{2-[(4,6-dimethoxypyrimidin-2-yl)oxy]benzyl}aniline, and the following compounds:

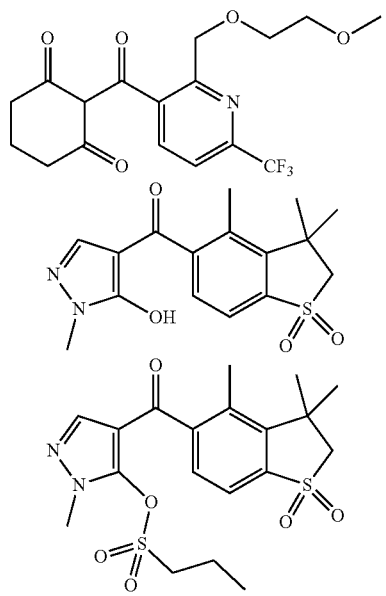

-continued

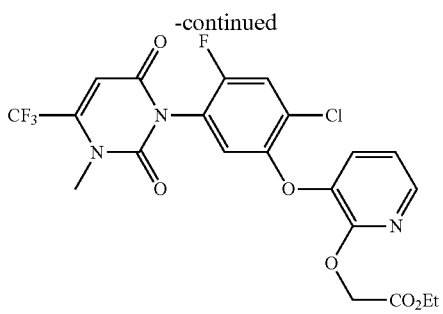

Examples for plant growth regulators are:

Acibenzolar, acibenzolar-S-methyl, 5-aminolevulinic acid, ancymidol, 6-benzylaminopurine, Brassinolid, catechine, chlormequat chloride, cloprop, cyclanilide, 3-(cycloprop-1-enyl) propionic acid, daminozide, dazomet, n-decanol, dikegulac, dikegulac-sodium, endothal, endothal-dipotassium, -disodium, and -mono(N,N-dimethylalkylammonium), ethephon, flumetralin, flurenol, flurenol-butyl, flurprimidol, forchlorfenuron, gibberellic acid, inabenfide, indol-3-acetic acid (IAA), 4-indol-3-ylbutyric acid, isoprothiolane, probenazole, jasmonic acid, maleic hydrazide, mepiquat chloride, 1-methylcyclopropene, methyl jasmonate, 2-(1-naphthyl)acetamide, 1-naphthylacetic acid, 2-naphthyloxyacetic acid, nitrophenolate-mixture, paclobutrazol, N-(2-phenylethyl)-beta-alanine, N-phenylphthalamic acid, prohexadione, prohexadione-calcium, prohydrojasmone, salicylic acid, strigolactone, tecnazene, thidiazuron, triacontanol, trinexapac, trinexapac-ethyl, tsitodef, uniconazole, uniconazole-P.

Methods and Uses

The compounds of formula (I) and compositions comprising thereof have potent microbicidal activity and/or plant defense modulating potential. They can be used for controlling unwanted microorganisms, such as unwanted fungi and bacteria. They can be particularly useful in crop protection (they control microorganisms that cause plants diseases) or for protecting materials (e.g. industrial materials, timber, storage goods) as described in more details herein below. More specifically, the compounds of formula (I) and compositions comprising thereof can be used to protect seeds, germinating seeds, emerged seedlings, plants, plant parts, fruits, harvest goods and/or the soil in which the plants grow from unwanted microorganisms.

Control or controlling as used herein encompasses protective, curative and eradicative treatment of unwanted microorganisms. Unwanted microorganisms may be pathogenic bacteria, pathogenic virus, pathogenic oomycetes or pathogenic fungi, more specifically phytopathogenic bacteria, phytopathogenic virus, phytopathogenic oomycetes or phytopathogenic fungi. As detailed herein below, these phytopathogenic microorganisms are the causal agents of a broad spectrum of plants diseases.

More specifically, the compounds of formula (I) and compositions comprising thereof can be used as fungicides. For the purpose of the specification, the term "fungicide" refers to a compound or composition that can be used in crop protection for the control of unwanted fungi, such as Plasmodiophoromycetes, Chytridiomycetes, Zygomycetes, Ascomycetes, Basidiomycetes and Deuteromycetes and/or for the control of Oomycetes.

The compounds of formula (I) and compositions comprising thereof may also be used as antibacterial agent. In particular, they may be used in crop protection, for example for the control of unwanted bacteria, such as Pseudomonadaceae, Rhizobiaceae, Xanthomonadaceae, Enterobacteriaceae, Corynebacteriaceae and Streptomycetaceae.

The compounds of formula (I) and compositions comprising thereof may also be used as antiviral agent in crop protection. For example the compounds of formula (I) and compositions comprising thereof may have effects on diseases from plant viruses, such as the tobacco mosaic virus (TMV), tobacco rattle virus, tobacco stunt virus (TStuV), tobacco leaf curl virus (VLCV), tobacco nervilia mosaic virus (TVBMV), tobacco necrotic dwarf virus (TNDV), tobacco streak virus (TSV), potato virus X (PVX), potato viruses Y, S, M, and A, potato acuba mosaic virus (PAMV), potato mop-top virus (PMTV), potato leaf-roll virus (PLRV), alfalfa mosaic virus (AMV), cucumber mosaic virus (CMV), cucumber green mottlemosaic virus (CGMMV), cucumber yellows virus (CuYV), watermelon mosaic virus (WMV), tomato spotted wilt virus (TSWV), tomato ringspot virus (TomRSV), sugarcane mosaic virus (SCMV), rice drawf virus, rice stripe virus, rice black-streaked drawf virus, strawberry mottle virus (SMoV), strawberry vein banding virus (SVBV), strawberry mild yellow edge virus (SMYEV), strawberry crinkle virus (SCrV), broad beanwilt virus (BBWV), and melon necrotic spot virus (MNSV).

The present invention also relates to a method for controlling unwanted microorganisms, in particular unwanted phytopathogenic microorganisms such as unwanted fungi, oomycetes and bacteria, comprising the step of applying one or more compounds of formula (I) or a composition comprising thereof to the microorganisms and/or their habitat (to the plants, plant parts, seeds, fruits or to the soil in which the plants grow).

Typically, when the compounds of formula (I) and compositions comprising thereof are used in curative or protective methods for controlling phytopathogenic fungi and/or phytopathogenic oomycetes, an effective and plant-compatible amount thereof is applied to the plants, plant parts, fruits, seeds or to the soil or substrates in which the plants grow. Suitable substrates that may be used for cultivating plants include inorganic based substrates, such as mineral wool, in particular stone wool, perlite, sand or gravel; organic substrates, such as peat, pine bark or sawdust; and petroleum based substrates such as polymeric foams or plastic beads. Effective and plant-compatible amount means an amount that is sufficient to control or destroy the fungi present or liable to appear on the cropland and that does not entail any appreciable symptom of phytotoxicity for said crops. Such an amount can vary within a wide range depending on the fungus to be controlled, the type of crop, the crop growth stage, the climatic conditions and the respective compounds of formula (I) and compositions comprising thereof. This amount can be determined by systematic field trials that are within the capabilities of a person skilled in the art.

Plants and Plant Parts

The compounds of formula (I) and compositions comprising thereof may be applied to any plants or plant parts.

Plants mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the genetically modified plants (GMO or transgenic plants) and the plant cultivars which are protectable and non-protectable by plant breeders' rights.

Genetically modified plants (GMO or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome. This gene gives the transformed plant new or improved agronomic or other properties by expressing a protein or polypeptide of interest or by downregulating or silencing other gene(s) which are present in the plant (using for example, antisense technology, cosuppression technology, RNA interference-RNAi-technology or microRNA-miRNA-technology). A heterologous gene that is located in the genome is also called a transgene. A transgene that is defined by its particular location in the plant genome is called a transformation or transgenic event.

Plant cultivars are understood to mean plants which have new properties ("traits") and have been obtained by conventional breeding, by mutagenesis or by recombinant DNA techniques. They can be cultivars, varieties, bio- or genotypes.

Plant parts are understood to mean all parts and organs of plants above and below the ground, such as shoots, leaves, needles, stalks, stems, flowers, fruit bodies, fruits, seeds, roots, tubers and rhizomes. The plant parts also include harvested material and vegetative and generative propagation material, for example cuttings, tubers, rhizomes, slips and seeds.

Plants which may be treated in accordance with the methods of the invention include the following: cotton, flax, grapevine, fruit, vegetables, such as Rosaceae sp. (for example pome fruits such as apples and pears, but also stone fruits such as apricots, cherries, almonds and peaches, and soft fruits such as strawberries), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for example banana trees and plantations), Rubiaceae sp. (for example coffee), Theaceae sp., Sterculiceae sp., Rutaceae sp. (for example lemons, oranges and grapefruit); Solanaceae sp. (for example tomatoes), Liliaceae sp., Asteraceae sp. (for example lettuce), Umbelliferae sp., Cruciferae sp., Chenopodiaceae sp., Cucurbitaceae sp. (for example cucumber), Alliaceae sp. (for example leek, onion), Papilionaceae sp. (for example peas); major crop plants, such as Gramineae sp. (for example maize, turf, cereals such as wheat, rye, rice, barley, oats, millet and triticale), Asteraceae sp. (for example sunflower), Brassicaceae sp. (for example white cabbage, red cabbage, broccoli, cauliflower, Brussels sprouts, pak choi, kohlrabi, radishes, and oilseed rape, mustard, horseradish and cress), Fabacae sp. (for example bean, peanuts), Papilionaceae sp. (for example soya bean), Solanaceae sp. (for example potatoes), Chenopodiaceae sp. (for example sugar beet, fodder beet, swiss chard, beetroot); useful plants and ornamental plants for gardens and wooded areas; and genetically modified varieties of each of these plants.

Plants and plant cultivars which may be treated by the above disclosed methods include plants and plant cultivars which are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may be treated by the above disclosed methods include those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may be treated by the above disclosed methods include those plants characterized by enhanced yield characteristics. Increased yield in said plants may be the result of, for example, improved plant physiology, growth and development, such as water use efficiency, water retention efficiency, improved nitrogen use, enhanced carbon assimilation, improved photosynthesis, increased germination efficiency and accelerated maturation. Yield may furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content and composition for example cotton or starch, protein content, oil content and composition, nutritional value, reduction in anti-nutritional compounds, improved processability and better storage stability.

Plants and plant cultivars which may be treated by the above disclosed methods include plants and plant cultivars which are hybrid plants that already express the characteristic of heterosis or hybrid vigor which results in generally higher yield, vigor, health and resistance towards biotic and abiotic stresses.

Plants and plant cultivars (obtained by plant biotechnology methods such as genetic engineering) which may be treated by the above disclosed methods include plants and plant cultivars which are herbicide-tolerant plants, i.e. plants made tolerant to one or more given herbicides. Such plants can be obtained either by genetic transformation, or by selection of plants containing a mutation imparting such herbicide tolerance.

Plants and plant cultivars (obtained by plant biotechnology methods such as genetic engineering) which may be treated by the above disclosed methods include plants and plant cultivars which are insect-resistant transgenic plants, i.e. plants made resistant to attack by certain target insects. Such plants can be obtained by genetic transformation, or by selection of plants containing a mutation imparting such insect resistance.

Plants and plant cultivars (obtained by plant biotechnology methods such as genetic engineering) which may be treated by the above disclosed methods include plants and plant cultivars which are disease-resistant transgenic plants, i.e. plants made resistant to attack by certain target insects. Such plants can be obtained by genetic transformation, or by selection of plants containing a mutation imparting such insect resistance.

Plants and plant cultivars (obtained by plant biotechnology methods such as genetic engineering) which may be treated by the above disclosed methods include plants and plant cultivars which are tolerant to abiotic stresses. Such plants can be obtained by genetic transformation, or by selection of plants containing a mutation imparting such stress resistance.

Plants and plant cultivars (obtained by plant biotechnology methods such as genetic engineering) which may be treated by the above disclosed methods include plants and plant cultivars which show altered quantity, quality and/or storage-stability of the harvested product and/or altered properties of specific ingredients of the harvested product.

Plants and plant cultivars (obtained by plant biotechnology methods such as genetic engineering) which may be treated by the above disclosed methods include plants and plant cultivars, such as cotton plants, with altered fiber characteristics. Such plants can be obtained by genetic transformation, or by selection of plants contain a mutation imparting such altered fiber characteristics.

Plants and plant cultivars (obtained by plant biotechnology methods such as genetic engineering) which may be treated by the above disclosed methods include plants and plant cultivars, such as oilseed rape or related *Brassica* plants, with altered oil profile characteristics. Such plants can be obtained by genetic transformation, or by selection of plants contain a mutation imparting such altered oil profile characteristics.

Plants and plant cultivars (obtained by plant biotechnology methods such as genetic engineering) which may be treated by the above disclosed methods include plants and plant cultivars, such as oilseed rape or related Brassica plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Plants and plant cultivars (obtained by plant biotechnology methods such as genetic engineering) which may be treated by the above disclosed methods include plants and plant cultivars, such as Tobacco plants, with altered post-translational protein modification patterns.

Pathogens

Non-limiting examples of pathogens of fungal diseases which may be treated in accordance with the invention include:

diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;

diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* or *Phakopsora meibomiae*; *Puccinia* species, for example *Puccinia recondita, Puccinia graminis* oder *Puccinia striiformis*; *Uromyces* species, for example *Uromyces appendiculatus*;

diseases caused by pathogens from the group of the Oomycetes, for example *Albugo* species, for example *Albugo candida*; *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimurn*;

leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus* (conidial form: *Drechslera*, syn: *Helminthosporium*) or *Cochliobolus miyabeanus*; *Colletotrichum* species, for example *Colletotrichum lindemuthanium*; *Corynespora* species, for example *Corynespora cassiicola*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium leeticolor*; *Glomerella* species, for example *Glomerefla cingulata*; *Guignardia* species, for example *Guignardia bidwelli*; *Leptosphaeria* species, for example *Leptosphaeria maculans*; *Magnaporthe* species, for example *Magnaporthe grisea*; *Microdochium* species, for example *Microdochium nivale*; *Mycosphaerella* species, for example *Mycosphaerella graminicola, Mycosphaerella arachidicola* or *Mycosphaerella fijiensis*; *Phaeosphaeria* species, for example *Phaeosphaeria nodorum*; *Pyrenophora* species, for example *Pyrenophora teres* or *Pyrenophora tritici repentis*; *Ramularia* species, for example *Ramularia collo-cygni* or *Ramularia areola*; *Rhynchosporium* species, for example *Rhynchosporium secalis*; *Septoria* species, for example *Septoria apii* or *Septoria lycopersici*; *Stagonospora* species, for example *Stagonospora nodorum*; *Typhula* species, for example *Typhula incarnate*; *Venturia* species, for example *Venturia inaequalis*;

root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Plasmodiophora* species, for example *Plasmodiophora brassicae*; *Rhizoctonia* species, for example *Rhizoctonia solani*; *Sarocladium* species, for example *Sarocladium oryzae*; *Sclerotium* species, for example *Sclerotium oryzae*; *Tapesia* species, for example *Tapesia acuformis*; *Thielaviopsis* species, for example *Thielaviopsis basicola*;

ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Stagnospora* species, for example *Stagnospora nodorum*;

diseases caused by smut fungi, for example *Sphacelotheca* species, for example *Sphacelotheca reiliana*; *Tilletia* species, for example *Tilletia caries* or *Tilletia controversa*; *Urocystis* species, for example *Urocystis occulta*; *Ustilago* species, for example *Ustilago nuda*;

fruit rot caused, for example, by *Aspergillus* species, for example *Aspergillus flavus*; *Botrytis* species, for example *Botrytis cinerea*; *Monilinia* species, for example *Monilinia taxa*; *Penicillium* species, for example *Penicillium expansum* or *Penicillium purpurogenum*; *Rhizopus* species, for example *Rhizopus stolonifer*; *Sclerotinia* species, for example *Sclerotinia sclerotiorum*; *Verticilium* species, for example *Verticilium alboatrum*;

seed- and soil-borne rot and wilt diseases, and also diseases of seedlings, caused, for example, by *Alternaria* species, for example *Alternaria brassicicola*; *Aphanomyces* species, for example *Aphanomyces euteiches*; *Ascochyta* species, for example *Ascochyta lentis*; *Aspergillus* species, for example *Aspergillus flavus*; *Cladosporium* species, for example *Cladosporium herbarum*; *Cochliobolus* species, for example *Cochliobolus sativus* (conidial form: *Drechslera*, Bipolaris Syn: *Helminthosporium*); *Colletotrichum* species, for example *Colletotrichum coccodes*; *Fusarium* species, for example *Fusarium culmorum*; *Gibberella* species, for example *Gibberella zeae*; *Macrophomina* species, for example *Macrophomina phaseolina*; *Microdochium* species, for example *Microdochium nivale*; *Monographella* species, for example *Monographella niva-*

*lis*; *Penicillium* species, for example *Penicillium expansum*; *Phoma* species, for example *Phoma lingam*; *Phomopsis* species, for example *Phomopsis sojae*; *Phytophthora* species, for example *Phytophthora cactorum*; *Pyrenophora* species, for example *Pyrenophora graminea*; *Pyricularia* species, for example *Pyricularia oryzae*; *Pythium* species, for example *Pythium ultimum*; *Rhizoctonia* species, for example *Rhizoctonia solani*; *Rhizopus* species, for example *Rhizopus oryzae*; *Sclerotium* species, for example *Sclerotium rolfsii*; *Septoria* species, for example *Septoria nodorum*; *Typhula* species, for example *Typhula incarnata*; *Verticillium* species, for example *Verticillium dahliae*;

cancers, galls and witches' broom caused, for example, by *Nectria* species, for example *Nectria galligena*;

wilt diseases caused, for example, by *Verticillium* species, for example *Verticillium longisporum*; *Fusarium* species, for example *Fusarium oxysporum*;

deformations of leaves, flowers and fruits caused, for example, by *Exobasidium* species, for example *Exobasidium vexans*; *Taphrina* species, for example *Taphrina deformans*;

degenerative diseases in woody plants, caused, for example, by *Esca* species, for example *Phaeomoniella chlamydospora*, *Phaeoacremonium aleophilum* or *Fomitiporia mediterranea*; *Ganoderma* species, for example *Ganoderma boninense*;

diseases of plant tubers caused, for example, by *Rhizoctonia* species, for example *Rhizoctonia solani*; *Helminthosporium* species, for example *Helminthosporium solani*;

diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*; *Liberibacter* species, for example *Liberibacter asiaticus*; *Xyella* species, for example *Xylella fastidiosa*; *Ralstonia* species, for example *Ralstonia solanacearum*; *Dickeya* species, for example *Dickeya solani*; *Clavibacter* species, for example *Clavibacter michiganensis*; *Streptomyces* species, for example *Streptomyces scabies*.

diseases of soya beans:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina tritoni*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*, *Phakopsora meibomiae*), scab (*Sphaceloma glycines*), stemphylium leaf blight (*Stemphylium botryosum*), sudden death syndrome (*Fusarium virguliforme*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum*, *Fusarium orthoceras*, *Fusarium semitectum*, *Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum*, *Pythium iffegulare*, *Pythium debaryanum*, *Pythium myriotyium*, *Pythium ultimum*), rhizoctonia root rot, stem decay, and damping-off (*Rhizoctonia solan*), sclerotinia stem decay (*Sclerotinia sclerotiorum*), sclerotinia southern blight (*Sclerotinia rolfsii*), thielaviopsis root rot (*Thielaviopsis basicola*).

Mycotoxins

In addition, the compounds of formula (I) and compositions comprising thereof may reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum*, *F. asiaticum*, *F. avenaceum*, *F. crookwellense*, *F. culmorum*, *F. graminearum* (*Gibberella zeae*), *F. equiseti*, *F. fujikoroi*, *F. musarum*, *F. oxysporum*, *F. proliferatum*, *F. poae*, *F. pseudograminearum*, *F. sambucinum*, *F. scirpi*, *F. semitectum*, *F. solani*, *F. sporotrichoides*, *F. langsethiae*, *F. subglutinans*, *F. tricinctum*, *F. verticillioides* etc., and also by *Aspergillus* spec., such as *A. flavus*, *A. parasiticus*, *A. nomius*, *A. ochraceus*, *A. clavatus*, *A. terreus*, *A. versicolor*, *Penicillium* spec., such as *P. verrucosum*, *P. viridicatum*, *P. citrinum*, *P. expansum*, *P. claviforme*, *P. roqueforti*, *Claviceps* spec., such as *C. purpurea*, *C. fusiformis*, *C. paspali*, *C. africana*, *Stachybotrys* spec. and others.

Material Protection

The compounds of formula (I) and compositions comprising thereof may also be used in the protection of materials, especially for the protection of industrial materials against attack and destruction by phytopathogenic fungi.

In addition, the compounds of formula (I) and compositions comprising thereof may be used as antifouling compositions, alone or in combinations with other active ingredients.

Industrial materials in the present context are understood to mean inanimate materials which have been prepared for use in industry. For example, industrial materials which are to be protected from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The compounds of formula (I) and compositions comprising thereof may prevent adverse effects, such as rotting, decay, discoloration, decoloration or formation of mould.

In the case of treatment of wood the compounds of formula (I) and compositions comprising thereof may also be used against fungal diseases liable to grow on or inside timber.

Timber means all types of species of wood, and all types of working of this wood intended for construction, for example solid wood, high-density wood, laminated wood, and plywood. In addition, the compounds of formula (I) and compositions comprising thereof may be used to protect objects which come into contact with saltwater or brackish water, especially hulls, screens, nets, buildings, moorings and signalling systems, from fouling.

The compounds of formula (I) and compositions comprising thereof may also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, may be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The compounds of formula (I) and compositions comprising thereof may prevent adverse effects, such as rotting, decay, discoloration, decoloration or formation of mould.

Microorganisms capable of degrading or altering industrial materials include, for example, bacteria, fungi, yeasts, algae and slime organisms. The compounds of formula (I) and compositions comprising thereof preferably act against fungi, especially moulds, wood-discoloring and wood-destroying fungi (*Ascomycetes, Basidiomycetes, Deuteromycetes* and *Zygomycetes*), and against slime organisms and algae. Examples include microorganisms of the following genera: *Alternaria*, such as *Alternaria tenuis*; *Aspergillus*, such as *Aspergillus niger*, *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*, *Aureobasidium*, such as *Aureobasidium pullulans*; *Sclerophoma*, such as *Sclerophoma pityophila*; *Trichoderma*, such as *Trichoderma viride*; *Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli*; *Pseudomonas*, such as *Pseudomonas aeruginosa*; *Staphylococcus*, such as *Staphylococcus aureus*, *Candida* spp. and *Saccharomyces* spp., such as *Saccharomyces cerevisae*.

Seed Treatment

The compounds of formula (I) and compositions comprising thereof may also be used to protect seeds from unwanted microorganisms, such as phytopathogenic microorganisms, for instance phytopathogenic fungi or phytopathogenic oomycetes. The term seed(s) as used herein include dormant seeds, primed seeds, pregerminated seeds and seeds with emerged roots and leaves.

Thus, the present invention also relates to a method for protecting seeds from unwanted microorganisms which comprises the step of treating the seeds with the compounds of formula (I) and compositions comprising thereof.

The treatment of seeds with the compounds of formula (I) and compositions comprising thereof protects the seeds from phytopathogenic microorganisms, but also protects the germinating seeds, the emerging seedlings and the plants after emergence from the treated seeds. Therefore, the present invention also relates to a method for protecting seeds, germinating seeds and emerging seedlings.

The seeds treatment may be performed prior to sowing, at the time of sowing or shortly thereafter.

When the seeds treatment is performed prior to sowing (e.g. so-called on-seed applications), the seeds treatment may be performed as follows: the seeds may be placed into a mixer with a desired amount of the compounds of formula (I) or compositions comprising thereof, the seeds and the compounds of formula (I) or compositions comprising thereof are mixed until an homogeneous distribution on seeds is achieved. If appropriate, the seeds may then be dried.

The invention also relates to seeds coated with the compounds of formula (I) or compositions comprising thereof.

Preferably, the seeds are treated in a state in which it is sufficiently stable for no damage to occur in the course of treatment. In general, seeds can be treated at any time between harvest and shortly after sowing. It is customary to use seeds which have been separated from the plant and freed from cobs, shells, stalks, coats, hairs or the flesh of the fruits. For example, it is possible to use seeds which have been harvested, cleaned and dried down to a moisture content of less than 15% by weight. Alternatively, it is also possible to use seeds which, after drying, for example, have been treated with water and then dried again, or seeds just after priming, or seeds stored in primed conditions or pre-germinated seeds, or seeds sown on nursery trays, tapes or paper.

The amount of the compounds of formula (I) or compositions comprising thereof applied to the seeds is typically such that the germination of the seed is not impaired, or that the resulting plant is not damaged. This must be ensured particularly in case the compounds of formula (I) would exhibit phytotoxic effects at certain application rates. The intrinsic phenotypes of transgenic plants should also be taken into consideration when determining the amount of the compounds of formula (I) to be applied to the seed in order to achieve optimum seed and germinating plant protection with a minimum amount of compound being employed.

The compounds of formula (I) can be applied as such, directly to the seeds, i.e. without the use of any other components and without having been diluted. Also a composition comprising one or more compounds of formula (I) can be applied to the seeds.

The compounds of formula (I) and compositions comprising thereof are suitable for protecting seeds of any plant variety. Preferred seeds are that of cereals (such as wheat, barley, rye, millet, triticale, and oats), oilseed rape, maize, cotton, soybean, rice, potatoes, sunflower, beans, coffee, peas, beet (e.g. sugar beet and fodder beet), peanut, vegetables (such as tomato, cucumber, onions and lettuce), lawns and ornamental plants. More preferred are seeds of wheat, soybean, oilseed rape, maize and rice.

The compounds of formula (I) and compositions comprising thereof may be used for treating transgenic seeds, in particular seeds of plants capable of expressing a polypeptide or protein which acts against pests, herbicidal damage or abiotic stress, thereby increasing the protective effect. Seeds of plants capable of expressing a polypeptide or protein which acts against pests, herbicidal damage or abiotic stress may contain at least one heterologous gene which allows the expression of said polypeptide or protein. These heterologous genes in transgenic seeds may originate, for example, from microorganisms of the species *Bacillus, Rhizobium, Pseudomonas, Serratia, Trichoderma, Clavibacter, Glomus* or *Gliocladium*. These heterologous genes preferably originate from *Bacillus* sp., in which case the gene product is effective against the European corn borer and/or the Western corn rootworm. Particularly preferably, the heterologous genes originate from *Bacillus thuringiensis*.

Application

The compounds of formula (I) can be applied as such, or for example in the form of as ready-to-use solutions, emulsions, water- or oil-based suspensions, powders, wettable powders, pastes, soluble powders, dusts, soluble granules, granules for broadcasting, suspoemulsion concentrates, natural products impregnated with the compounds of formula (I), synthetic substances impregnated with the compounds of formula (I), fertilizers or microencapsulations in polymeric substances.

Application is accomplished in a customary manner, for example by watering, spraying, atomizing, broadcasting, dusting, foaming, spreading-on and the like. It is also possible to deploy the compounds of formula (I) by the ultra-low volume method, via a drip irrigation system or drench application, to apply it in-furrow or to inject it into the soil stem or trunk. It is further possible to apply the compounds of formula (I) by means of a wound seal, paint or other wound dressing.

The effective and plant-compatible amount of the compound(s) of formula (I) which is applied to the plants, plant parts, fruits, seeds or soil will depend on various factors, such as the compound/composition employed, the subject of the treatment (plant, plant part, fruit, seed or soil), the type of treatment (dusting, spraying, seed dressing), the purpose of the treatment (curative and protective), the type of microorganisms, the development stage of the microorganisms, the sensitivity of the microorganisms, the crop growth stage and the environmental conditions.

When the compounds of formula (I) are used as a fungicide, the application rates can vary within a relatively wide range, depending on the kind of application. For the treatment of plant parts, such as leaves, the application rate may range from 0.1 to 10 000 g/ha, preferably from 10 to 1000 g/ha, more preferably from 50 to 300 g/ha (in the case of application by watering or dripping, it is even possible to reduce the application rate, especially when inert substrates such as rockwool or perlite are used). For the treatment of seeds, the application rate may range from 0.1 to 200 g per 100 kg of seeds, preferably from 1 to 150 g per 100 kg of seeds, more preferably from 2.5 to 25 g per 100 kg of seeds, even more preferably from 2.5 to 12.5 g per 100 kg of seeds. For the treatment of soil, the application rate may range from 0.1 to 10 000 g/ha, preferably from 1 to 5000 g/ha.

These application rates are merely examples and are not intended to limit the scope of the present invention.

Aspects of the present teaching may be further understood in light of the following examples, which should not be construed as limiting the scope of the present teaching in any way.

EXAMPLES

Preparation Examples

Preparation of 7,8-difluoro-N-[3-fluoro-2-(1-methyl-1H-pyrazol-5-yl)phenyl]-2-methylquinolin-3-amine (Compound I-050)

Step 1: preparation of 5-(2-bromo-6-fluoro-phenyl)-1-methyl-pyrazole

To a solution of 10 g (36.7 mmol) of 1-(2-bromo-6-fluoro-phenyl)-3-(dimethylamino)prop-2-en-1-one in ethanol (70 mL), 19.2 mL (110 mmol) of N,N-diisopropylethylamine were added. Then, 7.95 g (55 mmol) of methylhydrazine sulfate (solid) were added slowly and portionwise. The resulting mixture was heated to reflux for 7 h then cooled to room temperature and concentrated under vacuum. The residue obtained was purified by column chromatography on silica gel (gradient n-heptane/ethyl acetate) to yield 7.4 g (77%) of 5-(2-bromo-6-fluoro-phenyl)-1-methyl-pyrazole as a colorless liquid. Log P=2.40 [Method A]. Mass (M+H)=255. Purity=98% (LC-210 nm).

Step 2: Preparation of 7,8-difluoro-N-[3-fluoro-2-(1-methyl-1H-pyrazol-5-yl)phenyl]-2-methylquinolin-3-amine (Compound I-050)

Under argon, a mixture of 10 g (51.5 mmol) of 7,8-difluoro-2-methyl-quinolin-3-amine, 2.36 g (2.57 mmol) of tris(dibenzylideneacetone)dipalladium, 3.12 g (5.40 mmol) of 4,5-bis-(diphenylphosphino)9,9-dimethylxanthene, 50.3 g (154.5 mmol) of cesium carbonate were added in 180 mL of dry 1,4-dioxane. Afterwards, 16.2 g (61.8 mmol) of 5-(2-bromo-6-fluoro-phenyl)-1-methyl-pyrazole was diluted with 20 mL of dry 1,4-dioxane, and then added in the mixture. The resulting mixture was heated at 100° C. for 7 h. The reaction mixture was cooled to room temperature, and then diluted with water and extracted with ethyl acetate. Combined organic layers were washed with brine, then dried with magnesium sulfate and concentrated under vacuum. The residue obtained was purified by column chromatography on silica gel (gradient n-heptane/ethyl acetate) to yield 15.3 g (80%) of 7,8-difluoro-N-[3-fluoro-2-(1-methyl-1H-pyrazol-5-yl)phenyl]-2-methylquinolin-3-amine as a yellow solid. Log P=3.07 [Method A]. Mass (M+H)=369. Purity=98% (LC-210 nm).

Preparation of N-[3-fluoro-2-(1-methyl-1H-pyrazol-5-yl)phenyl]-3-methylquinoxalin-2-amine (Compound I-083)

In a 20 mL micro-wave tube, 420 mg (2.64 mmol) of 3-methylquinoxalin-2-amine, 808 mg (3.17 mmol) of 5-(2-bromo-6-fluoro-phenyl)-1-methyl-pyrazole, 121 mg (0.13 mmol) of tris(dibenzylideneacetone)dipalladium, 160 mg (0.28 mmol) of 4,5-bis-(diphenylphosphino)9,9-dimethylxanthene and 2.6 g (7.92 mmol) of cesium carbonate were added in 15 mL of dry 1,4-dioxane. The resulting mixture was heated at 140° C. for 1 h in micro-wave. The reaction mixture was cooled to room temperature, and then diluted with water and extracted with ethyl acetate. Combined organic layers were washed with brine, then dried over ChemElut cartridge and concentrated under vacuum. The residue obtained was purified by column chromatography on silica gel (gradient n-heptane/ethyl acetate) to yield 760 mg (83%) of N-[3-fluoro-2-(1-methyl-1H-pyrazol-5-yl)phenyl]-3-methylquinoxalin-2-amine as solid. Log P=2.82 [Method A]. Mass (M+H)=334. Purity=95% (LC-210 nm).

Preparation of N-[2-(1-ethyl-1H-pyrazol-5-yl)phenyl]-8-fluoroquinolin-3-amine (Compound I-080)

Step 1: Preparation of N-(2-bromophenyl)-8-fluoro-quinolin-3-amine

Under argon, a mixture of 2 g (12.3 mmol) of 8-fluoro-quinolin-3-amine, 904 mg (0.98 mmol) of tris(dibenzylideneacetone)dipalladium, 714 mg (1.23 mmol) of 4,5-bis-(diphenylphosphino)9,9-dimethylxanthene and 12 g (37 mmol) of cesium carbonate were added in 20 mL of dry 1,4-dioxane. Afterwards, a solution of 3.05 g (12.9 mmol) of 1,2-dibromobenzene in 10 mL of dry 1,4-dioxane was added to the mixture. The resulting mixture was heated at 100° C. for 6 h, then cooled to room temperature, diluted with water and extracted with ethyl acetate. The combined organic layers were washed with brine, then dried over ChemElut cartridge and concentrated under vacuum. The residue obtained was purified by column chromatography on silica gel (gradient n-heptane/ethyl acetate) to yield 1.4 g (35%) of N-(2-bromophenyl)-8-fluoro-quinolin-3-amine as solid. Log P=3.27 [Method A]. Mass (M+H)=317. Purity=98.5% (LC-210 nm).

Step 2: Preparation of 8-fluoro-N-[2-(4,4,5,5-tetramethyl-1,3,2-dioxaborolan-2-yl)phenyl]quinolin-3-amine (Compound VI-01)

Under argon, a mixture of 74 mg (0.23 mmol) of N-(2-bromophenyl)-8-fluoro-quinolin-3-amine, 71 mg 0.28 mmol) of 4,4,5,5-tetramethyl-2-(4,4,5,5-tetramethyl-1,3,2-dioxaborolan-2-yl)-1,3,2-dioxaborolane, mg (0.70 mmol) of potassium acetate and 19 mg (0.023 mmol) of [1,1'-Bis(diphenylphosphino)ferrocene]dichloropalladium(II) complex with CH$_2$Cl$_2$, were added in 2 mL of dry 1,4-dioxane. The resulting mixture was heated at 100° C. for 1 h. The reaction mixture was cooled to room temperature, then diluted with water and extracted with ethyl acetate. The combined organic layers were washed with brine, then dried over ChemElut cartridge and concentrated under vacuum. The residue obtained was purified by column chromatography on silica gel (gradient n-heptane/ethyl acetate) to yield 27 mg (32%) of 8-fluoro-N-[2-(4,4,5,5-tetramethyl-1,3,2-dioxaborolan-2-yl)phenyl]quinolin-3-amine as a yellow solid. Log P=4.87 [Method A]. Mass (M+H)=365. Purity=100% (LC-210 nm).

Step 3: Preparation of N-[2-(1-ethyl-1H-pyrazol-5-yl)phenyl]-8-fluoroquinolin-3-amine (Compound I-080)

Under argon, a mixture of 171 mg (0.35 mmol) of 8-fluoro-N-[2-(4,4,5,5-tetramethyl-1,3,2-dioxaborolan-2-yl)phenyl]quinolin-3-amine (compound VI-01), 94 mg (0.42 mmol) of 1-ethyl-5-iodo-pyrazole, 16 mg (0.018 mmol) of tris(dibenzylideneacetone)dipalladium, 14.5 mg (0.035 mmol) of 2-dicyclohexylphosphino-2',6'-dimethoxybiphenyl, SPhos and 134 mg (0.88 mmol) of cesium fluoride were added in 3 mL of dry 1,4-dioxane. The resulting mixture was heated at 90° C. for 4 h. The reaction mixture was cooled to room temperature, and then diluted with water and extracted with ethyl acetate. Combined organic layers were washed with brine, then dried over ChemElut cartridge and concentrated under vacuum. The residue obtained was purified by column chromatography on silica gel (gradient n-heptane/ ethyl acetate) to yield 24 mg (20%) of N-[2-(1-ethyl-1H-pyrazol-5-yl)phenyl]-8-fluoroquinolin-3-amine as solid. Log P=2.82 [Method A]. Mass (M+H)=333. Purity=99% (LC-210 nm.)

Preparation of N-[2-(1-benzyl-1H-pyrazol-5-yl)phenyl]-8-fluoroquinolin-3-amine (Compound I-096)

In a 5 mL micro-wave tube, 100 mg (0.32 mmol) of N-(2-bromophenyl)-8-fluoro-quinolin-3-amine, 108 mg (0.38 mmol) of 1-benzyl-5-(4,4,5,5-tetramethyl-1,3,2-dioxaborolan-2-yl)pyrazole, 14.4 mg (0.016 mmol) of tris(dibenzylideneacetone)dipalladium, 13 mg (0.032 mmol) of 2-dicyclohexylphosphino-2',6'-dimethoxybiphenyl (SPhos) and 120 mg (0.79 mmol) of cesium fluoride were added in 3 mL of dry 1,4-dioxane. The resulting mixture was heated at 140° C. for 1 h in micro-wave. The reaction mixture was cooled to room temperature, and then diluted with water and extracted with ethyl acetate. Combined organic layers were washed with brine, then dried over ChemElut cartridge and concentrated under vacuum. The residue obtained was purified by column chromatography on silica gel (gradient n-heptane/ethyl acetate) to yield 98 mg (78%) of N-[2-(1-benzyl-1H-pyrazol-5-yl)phenyl]-8-fluoroquinolin-3-amine as solid. Log P=3.49 [Method A]. Mass (M+H)=395. Purity=98% (LC-210 nm).

Preparation of 7,8-difluoro-N-[2-(1-isopropylpyrazol-3-yl)phenyl]-N,2-dimethyl-quinolin-3-amine (Compound I-046)

To a solution of 7,8-difluoro-N-[2-(1-isopropylpyrazol-3-yl)phenyl]-2-methyl-quinolin-3-amine (150 mg, 0.40 mmol) (compound I-043) in dry DMF (5 mL) at 0° C. under argon was added sodium hydride (60% dispersion in mineral oil, 32 mg, 0.80 mmol) followed by iodomethane (49 µL, 0.79 mmol). The mixture was allowed to warm to room temperature and was stirred for 2 h. The mixture was diluted with water and extracted with ethyl acetate. The combined organic layers were washed with a saturated aqueous NaHCO$_3$ solution, dried over magnesium sulfate, filtered and concentrated under reduced pressure. Purification by flash column chromatography on silica gel (gradient n-heptane/ethyl acetate) afforded the title compound as a yellow oil (116 mg, 75%). Log P=4.36 [Method A]. Mass (M+H)=393. Purity=100% (LC-210 nm).

Preparation of methyl 1-[2-(3-quinolylamino)phenyl]pyrazole-3-carboxylate (Compound I-062)

To a solution of N-(2-bromophenyl)quinolin-3-amine (164 mg, 0.55 mmol) in DMF (2.5 mL), were added methyl 1H-pyrazole-3-carboxylate (63 mg, 0.50 mmol), copper(1) iodide (10 mg, 0.05 mmol), L-proline (12 mg, 0.10 mmol) and potassium phosphate (212 mg, 1.0 mmol). The mixture was stirred at 120° C. for 18 h. The crude mixture was purified by preparative HPLC (CH$_3$CN/H$_2$O) to afford the title compound as a yellow solid (80 mg, 42%). Log P=2.16 [Method A]. Mass (M+H)=345. Purity=99% (LC-210 nm).

Preparation of N-{2-[5-({[tert-butyl(dimethyl)silyl]oxy}methyl)-1H-pyrazol-1-yl]phenyl}quinolin-3-amine (Compound I-069)

A mixture of 3-bromoquinoline (1.4 g, 6.7 mmol), 2-[5-({[tert-butyl(dimethyl)silyl]oxy}methyl)-1H-pyrazol-1-yl]aniline (1.7 g, 5.5 mmol), [1,1'-bis(di-tert-butylphosphino)ferrocene]dichloropalladium(II) (364 mg, 0.56 mmol) and cesium carbonate (5.5 g, 16.8 mmol) in 1,4-dioxane (15 mL) was heated to 100° C. for 18 h. The reaction was cooled to room temperature, diluted with water and extracted with ethyl acetate. The combined organic layers were washed with brine, dried over magnesium sulfate, filtered and concentrated under reduced pressure. Purification by flash column chromatography on silica gel (gradient petroleum ether/ ethyl acetate) afforded N-{2-[5-({[tert-butyl(dimethyl)silyl]oxy}methyl)-1H-pyrazol-1-yl]phenyl}quinolin-3-amine as a brown oil (1.7 g, 71%). Log P=4.92 [Method A]. Mass (M+H)=431. Purity=96% (LC-210 nm).

Preparation of tert-butyl {2-[5-({[tert-butyl(dimethyl)silyl]oxy}methyl)-1H-pyrazol-1-yl]phenyl}quinolin-3-ylcarbamate (Compound XX-07)

To a solution of N-{2-[5-({[tert-butyl(dimethyl)silyl]oxy}methyl)-1H-pyrazol-1-yl]phenyl}quinolin-3-amine (compound I-069) (150 mg, 0.35 mmol) and DMAP (45 mg, 0.35 mmol) in DCM (10 mL), was added di-tert-butyl dicarbonate (91 mg, 0.42 mmol). The reaction mixture was stirred at room temperature for 2 h, then diluted with water and extracted with dichloromethane. The combined organic layers were washed with brine, dried over magnesium sulfate, filtered and concentrated under reduced pressure. Purification by flash column chromatography on silica gel (gradient petroleum ether/ethyl acetate) afforded the title compound as a brown solid (185 mg, quantitative). Log P=5.84 [Method A]. Mass (M+H)=531. Purity=96% (LC-210 nm).

Preparation of methyl 1-[2-(quinolin-3-ylamino)phenyl]-1H-pyrazole-5-carboxylate (Compound I-064)

Methyl 1-(2-(tert-butoxycarbonyl(quinolin-3-yl)amino)phenyl)-1H-pyrazole-5-carboxylate (0.6 g, 1.35 mmol) (compound XX-05) was dissolved into a solution of HCl in 1,4-dioxane (4N, 10 mL) at 0° C. The resulting mixture was stirred at 0° C. for 1 h and concentrated under reduced pressure. The crude mixture was purified by preparative HPLC (CH$_3$CN/H$_2$O) to afford the title compound as a yellow solid (450 mg, 97%). Log P=2.02 [Method A]. Mass (M+H)=345. Purity=93% (LC-210 nm).

The following tables illustrate in a non-limiting manner examples of compounds according to the invention.

In the following, measurement of Log P values was performed according to EEC directive 79/831 Annex V.A8 by HPLC (High Performance Liquid Chromatography) on reversed phase columns with the following methods:

[a] Log P value is determined by measurement of LC-UV, in an acidic range, with 0.1% formic acid in water and acetonitrile as eluent (linear gradient from 10% acetonitrile to 95% acetonitrile).

[b] Log P value is determined by measurement of LC-UV, in a neutral range, with 0.001 molar ammonium acetate solution in water and acetonitrile as eluent (linear gradient from 10% acetonitrile to 95% acetonitrile).

[c] Log P value is determined by measurement of LC-UV, in an acidic range, with 0.1% phosphoric acid and acetonitrile as eluent (linear gradient from 10% acetonitrile to 95% acetonitrile).

If more than one Log P value is available within the same method, all the values are given and separated by "+".

Calibration was done with straight-chain alkan2-ones (with 3 to 16 carbon atoms) with known Log P values (measurement of Log P values using retention times with linear interpolation between successive alkanones). Lambda-max-values were determined using UV-spectra from 200 nm to 400 nm and the peak values of the chromatographic signals.

TABLE 1

Compounds according to formula (I)

| Example | (Y)$_p$–A–N=Z (Q$^1$) | L | n | (X)$_n$ | B–(W)$_m$ | logP |
|---|---|---|---|---|---|---|
| I-001 | quinolin-3-yl | NH | 0 | — | 1-methyl-1H-pyrazol-3-yl | 2.70 [a] |
| I-002 | 2-methylquinolin-3-yl | NH | 0 | — | 1-methyl-1H-pyrazol-3-yl | 2.01 [a] |
| I-003 | quinolin-3-yl | NH | 0 | — | 1-isopropyl-1H-pyrazol-3-yl | 3.70 [a] |
| I-004 | 2-methylquinolin-3-yl | NH | 0 | — | 1-isopropyl-1H-pyrazol-3-yl | 2.65 [a] |
| I-005 | quinolin-3-yl | NH | 0 | — | 1-tert-butyl-1H-pyrazol-3-yl | 4.27 [a] |
| I-006 | 2-methylquinolin-3-yl | NH | 0 | — | 1-tert-butyl-1H-pyrazol-3-yl | 3.01 [a] |
| I-007 | quinolin-3-yl | NH | 0 | — | 1-methyl-1H-pyrazol-5-yl | 1.90 [a] |
| I-008 | 2-methylquinolin-3-yl | NH | 0 | — | 1-methyl-1H-pyrazol-5-yl | 1.37 [a] |
| I-009 | quinolin-3-yl | NH | 0 | — | 1-tert-butyl-1H-pyrazol-5-yl | 3.19 [a] |
| I-010 | 2-methylquinolin-3-yl | NH | 0 | — | 1-tert-butyl-1H-pyrazol-5-yl | 2.58 [a] |
| I-011 | quinolin-3-yl | NH | 0 | — | 3-methyl-4,5-dihydro-1,2-oxazol-5-yl | 1.88 [a] |
| I-012 | 2-methylquinolin-3-yl | NH | 0 | — | 3-methyl-4,5-dihydro-1,2-oxazol-5-yl | 2.75 [b] |
| I-013 | 7,8-difluoro-2-methylquinolin-3-yl | NH | 0 | — | 3-methyl-4,5-dihydro-1,2-oxazol-5-yl | 3.15 [b] |

TABLE 1-continued

Compounds according to formula (I)

| Example | (Y)p-A(N=)(Q1-)(Z) group | L | n | (X)n | B group | logP |
|---|---|---|---|---|---|---|
| I-014 | 8-fluoroquinolin-3-yl | NH | 0 | — | 3-methyl-4,5-dihydro-1,2-oxazol-5-yl | 2.64 [b] |
| I-015 | quinolin-3-yl | NH | 0 | — | 3-ethyl-4,5-dihydro-1,2-oxazol-5-yl | 2.90 [b] |
| I-016 | 2-methylquinolin-3-yl | NH | 0 | — | 3-ethyl-4,5-dihydro-1,2-oxazol-5-yl | 3.11 [b] |
| I-017 | 7,8-difluoro-2-methylquinolin-3-yl | NH | 0 | — | 3-ethyl-4,5-dihydro-1,2-oxazol-5-yl | 3.50 [b] |
| I-018 | 8-fluoroquinolin-3-yl | NH | 0 | — | 3-ethyl-4,5-dihydro-1,2-oxazol-5-yl | 2.98 [b] |
| I-019 | quinolin-3-yl | NH | 0 | — | 3,5-dimethyl-4H-1,2-oxazol-5-yl | 2.96 [b] |
| I-020 | 8-fluoroquinolin-3-yl | NH | 0 | — | 3,5-dimethyl-4H-1,2-oxazol-5-yl | 3.02 [b] |
| I-021 | 2-methylquinolin-3-yl | NH | 0 | — | 3,5-dimethyl-4H-1,2-oxazol-5-yl | 3.12 [b] |
| I-022 | 7,8-difluoro-2-methylquinolin-3-yl | NH | 0 | — | 3,5-dimethyl-4H-1,2-oxazol-5-yl | 3.65 [b] |
| I-023 | quinolin-3-yl | NH | 0 | — | 3-ethyl-5-methyl-4H-1,2-oxazol-5-yl | 3.33 [b] |
| I-024 | 7,8-difluoro-2-methylquinolin-3-yl | NH | 0 | — | 3-ethyl-5-methyl-4H-1,2-oxazol-5-yl | 4.03 [b] |
| I-025 | quinolin-3-yl | NH | 1 | 3-F | 1-methyl-1H-pyrazol-3-yl | 3.01 [a] |
| I-026 | 2-methylquinolin-3-yl | NH | 1 | 3-F | 1-methyl-1H-pyrazol-3-yl | 2.43 [a] |
| I-027 | quinolin-3-yl | NH | 1 | 3-F | 1-isopropyl-1H-pyrazol-3-yl | 4.05 [a] |
| I-028 | 2-methylquinolin-3-yl | NH | 1 | 3-F | 1-isopropyl-1H-pyrazol-3-yl | 3.09 [a] |
| I-029 | quinolin-3-yl | NH | 1 | 3-F | 1-methyl-1H-pyrazol-5-yl | 2.26 [a] |
| I-030 | 2-methylquinolin-3-yl | NH | 1 | 3-F | 1-methyl-1H-pyrazol-5-yl | 1.79 [a] |
| I-031 | quinolin-3-yl | NH | 1 | 3-F | 1-isopropyl-1H-pyrazol-5-yl | 2.92 [a] |
| I-032 | quinolin-3-yl | NH | 1 | 3-F | 1-tert-butyl-1H-pyrazol-3-yl | 4.57 [a] |
| I-033 | 2-methylquinolin-3-yl | NH | 1 | 3-F | 1-tert-butyl-1H-pyrazol-3-yl | 3.39 [a] |
| I-034 | quinolin-3-yl | NH | 1 | 3-F | 3-methyl-4,5-dihydro-1,2-oxazol-5-yl | 2.84 [b] |
| I-035 | 2-methylquinolin-3-yl | NH | 1 | 3-F | 3-methyl-4,5-dihydro-1,2-oxazol-5-yl | 3.09 [b] |
| I-036 | 7,8-difluoro-2-methylquinolin-3-yl | NH | 1 | 3-F | 3-methyl-4,5-dihydro-1,2-oxazol-5-yl | 3.42 [b] |
| I-037 | quinolin-3-yl | NH | 0 | — | 5,5-dimethyl-4H-1,2-oxazol-3-yl | 3.42 [a] |
| I-038 | 8-fluoro-2-methylquinolin-3-yl | NH | 0 | — | 5,5-dimethyl-4H-1,2-oxazol-3-yl | 4.16 [a] |
| I-039 | 8-fluoroquinolin-3-yl | NH | 0 | — | 5,5-dimethyl-4H-1,2-oxazol-3-yl | 3.92 [a] |
| I-040 | 2-methylquinolin-3-yl | NH | 0 | — | 5,5-dimethyl-4H-1,2-oxazol-3-yl | 2.50 [a] |
| I-041 | 7,8-difluoro-2-methylquinolin-3-yl | NH | 0 | — | 5,5-dimethyl-4H-1,2-oxazol-3-yl | 4.51 [a] |
| I-042 | 7,8-difluoro-2-methylquinolin-3-yl | NH | 1 | 3-F | 3,5-dimethyl-4H-1,2-oxazol-5-yl | 4.23 [a] |
| I-043 | 7,8-difluoro-2-methylquinolin-3-yl | NH | 0 | — | 1-isopropyl-1H-pyrazol-3-yl | 5.00 [a] |
| I-044 | 7,8-difluoro-2-methylquinolin-3-yl | NH | 1 | 3-F | 1-isopropyl-1H-pyrazol-3-yl | 5.14 [a] |
| I-045 | quinolin-3-yl | NH | 0 | — | 2-isopropyl-1,3-thiazol-5-yl | 4.31 [a] |
| I-046 | 7,8-difluoro-2-methylquinolin-3-yl | NCH3 | 0 | — | 1-isopropyl-1H-pyrazol-3-yl | 4.36 [a] |
| I-047 | 7,8-difluoro-2-methylquinolin-3-yl | NCH3 | 1 | 3-F | 1-isopropyl-1H-pyrazol-3-yl | 3.85 [a] |
| I-048 | 7,8-difluoro-2-methylquinolin-3-yl | NH | 0 | — | 1-methyl-1H-pyrazol-3-yl | 4.24 [a] |
| I-049 | 7,8-difluoro-2-methylquinolin-3-yl | NH | 0 | — | 1-tert-butyl-1H-pyrazol-3-yl | 5.39 [a] |
| I-050 | 7,8-difluoro-2-methylquinolin-3-yl | NH | 1 | 3-F | 1-methyl-1H-pyrazol-5-yl | 3.09 [a] |
| I-051 | 7,8-difluoro-2-methylquinolin-3-yl | NH | 1 | 3-F | 1-isopropyl-1H-pyrazol-5-yl | 3.94 [a] |

TABLE 1-continued

Compounds according to formula (I)

| Example | (Y)p-A(N=Z)-Q¹- | L | n | (X)n | B-(W)m | logP |
|---|---|---|---|---|---|---|
| I-052 | 7,8-difluoro-2-methylquinolin-3-yl | NH | 1 | 3-F | 1-methyl-1H-pyrazol-3-yl | 4.44 [a] |
| I-053 | 7,8-difluoro-2-methylquinolin-3-yl | NH | 0 | — | 1-tert-butyl-1H-pyrazol-5-yl | 4.39 [a] |
| I-054 | quinolin-3-yl | NH | 0 | — | 4,5-dimethyl-1,3-thiazol-2-yl | 4.77 [a] |
| I-055 | quinolin-3-yl | NH | 0 | — | 4-isopropyl-1,3-thiazol-2-yl | 5.93 [a] |
| I-056 | quinolin-3-yl | NH | 1 | 3-F | 5,5-dimethyl-4H-1,2-oxazol-3-yl | 3.75 [a] |
| I-057 | 8-fluoro-2-methylquinolin-3-yl | NH | 0 | — | 4-methyl-4,5-dihydro-1,2-oxazol-3-yl | 3.73 [a] |
| I-058 | 7,8-difluoro-2-methylquinolin-3-yl | NH | 0 | — | 4-methyl-4,5-dihydro-1,2-oxazol-3-yl | 4.04 [a] |
| I-059 | quinolin-3-yl | NH | 0 | — | 4-methyl-4,5-dihydro-1,2-oxazol-3-yl | 2.88 [a] |
| I-060 | 7,8-difluoro-2-methylquinolin-3-yl | NH | 1 | 3-F | 5,5-dimethyl-4H-1,2-oxazol-3-yl | 4.80 [a] |
| I-061 | 7,8-difluoro-2,4-dimethylquinolin-3-yl | NH | 1 | 3-F | 1-methyl-1H-pyrazol-5-yl | 3.31 [a] |
| I-062 | quinolin-3-yl | NH | 0 | — | 3-(methoxycarbonyl)-1H-pyrazol-1-yl | 2.16 [a] |
| I-063 | quinolin-3-yl | NH | 0 | — | 5-(2-hydroxypropan-2-yl)-1H-pyrazol-1-yl | 1.79 [a] |
| I-064 | quinolin-3-yl | NH | 0 | — | 5-(methoxycarbonyl)-1H-pyrazol-1-yl | 2.02 [a] |
| I-065 | quinolin-3-yl | CH₂ | 0 | — | 1-methyl-1H-pyrazol-5-yl | 1.77 [a] |
| I-066 | quinolin-3-yl | NH | 0 | — | 5-prop-1-en-2-yl-1H-pyrazol-1-yl | 2.73 [a] |
| I-067 | quinolin-3-yl | CH₂ | 0 | — | 1,3,5-trimethyl-1H-pyrazol-4-yl | 1.94 [a] |
| I-068 | quinolin-3-yl | CH₂ | 0 | — | 1,3-dimethyl-1H-pyrazol-4-yl | 1.82 [a] |
| I-069 | quinolin-3-yl | NH | 0 | — | 5-[[tert-butyl(dimethyl)silyl]oxymethyl]-1H-pyrazol-1-yl | 4.92 [a] |
| I-070 | quinolin-3-yl | NH | 0 | — | 5-isopropyl-1H-pyrazol-1-yl | 2.92 [a] |
| I-071 | quinolin-3-yl | CH₂ | 0 | — | 1-isopropyl-1H-pyrazol-5-yl | 2.41 [a] |
| I-072 | quinolin-3-yl | CH₂ | 0 | — | 1-ethyl-1H-pyrazol-5-yl | 2.07 [a] |
| I-073 | quinolin-3-yl | CH₂ | 0 | — | 1-methyl-1H-imidazol-2-yl | 0.47 [a] |
| I-074 | quinolin-3-yl | CH₂ | 0 | — | 1-ethyl-1H-1,2,4-triazol-5-yl | 1.51 [a] |
| I-075 | quinolin-3-yl | NH | 1 | 3-F | 5-[[tert-butyl(dimethyl)silyl]oxymethyl]-1H-pyrazol-1-yl | 4.93 [a] |
| I-076 | quinolin-3-yl | NH | 1 | 3-F | 5-isopropyl-1H-pyrazol-1-yl | 3.15 [a] |
| I-077 | quinolin-3-yl | NH | 1 | 3-F | 5-(2-hydroxypropan-2-yl)-1H-pyrazol-1-yl | 1.96 [a] |
| I-078 | quinolin-3-yl | NH | 1 | 3-F | 5-(methoxycarbonyl)-1H-pyrazol-1-yl | 2.33 [a] |
| I-079 | quinolin-3-yl | NH | 1 | 3-F | 5-prop-1-en-2-yl-1H-pyrazol-1-yl | 2.95 [a] |
| I-080 | 8-fluoroquinolin-3-yl | NH | 0 | — | 1-ethyl-1H-pyrazol-5-yl | 2.84 [a] |
| I-081 | 8-fluoroquinolin-3-yl | NH | 1 | 3-F | 1-methyl-1H-pyrazol-5-yl | 2.70 [a] |
| I-082 | 7,8-difluoroquinolin-3-yl | NH | 1 | 3-F | 1-methyl-1H-pyrazol-5-yl | 2.92 [a] |
| I-083 | 3-methylquinoxalin-3-yl | NH | 1 | 3-F | 1-methyl-1H-pyrazol-5-yl | 2.82 [a] |
| I-084 | 5,6-difluoro-3-methylquinoxalin-2-yl | NH | 1 | 3-F | 1-methyl-1H-pyrazol-5-yl | 3.14 [a] |
| I-085 | 4-chloroquinolin-3-yl | NH | 1 | 3-F | 1-methyl-1H-pyrazol-5-yl | 3.11 [a] |
| I-086 | 4-methylquinolin-3-yl | NH | 1 | 3-F | 1-methyl-1H-pyrazol-5-yl | 2.04 [a] |
| I-087 | 7,8-difluoro-2-methylquinolin-3-yl | NH | 1 | 3-F | 1-ethyl-1H-pyrazol-5-yl | 3.37 [a] |
| I-088 | 7,8-difluoroquinolin-3-yl | NH | 1 | 3-F | 1-ethyl-1H-pyrazol-5-yl | 3.15 [a] |
| I-089 | 4-chloroquinolin-3-yl | NH | 1 | 3-F | 1-ethyl-1H-pyrazol-5-yl | 3.48 [a] |
| I-090 | 4-methylquinolin-3-yl | NH | 1 | 3-F | 1-ethyl-1H-pyrazol-5-yl | 2.35 [a] |
| I-091 | 3-methylquinoxalin-2-yl | NH | 1 | 3-F | 1-ethyl-1H-pyrazol-5-yl | 3.33 [a] |
| I-092 | 5,6-difluoro-3-methylquinoxalin-2-yl | NH | 1 | 3-F | 1-ethyl-1H-pyrazol-5-yl | 3.67 [a] |
| I-093 | 5,6-difluoroquinoxalin-2-yl | NH | 1 | 3-F | 1-ethyl-1H-pyrazol-5-yl | 3.44 [a] |
| I-094 | pyrazolo[1,5-a]pyrimidin-6-yl | NH | 1 | 3-F | 1-methyl-1H-pyrazol-5-yl | 2.00 [a] |
| I-095 | pyrazolo[1,5-a]pyrimidin-6-yl | NH | 1 | 3-F | 1-ethyl-1H-pyrazol-5-yl | 2.12 [a] |
| I-096 | 8-fluoroquinolin-3-yl | NH | 0 | — | 1-benzyl-1H-pyrazol-5-yl | 3.49 [a] |
| I-097 | 7,8-difluoro-2-methylquinolin-3-yl | NH | 0 | — | 1-benzyl-1H-pyrazol-5-yl | 4.08 [a] |

TABLE 1-continued

Compounds according to formula (I)

| Example | (Y)p–A(N=Z)–Q1– | L | n | (X)n | B–(W)m | logP |
|---|---|---|---|---|---|---|
| I-098 | 7,8-difluoroquinolin-3-yl | NH | 0 | — | 1-benzyl-1H-pyrazol-5-yl | 3.76 [a] |
| I-099 | 8-fluoroquinolin-3-yl | NH | 1 | 3-F | 1-isopropyl-1H-pyrazol-5-yl | 3.29 [a] |
| I-100 | 7,8-difluoroquinolin-3-yl | NH | 1 | 3-F | 1-isopropyl-1H-pyrazol-5-yl | 3.55 [a] |
| I-101 | 4-chloroquinolin-3-yl | NH | 1 | 3-F | 1-isopropyl-1H-pyrazol-5-yl | 3.96 [a] |
| I-102 | 4-methylquinolin-3-yl | NH | 1 | 3-F | 1-isopropyl-1H-pyrazol-5-yl | 2.76 [a] |
| I-103 | 3-methylquinoxalin-2-yl | NH | 1 | 3-F | 1-isopropyl-1H-pyrazol-5-yl | 3.97 [a] |
| I-104 | 5,6-difluoro-3-methylquinoxalin-2-yl | NH | 1 | 3-F | 1-isopropyl-1H-pyrazol-5-yl | 4.21 [a] |
| I-105 | 5,6-difluoroquinoxalin-2-yl | NH | 1 | 3-F | 1-isopropyl-1H-pyrazol-5-yl | 3.85 [a] |
| I-106 | pyrazolo[1,5-a]pyrimidin-6-yl | NH | 1 | 3-F | 1-isopropyl-1H-pyrazol-5-yl | 2.51 [a] |
| I-107 | 7,8-difluoro-2-methylquinolin-3-yl | NH | 1 | 3-F | 1,3-dimethyl-1H-pyrazol-5-yl | 3.23 [a] |
| I-108 | 8-fluoroquinolin-3-yl | NH | 0 | — | 1-phenyl-1H-pyrazol-5-yl | 3.29 [a] |
| I-109 | 7,8-difluoro-2-methylquinolin-3-yl | NH | 2 | 3-F, 6-CH3 | 1-methyl-1H-pyrazol-5-yl | 3.11 [a] |
| I-110 | 7,8-difluoro-2-methylquinolin-3-yl | NH | 3 | 3-F; 4,6-dimethyl | 1-methyl-1H-pyrazol-5-yl | 3.50 [a] |
| I-111 | 7,8-difluoro-2-methylquinolin-3-yl | NH | 2 | 3-F, 6-CH3 | 4-bromo-1-methyl-1H-pyrazol-5-yl | 3.59 [a] |
| I-112 | 7,8-difluoro-2,4-dimethylquinolin-3-yl | NH | 2 | 3-F; 4-CH3 | 4-bromo-1-methyl-1H-pyrazol-5-yl | 4.25 [a] |
| I-113 | 7,8-difluoro-2-methylquinolin-3-yl | NH | 3 | 3-F; 4,6-dimethyl | 1,4-dimethyl-1H-pyrazol-5-yl | 3.59 [a] |
| I-114 | 7,8-difluoro-2,4-dimethylquinolin-3-yl | NH | 2 | 3-F; 4-CH3 | 1-methyl-1H-pyrazol-5-yl | 3.72 [a] |
| I-115 | 7,8-difluoro-2-methylquinolin-3-yl | NH | 3 | 3-F; 4,6-dimethyl | 4-bromo-1-methyl-1H-pyrazol-5-yl | 3.99 [a] |
| I-116 | quinolin-3-yl | CH2 | 0 | — | 1-(tetrahydro-2H-pyran-2-yl)-1H-pyrazol-5-yl | 2.37 [a] |
| I-117 | 4-methylquinolin-3-yl | NH | 2 | 3,4-difluoro | 1-methyl-1H-pyrazol-5-yl | 1.95 [a] |
| I-118 | 5,6-difluoroquinoxalin-2-yl | NH | 1 | 3-F | 1-(2-phenylethyl)-1H-pyrazol-5-yl | 4.41 [a] |
| I-119 | 4-methylquinolin-3-yl | NH | 1 | 3-F | 1-(2-phenylethyl)-1H-pyrazol-5-yl | 3.29 [a] |
| I-120 | imidazo[1,2-a]pyrimidin-6-yl | NH | 1 | 3-F | 1-(2-phenylethyl)-1H-pyrazol-5-yl | 1.79 [a] |
| I-121 | 7,8-difluoroquinolin-3-yl | NH | 1 | 3-F | 1-(2-phenylethyl)-1H-pyrazol-5-yl | 4.08 [a] |
| I-122 | 7,8-difluoro-2-methylquinolin-3-yl | NH | 1 | 3-F | 1-(2-phenylethyl)-1H-pyrazol-5-yl | 4.34 [a] |
| I-123 | pyrazolo[1,5-a]pyrimidin-6-yl | NH | 1 | 3-F | 1-(2-phenylethyl)-1H-pyrazol-5-yl | 3.09 [a] |
| I-124 | 8-fluoroquinolin-3-yl | NH | 1 | 3-F | 1-(2-phenylethyl)-1H-pyrazol-5-yl | 3.29 [a] |
| I-125 | quinolin-3-yl | CH2 | 0 | — | 1-benzyl-1H-pyrazol-5-yl | 2.75 [a] |
| I-126 | quinolin-3-yl | CH2 | 0 | — | 1H-pyrazol-3-yl | 1.53 [a] |
| I-127 | 7,8-difluoroquinolin-3-yl | NH | 0 | — | 1-isopropyl-1H-pyrazol-5-yl | 3.30 [a] |
| I-128 | 8-fluoroquinolin-3-yl | NH | 0 | — | 1-isopropyl-1H-pyrazol-5-yl | 3.01 [a] |
| I-129 | 7,8-difluoro-2-methylquinolin-3-yl | NH | 0 | — | 1-isopropyl-1H-pyrazol-5-yl | 3.58 [a] |
| I-130 | 5,6-difluoro-3-methylquinoxalin-2-yl | NH | 2 | 3-F; 4-CH3 | 1-methyl-1H-pyrazol-5-yl | 3.37 [a] |
| I-131 | 5,6-difluoro-3-methylquinoxalin-2-yl | NH | 3 | 3-F; 4,6-dimethyl | 4-bromo-1-methyl-1H-pyrazol-5-yl | 3.74 [a] |
| I-132 | 5,6-difluoro-3-methylquinoxalin-2-yl | NH | 2 | 3-F; 4-CH3 | 4-bromo-1-methyl-1H-pyrazol-5-yl | 3.74 [a] |
| I-133 | 5,6-difluoro-3,8-dimethylquinoxalin-2-yl | NH | 3 | 3-F; 4,6-dimethyl | 4-bromo-1-methyl-1H-pyrazol-5-yl | 4.67 [a] |
| I-134 | 5,6-difluoro-3-methylquinoxalin-2-yl | NH | 3 | 3-F; 4,6-dimethyl | 1-methyl-1H-pyrazol-5-yl | 3.21 [a] |
| I-135 | 5,6-difluoroquinoxalin-2-yl | NH | 1 | 4-F | 1-ethyl-1H-pyrazol-5-yl | 3.27 [a] |
| I-136 | 5,6-difluoroquinoxalin-2-yl | NH | 0 | — | 1-(2-phenylethyl)-1H-pyrazol-5-yl | 4.27 [a] |

TABLE 1-continued

Compounds according to formula (I)

| Example | (Y)p-A(N=Z)-Q1- | L | n | (X)n | B-(W)m | logP |
|---|---|---|---|---|---|---|
| I-137 | pyrazolo[1,5-a]pyrimidin-6-yl | NH | 1 | 4-F | 1-methyl-1H-pyrazol-5-yl | 1.95 [a] |
| I-138 | pyrazolo[1,5-a]pyrimidin-6-yl | NH | 0 | — | 1-(2-phenylethyl)-1H-pyrazol-5-yl | 3.02 [a] |
| I-139 | pyrazolo[1,5-a]pyrimidin-6-yl | NH | 0 | — | 1-ethyl-1H-pyrazol-5-yl | 2.10 [a] |
| I-140 | pyrazolo[1,5-a]pyrimidin-6-yl | NH | 0 | — | 1-methyl-1H-pyrazol-5-yl | 1.88 [a] |
| I-141 | pyrazolo[1,5-a]pyrimidin-6-yl | NH | 1 | 4-F | 1-(2-phenylethyl)-1H-pyrazol-5-yl | 3.02 [a] |
| I-142 | pyrazolo[1,5-a]pyrimidin-6-yl | NH | 1 | 4-F | 1-ethyl-1H-pyrazol-5-yl | 2.17 [a] |
| I-143 | 8-fluoroquinolin-3-yl | NH | 1 | 4-F | 1-methyl-1H-pyrazol-5-yl | 2.64 [a] |
| I-144 | 7,8-difluoro-2-methylquinolin-3-yl | NH | 1 | 4-F | 1-ethyl-1H-pyrazol-5-yl | 3.27 [a] |
| I-145 | 7,8-difluoro-2-methylquinolin-3-yl | NH | 1 | 4-F | 1-(2-phenylethyl)-1H-pyrazol-5-yl | 4.20 [a] |
| I-146 | 7,8-difluoro-2-methylquinolin-3-yl | NH | 0 | — | 1-(2-phenethyl)-1H-pyrazol-5-yl | 4.27 [a] |
| I-147 | 7,8-difluoro-2-methylquinolin-3-yl | NH | 1 | 4-F | 1-methyl-1H-pyrazol-5-yl | 2.96 [a] |
| I-148 | 7,8-difluoro-2-methylquinolin-3-yl | NH | 0 | — | 1-methyl-1H-pyrazol-5-yl | 2.92 [a] |
| I-149 | 7,8-difluoro-2-methylquinolin-3-yl | NH | 0 | — | 1-ethyl-1H-pyrazol-5-yl | 3.27 [a] |
| I-150 | 8-fluoroquinolin-3-yl | NH | 1 | 4-F | 1-ethyl-1H-pyrazol-5-yl | 2.90 [a] |
| I-151 | 7,8-difluoroquinolin-3-yl | NH | 0 | — | 1-ethyl-1H-pyrazol-5-yl | 3.09 [a] |
| I-152 | 7,8-difluoroquinolin-3-yl | NH | 0 | — | 1-methyl-1H-pyrazol-5-yl | 2.80 [a] |
| I-153 | 7,8-difluoroquinolin-3-yl | NH | 1 | 4-F | 1-methyl-1H-pyrazol-5-yl | 2.86 [a] |
| I-154 | 7,8-difluoroquinolin-3-yl | NH | 0 | — | 1-(2-phenylethyl)-1H-pyrazol-5-yl | 4.03 [a] |
| I-155 | 4-methylquinolin-3-yl | NH | 0 | — | 1-ethyl-1H-pyrazol-5-yl | 1.95 [a] |
| I-156 | 4-methylquinolin-3-yl | NH | 0 | — | 1-methyl-1H-pyrazol-5-yl | 1.69 [a] |
| I-157 | 4-methylquinolin-3-yl | NH | 1 | 4-F | 1-methyl-1H-pyrazol-5-yl | 1.72 [a] |
| I-158 | 3-methylquinoxalin-2-yl | NH | 0 | — | 1-methyl-1H-pyrazol-5-yl | 2.57 [a] |
| I-159 | 3-methylquinoxalin-2-yl | NH | 0 | — | 1-ethyl-1H-pyrazol-5-yl | 3.06 [a] |
| I-160 | 3-methylquinoxalin-2-yl | NH | 1 | 4-F | 1-ethyl-1H-pyrazol-5-yl | 3.08 [a] |
| I-161 | 3-methylquinoxalin-2-yl | NH | 1 | 4-F | 1-(2-phenylethyl)-1H-pyrazol-5-yl | 4.20 [a] |
| I-162 | 8-fluoroquinolin-3-yl | NH | 0 | — | 1-methyl-1H-pyrazol-5-yl | 2.55 [a] |
| I-163 | 7,8-difluoroquinolin-3-yl | NH | 1 | 4-F | 1-ethyl-1H-pyrazol-5-yl | 3.17 [a] |
| I-164 | 4-chloroquinolin-3-yl | NH | 0 | — | 1-ethyl-1H-pyrazol-5-yl | 3.27 [a] |
| I-165 | 4-chloroquinolin-3-yl | NH | 0 | — | 1-methyl-1H-pyrazol-5-yl | 2.86 [a] |
| I-166 | 4-chloroquinolin-3-yl | NH | 1 | 4-F | 1-methyl-1H-pyrazol-5-yl | 2.90 [a] |
| I-167 | 4-chloroquinolin-3-yl | NH | 0 | — | 1-(2-phenylethyl)-1H-pyrazol-5-yl | 4.39 [a] |
| I-168 | 4-chloroquinolin-3-yl | NH | 1 | 4-F | 1-(2-phenylethyl)-1H-pyrazol-5-yl | 4.30 [a] |
| I-169 | 4-chloroquinolin-3-yl | NH | 1 | 4-F | 1-ethyl-1H-pyrazol-5-yl | 3.27 [a] |
| I-170 | 4-methylquinolin-3-yl | NH | 1 | 4-F | 1-ethyl-1H-pyrazol-5-yl | 1.98 [a] |
| I-171 | 3-methylquinoxalin-2-yl | NH | 0 | — | 1-(2-phenylethyl)-1H-pyrazol-5-yl | 4.25 [a] |
| I-172 | 5,6-difluoro-3-methylquinoxalin-2-yl | NH | 0 | — | 1-(2-phenylethyl)-1H-pyrazol-5-yl | 4.56 [a] |
| I-173 | 5,6-difluoro-3-methylquinoxalin-2-yl | NH | 1 | 4-F | 1-(2-phenylethyl)-1H-pyrazol-5-yl | 4.49 [a] |
| I-174 | 5,6-difluoroquinoxalin-2-yl | NH | 0 | — | 1-methyl-1H-pyrazol-5-yl | 2.84 [a] |
| I-175 | 5,6-difluoroquinoxalin-2-yl | NH | 0 | — | 1-ethyl-1H-pyrazol-5-yl | 3.21 [a] |
| I-176 | 3-methylquinoxalin-2-yl | NH | 2 | 3-F, 6-CH3 | 1-methyl-1H-pyrazol-5-yl | 2.43 [a] |
| I-177 | 3-methylquinoxalin-2-yl | NH | 2 | 3-F; 4-CH3 | 4-bromo-1-methyl-1H-pyrazol-5-yl | 3.50 [a] |
| I-178 | 3-methylquinoxalin-2-yl | NH | 2 | 3-F; 4-CH3 | 1-methyl-1H-pyrazol-5-y | 3.09 [a] |
| I-179 | quinolin-3-yl | CH2 | 0 | — | 1-[(4-fluorophenyl)methyl]-1H-pyrazol-5-yl | 2.86 [a] |
| I-180 | 5,6-difluoro-3-methylquinoxalin-2-yl | NH | 0 | — | 1-methyl-1H-pyrazol-5-yl | 3.00 [a] |
| I-181 | 5,6-difluoro-3-methylquinoxalin-2-yl | NH | 1 | 4-F | 1-methyl-1H-pyrazol-5-yl | 3.00 [a] |
| I-182 | 8-fluoroquinolin-3-yl | NH | 1 | 4-F | 1-(2-phenylethyl)-1H-pyrazol-5-yl | 3.76 [a] |

TABLE 1-continued

Compounds according to formula (I)

| Example | (Y)p–A(Q¹)(N=Z) | L | n | (X)n | B(W)m | logP |
|---|---|---|---|---|---|---|
| I-183 | 7,8-difluoroquinolin-3-yl | NH | 1 | 4-F | 1-(2-phenylethyl)-1H-pyrazol-5-yl | 3.97 [a] |
| I-184 | 8-fluoroquinolin-3-yl | NH | 0 | — | 1-(2-phenylethyl)-1H-pyrazol-5-yl | 3.81 [a] |
| I-185 | 3-methylquinoxalin-2-yl | NH | 1 | 4-F | 1-methyl-1H-pyrazol-5-yl | 2.56 [a] |
| I-186 | 4-methylquinolin-3-yl | NH | 1 | 4-F | 1-(2-phenylethyl)-1H-pyrazol-5-yl | 2.76 [a] |
| I-187 | 4-methylquinolin-3-yl | NH | 0 | — | 1-(2-phenylethyl)-1H-pyrazol-5-yl | 2.85 [a] |
| I-188 | 5,6-difluoroquinoxalin-2-yl | NH | 1 | 4-F | 1-(2-phenylethyl)-1H-pyrazol-5-yl | 4.18 [a] |
| I-189 | 5,6-difluoroquinoxalin-2-yl | NH | 1 | 4-F | 1-methyl-1H-pyrazol-5-yl | 2.82 [a] |
| I-190 | 5,6-difluoro-3-methylquinoxalin-2-yl | NH | 1 | 4-F | 1-ethyl-1H-pyrazol-5-yl | 3.40 [a] |
| I-191 | 5,6-difluoro-3-methylquinoxalin-2-yl | NH | 0 | — | 1-ethyl-1H-pyrazol-5-yl | 3.42 [a] |
| I-192 | 3-methylquinoxalin-2-yl | NH | 1 | 3-F | 1,4-dimethyl-1H-pyrazol-5-yl | 3.02 [a] |
| I-193 | 3-methylquinoxlin-2-yl | NH | 2 | 3-F; 4-CH3 | 1,4-dimethyl-1H-pyrazol-5-yl | 3.33 [a] |
| I-194 | 7,8-difluoro-2,4-dimethylquinolin-3-yl | NH | 1 | 3-F | 1,4-dimethyl-1H-pyrazol-5-yl | 2.86 [a] |
| I-195 | 7,8-difluoro-4-methylquinolin-3-yl | NH | 1 | 3-F | 1-methyl-1H-pyrazol-5-yl | 3.11 [a] |
| I-196 | 4-methylquinolin-3-yl | NH | 3 | 3-F; 4,6-dimethyl | 1-methyl-1H-pyrazol-5-yl | 1.75 [a] |
| I-197 | 4-methylquinolin-3-yl | NH | 2 | 3-F; 4-CH3 | 1-methyl-1H-pyrazol-5-yl | 2.15 [a] |
| I-198 | 4-methylquinolin-3-yl | NH | 2 | 3-F; 4-CH3 | 1,4-dimethyl-1H-pyrazol-5-yl | 2.40 [a] |
| I-199 | quinolin-3-yl | CH2 | 0 | — | 4-carboxy-1,3-thiazol-5-yl | 1.37 [a] |
| I-200 | 4-(difluoromethyl)quinolin-3-yl | CH2 | 0 | — | 1-methyl-1H-pyrazol-5-yl | 2.92 [a] |
| I-201 | 2-(difluoromethyl)quinolin-3-yl | CH2 | 0 | — | 1-methyl-1H-pyrazol-5-yl | 3.33 [a] |
| I-202 | quinolin-3-yl | CH2 | 0 | — | 1-[(4-fluorophenyl)methyl]-1H-pyrazol-3-yl | 2.86 [a] |
| I-203 | quinolin-3-yl | CH2 | 0 | — | 3-isopropyl-1H-pyrazol-1-yl | 2.43 [a] |
| I-204 | quinolin-3-yl | CH2 | 0 | — | 1-tert-butyl-1H-pyrazol-5-yl | 2.77 [a] |
| I-205 | quinolin-3-yl | CH2 | 0 | — | 1-tert-butyl-1H-pyrazol-3-yl | 2.82 [a] |
| I-206 | 8-fluoroquinolin-3-yl | NH | 2 | 3-F; 4-CH3 | 1-methyl-1H-pyrazol-5-yl | 2.99 [a] |
| I-207 | 8-fluoro-4-methylquinolin-3-yl | NH | 1 | 3-F | 1-methyl-1H-pyrazol-5-yl | 2.80 [a] |
| I-208 | 8-fluoro-4-methylquinolin-3-yl | NH | 1 | 3-F | 1,4-dimethyl-1H-pyrazol-5-yl | 3.06 [a] |
| I-209 | 8-fluoro-4-methylquinolin-3-yl | NH | 2 | 3-F; 4-CH3 | 1-methyl-1H-pyrazol-5-yl | 3.17 [a] |
| I-210 | pyrazolo[1,5-a]pyrimidin-6-yl | NH | 1 | 4-CH3 | 1-methyl-1H-pyrazol-5-yl | 2.15 [a] |
| I-211 | pyrazolo[1,5-a]pyrimidin-6-yl | NH | 1 | 4-Cl | 1-methyl-1H-pyrazol-5-yl | 2.34 [a] |
| I-212 | 4-chloroquinolin-3-yl | NH | 1 | 4-CH3 | 1-methyl-1H-pyrazol-5-yl | 3.24 [a] |
| I-213 | 5,6-difluoro-3-methylquinoxalin-2-yl | NH | 1 | 4-CH3 | 1-methyl-1H-pyrazol-5-yl | 3.35 [a] |
| I-214 | 5,6-difluoro-3-methylquinoxalin-2-yl | NH | 1 | 4-Cl | 1-methyl-1H-pyrazol-5-yl | 3.69 [a] |
| I-215 | 8-methylquinolin-3-yl | NH | 1 | 4-CH3 | 1-methyl-1H-pyrazol-5-yl | 2.62 [a] |
| I-216 | 4-methylquinolin-3-yl | NH | 1 | 4-CH3 | 1-methyl-1H-pyrazol-5-yl | 1.86 [a] |
| I-217 | 4-methylquinolin-3-yl | NH | 1 | 4-Cl | 1-methyl-1H-pyrazol-5-yl | 2.30 [a] |
| I-218 | 5,6-difluoroquinoxalin-2-yl | NH | 1 | 4-CH3 | 1-methyl-1H-pyrazol-5-yl | 3.23 [a] |
| I-219 | 4-chloroquinolin-3-yl | NH | 1 | 4-Cl | 1-methyl-1H-pyrazol-5-yl | 3.51 [a] |
| I-220 | 5,6-difluoroquinoxalin-2-yl | NH | 1 | 4-Cl | 1-methyl-1H-pyrazol-5-yl | 3.58 [a] |
| I-221 | 8-(trifluoromethyl)quinolin-3-yl | NH | 1 | 4-CH3 | 1-methyl-1H-pyrazol-5-yl | 3.87 [a] |
| I-222 | 8-(trifluoromethyl)quinolin-3-yl | NH | 1 | 4-Cl | 1-methyl-1H-pyrazol-5-yl | 4.03 [a] |
| I-223 | 3-methylquinoxalin-2-yl | NH | 1 | 4-CH3 | 1-methyl-1H-pyrazol-5-yl | 2.92 [a] |
| I-224 | 3-methylquinoxalin-2-yl | NH | 1 | 4-Cl | 1-methyl-1H-pyrazol-5-yl | 3.31 [a] |
| I-225 | 8-methylquinolin-3-yl | NH | 1 | 4-Cl | 1-methyl-1H-pyrazol-5-yl | 3.13 [a] |
| I-226 | 8-fluoroquinolin-3-yl | NH | 1 | 4-Cl | 1-methyl-1H-pyrazol-5-yl | 3.13 [a] |
| I-227 | 7,8-difluoroquinolin-3-yl | NH | 1 | 4-CH3 | 1-methyl-1H-pyrazol-5-yl | 3.21 [a] |
| I-228 | 7,8-difluoroquinolin-3-yl | NH | 1 | 4-Cl | 1-methyl-1H-pyrazol-5-yl | 3.37 [a] |

TABLE 1-continued

Compounds according to formula (I)

| Example | (Y)p–A(–N=)–Q¹–Z | L | n | (X)n | B (W)m | logP |
|---|---|---|---|---|---|---|
| I-229 | 7,8-difluoro-2-methylquinolin-3-yl | NH | 1 | 4-CH₃ | 1-methyl-1H-pyrazol-5-yl | 3.33 [a] |
| I-230 | 7,8-difluoro-2-methylquinolin-3-yl | NH | 1 | 4-Cl | 1-methyl-1H-pyrazol-5-yl | 3.51 [a] |
| I-231 | 8-fluoroquinolin-3-yl | NH | 1 | 4-CH₃ | 1-methyl-1H-pyrazol-5-yl | 2.92 [a] |
| I-232 | 5,6-difluoro-3-methylquinoxalin-2-yl | NH | 2 | 3,4-difluoro | 1-methyl-1H-pyrazol-5-yl | 3.46 [a] |
| I-233 | 7,8-difluoro-2-methylquinolin-3-yl | NH | 1 | 4-OCF₃ | 1-methyl-1H-pyrazol-5-yl | 3.61 [a] |
| I-234 | 7,8-difluoro-2-methylquinolin-3-yl | NH | 2 | 3,4-difluoro | 1-methyl-1H-pyrazol-5-yl | 3.27 [a] |
| I-235 | 5,6-difluoro-3-methylquinoxalin-2-yl | NH | 1 | 4-OCF₃ | 1-methyl-1H-pyrazol-5-yl | 3.96 [a] |
| I-236 | 8-fluoroquinolin-3-yl | NH | 2 | 3,4-difluoro | 1-methyl-1H-pyrazol-5-yl | 2.74 [a] |
| I-237 | 4-chloroquinolin-3-yl | NH | 2 | 3,4-difluoro | 1-methyl-1H-pyrazol-5-yl | 3.05 [a] |
| I-238 | 7,8-difluoroquinolin-3-yl | NH | 2 | 3,4-difluoro | 1-methyl-1H-pyrazol-5-yl | 3.01 [a] |
| I-239 | pyrazolo[1,5-a]pyrimidin-6-yl | NH | 2 | 3,4-difluoro | 1-methyl-1H-pyrazol-5-yl | 2.11 [a] |
| I-240 | 8-methylquinolin-3-yl | NH | 2 | 3,4-difluoro | 1-methyl-1H-pyrazol-5-yl | 2.87 [a] |
| I-241 | 8-(trifluoromethyl)quinolin-3-yl | NH | 2 | 3,4-difluoro | 1-methyl-1H-pyrazol-5-yl | 3.54 [a] |
| I-242 | 8-fluoroquinolin-3-yl | NH | 2 | 3,4-difluoro | 1-ethyl-1H-pyrazol-5-yl | 2.98 [a] |
| I-243 | 7,8-difluoro-2-methylquinolin-3-yl | NH | 2 | 3,4-difluoro | 1-ethyl-1H-pyrazol-5-yl | 3.39 [a] |
| I-244 | quinolin-3-yl | NH | 1 | 4-F | 1-methyl-1H-imidazol-5-yl | 1.11 [a] |
| I-245 | 7,8-difluoroquinolin-3-yl | NH | 2 | 3,4-difluoro | 1-ethyl-1H-pyrazol-5-yl | 3.28 [a] |
| I-246 | 4-chloroquinolin-3-yl | NH | 2 | 3,4-difluoro | 1-ethyl-1H-pyrazol-5-yl | 3.39 [a] |
| I-247 | 3-methylquinoxalin-2-yl | NH | 2 | 3,4-difluoro | 1-ethyl-1H-pyrazol-5-yl | 3.33 [a] |
| I-248 | 8-methylquinolin-3-yl | NH | 1 | 4-F | 1-methyl-1H-imidazol-5-yl | 1.51 [a] |
| I-249 | 8-(trifluoromethyl)quinolin-3-yl | NH | 1 | 4-F | 1-methyl-1H-imidazol-5-yl | 1.96 [a] |
| I-250 | 5,6-difluoroquinoxalin-2-yl | NH | 2 | 3,4-difluoro | 1-ethyl-1H-pyrazol-5-yl | 3.79 [a] |
| I-251 | 5,6-difluoro-3-methylquinoxalin-2-yl | NH | 2 | 3,4-difluoro | 1-ethyl-1H-pyrazol-5-yl | 3.92 [a] |
| I-252 | 8-fluoroquinolin-3-yl | CH₂ | 1 | 4-F | 1-methyl-1H-pyrazol-5-yl | 2.70 [a] |
| I-253 | 8-fluoroquinolin-3-yl | NH | 1 | 4-OCF₃ | 1-methyl-1H-pyrazol-5-yl | 3.37 [a] |
| I-254 | 3-methylquinoxalin-2-yl | NH | 1 | 4-OCF₃ | 1-methyl-1H-pyrazol-5-yl | 3.63 [a] |
| I-255 | 7,8-difluoroquinolin-3-yl | NH | 1 | 4-OCF₃ | 1-methyl-1H-pyrazol-5-yl | 3.62 [a] |
| I-256 | 4-chloroquinolin-3-yl | NH | 1 | 4-OCF₃ | 1-methyl-1H-pyrazol-5-yl | 3.83 [a] |
| I-257 | 4-methylquinolin-3-yl | NH | 1 | 4-OCF₃ | 1-methyl-1H-pyrazol-5-yl | 2.68 [a] |
| I-258 | 5,6-difluoroquinoxalin-2-yl | NH | 1 | 4-OCF₃ | 1-methyl-1H-pyrazol-5-yl | 3.80 [a] |
| I-259 | pyrazolo[1,5-a]pyrimidin-6-yl | NH | 1 | 4-OCF₃ | 1-methyl-1H-pyrazol-5-yl | 2.66 [a] |
| I-260 | 4-methylquinolin-3-yl | NH | 3 | 3,4,6-trifluoro | 1-ethyl-1H-pyrazol-5-yl | 1.98 [a] |
| I-261 | 4-methylquinolin-3-yl | NH | 2 | 3,4-difluoro | 1-ethyl-1H-pyrazol-5-yl | 2.39 [a] |

TABLE 1-continued

Compounds according to formula (I)

| Example | A (Y)p Q¹ / N Z | L | n | (X)n | B (W)m | logP |
|---|---|---|---|---|---|---|
| I-262 | 4-methylquinolin-3-yl | NH | 2 | 3,6-difluoro | 1-ethyl-1H-pyrazol-5-yl | 1.88 [a] |
| I-263 | 4-methylquinolin-3-yl | NH | 2 | 3,6-difluoro | 1-ethyl-4-fluoro-1H-pyrazol-5-yl | 2.25 [a] |
| I-264 | 4,7,8-trifluoroquinolin-3-yl | NH | 2 | 3,6-difluoro | 1-ethyl-1H-pyrazol-5-yl | 3.19 [a] |
| I-265 | 7,8-difluoroquinolin-3-yl | NH | 2 | 3,6-difluoro | 1-ethyl-1H-pyrazol-5-yl | 2.98 [a] |
| I-266 | 7,8-difluoro-4-oxo-1,4-dihydroquinolin-3-yl | NH | 1 | 3-F | 1-ethyl-1H-pyrazol-5-yl | 2.37 [a] |
| I-267 | 7,8-difluoro-4-oxo-1,4-dihydroquinolin-3-yl | NH | 2 | 3,6-difluoro | 1-ethyl-1H-pyrazol-5-yl | 2.20 [a] |
| I-268 | 4,7,8-trifluoroquinolin-3-yl | NH | 2 | 3,4-difluoro | 1-ethyl-1H-pyrazol-5-yl | 3.49 [a] |
| I-269 | 7,8-difluoro-4-oxo-1,4-dihydroquinolin-3-yl | NH | 2 | 3,4-difluoro | 1-ethyl-1H-pyrazol-5-yl | 2.49 [a] |
| I-270 | 7,8-difluoro-4-oxo-1,4-dihydroquinolin-3-yl | NH | 1 | 3-F | 1-methyl-1H-pyrazol-5-yl | 2.16 [a] |
| I-271 | 7,8-difluoroquinolin-3-yl | NH | 2 | 3,6-difluoro | 1-methyl-1H-pyrazol-5-yl | 2.71 [a] |
| I-272 | 7,8-difluoro-4-oxo-1,4-dihydroquinolin-3-yl | NH | 2 | 3,6-difluoro | 1-methyl-1H-pyrazol-5-yl | 2.00 [a] |
| I-273 | 4,7,8-trifluoroquinolin-3-yl | NH | 2 | 3,4-difluoro | 1-methyl-1H-pyrazol-5-yl | 3.11 [a] |
| I-274 | 7,8-difluoro-4-oxo-1,4-dihydroquinolin-3-yl | NH | 2 | 3,4-difluoro | 1-methyl-1H-pyrazol-5-yl | 2.23 [a] |
| I-275 | 4,7,8-trifluoroquinolin-3-yl | NH | 1 | 3-F | 1-methyl-1H-pyrazol-5-yl | 3.08 [a] |
| I-277 | 7,8-difluoro-2-methylquinolin-3-yl | CH₂ | 0 | — | 1-ethyl-1H-pyrazol-5-yl | 3.33 [a] |
| I-279 | 7,8-difluoro-2-methylquinolin-3-yl | NH | 1 | 4-F | 1-tert-butyl-1H-pyrazol-5-yl | 4.25 [a] |
| I-281 | 7,8-difluoro-2-methylquinolin-3-yl | NH | 1 | 4-F | 1-(2,2,2-trifluoroethyl)-1H-pyrazol-5-yl | 4.49 [a] |
| I-282 | 7,8-difluoro-2-methylquinolin-3-yl | NH | 1 | 3-F | 1-methyl-4-(trifluoromethyl)-1H-pyrazol-5-yl | 3.76 [a] |
| I-284 | 7,8-difluoro-2-methylquinolin-3-yl | NH | 1 | 3-F | 1,3,5-trimethyl-1H-pyrazol-4-yl | 3.19 [a] |
| I-285 | 7,8-difluoro-2-methylquinolin-3-yl | NH | 1 | 3-F | 1-(2,2,2-trifluoroethyl)-1H-pyrazol-5-yl | 4.58 [a] |
| I-287 | 7,8-difluoro-2-methylquinolin-3-yl | NH | 1 | 3-F | 1,4-dimethyl-1H-pyrazol-5-yl | 3.23 [a] |
| I-288 | 7,8-difluoro-2-methylquinolin-3-yl | CH₂ | 0 | — | 1-benzyl-1H-pyrazol-5-yl | 4.13 [a] |
| I-289 | 7,8-difluoro-2-methylquinolin-3-yl | CH₂ | 0 | — | 1-(2-methylpropyl)-1H-pyrazol-5-yl | 4.11 [a] |
| I-290 | 7,8-difluoro-2-methylquinolin-3-yl | CH₂ | 0 | — | 1-methyl-1H-pyrazol-5-yl | 3.00 [a] |
| I-291 | 7,8-difluoro-2-methylquinolin-3-yl | NH | 1 | 4-F | 1-isopropyl-1H-pyrazol-5-yl | 3.59 [a] |
| I-292 | 7,8-difluoro-2-methylquinolin-3-yl | CH₂ | 0 | — | 1,4-dimethyl-1H-pyrazol-5-yl | 3.21 [a] |
| I-293 | 7,8-difluoro-2-methylquinolin-3-yl | CH₂ | 0 | — | 1-propyl-1H-pyrazol-5-yl | 3.72 [a] |
| I-294 | 7,8-difluoro-2-methylquinolin-3-yl | CH₂ | 0 | — | 4-chloro-1-methyl-1H-pyrazol-5-yl | 3.55 [a] |
| I-295 | 7,8-difluoro-2-methylquinolin-3-yl | NH | 1 | 4-F | 1-isopropyl-3-(trifluoromethyl)-1H-pyrazol-5-yl | 4.53 [a] |

TABLE 1-continued

Compounds according to formula (I)

| Example | (Y)p-A(Q1)(N=Z) | L | n | (X)n | B(W)m | logP |
|---|---|---|---|---|---|---|
| I-296 | 7,8-difluoro-2-methylquinolin-3-yl | NH | 1 | 4-F | 1-cyclopropyl-1H-pyrazol-5-yl | 3.41 [a] |
| I-297 | 7,8-difluoro-2-methylquinolin-3-yl | NH | 1 | 4-F | 1,4-dimethyl-1H-pyrazol-5-yl | 3.13 [a] |
| I-298 | 7,8-difluoro-2-methylquinolin-3-yl | NH | 1 | 4-F | 1,3-dimethyl-1H-pyrazol-5-yl | 3.11 [a] |
| I-299 | 7,8-difluoro-2-methylquinolin-3-yl | NH | 1 | 3-F | 1-benzyl-1H-pyrazol-5-yl | 4.03 [a] |
| I-300 | 7,8-difluoro-2-methylquinolin-3-yl | NH | 1 | 4-F | 1-methyl-3-(trifluoromethyl)-1H-pyrazol-5-yl | 3.83 [a] |
| I-301 | 7,8-difluoro-2-methylquinolin-3-yl | NH | 1 | 4-F | 1-propyl-1H-pyrazol-5-yl | 3.59 [a] |
| I-302 | 7,8-difluoro-2-methylquinolin-3-yl | NH | 1 | 3-F | 1-cyclopropyl-1H-pyrazol-5-yl | 3.50 [a] |
| I-303 | 7,8-difluoro-2-methylquinolin-3-yl | NH | 1 | 3-F | 1-methyl-3-(trifluoromethyl)-1H-pyrazol-5-yl | 3.94 [a] |
| I-304 | 7,8-difluoro-2-methylquinolin-3-yl | NH | 1 | 3-F | 4-chloro-1-methyl-1H-pyrazol-5-yl | 3.46 [a] |
| I-305 | 7,8-difluoro-2-methylquinolin-3-yl | NH | 1 | 3-F | 1-isopropyl-3-(trifluoromethyl)-1H-pyrazol-5-yl | 4.76 [a] |
| I-306 | 7,8-difluoro-2-methylquinolin-3-yl | NH | 1 | 3-F | 1-(2-methylpropyl)-1H-pyrazol-5-yl | 4.06 [a] |
| I-307 | 7,8-difluoro-2-methylquinolin-3-yl | CH2 | 0 | — | 1-tert-butyl-1H-pyrazol-5-yl | 4.20 [a] |
| I-308 | 7,8-difluoro-2-methylquinolin-3-yl | NH | 1 | 4-F | 1-methyl-4-(trifluoromethyl)-1H-pyrazol-5-yl | 3.72 [a] |
| I-309 | 4,7,8-trifluoroquinolin-3-yl | NH | 2 | 3,6-difluoro | 1-methyl-1H-pyrazol-5-yl | 2.86 [a] |
| I-310 | 3-methylquinoxalin-2-yl | NH | 2 | 3,6-difluoro | 1-ethyl-1H-pyrazol-5-yl | 2.61 [a] |
| I-311 | 3-methylquinoxalin-2-yl | NH | 2 | 3,6-difluoro | 1-ethyl-4-fluoro-1H-pyrazol-5-yl | 2.88 [a] |
| I-312 | 3-methylquinoxalin-2-yl | NH | 1 | 3-F | 1-ethyl-4-fluoro-1H-pyrazol-5-yl | 3.29 [a] |
| I-313 | 3-(fluoromethyl)quinoxalin-2-yl | NH | 2 | 3,6-difluoro | 1-ethyl-1H-pyrazol-5-yl | 2.96 [a] |
| I-314 | 3-methylquinoxalin-2-yl | NH | 3 | 3,4,6-trifluoro | 1-ethyl-4-fluoro-1H-pyrazol-5-yl | 3.15 [a] |
| I-315 | 4-chloroquinolin-3-yl | NH | 2 | 3,6-difluoro | 1-ethyl-1H-pyrazol-5-yl | 3.17 [a] |
| I-316 | 4-chloroquinolin-3-yl | NH | 2 | 3,4-difluoro | 4-chloro-1-ethyl-1H-pyrazol-5-yl | 4.08 [a] |
| I-317 | 4-chloroquinolin-3-yl | NH | 3 | 3,4,6-trifluoro | 1-ethyl-1H-pyrazol-5-yl | 3.25 [a] |
| I-318 | 4-chloroquinolin-3-yl | NH | 2 | 3,6-difluoro | 1-ethyl-4-fluoro-1H-pyrazol-5-yl | 3.39 [a] |
| I-319 | 3-methylquinoxalin-2-yl | NH | 2 | 3,4-difluoro | 1-ethyl-4-fluoro-1H-pyrazol-5-yl | 3.31 [a] |
| I-320 | 7,8-difluoro-2-methylquinolin-3-yl | CH2 | 0 | — | 1,3-dimethyl-1H-pyrazol-5-yl | 3.19 [a] |
| I-321 | 7,8-difluoro-2-methylquinolin-3-yl | CH2 | 0 | — | 1-allyl-1H-pyrazol-5-yl | 3.87 [a] |
| I-322 | 7,8-difluoro-2-methylquinolin-3-yl | NH | 1 | 4-F | 4-chloro-1-methyl-1H-pyrazol-5-yl | 3.50 [a] |
| I-323 | 7,8-difluoro-2-methylquinolin-3-yl | NH | 1 | 3-F | 1-tert-butyl-1H-pyrazol-5-yl | 4.32 [a] |
| I-324 | 7,8-difluoro-2-methylquinolin-3-yl | NH | 1 | 3-F | 1-propyl-1H-pyrazol-5-yl | 3.76 [a] |

TABLE 1-continued

Compounds according to formula (I)

| Example | (Y)p-A-Q1-Z (with N) | L | n | (X)n | B (W)m | logP |
|---|---|---|---|---|---|---|
| I-325 | 7,8-difluoro-2-methylquinolin-3-yl | NH | 1 | 4-F | 1-(2-methylpropyl)-1H-pyrazol-5-yl | 3.99 [a] |
| I-326 | 7,8-difluoro-2-methylquinolin-3-yl | NH | 1 | 4-F | 1-benzyl-1H-pyrazol-5-yl | 3.99 [a] |
| I-327 | 7,8-difluoro-2-methylquinolin-3-yl | CH$_2$ | 0 | — | 1-isopropyl-1H-pyrazol-5-yl | 3.76 [a] |
| I-328 | 3-methylquinoxalin-2-yl | NH | 3 | 3,4,6-trifluoro | 1-ethyl-1H-pyrazol-5-yl | 2.84 [a] |
| I-329 | 3-(difluoromethyl)quinoxalin-2-yl | NH | 2 | 3,6-difluoro | 1-ethyl-1H-pyrazol-5-yl | 3.31 [a] |
| I-330 | 7,8-difluoro-2-methylquinolin-3-yl | CH$_2$ | 1 | 3-Cl | 1-methyl-1H-pyrazol-5-yl | 3.31 [a] |
| I-331 | 7,8-difluoro-2-methylquinolin-3-yl | CH$_2$ | 1 | 3-F | 1-ethyl-1H-pyrazol-5-yl | 3.35 [a] |
| I-332 | 7,8-difluoro-2-methylquinolin-3-yl | CH$_2$ | 1 | 3-F | 1-methyl-1H-pyrazol-5-yl | 3.06 [a] |
| I-333 | 7,8-difluoro-2-methylquinolin-3-yl | CH$_2$ | 1 | 4-F | 1-ethyl-1H-pyrazol-5-yl | 3.46 [a] |
| I-334 | 7,8-difluoro-2-methylquinolin-3-yl | CH$_2$ | 1 | 3-Cl | 1-ethyl-1H-pyrazol-5-yl | 3.65 [a] |
| I-335 | 7,8-difluoro-2-methylquinolin-3-yl | CH$_2$ | 1 | 4-F | 1-methyl-1H-pyrazol-5-yl | 3.15 [a] |
| I-336 | 8-(trifluoromethyl)quinolin-3-yl | CH$_2$ | 0 | — | 1-ethyl-1H-pyrazol-5-yl | 3.79 [a] |
| I-337 | 8-(trifluoromethyl)quinolin-3-yl | CH$_2$ | 0 | — | 1-methyl-1H-pyrazol-5-yl | 3.48 [a] |
| I-338 | 8-chloroquinolin-3-yl | CH$_2$ | 0 | — | 1-benzyl-1H-pyrazol-5-yl | 4.08 [a] |
| I-339 | 5,6-difluoro-3-methylquinoxalin-2-yl | CH$_2$ | 0 | — | 1-ethyl-1H-pyrazol-5-yl | 3.31 [a] |
| I-340 | 8-chloroquinolin-3-yl | CH$_2$ | 0 | — | 1-methyl-1H-pyrazol-5-yl | 2.94 [a] |
| I-341 | 8-chloroquinolin-3-yl | CH$_2$ | 0 | — | 1-benzyl-1H-pyrazol-5-yl | 3.63 [a] |
| I-342 | 5,6-difluoro-3-methylquinoxalin-2-yl | CH$_2$ | 0 | — | 1-benzyl-1H-pyrazol-5-yl | 4.15 [a] |
| I-343 | 7,8-difluoroquinolin-3-yl | CH$_2$ | 0 | — | 1-ethyl-1H-pyrazol-5-yl | 3.11 [a] |
| I-344 | 5,6-difluoro-3-methylquinoxalin-3-yl | CH$_2$ | 0 | — | 1-methyl-1H-pyrazol-5-yl | 2.96 [a] |
| I-345 | 5,6-difluoro-3-methylquinoxalin-2-yl | CH$_2$ | 0 | — | 1-isopropyl-1H-pyrazol-5-yl | 3.76 [a] |
| I-346 | 8-chloroquinolin-3-yl | CH$_2$ | 0 | — | 1-ethyl-1H-pyrazol-5-yl | 3.25 [a] |
| I-347 | 2-methylquinolin-3-yl | CH$_2$ | 0 | — | 1-isopropyl-1H-pyrazol-5-yl | 1.73 [a] |
| I-348 | 2-methylquinolin-3-yl | CH$_2$ | 0 | — | 1-methyl-1H-pyrazol-5-yl | 1.36 [a] |
| I-349 | 2-methylquinolin-3-yl | CH$_2$ | 0 | — | 1-ethyl-1H-pyrazol-5-yl | 1.53 [a] |
| I-350 | 7,8-difluoro-2-methylquinolin-3-yl | CH$_2$ | 1 | 4-Cl | 1-methyl-1H-pyrazol-5-yl | 3.55 [a] |
| I-351 | 7,8-difluoro-2-methylquinolin-3-yl | CH$_2$ | 1 | 4-Cl | 1-ethyl-1H-pyrazol-5-yl | 3.87 [a] |
| I-352 | 8-fluoroquinolin-3-yl | CH$_2$ | 0 | — | 1-isopropyl-1H-pyrazol-5-yl | 3.19 [a] |
| I-353 | 8-fluoroquinolin-3-yl | CH$_2$ | 0 | — | 1-methyl-1H-pyrazol-5-yl | 2.57 [a] |
| I-354 | 8-fluoroquinolin-3-yl | CH$_2$ | 0 | — | 1-ethyl-1H-pyrazol-5-yl | 2.86 [a] |
| I-355 | 7,8-difluoroquinolin-3-yl | CH$_2$ | 0 | — | 1-methyl-1H-pyrazol-5-yl | 2.84 [a] |
| I-356 | quinoxalin-2-yl | CH$_2$ | 0 | — | 1-isopropyl-1H-pyrazol-5-yl | 3.06 [a] |
| I-357 | quinoxalin-2-yl | CH$_2$ | 0 | — | 1-methyl-1H-pyrazol-5-yl | 2.34 [a] |

TABLE 1-continued

Compounds according to formula (I)

| Example | A ring (with Y, Q¹, N, Z) | L | n | (X)ₙ | B ring (with W) | logP |
|---|---|---|---|---|---|---|
| I-358 | quinoxalin-2-yl | CH₂ | 0 | — | 1-ethyl-1H-pyrazol-5-yl | 2.64 [a] |
| I-359 | 8-fluoroquinolin-3-yl | CH₂ | 0 | — | 1-benzyl-1H-pyrazol-5-yl | 3.65 [a] |
| I-360 | 8-fluoroquinolin-3-yl | CF₂ | 0 | — | 1-methyl-1H-pyrazol-5-yl | 2.90 [a] |

In table 1, the point of attachment of the (X)ₙ residue to the phenyl ring is based on the above numbering of the phenyl ring.

The compounds of formula (I) which are mentioned in table 1 hereinbelow were prepared in accordance with the procedures detailed hereinabove in connection with specific examples and with the general description of the processes herein disclosed.

TABLE 2

Further compounds according to formula (I)

| Example | A ring (with Y, Q¹, N, Z) | L | n | (X)ₙ | B ring (with W) |
|---|---|---|---|---|---|
| I-361 | 8-fluoroquinolin-3-yl | NH₂ | 1 | 3-F | (4,4-dimethyl-1,5-dihydroimidazol-2-yl) |
| I-362 | 8-fluoroquinolin-3-yl | NH₂ | 1 | 3-F | oxazol-4-yl |
| I-363 | 8-fluoroquinolin-3-yl | NH₂ | 1 | 3-F | (4-methyl-1,3-dioxolan-2-yl) |
| I-364 | 8-fluoroquinolin-3-yl | CH₂ | 1 | 3-F | (4,4-dimethyl-1,5-dihydroimidazol-2-yl) |
| I-365 | 8-fluoroquinolin-3-yl | CH₂ | 1 | 3-F | oxazol-4-yl |
| I-366 | 8-fluoroquinolin-3-yl | CH₂ | 1 | 3-F | (4-methyl-1,3-dioxolan-2-yl) |
| I-367 | 8-fluoroquinolin-3-yl | NH₂ | 1 | 3-F | isoxazol-3-yl |
| I-368 | 8-fluoroquinolin-3-yl | CH₂ | 1 | 3-F | isoxazol-3-yl |

TABLE 3

Compounds according to formula (VI)

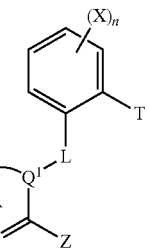

(VI)

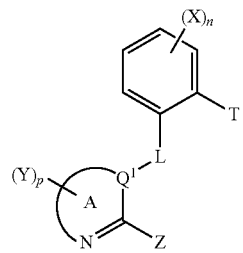

| Example | L | (X)$_n$ | T | LogP |
|---|---|---|---|---|
| VI-01 | 8-fluoroquinolin-3-yl | NH | — | 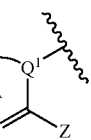 4.87 [a] |
| VI-02 | quinolin-3-yl | NH | — | 4.29 [a] |
| VI-03 | quinolin-3-yl | CH$_2$ | — | 3.39 [a] |

TABLE 4

Compounds according to formula (XX)

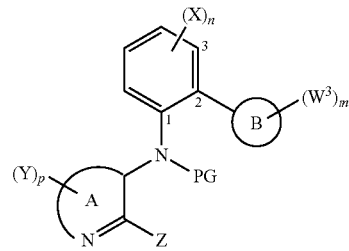

(XX)

In table 4, the point of attachment of the (X)$_n$ residue to the phenyl ring is based on the above numbering of the phenyl ring.

| Example | 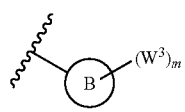 | PG | (X)$_n$ |  | LogP |
|---|---|---|---|---|---|
| XX-01 | quinolin-3-yl | tert-butoxycarbonyl | — | 5-carboxy-1H-pyrazol-1-yl | 2.42[a] |
| XX-02 | quinolin-3-yl | tert-butoxycarbonyl | 3-F | 5-carboxy-1H-pyrazol-1-yl | 2.62[a] |
| XX-03 | quinolin-3-yl | tert-butoxycarbonyl | 3-F | 5-(methoxycarbonyl)-1H-pyrazol-1-yl | 3.36[a] |
| XX-04 | quinolin-3-yl | tert-butoxycarbonyl | — | 5-prop-1-en-2-yl-1H-pyrazol-1-yl | 3.67[a] |
| XX-05 | quinolin-3-yl | tert-butoxycarbonyl | — | 5-(methoxycarbonyl)-1H-pyrazol-1-yl | 3.19[a] |
| XX-06 | quinolin-3-yl | tert-butoxycarbonyl | — | 5-formyl-1H-pyrazol-1-yl | 3.06[a] |
| XX-07 | quinolin-3-yl | tert-butoxycarbonyl | — | 5-[[tert-butyl(dimethyl)silyl]oxymethyl]-1H-pyrazol-1-yl | 5.84[a] |
| XX-08 | quinolin-3-yl | tert-butoxycarbonyl | 3-F | 5-(hydroxymethyl)-1H-pyrazol-1-yl | 2.47[a] |
| XX-09 | quinolin-3-yl | tert-butoxycarbonyl | 3-F | 5-[[tert-butyl(dimethyl)silyl]oxymethyl]-1H-pyrazol-1-yl | 5.80[a] |
| XX-10 | quinolin-3-yl | tert-butoxycarbonyl | 3-F | 5-formyl-1H-pyrazol-1-yl | 3.24[a] |
| XX-11 | quinolin-3-yl | tert-butoxycarbonyl | 3-F | 5-(2-hydroxypropan-2-yl)-1H-pyrazol-1-yl | 3.33[a] |
| XX-12 | quinolin-3-yl | tert-butoxycarbonyl | — | 5-(hydroxymethyl)-1H-pyrazol-1-yl | 2.35[a] |

TABLE 5

Compounds according to formula (IXa)

(IXa)

| Example | Hal | $X_a$ | $W^4$ | LogP |
|---|---|---|---|---|
| IXa-01 | Br | F | Me | 2.40[a] |
| IXa-02 | Br | F | isopropyl | 3.09[a] |
| IXa-03 | Br | F | tert-butyl | 3.61[a] |
| IXa-04 | Br | F | Et | 2.71[a] |
| IXa-05 | Br | F | 2-phenylethyl | 3.83[a] |

Note:
M = Methyl,
Et = Ethyl

TABLE 6

Compounds according to formula (IXb)

(IXb)

| Example | $X_a$ | R | W | LogP |
|---|---|---|---|---|
| IXb-01 | F | Br | CH$_2$OH | 1.27[a] |
| IXb-02 | F | Br | [tert-butyl(dimethyl)silyl]oxymethyl | 4.96[a] |
| IXb-03 | F | Br | methoxycarbonyl | 2.53[a] |
| IXb-04 | F | NH$_2$ | [tert-butyl(dimethyl)silyl]oxymethyl | 4.10[a] |

NMR-Peak Lists

1H-NMR data of selected examples are written in form of 1H-NMR-peak lists. To each signal peak are listed the δ-value in ppm and the signal intensity in round brackets. Between the δ-value-signal intensity pairs are semicolons as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contains therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-D$_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

NMR-Peak Lists for Compounds of Formula (I)

I-001: $^1$H-NMR (400.0 MHz, d$_6$-DMSO):

δ=9.9009 (2.4); 8.7980 (2.7); 8.7914 (2.6); 7.9421 (2.4); 7.9358 (2.4); 7.9150 (1.3); 7.9105 (1.3); 7.8924 (1.5); 7.8221 (3.9); 7.8165 (3.5); 7.8098 (1.8); 7.8036 (3.1); 7.7835 (1.8); 7.5463 (2.0); 7.5258 (3.6); 7.5156 (1.7); 7.5087 (2.9); 7.5012 (1.6); 7.4965 (1.5); 7.4925 (1.3); 7.4790 (0.5); 7.3139 (0.9); 7.2930 (1.6); 7.2751 (0.9); 7.0409 (1.1); 7.0221 (2.0); 7.0038 (1.0); 6.7832 (3.3); 6.7775 (3.2); 3.9744 (16.0); 3.9037 (2.3); 3.3439 (5.3); 3.1701 (0.8); 2.5065 (41.1); 2.5026 (50.1); −0.0002 (7.3)

I-002: $^1$H-NMR (400.0 MHz, d$_6$-DMSO):

δ=9.9413 (2.8); 8.0311 (3.9); 7.8538 (4.4); 7.8485 (3.6); 7.8319 (1.8); 7.8157 (1.6); 7.8123 (1.6); 7.7962 (1.7); 7.7927 (1.6); 7.7782 (1.4); 7.7601 (1.6); 7.7578 (1.6); 7.5578 (1.7); 7.5374 (2.0); 7.5111 (0.7); 7.5079 (0.7); 7.4939 (1.3); 7.4907 (1.5); 7.4736 (1.1); 7.4700 (1.0); 7.4456 (1.2); 7.4281 (1.5); 7.4110 (0.6); 7.3158 (0.8); 7.3126 (0.8); 7.2949 (1.5); 7.2772 (0.8); 7.2741 (0.8); 7.0226 (1.0); 7.0047 (1.8); 6.9864 (0.9); 6.8287 (3.3); 6.8228 (3.3); 3.9696 (16.0); 3.9035 (4.0); 3.3262 (30.8); 3.1762 (0.3); 3.1635 (0.3); 2.7865 (14.4); 2.5068 (42.9); 2.5025 (56.0); 2.4982 (40.6); 2.3292 (0.3); 0.0077 (0.3); −0.0003 (10.1); −0.0082 (0.4)

I-003: $^1$H-NMR (400.0 MHz, d$_6$-DMSO):

δ=10.1122 (2.6); 8.7705 (2.7); 8.7638 (2.6); 7.9540 (2.4); 7.9478 (2.2); 7.9050 (4.1); 7.8992 (3.9); 7.8839 (1.4); 7.8278 (1.3); 7.8110 (2.7); 7.8044 (1.6); 7.7947 (1.8); 7.5916 (1.8); 7.5711 (2.0); 7.5322 (0.5); 7.5199 (1.5); 7.5136 (2.1); 7.5045 (2.8); 7.4951 (2.1); 7.4896 (1.3); 7.4767 (0.4); 7.3284 (0.8); 7.3255 (0.8); 7.3078 (1.5); 7.2898 (0.8); 7.0490 (1.0); 7.0300 (1.8); 7.0115 (0.9); 6.7899 (3.2); 6.7840 (3.0); 4.6729 (0.4); 4.6559 (1.1); 4.6394 (1.4); 4.6228 (1.1); 4.6063 (0.4); 3.9040 (2.8); 3.3384 (6.2); 3.1705 (0.6); 2.5070 (41.7); 2.5030 (51.4); 2.4990 (37.4); 1.6190 (0.5); 1.5132 (16.0); 1.4966 (15.8); −0.0002 (9.2)

I-004: $^1$H-NMR (400.0 MHz, d$_6$-DMSO):

δ=9.8167 (2.7); 8.0426 (3.4); 7.9308 (3.2); 7.9248 (3.2); 7.8577 (1.6); 7.8373 (1.7); 7.8133 (1.5); 7.8100 (1.5); 7.7938 (1.6); 7.7904 (1.7); 7.7807 (1.4); 7.7625 (1.5); 7.5328 (1.7); 7.5234 (0.8); 7.5202 (0.9); 7.5130 (2.1); 7.5065 (1.4); 7.5032 (1.5); 7.4860 (1.0); 7.4826 (0.9); 7.4513 (1.1); 7.4337 (1.4); 7.4160 (0.7); 7.2994 (0.8); 7.2960 (0.8); 7.2783 (1.5); 7.2608 (0.8); 7.2575 (0.8);

7.0136 (1.0); 6.9958 (1.7); 6.9781 (0.8); 6.8297 (3.2); 6.8237 (3.2); 4.6608 (0.4); 4.6445 (1.0); 4.6277 (1.4); 4.6110 (1.0); 4.5946 (0.4); 3.9040 (4.5); 3.3276 (11.4); 3.1703 (0.6); 2.7930 (13.6); 2.5075 (39.9); 2.5031 (51.8); 2.4987 (37.6); 1.6270 (0.6); 1.5655 (0.8); 1.4981 (16.0); 1.4814 (15.8); 0.0080 (0.3); −0.0002 (10.0); −0.0083 (0.4)

I-005: $^{1}$H-NMR (400.0 MHz, $d_{6}$-DMSO):

δ=10.2259 (0.8); 8.7540 (0.9); 8.7472 (0.9); 7.9812 (1.7); 7.9751 (1.7); 7.9068 (0.4); 7.9008 (0.3); 7.8836 (0.4); 7.8367 (0.4); 7.8267 (0.7); 7.8230 (0.7); 7.8131 (0.5); 7.8073 (0.6); 7.8042 (0.6); 7.6123 (0.6); 7.5919 (0.6); 7.5238 (0.5); 7.5178 (0.7); 7.5085 (0.9); 7.4991 (0.7); 7.4939 (0.4); 7.3121 (0.5); 7.0477 (0.4); 7.0289 (0.6); 6.8221 (1.0); 6.8159 (1.0); 3.9041 (1.3); 3.3420 (2.0); 3.1703 (0.4); 2.5072 (13.5); 2.5030 (17.6); 2.4989 (13.0); 1.6188 (16.0); −0.0002 (3.1)

I-006: $^{1}$H-NMR (400.0 MHz, $d_{6}$-DMSO):

δ=9.5430 (1.0); 8.0318 (1.2); 7.9756 (1.1); 7.9694 (1.1); 7.8669 (0.6); 7.8463 (0.6); 7.8011 (0.5); 7.7813 (1.1); 7.7616 (0.6); 7.5231 (0.5); 7.5055 (0.3); 7.4586 (0.4); 7.4333 (0.7); 7.4122 (0.7); 7.2491 (0.5); 6.9994 (0.4); 6.9811 (0.6); 6.8228 (1.1); 6.8166 (1.0); 3.9039 (1.4); 3.3271 (5.4); 2.7770 (4.5); 2.5072 (14.7); 2.5032 (18.5); 1.5926 (16.0); −0.0002 (3.2)

I-007: $^{1}$H-NMR (400.0 MHz, $d_{6}$-DMSO):

δ=8.6458 (2.6); 8.6392 (2.6); 8.0027 (2.9); 7.8349 (1.1); 7.8284 (0.9); 7.8216 (0.6); 7.8118 (1.2); 7.6970 (1.1); 7.6800 (1.0); 7.6734 (1.3); 7.4816 (2.4); 7.4755 (2.4); 7.4567 (3.8); 7.4475 (5.5); 7.4335 (2.9); 7.4239 (2.4); 7.4069 (0.4); 7.3660 (4.4); 7.3615 (3.4); 7.3497 (2.1); 7.2030 (0.8); 7.1926 (1.1); 7.1827 (1.1); 7.1733 (1.1); 7.1627 (0.6); 6.3080 (3.4); 6.3036 (3.2); 3.9031 (2.7); 3.6511 (16.0); 3.3255 (24.6); 3.1756 (0.4); 3.1626 (0.4); 2.5061 (41.6); 2.5020 (52.5); 2.4978 (38.2); 1.2343 (1.4); −0.0002 (9.1); −0.0082 (0.4)

I-008: $^{1}$H-NMR (400.0 MHz, $d_{6}$-DMSO):

δ=7.7631 (1.5); 7.7431 (1.7); 7.6444 (1.4); 7.6259 (1.5); 7.4642 (0.7); 7.4605 (0.8); 7.4517 (0.8); 7.4422 (1.5); 7.4346 (1.3); 7.4312 (1.6); 7.4265 (1.4); 7.4221 (1.1); 7.4139 (1.0); 7.4105 (1.0); 7.3720 (2.4); 7.3538 (3.0); 7.3369 (0.7); 7.2748 (3.9); 7.2618 (2.5); 7.2417 (3.3); 7.2371 (3.3); 7.2114 (2.1); 7.2056 (1.4); 7.1908 (2.0); 7.1873 (2.2); 7.1682 (0.8); 6.2703 (3.3); 6.2658 (3.3); 3.9029 (4.0); 3.6907 (16.0); 3.3270 (34.8); 3.1754 (0.3); 2.5416 (13.9); 2.5240 (4.8); 2.5061 (35.2); 2.5017 (46.7); 2.4973 (34.1); −0.0002 (6.4)

I-009: $^{1}$H-NMR (400.0 MHz, $d_{6}$-DMSO):

δ=8.7141 (0.9); 8.7079 (0.9); 7.8664 (0.5); 7.8460 (0.6); 7.7704 (0.5); 7.7526 (0.5); 7.7477 (0.6); 7.7322 (0.9); 7.7266 (0.9); 7.4925 (0.5); 7.4886 (0.5); 7.4743 (2.2); 7.4611 (0.5); 7.4158 (1.5); 7.4085 (1.0); 7.3304 (1.2); 7.2879 (0.6); 7.2696 (0.7); 7.0699 (0.4); 6.2145 (1.3); 3.9034 (1.2); 3.3258 (10.6); 2.5024 (21.4); 1.4039 (16.0); −0.0002 (3.0)

I-010: $^{1}$H-NMR (400.0 MHz, $d_{6}$-DMSO):

δ=7.8375 (0.5); 7.8150 (2.0); 7.7933 (0.5); 7.7903 (0.5); 7.5300 (0.4); 7.5271 (0.4); 7.4937 (1.1); 7.4895 (1.1); 7.4415 (0.4); 7.3766 (0.4); 7.3103 (0.4); 7.3065 (0.4); 7.2914 (0.5); 7.2877 (0.4); 7.0924 (0.6); 7.0725 (0.5); 7.0258 (0.5); 7.0238 (0.5); 6.3402 (0.8); 6.2842 (1.1); 6.2800 (1.1); 3.9032 (1.3); 3.3252 (11.9); 2.5108 (6.2); 2.5066 (12.9); 2.5021 (17.0); 2.4976 (12.1); 2.4933 (5.8); 2.4002 (4.4); 1.4232 (16.0); −0.0002 (3.5)

I-011: $^{1}$H-NMR (400.0 MHz, $d_{6}$-DMSO):

δ=8.6958 (3.9); 8.6890 (3.9); 7.9665 (4.0); 7.8682 (1.6); 7.8576 (1.5); 7.8439 (1.7); 7.7004 (1.6); 7.6951 (1.4); 7.6875 (1.7); 7.6836 (1.2); 7.6764 (1.9); 7.6685 (0.4); 7.4615 (0.7); 7.4475 (4.2); 7.4446 (4.5); 7.4375 (3.5); 7.4255 (5.7); 7.4132 (0.6); 7.3455 (4.9); 7.3362 (6.0); 7.3203 (3.3); 7.3137 (3.3); 7.2061 (1.2); 7.1963 (1.4); 7.1858 (1.5); 7.1762 (1.5); 7.1655 (0.8); 5.7788 (1.4); 5.7587 (1.6); 5.7517 (1.6); 5.7315 (1.4); 3.9035 (3.5); 3.4380 (1.0); 3.4111 (1.0); 3.3936 (1.2); 3.3672 (1.3); 3.3253 (21.4); 2.8904 (1.0); 2.8298 (1.2); 2.8108 (1.1); 2.7868 (1.0); 2.7676 (1.0); 2.7313 (0.9); 2.6757 (0.4); 2.6712 (0.6); 2.6665 (0.4); 2.5244 (1.7); 2.5107 (38.9); 2.5065 (79.1); 2.5020 (104.0); 2.4976 (74.2); 2.3332 (0.4); 2.3286 (0.6); 2.3242 (0.4); 2.0750 (0.6); 1.8992 (16.0); −0.0001 (6.3)

I-012: $^{1}$H-NMR (400.1 MHz, $d_{6}$-DMSO):

δ=8.1437 (0.7); 7.8214 (1.9); 7.8008 (2.0); 7.6411 (1.6); 7.6230 (1.9); 7.4525 (2.3); 7.4334 (2.8); 7.4186 (1.3); 7.4150 (1.2); 7.3884 (1.3); 7.3859 (1.4); 7.3676 (2.2); 7.3479 (2.3); 7.3442 (1.8); 7.3284 (1.2); 7.3248 (1.0); 7.2173 (1.4); 7.2003 (5.2); 7.1799 (0.9); 7.1566 (2.4); 7.1456 (4.9); 7.1380 (2.2); 5.7513 (6.2); 5.6888 (1.1); 5.6674 (1.4); 5.6617 (1.4); 5.6402 (1.2); 3.3302 (1.5); 3.3044 (2.0); 3.2885 (1.6); 3.2606 (1.1); 2.8699 (1.0); 2.8488 (0.9); 2.8260 (0.8); 2.8047 (0.8); 2.6649 (0.5); 2.6392 (16.0); 2.5052 (19.4); 2.5009 (25.7); 2.4966 (18.9); 1.8773 (12.6); −0.0002 (4.2)

I-013: $^{1}$H-NMR (400.1 MHz, $d_{6}$-DMSO):

δ=7.5407 (0.6); 7.5242 (0.8); 7.5159 (1.4); 7.5021 (1.2); 7.4877 (1.0); 7.4694 (2.6); 7.4486 (2.6); 7.4213 (0.5); 7.3968 (0.9); 7.3934 (0.9); 7.3776 (2.0); 7.3745 (2.0); 7.3576 (4.6); 7.2730 (1.4); 7.2544 (2.0); 7.2356 (0.8); 7.2093 (2.3); 7.1898 (1.9); 7.1278 (3.5); 5.6669 (1.2); 5.6457 (1.4); 5.6398 (1.4); 5.6184 (1.2); 3.3045 (27.5); 3.2855 (0.9); 3.2685 (1.0); 3.2411 (1.0); 2.8515 (1.1); 2.8311 (1.0); 2.8084 (0.8); 2.7874 (0.8); 2.6923 (16.0); 2.6704 (0.3); 2.5055 (33.2); 2.5012 (44.1); 2.4970 (33.0); 2.0725 (9.5); 1.8721 (13.2); −0.0002 (7.0)

I-014: $^{1}$H-NMR (400.1 MHz, $d_{6}$-DMSO):

δ=8.7211 (3.9); 8.7146 (3.9); 8.1425 (4.5); 7.5075 (2.2); 7.4872 (3.1); 7.4627 (2.3); 7.4438 (2.9); 7.4144 (1.0); 7.4014 (1.2); 7.3948 (1.8); 7.3818 (1.9); 7.3669 (5.0); 7.3576 (6.6); 7.3027 (3.3); 7.2472 (1.3); 7.2355 (2.6); 7.2274 (1.8); 7.2168 (2.6); 7.2066 (2.3); 7.1881 (1.2); 5.7657 (1.5); 5.7513 (7.4); 5.7387 (1.7); 5.7184 (1.5); 3.4284 (1.1); 3.4012 (1.1); 3.3852 (1.3); 3.3576 (1.2); 3.3051 (43.8); 2.8277 (1.3); 2.8076 (1.2); 2.7843 (1.1); 2.7642 (1.1); 2.6698 (0.4); 2.5050 (50.5); 2.5010 (65.4); 2.4973 (49.5); 2.3281 (0.4); 1.8974 (16.0); −0.0002 (8.7)

I-015: $^{1}$H-NMR (400.1 MHz, $d_{6}$-DMSO):

δ=8.6967 (5.1); 8.6899 (5.2); 7.9258 (5.8); 7.8687 (2.1); 7.8583 (2.0); 7.8449 (2.4); 7.6997 (2.1); 7.6949 (1.6); 7.6868 (2.3); 7.6831 (1.8); 7.6759 (2.5); 7.4608 (0.9); 7.4434 (5.3); 7.4372 (6.2); 7.4232 (6.6); 7.4122 (0.9); 7.3449 (7.0); 7.3339 (9.6); 7.3249 (5.0); 7.2040 (1.5); 7.1937 (2.2); 7.1838 (2.1); 7.1740 (2.0); 7.1633 (1.0); 5.7717 (1.9); 5.7512 (6.6); 5.7448 (2.4); 5.7243 (1.9); 3.4485 (1.6); 3.4212 (1.6); 3.4054 (1.9); 3.3781 (1.7); 3.3077 (46.0); 2.8433 (1.8); 2.8232 (1.8); 2.8003 (1.6); 2.7801 (1.6); 2.5052 (40.0); 2.5011 (52.6); 2.4970 (39.4); 2.3182 (1.8); 2.2993 (5.4); 2.2806 (5.5); 2.2619 (1.9); 1.0549 (7.9); 1.0362 (16.0); 1.0174 (7.4); −0.0002 (7.1)

I-016: $^{1}$H-NMR (400.1 MHz, $d_{6}$-DMSO):

δ=7.8204 (1.9); 7.7997 (2.1); 7.6467 (1.7); 7.6269 (2.0); 7.4541 (1.0); 7.4399 (3.2); 7.4201 (3.3); 7.3878 (1.7); 7.3675 (2.4); 7.3475 (2.0); 7.3282 (1.3); 7.3248 (1.2); 7.2117 (1.4); 7.1929 (2.3); 7.1724 (9.1); 7.1633 (3.1); 7.1426 (2.1); 5.7508 (6.1); 5.6821 (1.5); 5.6607 (1.4); 5.6552 (1.4); 5.6336 (1.2); 3.3487 (1.0); 3.3210 (1.4); 3.3041 (41.5); 3.2784 (1.6); 2.8808 (1.1); 2.8595 (1.1);

2.8377 (1.0); 2.8164 (1.0); 2.6692 (0.4); 2.6643 (0.4); 2.6545 (0.4); 2.6358 (16.0); 2.5045 (42.3); 2.5002 (58.2); 2.4961 (45.6); 2.4200 (0.5); 2.3319 (0.4); 2.3272 (0.4); 2.2933 (1.0); 2.2748 (2.9); 2.2561 (3.1); 2.2376 (1.2); 1.0169 (4.8); 0.9982 (9.9); 0.9795 (4.7); 0.0079 (0.4); −0.0002 (9.7)

I-017: $^1$H-NMR (400.1 MHz, $d_6$-DMSO):

δ=7.5457 (0.6); 7.5223 (1.4); 7.5087 (1.3); 7.4903 (1.0); 7.4724 (1.1); 7.4633 (2.5); 7.4412 (2.7); 7.4239 (0.6); 7.3961 (0.9); 7.3928 (0.9); 7.3770 (1.9); 7.3740 (1.9); 7.3581 (1.4); 7.3547 (1.4); 7.3348 (3.7); 7.2686 (1.4); 7.2499 (2.1); 7.2313 (1.0); 7.2130 (2.4); 7.1935 (2.0); 7.1531 (3.7); 5.7514 (0.9); 5.6624 (1.2); 5.6412 (1.5); 5.6352 (1.5); 5.6139 (1.2); 3.3306 (1.1); 3.3040 (41.1); 3.2879 (2.1); 3.2602 (1.3); 2.8662 (1.2); 2.8453 (1.2); 2.8230 (1.0); 2.8021 (1.0); 2.6910 (16.0); 2.6702 (0.8); 2.5051 (46.1); 2.5009 (61.5); 2.4969 (47.2); 2.3280 (0.4); 2.2893 (1.0); 2.2706 (3.2); 2.2520 (3.4); 2.2332 (1.3); 1.0193 (5.0); 1.0005 (10.3); 0.9818 (4.9); −0.0002 (9.4)

I-018: $^1$H-NMR (400.1 MHz, $d_6$-DMSO):

δ=8.7236 (4.7); 8.7170 (4.8); 8.1248 (5.0); 7.5102 (2.4); 7.4898 (3.4); 7.4567 (2.7); 7.4377 (3.3); 7.4149 (1.4); 7.4021 (1.5); 7.3952 (2.2); 7.3822 (2.3); 7.3681 (6.5); 7.3588 (7.7); 7.3364 (0.5); 7.3193 (2.7); 7.3142 (3.7); 7.3097 (2.9); 7.2564 (0.4); 7.2459 (1.6); 7.2358 (3.6); 7.2257 (2.2); 7.2157 (3.3); 7.2056 (2.8); 7.1891 (1.5); 7.1867 (1.5); 5.7594 (1.7); 5.7517 (2.9); 5.7392 (2.0); 5.7323 (2.1); 5.7120 (1.8); 3.4420 (1.4); 3.4147 (1.5); 3.3990 (1.7); 3.3716 (1.6); 3.3058 (40.1); 2.8389 (1.6); 2.8188 (1.6); 2.7958 (1.4); 2.7756 (1.4); 2.6703 (0.4); 2.5098 (22.2); 2.5057 (45.0); 2.5013 (62.0); 2.4968 (47.0); 2.4927 (25.2); 2.3326 (0.4); 2.3279 (0.4); 2.3162 (1.7); 2.2975 (4.9); 2.2787 (5.1); 2.2601 (1.9); 1.0541 (7.7); 1.0354 (16.0); 1.0167 (7.5); 0.9255 (0.4); 0.0079 (0.4); −0.0002 (10.3); −0.0083 (0.6)

I-019: $^1$H-NMR (400.1 MHz, $d_6$-DMSO):

δ=8.6907 (3.6); 8.6839 (3.8); 7.8611 (1.5); 7.8506 (1.4); 7.8372 (1.8); 7.6767 (1.6); 7.6717 (1.3); 7.6638 (1.7); 7.6601 (1.4); 7.6527 (2.0); 7.6210 (2.4); 7.6017 (2.6); 7.5143 (4.0); 7.4516 (0.3); 7.4456 (0.7); 7.4318 (2.9); 7.4212 (3.4); 7.4135 (2.3); 7.4096 (3.0); 7.3969 (0.9); 7.3665 (5.0); 7.3569 (5.8); 7.2410 (4.0); 7.2329 (4.2); 7.2214 (1.8); 7.2110 (1.6); 7.2006 (0.9); 5.7510 (1.9); 3.3050 (51.7); 3.1501 (7.2); 2.6694 (0.4); 2.5049 (48.0); 2.5007 (64.6); 2.4965 (49.4); 2.3275 (0.4); 2.3230 (0.4); 1.8868 (1.3); 1.8468 (14.8); 1.6852 (1.6); 1.5873 (16.0); −0.0002 (7.5)

I-020: $^1$H-NMR (400.1 MHz, $d_6$-DMSO):

δ=8.7275 (3.6); 8.7210 (3.7); 7.7171 (4.4); 7.6999 (0.6); 7.6957 (0.5); 7.6688 (0.4); 7.6429 (2.3); 7.6236 (2.8); 7.4877 (2.0); 7.4672 (2.9); 7.3983 (1.5); 7.3818 (5.1); 7.3728 (6.6); 7.3593 (1.5); 7.3459 (1.0); 7.2804 (1.2); 7.2712 (1.3); 7.2601 (1.6); 7.2505 (1.6); 7.2392 (0.9); 7.2176 (4.0); 7.2016 (1.4); 7.1924 (1.6); 7.1736 (1.2); 5.7512 (2.4); 3.3037 (50.6); 3.2797 (1.2); 3.2361 (0.3); 3.1846 (0.5); 3.1413 (3.7); 3.1291 (3.6); 3.0852 (0.6); 2.6700 (0.4); 2.5051 (56.2); 2.5008 (75.4); 2.4967 (57.9); 2.3279 (0.5); 1.8872 (2.3); 1.8419 (15.1); 1.6854 (3.2); 1.5788 (16.0); 1.2371 (0.6); −0.0002 (12.0)

I-021: $^1$H-NMR (400.1 MHz, $d_6$-DMSO):

δ=8.1573 (1.5); 7.8214 (1.9); 7.8009 (2.1); 7.6551 (1.7); 7.6373 (1.9); 7.6349 (1.9); 7.5648 (1.7); 7.5618 (1.8); 7.5452 (1.9); 7.5421 (2.0); 7.4547 (0.8); 7.4512 (0.9); 7.4374 (1.8); 7.4342 (1.8); 7.4172 (1.4); 7.4133 (1.2); 7.3896 (2.0); 7.3699 (3.1); 7.3518 (2.1); 7.3480 (1.9); 7.3404 (4.9); 7.3160 (2.6); 7.2988 (1.3); 7.1930 (1.1); 7.1900 (1.2); 7.1730 (1.8); 7.1558 (0.9); 7.1526 (0.8); 7.0887 (3.4); 5.7515 (0.8); 3.3066 (2.3); 3.2628 (2.5); 3.1223 (2.3); 3.0787 (1.5); 2.6433 (16.0); 2.5057 (23.0); 2.5014 (31.0); 2.4971 (23.4); 2.0722 (2.4); 1.8701 (12.9); 1.5718 (13.2); 1.2331 (0.5); −0.0002 (5.3)

I-022: $^1$H-NMR (400.1 MHz, $d_6$-DMSO):

δ=7.5906 (1.9); 7.5739 (2.0); 7.5711 (2.0); 7.5596 (0.7); 7.5420 (0.8); 7.5335 (1.3); 7.5201 (1.2); 7.4955 (1.0); 7.4774 (1.1); 7.4702 (1.3); 7.4524 (1.1); 7.4288 (0.5); 7.4102 (0.8); 7.4069 (0.8); 7.3978 (1.4); 7.3901 (2.3); 7.3726 (2.0); 7.3691 (2.3); 7.3338 (4.2); 7.3200 (1.5); 7.2431 (1.2); 7.2403 (1.2); 7.2227 (2.0); 7.2068 (4.3); 5.7515 (0.9); 3.3042 (36.5); 3.2827 (1.4); 3.2387 (2.1); 3.1179 (2.4); 3.0744 (1.4); 2.6934 (16.0); 2.6707 (0.4); 2.5056 (41.6); 2.5013 (55.2); 2.4971 (41.2); 1.8627 (13.4); 1.6463 (1.3); 1.5565 (13.5); −0.0002 (8.3)

I-023: $^1$H-NMR (400.1 MHz, CDCl3):

δ=8.6909 (3.3); 8.6842 (3.4); 7.9997 (1.9); 7.9793 (2.1); 7.6039 (1.6); 7.5844 (5.0); 7.5074 (0.7); 7.5037 (0.9); 7.4899 (1.6); 7.4867 (1.9); 7.4758 (2.3); 7.4705 (2.0); 7.4657 (1.8); 7.4574 (4.2); 7.4409 (1.8); 7.4241 (0.7); 7.4214 (0.7); 7.3706 (2.0); 7.3510 (2.3); 7.3316 (1.1); 7.3288 (1.1); 7.3109 (2.0); 7.2932 (1.0); 7.2905 (1.0); 7.2585 (3.2); 7.0737 (1.4); 7.0548 (2.6); 7.0424 (2.7); 5.2910 (4.8); 3.3664 (1.9); 3.3243 (2.2); 2.8958 (2.7); 2.8537 (2.3); 2.3664 (0.9); 2.3375 (2.8); 2.3187 (3.0); 2.3000 (1.1); 1.7998 (0.4); 1.7114 (16.0); 1.2562 (0.6); 1.0995 (5.2); 1.0808 (10.3); 1.0619 (4.9); −0.0002 (3.0)

I-024: $^1$H-NMR (400.1 MHz, $d_6$-DMSO):

δ=7.8185 (0.4); 7.8119 (0.3); 7.7927 (0.4); 7.7885 (0.3); 7.7789 (0.4); 7.5887 (1.7); 7.5857 (1.9); 7.5689 (2.0); 7.5660 (2.2); 7.5450 (0.8); 7.5360 (1.3); 7.5224 (1.1); 7.4981 (1.0); 7.4796 (1.2); 7.4726 (1.5); 7.4640 (1.0); 7.4589 (1.2); 7.4546 (1.2); 7.4313 (0.5); 7.4126 (0.7); 7.4092 (0.7); 7.3925 (1.9); 7.3750 (2.2); 7.3682 (4.0); 7.3490 (2.8); 7.3381 (0.6); 7.3323 (1.3); 7.2357 (1.1); 7.2325 (1.2); 7.2159 (1.8); 7.1911 (3.7); 5.7512 (2.3); 3.3025 (48.3); 3.2745 (1.5); 3.2312 (2.3); 3.1063 (2.6); 3.0630 (1.6); 2.7090 (0.4); 2.6923 (16.0); 2.6744 (0.5); 2.6699 (0.6); 2.5052 (58.3); 2.5008 (78.5); 2.4965 (58.2); 2.3323 (0.4); 2.3276 (0.5); 2.3231 (0.4); 2.3033 (0.4); 2.2836 (0.8); 2.2638 (1.8); 2.2443 (2.7); 2.2249 (1.9); 2.2054 (0.7); 2.1852 (0.4); 1.5637 (12.9); 0.9534 (5.1); 0.9347 (10.8); 0.9160 (4.9); 0.0079 (0.6); −0.0002 (12.6); −0.0083 (0.6)

I-025: $^1$H-NMR (400.1 MHz, $d_6$-DMSO):

δ=9.9422 (2.8); 8.8040 (2.9); 8.7973 (2.9); 8.0269 (2.3); 8.0204 (2.2); 7.9359 (1.5); 7.9160 (1.6); 7.8904 (3.0); 7.8847 (3.0); 7.8626 (1.4); 7.8600 (1.4); 7.8433 (1.7); 7.8391 (1.5); 7.5873 (0.6); 7.5833 (0.7); 7.5702 (1.5); 7.5662 (1.4); 7.5505 (1.7); 7.5461 (2.4); 7.5425 (1.7); 7.5267 (1.4); 7.5236 (1.4); 7.5097 (0.7); 7.5062 (0.6); 7.3393 (0.6); 7.3351 (0.9); 7.3187 (3.6); 7.3144 (2.8); 7.3053 (1.5); 7.3010 (1.4); 7.2858 (1.2); 7.2803 (0.5); 7.2652 (0.5); 6.8778 (0.8); 6.8719 (0.8); 6.8606 (0.8); 6.8546 (0.8); 6.8496 (1.0); 6.8460 (0.9); 6.8303 (0.8); 6.8267 (0.8); 6.6539 (1.6); 6.6481 (1.7); 6.6416 (1.8); 6.6358 (1.6); 4.0071 (16.0); 3.9808 (0.6); 3.3255 (29.2); 2.5170 (16.7); 2.5128 (31.5); 2.5083 (41.2); 2.5039 (29.8); 2.4996 (14.7); 2.4612 (0.7); 0.0148 (2.4); 0.0069 (42.7); −0.0013 (2.2)

I-026: $^1$H-NMR (400.1 MHz, $d_6$-DMSO):

δ=10.0361 (3.4); 8.0751 (4.4); 7.9203 (3.2); 7.9149 (3.2); 7.8752 (2.0); 7.8546 (2.2); 7.8112 (1.8); 7.7918 (2.0); 7.5509 (1.0); 7.5336 (1.9); 7.5160 (1.3); 7.5131 (1.2); 7.4730 (1.5); 7.4549 (1.5); 7.4373 (0.9); 7.3205 (0.9); 7.3096 (3.2); 7.3003 (4.4); 7.2828 (1.2); 7.2619 (0.4); 6.8686 (0.8); 6.8581 (1.0); 6.8453 (0.9); 6.8400 (1.0);

6.8352 (1.0); 6.8218 (0.8); 6.8173 (0.8); 6.7033 (1.7); 6.6977 (1.8); 6.6899 (1.8); 6.6843 (1.6); 4.0065 (16.0); 3.3444 (6.5); 2.7509 (14.8); 2.5079 (9.7); 1.5434 (0.3); 0.0029 (6.2)

I-027: $^1$H-NMR (400.1 MHz, $d_6$-DMSO):

δ=10.2003 (2.7); 8.7726 (2.7); 8.7658 (2.7); 8.0167 (2.2); 8.0102 (2.0); 7.9672 (3.1); 7.9613 (3.0); 7.9280 (1.2); 7.9249 (1.3); 7.9056 (1.4); 7.8579 (1.2); 7.8551 (1.1); 7.8388 (1.5); 7.8343 (1.3); 7.5779 (0.5); 7.5737 (0.7); 7.5607 (1.4); 7.5566 (1.3); 7.5415 (2.6); 7.5364 (2.4); 7.5216 (1.3); 7.5182 (1.3); 7.5044 (0.6); 7.5009 (0.6); 7.3918 (1.3); 7.3727 (2.6); 7.3422 (1.2); 7.3267 (1.3); 7.3221 (1.4); 7.3063 (1.3); 7.3019 (0.7); 7.2858 (0.5); 6.8970 (0.9); 6.8943 (0.9); 6.8769 (0.9); 6.8743 (0.9); 6.8686 (1.0); 6.8663 (1.0); 6.8484 (0.8); 6.8462 (0.8); 6.6716 (1.5); 6.6656 (1.6); 6.6586 (1.6); 6.6527 (1.4); 4.7134 (0.4); 4.6968 (1.1); 4.6802 (1.4); 4.6636 (1.1); 4.6470 (0.4); 3.3300 (17.2); 2.5170 (8.6); 2.5127 (15.8); 2.5083 (20.3); 2.5038 (14.5); 2.4996 (7.0); 1.6638 (0.9); 1.5466 (0.3); 1.5160 (16.0); 1.4994 (15.8); 1.2377 (0.4); 0.0137 (1.0); 0.0058 (14.0); −0.0024 (0.7)

I-028: $^1$H-NMR (400.1 MHz, $d_6$-DMSO):

δ=9.8729 (2.9); 8.0766 (3.8); 7.9983 (3.1); 7.9923 (3.0); 7.8816 (1.7); 7.8610 (1.9); 7.8168 (1.5); 7.7790 (1.7); 7.5696 (0.8); 7.5662 (0.8); 7.5523 (1.4); 7.5490 (1.6); 7.5317 (1.2); 7.5282 (1.0); 7.5088 (0.4); 7.4959 (0.5); 7.4833 (1.4); 7.4632 (1.7); 7.4459 (0.8); 7.4009 (1.4); 7.3903 (1.7); 7.3730 (1.2); 7.3537 (0.3); 7.3122 (0.4); 7.2914 (1.1); 7.2750 (3.6); 7.2652 (2.7); 7.2546 (0.7); 6.8622 (0.8); 6.8570 (0.7); 6.8445 (0.8); 6.8391 (0.8); 6.8336 (0.8); 6.8225 (0.9); 6.8106 (0.6); 6.7103 (1.5); 6.7043 (1.6); 6.6966 (1.6); 6.6906 (1.4); 4.7055 (0.4); 4.6888 (1.1); 4.6722 (1.5); 4.6555 (1.1); 4.6388 (0.5); 3.3288 (31.0); 2.7545 (13.7); 2.5155 (32.5); 2.5111 (41.7); 2.5068 (29.9); 1.6586 (1.8); 1.6019 (0.3); 1.5115 (16.0); 1.4948 (15.9); 1.4630 (0.4); 0.0172 (2.5); 0.0093 (42.7); 0.0011 (2.1)

I-029: $^1$H-NMR (400.1 MHz, $d_6$-DMSO):

δ=8.6729 (3.4); 8.6664 (3.3); 7.9764 (3.8); 7.8725 (1.8); 7.8530 (2.0); 7.7693 (1.7); 7.7506 (2.0); 7.7463 (1.8); 7.6803 (3.1); 7.6743 (2.9); 7.5277 (0.7); 7.5239 (0.9); 7.5106 (1.9); 7.5069 (1.8); 7.4924 (3.7); 7.4873 (3.2); 7.4739 (3.4); 7.4566 (2.7); 7.4447 (4.4); 7.4401 (4.4); 7.2561 (2.6); 7.2355 (2.2); 7.0151 (1.3); 6.9933 (2.2); 6.9714 (1.2); 6.3563 (4.0); 6.3518 (3.8); 3.6624 (16.0); 3.6328 (0.3); 3.3372 (16.5); 2.5118 (15.3); 2.5079 (19.0); 2.0811 (0.6); 1.2402 (0.6); 0.0056 (11.5)

I-030: $^1$H-NMR (400.1 MHz, $d_6$-DMSO):

δ=7.8168 (2.2); 7.7960 (2.5); 7.7587 (2.0); 7.7400 (2.2); 7.5956 (5.2); 7.5408 (1.2); 7.5376 (1.2); 7.5236 (1.8); 7.5203 (2.2); 7.5030 (1.4); 7.4995 (1.3); 7.4493 (1.1); 7.4419 (1.7); 7.4397 (1.7); 7.4286 (2.3); 7.4221 (2.4); 7.4119 (2.2); 7.4081 (1.6); 7.3914 (1.2); 7.3764 (0.4); 7.3444 (4.7); 7.3398 (4.7); 7.3274 (3.8); 6.9675 (1.3); 6.9453 (2.3); 6.9237 (1.2); 6.8512 (2.6); 6.8307 (2.4); 6.3403 (4.6); 6.3356 (4.4); 3.6744 (16.0); 3.3827 (0.4); 3.3317 (131.4); 3.2955 (1.2); 2.6767 (0.3); 2.5123 (57.2); 2.5079 (53.1); 2.5035 (37.8); 1.7602 (0.6); 0.0140 (2.1); 0.0062 (38.2); −0.0019 (2.0)

I-031: $^1$H-NMR (400.1 MHz, $d_6$-DMSO):

δ=8.7097 (7.2); 8.7031 (7.2); 7.8817 (3.7); 7.8621 (4.1); 7.7922 (3.5); 7.7895 (3.3); 7.7731 (4.6); 7.7688 (4.6); 7.7572 (13.9); 7.7511 (7.4); 7.5965 (0.6); 7.5711 (7.8); 7.5669 (7.7); 7.5393 (1.7); 7.5354 (2.0); 7.5222 (3.7); 7.5183 (3.5); 7.5022 (5.3); 7.4973 (5.8); 7.4870 (2.4); 7.4804 (3.9); 7.4777 (4.0); 7.4665 (4.1); 7.4498 (3.7); 7.4293 (1.9); 7.2466 (5.4); 7.2260 (4.4); 7.1639 (0.3); 7.0044 (2.6); 6.9823 (4.6); 6.9611 (2.4); 6.3764 (8.9); 6.3720 (8.6); 4.2212 (0.8); 4.2049 (2.1); 4.1887 (2.8); 4.1723 (2.1); 4.1560 (0.8); 3.3290 (125.7); 2.6767 (0.4); 2.6727 (0.3); 2.5121 (57.1); 2.5077 (74.0); 2.5033 (53.2); 2.3346 (0.4); 1.3241 (0.8); 1.2988 (15.2); 1.2825 (14.9); 1.2475 (16.0); 1.2312 (15.6); 1.2167 (1.4); 1.2073 (0.8); 1.2001 (1.0); 0.0137 (3.6); 0.0059 (58.2); −0.0022 (2.6)

I-032: $^1$H-NMR (400.1 MHz, $d_6$-DMSO):

δ=10.3162 (1.4); 8.7550 (1.2); 8.7500 (1.2); 8.0319 (2.4); 7.9254 (0.8); 7.9059 (0.9); 7.8608 (0.9); 7.8428 (0.8); 7.5759 (0.4); 7.5595 (0.8); 7.5405 (1.3); 7.5228 (0.8); 7.5055 (0.4); 7.4117 (0.9); 7.3916 (1.6); 7.3729 (0.6); 7.3466 (0.5); 7.3269 (0.7); 7.3102 (0.6); 6.8974 (0.5); 6.8760 (0.6); 6.8704 (0.6); 6.8492 (0.4); 6.6941 (0.9); 6.6872 (0.8); 3.3249 (15.2); 2.5079 (8.7); 1.6244 (16.0); 0.0049 (3.7)

I-033: $^1$H-NMR (400.1 MHz, $d_6$-DMSO):

δ=9.5774 (1.0); 8.0664 (1.4); 8.0402 (1.1); 8.0341 (1.1); 7.8879 (0.6); 7.8670 (0.7); 7.8147 (0.6); 7.7952 (0.6); 7.5674 (0.6); 7.5497 (0.4); 7.5468 (0.3); 7.4851 (0.4); 7.4664 (0.6); 7.2520 (0.4); 7.2358 (0.4); 7.1415 (0.8); 7.1209 (0.5); 6.8352 (0.4); 6.8149 (0.4); 6.8072 (0.4); 6.7021 (0.5); 6.6960 (0.6); 6.6885 (0.6); 6.6825 (0.5); 3.3260 (4.0); 7.2291 (4.6); 2.5121 (4.6); 2.5081 (5.9); 2.5040 (4.5); 1.6017 (16.0); 0.0053 (4.5)

I-034: $^1$H-NMR (400.1 MHz, CDCl3):

δ=8.6882 (3.5); 8.6818 (3.5); 8.0266 (2.4); 8.0059 (2.6); 7.6504 (2.1); 7.6279 (5.4); 7.6211 (3.5); 7.5592 (1.0); 7.5404 (2.1); 7.5220 (1.6); 7.4998 (1.9); 7.4804 (2.3); 7.4628 (0.9); 7.2760 (0.7); 7.2589 (12.1); 7.2398 (1.9); 7.2202 (1.3); 7.1956 (3.4); 7.1754 (1.7); 6.7822 (1.9); 6.7702 (3.0); 6.7640 (2.8); 6.7387 (1.3); 6.0701 (1.5); 6.0416 (3.2); 6.0133 (1.6); 5.2959 (0.5); 3.2762 (0.9); 3.2478 (0.9); 3.2330 (1.7); 3.2049 (1.6); 3.1460 (1.5); 3.1172 (1.5); 3.1035 (0.8); 3.0742 (0.7); 1.9634 (16.0); 1.5776 (5.0); −0.0002 (9.5)

I-035: $^1$H-NMR (400.1 MHz, CDCl3):

δ=7.9700 (1.6); 7.9492 (1.8); 7.6905 (4.2); 7.6034 (1.4); 7.5832 (1.8); 7.5468 (0.8); 7.5433 (0.8); 7.5295 (1.4); 7.5260 (1.7); 7.5086 (1.1); 7.5051 (1.0); 7.4449 (1.3); 7.4425 (1.4); 7.4250 (1.8); 7.4076 (0.8); 7.4051 (0.8); 7.2588 (16.9); 7.2428 (0.9); 7.2384 (1.5); 7.2225 (1.5); 7.2181 (1.0); 7.2020 (0.9); 7.0798 (2.1); 7.0593 (1.6); 6.7965 (1.8); 6.7635 (1.0); 6.7614 (1.1); 6.7394 (1.5); 6.7179 (1.0); 6.7158 (0.9); 6.0750 (1.2); 6.0462 (2.3); 6.0176 (1.3); 5.2962 (1.1); 3.2570 (0.6); 3.2281 (0.6); 3.2131 (1.2); 3.1854 (1.2); 3.1442 (1.0); 3.1146 (1.0); 3.1013 (0.5); 3.0719 (0.4); 2.6853 (16.0); 1.9592 (11.5); 1.8699 (0.4); 1.7720 (0.3); 1.7299 (0.5); 1.6915 (0.5); 1.6338 (0.4); −0.0002 (14.4); −0.0083 (0.8)

I-036: $^1$H-NMR (400.1 MHz, CDCl3):

δ=7.6537 (3.2); 7.3355 (0.3); 7.3200 (0.6); 7.3122 (3.8); 7.2981 (2.8); 7.2900 (1.5); 7.2838 (0.9); 7.2749 (1.4); 7.2604 (7.3); 7.2473 (1.6); 7.2429 (1.0); 7.2267 (0.8); 7.0893 (2.2); 7.0688 (1.8); 6.8731 (2.0); 6.7976 (1.1); 6.7752 (1.6); 6.7530 (1.0); 6.0640 (1.2); 6.0353 (2.4); 6.0067 (1.3); 5.2971 (0.7); 3.2735 (0.7); 3.2456 (0.8); 3.2305 (1.2); 3.2027 (1.1); 3.0901 (1.0); 3.0604 (1.0); 3.0471 (0.6); 3.0174 (0.6); 2.7315 (16.0); 1.9574 (12.1); 1.5917 (1.0); −0.0002 (5.8)

I-037: $^1$H-NMR (300.2 MHz, CDCl3):

δ=9.5085 (2.4); 8.8858 (4.0); 8.8771 (4.0); 8.0996 (1.9); 8.0718 (2.1); 7.9682 (3.0); 7.9597 (2.9); 7.7411 (1.6); 7.7373 (1.7); 7.7145 (2.2); 7.7099 (2.2); 7.6395 (1.0); 7.6344 (1.1); 7.6165 (1.9); 7.6116 (2.2); 7.6066 (1.1); 7.5889 (1.7); 7.5836 (1.4); 7.5495 (1.8); 7.5452 (1.8); 7.5262 (1.4); 7.5225 (2.2); 7.5188 (1.6); 7.4997 (0.9);

7.4957 (0.8); 7.4604 (1.9); 7.4570 (1.7); 7.4312 (3.3); 7.4273 (2.2); 7.3258 (1.1); 7.3211 (1.4); 7.3014 (3.3); 7.2967 (5.9); 7.2715 (5.1); 6.9453 (1.5); 6.9416 (1.5); 6.9213 (1.9); 6.9168 (2.4); 6.8952 (1.2); 6.8915 (1.2); 3.2936 (16.0); 2.2500 (1.0); 2.0717 (0.6); 1.5474 (44.8); 1.3343 (0.4); 1.3093 (0.6); 1.2990 (1.3); 1.2861 (0.9); 0.9388 (0.5); 0.9170 (1.6); 0.8938 (0.6); 0.0386 (0.6)

I-038: $^1$H-NMR (300.2 MHz, CDCl3):

δ=9.4600 (1.8); 8.0809 (2.5); 8.0768 (2.5); 7.4693 (0.9); 7.4651 (1.0); 7.4420 (2.0); 7.4377 (1.9); 7.4187 (1.1); 7.4146 (1.5); 7.4042 (0.4); 7.3963 (1.2); 7.3898 (2.8); 7.3858 (3.1); 7.3709 (1.3); 7.3600 (0.8); 7.3499 (1.0); 7.3448 (1.8); 7.3344 (1.8); 7.3287 (2.1); 7.3220 (2.0); 7.3083 (2.0); 7.3030 (2.2); 7.2998 (1.9); 7.2901 (1.2); 7.2849 (1.1); 7.2650 (0.8); 7.2599 (0.8); 7.2538 (1.1); 7.2492 (1.1); 7.2285 (0.7); 7.2239 (0.7); 6.9759 (1.0); 6.9716 (1.1); 6.9523 (1.1); 6.9473 (1.6); 6.9261 (0.8); 6.9219 (0.8); 3.3123 (11.1); 2.8355 (16.0); 2.0746 (0.4); 1.9595 (1.0); 1.5545 (31.7); 1.3398 (0.5); 1.3123 (0.8); 1.2971 (2.7); 1.2651 (0.3); 0.9357 (1.0); 0.9139 (3.2); 0.8907 (1.2); 0.0347 (0.6)

I-039: $^1$H-NMR (400.0 MHz, d$_6$-DMSO):

δ=9.3397 (1.7); 8.8264 (1.5); 8.8200 (1.6); 8.0694 (1.2); 7.6837 (0.9); 7.6630 (1.1); 7.5363 (1.0); 7.5283 (0.5); 7.5157 (1.7); 7.5089 (1.0); 7.4958 (0.6); 7.4890 (0.6); 7.4761 (1.4); 7.4213 (0.5); 7.4007 (1.0); 7.3886 (0.8); 7.3841 (0.6); 7.3697 (0.6); 7.3613 (0.6); 7.3437 (0.5); 7.0685 (0.6); 7.0501 (1.1); 7.0318 (0.5); 3.9036 (1.4); 3.3451 (8.0); 3.3353 (102.7); 2.5072 (34.2); 2.5030 (44.8); 2.4988 (33.0); 1.3944 (16.0); 1.2342 (0.4); −0.0002 (3.2)

I-040: $^1$H-NMR (300.2 MHz, CDCl3):

δ=9.3797 (1.6); 8.0816 (3.5); 8.0457 (1.4); 8.0177 (1.5); 7.7199 (1.1); 7.7167 (1.2); 7.6930 (1.4); 7.6896 (1.5); 7.6407 (0.8); 7.6358 (0.8); 7.6176 (1.2); 7.6128 (1.5); 7.6079 (0.7); 7.5898 (1.0); 7.5848 (0.9); 7.5111 (1.1); 7.5075 (1.1); 7.4843 (1.5); 7.4614 (0.8); 7.4578 (0.7); 7.4436 (0.3); 7.3275 (1.7); 7.3253 (1.6); 7.3124 (3.9); 7.3101 (3.4); 7.2998 (7.7); 6.9444 (0.9); 6.9308 (1.1); 6.9192 (1.0); 6.9149 (0.6); 6.9064 (0.9); 6.8996 (0.4); 6.8903 (0.7); 3.3289 (11.0); 2.7888 (16.0); 2.0832 (0.5); 1.8508 (1.2); 1.5657 (31.6); 1.3208 (0.5); 1.3059 (1.4); 1.2975 (1.3); 0.9436 (0.5); 0.9218 (1.6); 0.8986 (0.6); 0.0407 (1.9)

I-041: $^1$H-NMR (300.2 MHz, CDCl3):

δ=9.4312 (1.8); 8.0597 (2.6); 8.0565 (2.6); 7.4482 (0.7); 7.4436 (0.6); 7.4375 (0.4); 7.4314 (0.6); 7.4255 (0.6); 7.4182 (1.0); 7.4129 (1.2); 7.4008 (1.0); 7.3951 (1.0); 7.3777 (1.1); 7.3554 (1.2); 7.3451 (1.7); 7.3386 (9.1); 7.3285 (3.3); 7.3229 (2.2); 7.3155 (4.2); 7.3106 (1.4); 7.2998 (1.6); 7.2926 (0.9); 6.9805 (1.0); 6.9710 (0.9); 6.9647 (0.4); 6.9574 (0.8); 6.9513 (0.9); 6.9460 (0.9); 6.9362 (0.6); 6.9264 (0.8); 3.3227 (11.5); 2.8307 (16.0); 1.7987 (1.6); 1.5610 (33.0); 1.3165 (0.4); 1.2988 (1.5); 1.2933 (1.4); 0.9369 (0.5); 0.9151 (1.8); 0.8919 (0.6); 0.1158 (0.4); 0.0351 (1.3)

I-042: $^1$H-NMR (300.2 MHz, CDCl3):

δ=8.4081 (1.7); 7.8410 (2.6); 7.8367 (2.4); 7.3939 (0.4); 7.3758 (0.5); 7.3717 (0.5); 7.3612 (1.9); 7.3554 (1.6); 7.3453 (1.3); 7.3412 (1.5); 7.3358 (1.3); 7.3249 (1.4); 7.2999 (21.1); 7.2733 (0.5); 7.2394 (0.6); 7.2182 (0.7); 7.2120 (1.4); 7.1910 (1.4); 7.1848 (1.0); 7.1637 (0.9); 7.0646 (2.0); 7.0370 (1.4); 6.7446 (1.0); 6.7407 (1.0); 6.7176 (0.9); 6.7136 (0.9); 6.7058 (1.0); 6.7018 (1.0); 6.6789 (0.9); 6.6674 (0.9); 3.5425 (0.5); 3.5305 (0.5); 3.4802 (1.0); 3.4717 (0.9); 3.4683 (0.9); 3.3572 (1.1); 3.3414 (1.1); 3.2983 (0.6); 3.2826 (0.6); 2.8448 (16.0); 2.1012 (10.7); 1.6801 (10.8); 1.5935 (4.1); 1.3455 (0.5); 1.3057 (2.9); 0.9427 (1.1); 0.9209 (3.5); 0.8977 (1.2); 0.0496 (0.9); 0.0388 (23.0); 0.0279 (0.9)

I-043: $^1$H-NMR (300.2 MHz, CDCl3):

δ=9.8061 (1.7); 8.0215 (2.4); 8.0180 (2.3); 7.7554 (1.4); 7.7505 (1.4); 7.7294 (1.5); 7.7245 (1.4); 7.5778 (1.4); 7.5748 (1.4); 7.5503 (1.7); 7.5473 (1.7); 7.5282 (2.8); 7.5201 (2.8); 7.3798 (0.4); 7.3621 (0.5); 7.3570 (0.5); 7.3490 (1.2); 7.3455 (1.3); 7.3309 (2.0); 7.3263 (1.6); 7.3195 (1.0); 7.3093 (1.1); 7.2996 (3.2); 7.2768 (1.2); 7.2734 (1.0); 7.2682 (1.0); 7.2464 (0.4); 7.0738 (1.0); 7.0700 (0.9); 7.0478 (1.5); 7.0237 (0.8); 7.0199 (0.7); 6.6756 (2.9); 6.6675 (2.8); 4.6376 (0.4); 4.6153 (1.0); 4.5930 (1.3); 4.5707 (1.0); 4.5484 (0.4); 4.1738 (0.5); 4.1500 (0.5); 2.9630 (13.3); 2.0852 (2.2); 1.8857 (0.4); 1.6134 (16.0); 1.5910 (15.8); 1.3227 (0.6); 1.2989 (1.4); 1.2751 (0.6); 0.0433 (0.7)

I-044: $^1$H-NMR (499.9 MHz, CDCl3):

δ=9.9386 (2.0); 7.9598 (3.1); 7.5297 (3.1); 7.5249 (3.2); 7.3502 (0.5); 7.3473 (0.6); 7.3399 (0.6); 7.3367 (0.7); 7.3320 (1.1); 7.3290 (1.1); 7.3217 (1.0); 7.3186 (1.0); 7.2995 (0.9); 7.2858 (0.9); 7.2803 (1.2); 7.2666 (1.1); 7.2585 (3.2); 7.2480 (0.6); 7.2357 (1.4); 7.2198 (2.4); 7.1931 (1.0); 7.1810 (1.0); 7.1769 (1.4); 7.1648 (1.4); 7.1607 (0.7); 7.1484 (0.6); 6.8037 (1.5); 6.7989 (1.6); 6.7929 (1.7); 6.7881 (1.6); 6.7577 (0.7); 6.7555 (1.0); 6.7417 (1.0); 6.7395 (1.0); 6.7351 (1.1); 6.7331 (1.1); 6.7190 (0.9); 6.7170 (0.9); 5.2948 (3.5); 4.6093 (0.5); 4.5959 (1.2); 4.5825 (1.6); 4.5691 (1.2); 4.5557 (0.5); 2.8878 (16.0); 1.6334 (2.0); 1.5787 (18.4); 1.5653 (18.7); −0.0002 (3.1)

I-045: $^1$H-NMR (300.2 MHz, CDCl3):

δ=10.1173 (3.5); 8.8137 (6.2); 8.8047 (6.3); 8.0422 (2.3); 8.0380 (2.5); 8.0157 (2.4); 8.0125 (2.8); 7.8912 (4.6); 7.8824 (4.5); 7.7409 (0.3); 7.7145 (3.3); 7.7095 (3.5); 7.6968 (2.6); 7.6888 (5.2); 7.6837 (3.9); 7.6716 (3.6); 7.6653 (3.3); 7.6400 (3.3); 7.6368 (3.3); 7.6125 (4.1); 7.6094 (3.9); 7.5667 (1.3); 7.5610 (1.6); 7.5438 (3.6); 7.5380 (3.0); 7.5340 (1.7); 7.5182 (6.6); 7.5112 (5.9); 7.4918 (2.6); 7.4871 (2.7); 7.4689 (1.1); 7.4640 (0.9); 7.4308 (16.0); 7.4159 (0.6); 7.3829 (1.9); 7.3778 (2.0); 7.3581 (2.8); 7.3543 (3.2); 7.3312 (1.9); 7.3262 (1.7); 7.2998 (25.5); 7.2762 (0.8); 7.0660 (2.3); 7.0622 (2.4); 7.0402 (3.5); 7.0377 (3.5); 7.0159 (1.9); 7.0120 (1.8); 3.4939 (1.1); 3.4709 (2.7); 3.4480 (3.7); 3.4251 (2.8); 3.4022 (1.2); 1.6224 (8.9); 1.5634 (46.2); 1.5405 (45.0); 1.4775 (0.5); 1.4546 (1.1); 1.1231 (0.4); 0.9226 (0.4); 0.0513 (0.9); 0.0405 (25.7); 0.0296 (0.8)

I-046: $^1$H-NMR (300.2 MHz, CDCl3):

δ=8.0319 (2.2); 8.0248 (1.8); 8.0083 (2.1); 8.0007 (1.6); 7.6185 (4.0); 7.4768 (1.0); 7.4703 (0.9); 7.4594 (1.2); 7.4532 (1.4); 7.4465 (1.6); 7.4400 (1.6); 7.4184 (4.9); 7.4107 (3.4); 7.3586 (1.0); 7.3352 (1.5); 7.3274 (1.2); 7.3044 (1.7); 7.2988 (1.4); 7.2719 (0.7); 7.2552 (0.8); 7.2500 (0.8); 7.2310 (2.3); 7.2255 (1.9); 7.2068 (3.8); 7.2001 (2.5); 7.1813 (2.2); 7.1746 (1.6); 7.1566 (0.9); 7.1502 (0.5); 6.8161 (4.9); 6.8084 (3.5); 6.7911 (2.4); 6.7865 (1.7); 6.7660 (2.2); 6.7606 (1.5); 5.3229 (1.8); 5.3164 (4.1); 4.5842 (0.5); 4.5619 (1.2); 4.5396 (1.7); 4.5173 (1.2); 4.4951 (0.5); 3.1668 (15.3); 2.3476 (16.0); 2.0455 (0.4); 1.5456 (10.3); 1.5393 (19.2); 1.5234 (10.2); 1.5169 (18.5); 1.4551 (0.3); 1.2947 (0.6); 0.9089 (0.4); 0.0302 (0.6)

I-047: $^1$H-NMR (300.2 MHz, CDCl3):

δ=7.4804 (2.4); 7.4759 (2.4); 7.3822 (0.4); 7.3771 (0.4); 7.3647 (0.5); 7.3590 (0.5); 7.3517 (0.9); 7.3466 (1.0); 7.3343 (0.9); 7.3288 (0.9); 7.3121 (1.3); 7.3001 (0.7); 7.2855 (1.7); 7.2793 (1.2); 7.2642 (1.5); 7.2578 (1.7);

7.2486 (0.5); 7.2369 (0.8); 7.2257 (0.4); 7.1921 (2.9); 7.1846 (2.9); 6.9405 (0.9); 6.9374 (0.9); 6.9100 (1.6); 6.8826 (0.9); 6.8791 (1.1); 6.8726 (1.8); 6.8454 (1.5); 6.1061 (1.9); 6.1038 (2.0); 6.0986 (2.0); 5.3086 (4.0); 4.3828 (0.4); 4.3605 (1.0); 4.3381 (1.4); 4.3159 (1.0); 4.2936 (0.4); 3.1861 (14.3); 2.4636 (13.4); 1.3623 (16.0); 1.3399 (15.7); 0.0207 (0.5)

I-048: $^1$H-NMR (300.2 MHz, CDCl3):

δ=9.8316 (1.4); 8.0099 (2.3); 8.0059 (2.2); 7.7563 (1.2); 7.7512 (1.3); 7.7304 (1.4); 7.7253 (1.4); 7.5894 (1.3); 7.5863 (1.3); 7.5619 (1.6); 7.5588 (1.6); 7.4697 (2.4); 7.4618 (2.4); 7.3867 (0.4); 7.3691 (0.5); 7.3643 (0.4); 7.3523 (1.3); 7.3484 (1.0); 7.3388 (2.1); 7.3340 (1.2); 7.3178 (2.0); 7.3062 (1.7); 7.2998 (19.8); 7.2857 (1.1); 7.2771 (0.4); 7.2545 (0.4); 7.0875 (0.9); 7.0836 (0.9); 7.0614 (1.4); 7.0594 (1.4); 7.0372 (0.7); 7.0335 (0.7); 6.6822 (3.0); 6.6743 (3.0); 4.0237 (16.0); 2.9480 (14.0); 1.5955 (15.2); 1.2938 (0.4); 0.0504 (0.7); 0.0396 (19.4); 0.0287 (0.8)

I-049: $^1$H-NMR (300.2 MHz, CDCl3):

δ=9.5880 (0.5); 8.0293 (0.6); 8.0258 (0.6); 7.7549 (0.4); 7.7499 (0.4); 7.7289 (0.4); 7.7239 (0.4); 7.6300 (1.0); 7.6217 (1.0); 7.5083 (0.4); 7.5051 (0.4); 7.4808 (0.5); 7.4776 (0.5); 7.3599 (0.3); 7.3567 (0.4); 7.3437 (0.5); 7.3379 (0.3); 7.3129 (0.4); 7.2999 (2.9); 7.2934 (0.5); 7.2706 (0.4); 7.0370 (0.4); 7.0351 (0.4); 6.6739 (0.9); 6.6655 (0.9); 2.9624 (4.2); 1.8250 (0.5); 1.7114 (0.5); 1.6834 (16.0); 1.6177 (2.5); 1.3067 (0.8); 0.9221 (1.0); 0.8988 (0.4); 0.0402 (2.6)

I-050: $^1$H-NMR (499.9 MHz, CDCl3):

δ=7.8887 (3.7); 7.6700 (3.4); 7.6667 (3.1); 7.4174 (0.6); 7.4072 (0.7); 7.3992 (1.2); 7.3890 (1.2); 7.3603 (1.1); 7.3446 (2.4); 7.3396 (1.5); 7.3316 (1.8); 7.3272 (1.8); 7.3154 (0.9); 7.3070 (0.6); 7.2640 (2.8); 6.9462 (2.4); 6.9296 (2.2); 6.8092 (1.2); 6.7918 (2.2); 6.7749 (1.2); 6.4499 (3.6); 6.4465 (3.3); 5.7779 (2.4); 3.8014 (14.6); 2.5776 (16.0); 1.6768 (8.3); −0.0002 (2.2)

I-051: $^1$H-NMR (499.9 MHz, d$_6$-DMSO):

δ=7.7555 (8.1); 7.6952 (1.7); 7.6841 (1.9); 7.6791 (2.2); 7.6771 (2.2); 7.6678 (2.1); 7.5716 (1.5); 7.5566 (1.8); 7.5516 (2.2); 7.5370 (2.2); 7.5174 (1.6); 7.5115 (7.6); 7.5084 (7.6); 7.4513 (1.5); 7.4349 (3.4); 7.4213 (3.4); 7.4050 (1.6); 7.1504 (8.1); 6.9925 (2.6); 6.9753 (4.7); 6.9577 (2.4); 6.8407 (5.3); 6.8244 (5.0); 6.3958 (8.6); 6.3924 (8.5); 4.2375 (0.8); 4.2245 (2.0); 4.2114 (2.9); 4.1983 (2.1); 4.1852 (0.8); 3.3157 (17.0); 2.8920 (0.8); 2.7331 (0.8); 2.5157 (35.7); 2.5069 (7.6); 2.5034 (9.2); 2.5001 (6.9); 1.3146 (15.3); 1.3015 (15.2); 1.2635 (16.0); 1.2504 (15.8); −0.0002 (6.0)

I-052: $^1$H-NMR (300.2 MHz, CDCl3):

δ=10.0414 (1.4); 7.9952 (2.2); 7.9911 (2.2); 7.5102 (2.4); 7.5024 (2.4); 7.4048 (0.4); 7.3870 (0.5); 7.3822 (0.5); 7.3740 (1.1); 7.3704 (1.2); 7.3561 (1.9); 7.3348 (1.0); 7.3246 (1.2); 7.3183 (1.0); 7.3136 (1.0); 7.2998 (12.8); 7.2904 (2.5); 7.2861 (1.9); 7.2725 (1.4); 7.2536 (0.9); 7.2468 (1.1); 7.2268 (1.2); 7.2193 (0.5); 7.1993 (0.5); 6.8521 (1.5); 6.8442 (1.5); 6.8344 (1.6); 6.8263 (2.0); 6.8201 (0.9); 6.7996 (0.7); 6.7943 (0.8); 6.7876 (0.9); 6.7834 (0.8); 6.7611 (0.7); 6.7568 (0.7); 5.3392 (0.6); 4.0461 (16.0); 2.9193 (14.0); 1.6093 (11.5); 1.2932 (0.3); 0.0497 (0.4); 0.0389 (11.9); 0.0280 (0.4)

I-053: $^1$H-NMR (300.2 MHz, CDCl3):

δ=7.9055 (2.7); 7.9016 (2.7); 7.6571 (3.5); 7.6514 (3.5); 7.4650 (0.6); 7.4599 (0.7); 7.4333 (1.7); 7.4137 (1.4); 7.4085 (1.7); 7.3990 (2.9); 7.3951 (1.9); 7.3805 (2.6); 7.3742 (2.2); 7.3696 (1.7); 7.3594 (1.2); 7.3458 (2.4); 7.3424 (2.3); 7.3273 (1.3); 7.3182 (1.8); 7.2997 (5.9); 7.2817 (0.4); 7.1122 (1.2); 7.1083 (1.1); 7.0875 (1.8); 7.0837 (1.7); 7.0627 (0.9); 7.0587 (0.8); 6.3242 (3.6); 6.3185 (3.6); 5.5725 (2.0); 2.5224 (16.0); 1.6621 (3.6); 1.5885 (0.4); 1.5434 (0.5); 1.5223 (64.4); 1.4952 (0.4); 1.2915 (0.4); 0.0367 (4.7)

I-054: $^1$H-NMR (300.2 MHz, CDCl3):

δ=11.0923 (1.8); 8.8992 (3.2); 8.8904 (3.3); 8.0870 (1.5); 8.0598 (1.7); 8.0126 (2.4); 8.0039 (2.4); 7.7539 (1.4); 7.7428 (1.8); 7.7383 (2.0); 7.7313 (2.0); 7.7261 (1.9); 7.7167 (1.9); 7.7120 (1.9); 7.6457 (0.3); 7.6263 (0.7); 7.6211 (0.9); 7.6034 (1.6); 7.5984 (1.7); 7.5764 (1.6); 7.5705 (1.4); 7.5611 (2.2); 7.5533 (1.7); 7.5338 (3.2); 7.5084 (0.7); 7.5042 (0.6); 7.3456 (1.0); 7.3413 (1.0); 7.3175 (1.9); 7.3000 (55.2); 6.9712 (1.2); 6.9674 (1.3); 6.9447 (2.0); 6.9209 (1.0); 6.9172 (1.0); 2.4475 (15.3); 2.4413 (16.0); 2.0487 (0.3); 1.5912 (24.1); 0.0499 (2.1); 0.0392 (59.9); 0.0283 (2.1)

I-055: $^1$H-NMR (300.2 MHz, CDCl3):

δ=11.2716 (5.6); 8.9104 (10.7); 8.9014 (10.9); 8.0867 (5.0); 8.0594 (5.4); 8.0279 (7.9); 8.0192 (7.8); 7.8416 (5.6); 7.8368 (5.9); 7.8153 (6.1); 7.8105 (6.1); 7.7592 (4.3); 7.7552 (4.1); 7.7330 (5.8); 7.7278 (5.7); 7.6352 (5.8); 7.6324 (6.0); 7.6243 (2.8); 7.6189 (3.1); 7.6072 (7.6); 7.6037 (8.5); 7.5963 (5.4); 7.5915 (2.7); 7.5744 (5.2); 7.5684 (4.2); 7.5592 (5.0); 7.5541 (5.3); 7.5322 (5.1); 7.5283 (4.3); 7.5096 (2.1); 7.5052 (1.9); 7.3890 (3.1); 7.3841 (3.1); 7.3644 (4.1); 7.3604 (5.6); 7.3369 (2.9); 7.3321 (2.8); 7.2980 (16.8); 6.9974 (4.0); 6.9938 (4.1); 6.9708 (6.5); 6.9470 (3.6); 6.9434 (3.3); 6.8929 (16.0); 6.8902 (15.2); 3.2471 (1.2); 3.2241 (3.1); 3.2219 (2.9); 3.2012 (4.2); 3.1990 (4.0); 3.1783 (3.2); 3.1762 (3.0); 3.1554 (1.3); 2.0402 (3.8); 1.7224 (1.4); 1.6524 (0.5); 1.6295 (0.4); 1.4434 (77.1); 1.4205 (75.2); 1.3766 (0.3); 1.2949 (1.3); 1.2311 (0.4); 1.2082 (0.4)

I-056: $^1$H-NMR (300.2 MHz, CDCl3):

δ=9.7449 (4.2); 8.8708 (7.7); 8.8621 (7.8); 8.1069 (3.8); 8.0789 (4.2); 7.9477 (5.7); 7.9393 (5.6); 7.7557 (3.1); 7.7514 (3.3); 7.7290 (4.1); 7.7245 (4.3); 7.6667 (2.1); 7.6617 (2.3); 7.6437 (3.6); 7.6388 (4.5); 7.6338 (2.2); 7.6159 (3.3); 7.6107 (2.8); 7.5667 (3.4); 7.5626 (3.5); 7.5435 (2.6); 7.5397 (4.4); 7.5360 (3.0); 7.5168 (1.8); 7.5128 (1.7); 7.4010 (0.4); 7.3878 (0.3); 7.3716 (0.6); 7.3674 (0.9); 7.3551 (0.6); 7.3428 (1.0); 7.3352 (0.8); 7.3292 (1.1); 7.3144 (1.1); 7.3085 (0.9); 7.2981 (3.4); 7.2887 (0.8); 7.2815 (0.7); 7.2741 (0.6); 7.2654 (0.7); 7.2596 (0.6); 7.2427 (1.8); 7.2227 (2.1); 7.2153 (3.8); 7.1947 (3.4); 7.1883 (3.4); 7.1686 (3.3); 7.1489 (5.5); 7.1450 (7.0); 7.1206 (2.8); 7.1166 (2.7); 7.0903 (0.4); 7.0850 (0.4); 7.0622 (0.4); 6.6496 (2.6); 6.6454 (2.6); 6.6232 (2.5); 6.6190 (2.5); 6.6094 (2.7); 6.6045 (2.6); 6.5836 (2.4); 6.5787 (2.4); 3.4247 (16.0); 3.4096 (16.0); 2.0200 (0.8); 2.0131 (3.3); 1.7397 (0.4); 1.5302 (96.6); 1.4934 (0.3); 1.3168 (0.6); 1.2982 (1.0); 0.9368 (0.4); 0.9151 (1.2); 0.8918 (0.5); 0.0356 (2.1)

I-057: $^1$H-NMR (300.2 MHz, CDCl3):

δ=9.3815 (1.5); 8.0820 (2.4); 8.0778 (2.4); 7.5015 (1.4); 7.4976 (1.5); 7.4826 (1.1); 7.4763 (2.2); 7.4711 (1.8); 7.4554 (2.1); 7.4509 (2.0); 7.4422 (0.3); 7.4273 (1.0); 7.4110 (1.3); 7.4028 (2.0); 7.3856 (1.7); 7.3811 (2.6); 7.3759 (2.8); 7.3641 (1.4); 7.3594 (1.9); 7.3414 (1.4); 7.3367 (1.5); 7.3130 (0.8); 7.3084 (1.7); 7.3031 (1.3); 7.2982 (3.3); 7.2834 (0.9); 7.2783 (1.0); 7.2722 (1.2); 7.2675 (1.1); 7.2470 (0.9); 7.2423 (0.8); 7.0111 (1.0); 7.0059 (1.0); 6.9883 (1.0); 6.9843 (1.4); 6.9799 (1.0); 6.9619 (0.8); 6.9569 (0.8); 4.4646 (1.1); 4.4372 (1.9); 4.4353 (1.8); 4.4076 (1.8); 4.2942 (1.7); 4.2829 (1.8); 4.2672 (1.3); 4.2559 (1.4); 3.9427 (0.6); 3.9314 (0.6);

I-058: ¹H-NMR (300.2 MHz, CDCl3):

δ=9.3543 (1.6); 8.0569 (2.5); 8.0536 (2.5); 7.5002 (1.5); 7.4751 (2.0); 7.4577 (0.7); 7.4526 (0.7); 7.4403 (0.7); 7.4344 (0.7); 7.4272 (1.1); 7.4219 (1.2); 7.4097 (1.1); 7.4041 (1.2); 7.3895 (1.2); 7.3673 (1.3); 7.3575 (1.4); 7.3410 (1.8); 7.3365 (2.7); 7.3315 (2.8); 7.3224 (4.4); 7.3195 (4.2); 7.3037 (1.2); 7.2982 (5.4); 7.0102 (1.0); 7.0007 (0.9); 6.9918 (0.9); 6.9833 (1.3); 6.9733 (0.7); 6.9665 (0.8); 6.9558 (0.7); 4.4661 (1.2); 4.4386 (2.0); 4.4090 (1.8); 4.2990 (1.8); 4.2878 (1.9); 4.2720 (1.3); 4.2607 (1.4); 3.9450 (0.6); 3.9338 (0.6); 3.9214 (0.6); 3.9150 (0.6); 3.9102 (0.7); 3.9039 (0.5); 3.8913 (0.6); 3.8802 (0.5); 2.8266 (16.0); 1.6582 (5.3); 1.4348 (8.6); 1.4111 (8.5); 1.3393 (0.4); 1.3024 (1.6); 0.9396 (0.6); 0.9177 (2.0); 0.8944 (0.7); 0.0362 (4.5)

I-059: ¹H-NMR (300.2 MHz, CDCl3):

δ=9.4364 (8.1); 8.9015 (15.8); 8.8928 (16.0); 8.8713 (0.4); 8.1075 (7.9); 8.0796 (8.7); 7.9884 (12.1); 7.9799 (11.8); 7.8141 (0.4); 7.7648 (6.8); 7.7608 (7.0); 7.7382 (8.9); 7.7335 (9.1); 7.6605 (4.3); 7.6554 (4.7); 7.6374 (7.8); 7.6325 (9.2); 7.6275 (4.6); 7.6098 (7.2); 7.6045 (6.0); 7.5702 (7.2); 7.5659 (7.5); 7.5469 (5.5); 7.5431 (9.1); 7.5394 (6.5); 7.5203 (3.9); 7.5163 (3.7); 7.4829 (9.0); 7.4772 (13.9); 7.4726 (9.2); 7.4567 (10.1); 7.4483 (14.0); 7.4447 (12.4); 7.4030 (0.4); 7.3506 (5.3); 7.3462 (5.2); 7.3263 (6.8); 7.3225 (8.5); 7.2982 (29.4); 7.2522 (0.3); 7.1869 (0.3); 6.9882 (6.2); 6.9843 (6.3); 6.9615 (9.1); 6.9472 (0.8); 6.9381 (4.9); 6.9341 (4.8); 4.4585 (6.7); 4.4312 (11.9); 4.4018 (10.6); 4.3017 (10.7); 4.2907 (11.4); 4.2747 (7.7); 4.2637 (7.9); 3.9606 (1.0); 3.9496 (1.1); 3.9369 (3.3); 3.9259 (3.6); 3.9132 (3.7); 3.9070 (3.8); 3.9023 (4.0); 3.8961 (3.2); 3.8895 (1.7); 3.8833 (3.5); 3.8724 (2.9); 3.8598 (1.0); 3.8489 (0.9); 2.6763 (0.4); 2.1704 (0.4); 2.0401 (1.3); 1.7174 (5.6); 1.6492 (0.4); 1.6250 (0.4); 1.4836 (0.4); 1.4368 (50.2); 1.4131 (49.4); 1.3590 (0.8); 1.3360 (0.9); 1.2910 (0.6); 0.0482 (0.9); 0.0375 (23.1); 0.0266 (0.9)

I-060: ¹H-NMR (601.6 MHz, d₆-DMSO):

δ=9.2402 (1.7); 8.1238 (1.8); 7.8082 (0.3); 7.8116 (0.3); 7.7951 (0.3); 7.7456 (0.4); 7.7364 (0.4); 7.7318 (0.5); 7.7229 (0.4); 7.6226 (0.5); 7.6066 (0.5); 7.5944 (0.5); 7.4758 (0.4); 7.4640 (0.6); 7.3823 (0.3); 7.3727 (0.7); 7.3687 (0.8); 7.3578 (0.8); 7.3460 (0.5); 7.0761 (1.2); 7.0622 (1.0); 6.8591 (0.5); 6.8455 (0.6); 6.8397 (0.6); 6.8260 (0.5); 3.9009 (2.8); 3.3250 (0.3); 3.3060 (44.0); 2.6376 (7.8); 2.6152 (0.4); 2.6124 (0.6); 2.5215 (1.2); 2.5184 (1.5); 2.5152 (1.8); 2.5035 (70.6); 2.5006 (91.2); 2.4977 (68.5); 2.3848 (0.5); 1.3464 (16.0); 0.0051 (1.0); −0.0002 (21.0)

I-061: ¹H-NMR (499.9 MHz, d₆-DMSO):

δ=7.9417 (0.7); 7.9335 (0.7); 7.9311 (0.8); 7.9254 (0.8); 7.9229 (0.9); 7.9147 (0.8); 7.6947 (0.6); 7.6796 (0.7); 7.6751 (1.0); 7.6603 (1.0); 7.6559 (0.6); 7.6407 (0.5); 7.6154 (3.7); 7.6117 (3.8); 7.1834 (0.6); 7.1669 (1.4); 7.1531 (1.4); 7.1367 (0.7); 6.9605 (2.9); 6.6494 (1.0); 6.6320 (1.8); 6.6150 (1.0); 6.4892 (2.9); 6.4857 (2.9); 5.8744 (1.4); 5.8578 (1.4); 3.7580 (16.0); 3.3378 (1.4); 2.8974 (1.1); 2.7385 (1.0); 2.5091 (14.5); 2.4924 (14.4); −0.0002 (0.4)

I-062: ¹H-NMR (400.2 MHz, CDCl3):

δ=8.7713 (3.0); 8.2677 (3.6); 8.0217 (2.4); 8.0037 (2.5); 7.8493 (3.3); 7.8415 (5.1); 7.8352 (3.5); 7.8089 (0.7); 7.7747 (4.8); 7.6589 (2.4); 7.6416 (2.8); 7.6092 (0.7); 7.5585 (1.8); 7.5545 (1.8); 7.5411 (3.3); 7.5327 (3.9); 7.5268 (4.3); 7.5123 (3.7); 7.5069 (3.6); 7.4943 (2.6); 7.4888 (2.6); 7.4741 (2.8); 7.4574 (1.5); 7.4517 (1.4); 7.4065 (2.6); 7.4020 (2.6); 7.3867 (2.9); 7.3823 (2.9); 7.3509 (1.7); 7.3467 (1.7); 7.3283 (2.6); 7.3122 (1.5); 7.3080 (1.5); 7.2809 (1.0); 7.2724 (1.0); 7.0618 (1.8); 7.0566 (1.9); 7.0425 (2.8); 7.0378 (2.8); 7.0191 (4.3); 7.0136 (5.4); 7.0053 (3.4); 3.9830 (15.0); 3.9746 (16.0); 1.9968 (0.6); 1.9883 (0.6)

I-063: ¹H-NMR (300.1 MHz, CDCl3):

δ=8.5962 (0.6); 8.5868 (0.6); 8.5717 (0.4); 8.5462 (7.2); 8.5375 (7.2); 8.0008 (4.8); 7.9733 (5.3); 7.7534 (0.8); 7.7476 (0.7); 7.7403 (0.5); 7.7339 (0.5); 7.7015 (0.9); 7.6757 (15.6); 7.6698 (16.0); 7.6166 (4.0); 7.6124 (4.2); 7.5901 (5.7); 7.5855 (6.0); 7.5531 (2.4); 7.5479 (2.6); 7.5301 (5.1); 7.5252 (5.0); 7.5203 (2.7); 7.5029 (4.8); 7.4972 (3.9); 7.4811 (9.5); 7.4761 (5.9); 7.4555 (11.3); 7.4304 (10.1); 7.4249 (12.3); 7.4027 (5.4); 7.3981 (4.8); 7.3753 (2.0); 7.3709 (1.6); 7.2611 (92.1); 7.2244 (0.4); 7.1195 (3.4); 7.1126 (3.5); 7.0969 (3.4); 7.0933 (4.0); 7.0903 (4.1); 7.0872 (3.9); 7.0708 (2.6); 7.0642 (2.6); 6.9098 (0.7); 6.5143 (0.6); 6.5082 (0.7); 6.4985 (0.4); 6.3903 (11.7); 6.3839 (11.5); 6.2296 (3.4); 4.6737 (2.2); 3.4868 (0.7); 2.4698 (0.5); 2.3609 (0.5); 2.3266 (0.5); 2.0950 (1.1); 2.0198 (0.7); 2.0072 (1.8); 1.9694 (0.6); 1.8069 (0.3); 1.7393 (0.6); 1.6321 (0.3); 1.5792 (0.9); 1.5662 (0.7); 1.5493 (2.3); 1.5288 (106.8); 1.4757 (0.7); 1.3149 (0.5); 1.2529 (0.4); 0.0107 (2.6); −0.0002 (79.8); −0.0112 (2.9); −0.1987 (0.4)

I-064: ¹H-NMR (300.1 MHz, d₆-DMSO):

δ=8.5711 (1.5); 8.5630 (1.5); 8.0740 (1.0); 7.8631 (0.7); 7.8327 (0.9); 7.7031 (3.7); 7.6965 (3.8); 7.6859 (0.8); 7.6643 (0.8); 7.6556 (0.8); 7.5100 (0.7); 7.4879 (2.8); 7.4834 (2.3); 7.4757 (2.0); 7.4624 (4.3); 7.4363 (1.7); 7.4244 (2.4); 7.4201 (2.0); 7.3967 (1.7); 7.3056 (0.4); 7.2553 (0.8); 7.2484 (0.8); 7.2331 (0.8); 7.2274 (1.0); 7.2219 (0.7); 7.2077 (0.5); 7.2001 (0.5); 6.8647 (3.6); 6.8582 (3.5); 3.6626 (0.4); 3.5871 (16.0); 3.3897 (0.4); 2.5133 (6.5); 2.5074 (12.7); 2.5014 (16.8); 2.4955 (11.6); 2.4898 (5.4); 2.0742 (0.8); 0.0108 (0.4); 0.0000 (10.9); −0.0111 (0.4)

I-065: ¹H-NMR (300.2 MHz, CDCl3):

δ=8.6037 (2.0); 8.5970 (2.0); 8.0924 (1.4); 8.0647 (1.7); 7.7334 (1.3); 7.7199 (0.9); 7.7065 (2.0); 7.6963 (1.5); 7.6920 (1.2); 7.6688 (1.0); 7.6642 (0.7); 7.5918 (2.8); 7.5857 (2.8); 7.5700 (1.2); 7.5440 (1.6); 7.5195 (2.7); 7.4795 (1.1); 7.4754 (1.0); 7.4563 (3.1); 7.4538 (3.2); 7.4490 (2.6); 7.4306 (0.7); 7.4184 (1.0); 7.4109 (0.6); 7.3934 (1.3); 7.3860 (1.0); 7.3717 (0.7); 7.3641 (0.6); 7.3052 (6.0); 7.2978 (2.0); 7.2726 (1.2); 6.2319 (3.0); 6.2257 (2.9); 4.0884 (6.8); 3.3884 (16.0); 1.7851 (2.2); 0.0419 (3.2)

I-066: ¹H-NMR (300.1 MHz, d₆-DMSO):

δ=8.6237 (3.7); 8.6149 (3.8); 7.8535 (2.0); 7.8343 (6.0); 7.7088 (1.9); 7.7031 (1.4); 7.6937 (1.4); 7.6862 (1.7); 7.6771 (2.3); 7.6045 (5.8); 7.5984 (5.8); 7.5426 (3.8); 7.5343 (3.8); 7.4917 (1.4); 7.4839 (1.5); 7.4765 (3.0); 7.4692 (5.2); 7.4573 (10.3); 7.4443 (4.4); 7.4383 (4.5); 7.4228 (0.9); 7.4107 (0.8); 7.4058 (0.8); 7.3427 (2.4); 7.3177 (3.3); 7.3138 (2.9); 7.1850 (1.6); 7.1780 (1.6); 7.1629 (1.6); 7.1573 (2.1); 7.1366 (1.0); 7.1303 (1.0); 6.3901 (5.7); 6.3841 (5.6); 4.9899 (3.0); 4.9753 (4.2); 4.9708 (3.0); 4.7220 (4.7); 3.4067 (1.2); 2.5081 (14.7); 2.5025 (19.0); 2.4970 (13.9); 1.7869 (16.0); 1.5506 (0.9); 1.2333 (0.3); 0.0000 (9.9); −0.0109 (0.4)

Beginning of page (continuation of I-057):

3.9190 (0.6); 3.9125 (0.6); 3.9078 (0.7); 3.9013 (0.5); 3.8889 (0.6); 3.8776 (0.5); 2.8316 (16.0); 2.0390 (1.8); 1.7253 (2.8); 1.4323 (8.3); 1.4086 (8.3); 1.3015 (0.6); 0.9173 (0.6); 0.0362 (2.3)

I-067: $^1$H-NMR (300.2 MHz, CDCl3):

δ=8.5207 (2.4); 8.5134 (2.4); 8.2792 (1.5); 8.0974 (1.3); 8.0701 (1.5); 7.7176 (1.3); 7.7129 (1.1); 7.7076 (0.7); 7.6887 (2.8); 7.6796 (0.8); 7.6612 (1.0); 7.6563 (0.7); 7.5794 (1.9); 7.5752 (2.0); 7.5685 (1.6); 7.5644 (1.2); 7.5420 (1.5); 7.5177 (0.6); 7.5144 (0.6); 7.4081 (0.5); 7.3930 (2.0); 7.3878 (2.0); 7.3848 (2.3); 7.3714 (2.0); 7.3661 (1.8); 7.3525 (1.2); 7.3482 (1.0); 7.3419 (1.2); 7.3288 (1.3); 7.3206 (1.0); 7.3044 (8.2); 7.1518 (1.5); 7.1299 (1.2); 7.1243 (1.0); 5.3411 (0.4); 4.0203 (6.6); 3.7111 (15.4); 2.8932 (0.3); 2.8759 (0.3); 2.0642 (15.0); 1.6853 (16.0); 1.2955 (0.4); 0.0412 (5.4)

I-068: $^1$H-NMR (300.2 MHz, CDCl3):

δ=8.6421 (2.3); 8.6349 (2.4); 8.2564 (1.4); 8.1235 (1.3); 8.0957 (1.6); 7.7437 (1.3); 7.7308 (0.9); 7.7256 (0.9); 7.7172 (2.0); 7.7073 (1.5); 7.7027 (1.3); 7.6980 (0.8); 7.6797 (3.0); 7.6755 (2.6); 7.5791 (1.2); 7.5755 (1.1); 7.5526 (1.6); 7.5290 (0.6); 7.5255 (0.6); 7.3651 (0.6); 7.3603 (0.7); 7.3470 (4.2); 7.3362 (3.0); 7.3298 (4.6); 7.3158 (1.5); 7.3040 (12.6); 7.2878 (0.5); 7.2792 (1.3); 7.2739 (1.4); 7.2653 (0.7); 7.2584 (1.0); 7.2501 (0.7); 7.0444 (4.4); 4.1399 (6.8); 3.8414 (16.0); 2.4329 (0.5); 2.1350 (15.4); 1.2958 (0.4); 0.0524 (0.4); 0.0417 (8.6)

I-069: $^1$H-NMR (300.1 MHz, d$_6$-DMSO):

δ=8.6203 (0.9); 8.6112 (0.9); 7.9387 (0.9); 7.8191 (0.4); 7.6572 (0.4); 7.5834 (1.0); 7.5774 (1.0); 7.5674 (0.6); 7.5588 (0.6); 7.4978 (0.7); 7.4923 (0.7); 7.4754 (0.7); 7.4680 (0.9); 7.4554 (1.2); 7.4497 (0.6); 7.4429 (0.8); 7.4368 (0.4); 7.4216 (0.7); 7.4175 (0.5); 7.3952 (0.6); 7.3907 (0.4); 7.1614 (0.4); 6.3075 (0.9); 6.3016 (0.9); 4.5932 (2.3); 3.3177 (45.7); 2.5123 (4.0); 2.5063 (8.1); 2.5003 (10.8); 2.4943 (7.4); 2.4885 (3.3); 0.7349 (1.0); 0.7256 (16.0); 0.7162 (0.9); −0.0009 (6.0); −0.1166 (0.5); −0.1268 (12.7); −0.1372 (0.5)

I-070: $^1$H-NMR (300.1 MHz, d$_6$-DMSO):

δ=8.6468 (3.5); 8.6377 (3.5); 7.8580 (1.3); 7.8494 (1.2); 7.8364 (0.8); 7.8262 (1.6); 7.7351 (1.4); 7.7297 (1.2); 7.7127 (5.0); 7.7039 (2.2); 7.6911 (0.4); 7.6452 (2.7); 7.6366 (2.6); 7.5629 (3.5); 7.5575 (3.5); 7.5349 (0.7); 7.5296 (1.0); 7.5080 (3.1); 7.5021 (3.3); 7.4962 (2.0); 7.4912 (2.0); 7.4859 (2.3); 7.4755 (3.2); 7.4648 (4.4); 7.4525 (2.6); 7.4447 (2.0); 7.4278 (0.5); 7.3695 (1.6); 7.3658 (1.6); 7.3438 (2.3); 7.3394 (2.0); 7.1999 (1.2); 7.1938 (1.2); 7.1767 (1.3); 7.1734 (1.5); 7.1714 (1.5); 7.1508 (0.8); 7.1450 (0.8); 6.1907 (3.6); 6.1850 (3.6); 3.3403 (6.4); 2.8931 (0.4); 2.8704 (0.9); 2.8476 (1.3); 2.8248 (1.0); 2.8022 (0.4); 2.5099 (6.8); 2.5041 (8.9); 2.4983 (6.2); 1.5503 (1.0); 1.0173 (16.0); 0.9945 (15.6); −0.0002 (6.0)

I-071: $^1$H-NMR (300.2 MHz, CDCl3):

δ=8.6451 (9.4); 8.6379 (9.6); 8.0938 (5.7); 8.0661 (6.7); 7.7312 (5.7); 7.7149 (4.4); 7.7094 (7.8); 7.7051 (8.5); 7.6916 (6.5); 7.6869 (6.3); 7.6820 (3.5); 7.6632 (11.1); 7.6591 (11.9); 7.6235 (11.4); 7.6184 (11.5); 7.5626 (5.1); 7.5588 (5.3); 7.5359 (7.3); 7.5126 (3.0); 7.5089 (2.9); 7.4868 (1.8); 7.4816 (2.0); 7.4624 (6.4); 7.4548 (2.9); 7.4507 (2.1); 7.4379 (6.6); 7.4324 (6.8); 7.4173 (2.7); 7.4116 (5.2); 7.3885 (16.8); 7.3624 (6.5); 7.3134 (5.7); 7.3081 (9.0); 7.2986 (31.4); 7.2909 (3.7); 7.2869 (3.8); 7.2825 (4.9); 6.1587 (16.0); 6.1527 (16.0); 5.3353 (3.5); 4.2194 (0.3); 4.1980 (1.8); 4.1761 (4.4); 4.1540 (6.1); 4.1319 (5.0); 4.1098 (3.0); 4.0708 (3.6); 1.7640 (1.8); 1.3301 (6.3); 0.0471 (0.9); 0.0363 (29.3); 0.0254 (1.1)

I-072: $^1$H-NMR (300.2 MHz, CDCl3):

δ=8.6124 (4.1); 8.6050 (4.1); 8.0802 (2.2); 8.0528 (2.6); 8.0514 (2.6); 7.7145 (2.2); 7.6976 (1.9); 7.6922 (3.2); 7.6883 (3.3); 7.6744 (2.5); 7.6696 (2.4); 7.6648 (1.4); 7.6466 (1.9); 7.6417 (1.4); 7.6021 (5.5); 7.5960 (5.5); 7.5468 (5.2); 7.5430 (5.2); 7.5203 (2.9); 7.5167 (1.8); 7.4970 (1.2); 7.4933 (1.2); 7.4799 (0.7); 7.4750 (0.7); 7.4537 (1.9); 7.4494 (1.8); 7.4318 (3.0); 7.4267 (3.2); 7.4170 (2.6); 7.4120 (4.0); 7.3957 (2.4); 7.3915 (2.0); 7.3716 (2.6); 7.3653 (2.0); 7.3489 (1.4); 7.3425 (1.3); 7.2983 (3.9); 7.2930 (3.0); 7.2716 (1.7); 7.2682 (1.6); 6.1861 (5.9); 6.1800 (5.9); 4.0574 (9.2); 3.7234 (2.3); 3.6993 (7.2); 3.6752 (7.4); 3.6512 (2.4); 2.0168 (1.1); 1.2859 (0.4); 1.2348 (7.7); 1.2108 (16.0); 1.1866 (7.4); 0.0291 (1.3)

I-073: $^1$H-NMR (300.2 MHz, CDCl3):

δ=8.4621 (2.0); 8.4547 (2.0); 8.0429 (1.0); 8.0152 (1.3); 8.0127 (1.2); 7.6769 (1.1); 7.6724 (1.0); 7.6672 (0.6); 7.6513 (2.0); 7.6482 (2.5); 7.6392 (0.7); 7.6210 (0.9); 7.6160 (0.6); 7.5219 (1.0); 7.5181 (1.0); 7.4955 (2.2); 7.4912 (2.4); 7.4795 (2.2); 7.4727 (3.2); 7.4689 (2.2); 7.4505 (1.3); 7.4456 (1.3); 7.4251 (0.5); 7.4202 (0.5); 7.3709 (0.6); 7.3642 (0.5); 7.3458 (1.1); 7.3398 (1.0); 7.3229 (0.7); 7.3166 (0.7); 7.2985 (1.2); 7.2702 (1.5); 7.2461 (0.9); 7.2423 (0.8); 7.2276 (2.9); 7.2235 (2.9); 6.7975 (2.8); 6.7935 (2.7); 4.2688 (5.8); 2.8878 (16.0); 0.0263 (1.0)

I-074: $^1$H-NMR (300.2 MHz, CDCl3):

δ=8.5865 (4.2); 8.5791 (4.2); 8.0677 (8.6); 8.0491 (2.3); 8.0215 (2.7); 8.0193 (2.6); 7.6848 (2.5); 7.6802 (2.2); 7.6749 (1.4); 7.6592 (4.3); 7.6560 (5.2); 7.6470 (1.5); 7.6287 (1.9); 7.6237 (1.3); 7.5455 (3.5); 7.5400 (3.9); 7.5303 (2.5); 7.5264 (2.4); 7.5134 (2.5); 7.5082 (2.9); 7.5048 (3.2); 7.4998 (2.1); 7.4907 (3.3); 7.4859 (4.0); 7.4808 (4.2); 7.4761 (4.9); 7.4560 (1.3); 7.4510 (0.8); 7.4220 (1.4); 7.4158 (1.2); 7.3970 (2.3); 7.3907 (2.0); 7.3742 (1.3); 7.3678 (1.3); 7.3041 (3.0); 7.2988 (4.0); 7.2785 (1.9); 7.2763 (1.9); 4.2292 (11.8); 3.6498 (2.2); 3.6256 (7.0); 3.6014 (7.1); 3.5773 (2.3); 1.2763 (0.7); 1.0964 (7.7); 1.0722 (16.0); 1.0480 (7.4); 0.0192 (1.4)

I-075: $^1$H-NMR (300.1 MHz, d$_6$-DMSO):

δ=8.7964 (0.9); 8.7876 (1.0); 8.0139 (0.4); 8.0090 (0.4); 7.9841 (0.5); 7.9433 (1.1); 7.8939 (0.8); 7.8854 (1.1); 7.8601 (0.5); 7.8536 (0.5); 7.7572 (1.1); 7.7514 (1.1); 7.6578 (0.5); 7.6520 (0.4); 7.6331 (0.7); 7.6289 (0.6); 7.6091 (0.5); 7.6057 (0.5); 7.5868 (0.4); 7.5807 (0.5); 7.5590 (0.4); 7.3982 (0.6); 7.3702 (0.5); 7.1021 (0.5); 6.4934 (1.0); 6.4877 (1.0); 4.6946 (1.2); 4.6865 (1.2); 3.4494 (1.2); 2.6342 (0.9); 2.6285 (1.8); 2.6227 (2.3); 2.6170 (1.6); 0.8942 (1.6); 0.8499 (16.0); 0.1189 (1.3); 0.0000 (8.5)

I-076: $^1$H-NMR (300.1 MHz, d$_6$-DMSO):

δ=8.7185 (0.4); 8.7044 (6.6); 8.6956 (6.6); 8.1350 (0.6); 7.9009 (3.1); 7.8726 (8.9); 7.8636 (5.1); 7.8228 (2.9); 7.8189 (2.7); 7.7974 (3.7); 7.7914 (3.5); 7.6992 (6.4); 7.6420 (6.8); 7.6363 (6.8); 7.5795 (1.3); 7.5739 (1.6); 7.5565 (3.3); 7.5511 (2.8); 7.5305 (4.2); 7.5276 (4.3); 7.5227 (4.5); 7.5016 (3.8); 7.4967 (3.1); 7.4747 (3.8); 7.4532 (3.0); 7.4471 (2.0); 7.4255 (1.7); 7.2802 (4.2); 7.2522 (3.2); 7.0255 (2.1); 7.0222 (2.0); 6.9942 (3.8); 6.9664 (2.0); 6.9629 (1.7); 6.2692 (7.0); 6.2633 (6.9); 3.3761 (2.1); 3.2539 (0.4); 2.7410 (0.8); 2.7345 (0.7); 2.7279 (1.0); 2.7203 (2.0); 2.6968 (2.3); 2.6738 (1.8); 2.6514 (0.7); 2.5414 (0.6); 2.5139 (41.2); 2.5081 (81.1); 2.5022 (106.8); 2.4963 (73.6); 2.4908 (33.9); 2.2781 (0.5); 2.2720 (0.6); 2.2660 (0.4); 1.5515 (1.3); 1.1137 (15.4); 1.0909 (14.9); 1.0406 (16.0); 1.0178 (15.5); 0.0108 (0.4); −0.0001 (12.2); −0.0112 (0.4)

I-077: $^1$H-NMR (300.1 MHz, d$_6$-DMSO):

δ=8.6988 (4.5); 8.6899 (4.6); 7.9209 (5.9); 7.9137 (3.7); 7.8951 (2.6); 7.8540 (2.0); 7.8499 (1.8); 7.8286 (2.7);

7.8225 (2.3); 7.6462 (0.4); 7.6426 (0.4); 7.6224 (6.7); 7.6163 (6.6); 7.5961 (1.0); 7.5904 (1.1); 7.5730 (2.3); 7.5674 (2.1); 7.5473 (4.1); 7.5405 (4.0); 7.5164 (2.0); 7.4980 (0.9); 7.4932 (0.7); 7.4740 (0.9); 7.4524 (1.1); 7.4461 (2.1); 7.4248 (2.2); 7.4186 (1.5); 7.3971 (1.4); 7.3658 (4.5); 7.2832 (3.2); 7.2553 (2.3); 6.9628 (1.5); 6.9594 (1.5); 6.9318 (2.8); 6.9043 (1.4); 6.9007 (1.3); 6.4033 (6.6); 6.3972 (6.4); 5.7591 (1.4); 2.5135 (17.0); 2.5076 (33.0); 2.5017 (43.1); 2.4958 (29.1); 2.4901 (13.0); 2.4545 (0.5); 1.5534 (0.4); 1.5346 (0.5); 1.4783 (16.0); 1.3924 (0.7); 1.3169 (16.0); 1.2346 (0.3); 0.0108 (1.1); −0.0001 (26.7); −0.0112 (0.8)

I-078: $^1$H-NMR (300.1 MHz, d$_6$-DMSO):
δ=8.6295 (2.4); 8.6207 (2.4); 8.0815 (2.1); 7.8850 (1.0); 7.8795 (1.1); 7.8538 (1.3); 7.8170 (3.6); 7.8104 (3.6); 7.7452 (1.0); 7.7409 (0.9); 7.7362 (0.7); 7.7206 (1.3); 7.7136 (1.3); 7.6896 (1.8); 7.6817 (1.7); 7.5562 (0.4); 7.5502 (0.6); 7.5333 (1.3); 7.5273 (1.1); 7.5143 (1.4); 7.5085 (2.6); 7.5006 (1.2); 7.4881 (1.5); 7.4827 (1.9); 7.4597 (1.4); 7.4536 (0.8); 7.4318 (0.7); 7.2796 (1.6); 7.2517 (1.2); 7.0397 (0.8); 7.0364 (0.8); 7.0099 (4.7); 7.0035 (4.4); 6.9801 (0.8); 6.9768 (0.7); 3.7617 (0.6); 3.7255 (16.0); 3.6814 (0.3); 2.5141 (12.4); 2.5083 (24.0); 2.5024 (31.4); 2.4966 (21.7); −0.0001 (2.6)

I-079: $^1$H-NMR (300.1 MHz, d$_6$-DMSO):
δ=8.6974 (5.1); 8.6885 (5.2); 7.8988 (2.4); 7.8808 (6.3); 7.8273 (4.0); 7.8183 (4.2); 7.8094 (2.1); 7.7877 (2.8); 7.7816 (2.5); 7.7122 (6.6); 7.7059 (6.6); 7.5729 (0.9); 7.5672 (1.2); 7.5500 (2.5); 7.5444 (2.2); 7.5244 (4.7); 7.5175 (4.4); 7.4979 (2.1); 7.4933 (2.2); 7.4749 (1.0); 7.4678 (1.2); 7.4453 (1.2); 7.4393 (2.2); 7.4178 (2.3); 7.4117 (1.6); 7.3902 (1.4); 7.2675 (3.3); 7.2395 (2.5); 6.9760 (1.6); 6.9727 (1.6); 6.9448 (2.9); 6.9170 (1.5); 6.9134 (1.4); 6.5208 (6.3); 6.5145 (6.2); 5.0560 (3.1); 5.0512 (4.5); 5.0466 (3.1); 4.7913 (4.9); 3.3311 (21.8); 2.7281 (0.3); 2.5137 (21.0); 2.5080 (41.2); 2.5022 (54.0); 2.4964 (37.3); 2.2719 (0.3); 1.9139 (16.0); 0.0108 (1.4); −0.0001 (36.8); −0.0111 (1.2)

I-080: $^1$H-NMR (400.0 MHz, d$_6$-DMSO):
δ=8.6773 (5.0); 8.6709 (5.2); 8.1349 (5.7); 7.9549 (0.5); 7.5167 (2.9); 7.4909 (11.0); 7.4889 (10.9); 7.4797 (6.5); 7.4759 (4.0); 7.4586 (0.4); 7.4550 (0.5); 7.4179 (7.1); 7.4136 (8.2); 7.4015 (1.7); 7.3946 (2.3); 7.3817 (2.3); 7.3745 (1.4); 7.3623 (4.2); 7.3440 (3.8); 7.2513 (1.8); 7.2396 (3.8); 7.2305 (2.4); 7.2228 (2.6); 7.2195 (3.0); 7.2110 (3.2); 7.1942 (1.5); 7.1919 (1.6); 6.2997 (7.2); 6.2953 (7.2); 3.9429 (2.1); 3.9249 (7.0); 3.9069 (7.1); 3.8889 (2.2); 3.3500 (63.0); 3.3473 (58.1); 3.3450 (54.9); 2.8923 (3.2); 2.7340 (2.9); 2.5279 (0.5); 2.5145 (13.1); 2.5103 (27.6); 2.5058 (37.1); 2.5013 (26.9); 2.4970 (13.2); 1.2251 (0.4); 1.2102 (7.5); 1.1923 (16.0); 1.1743 (7.3); −0.0002 (1.4)

I-081: $^1$H-NMR (300.2 MHz, CDCl3):
δ=8.7386 (3.4); 8.7299 (3.4); 7.8543 (2.0); 7.8485 (2.4); 7.8407 (1.9); 7.7004 (4.4); 7.6941 (4.4); 7.5158 (0.7); 7.4998 (4.2); 7.4954 (2.5); 7.4883 (4.3); 7.4818 (2.3); 7.4679 (1.8); 7.4540 (0.3); 7.4381 (0.9); 7.4162 (0.8); 7.4099 (1.8); 7.3886 (1.8); 7.3823 (1.2); 7.3610 (1.1); 7.3340 (1.2); 7.3223 (1.0); 7.3159 (0.9); 7.3035 (1.4); 7.2984 (11.0); 7.2918 (1.4); 7.2760 (1.0); 7.2688 (1.0); 7.2500 (2.8); 7.2223 (2.0); 6.8842 (1.3); 6.8812 (1.3); 6.8542 (2.3); 6.8271 (1.2); 6.8240 (1.1); 6.4795 (5.0); 6.4732 (4.9); 6.0280 (2.2); 5.3353 (1.6); 3.8306 (16.0); 3.8275 (15.6); 1.6500 (9.6); 0.0353 (9.2); 0.0244 (0.3)

I-082: $^1$H-NMR (300.2 MHz, d$_6$-DMSO):
δ=8.7518 (3.2); 8.7433 (3.3); 8.2073 (3.8); 7.7380 (1.9); 7.7315 (2.4); 7.7248 (1.8); 7.6924 (0.5); 7.6737 (0.6); 7.6690 (0.6); 7.6578 (1.6); 7.6425 (2.5); 7.6204 (1.2); 7.6095 (1.3); 7.5863 (1.1); 7.5788 (0.5); 7.5553 (0.5); 7.5469 (0.8); 7.5244 (1.0); 7.5194 (1.8); 7.4971 (1.8); 7.4920 (1.2); 7.4697 (1.0); 7.4340 (4.9); 7.4277 (5.0); 7.3028 (2.5); 7.2755 (2.0); 7.0929 (1.2); 7.0902 (1.2); 7.0621 (2.2); 7.0342 (1.1); 7.0314 (1.1); 6.3554 (4.8); 6.3490 (4.8); 5.7784 (4.5); 3.6647 (15.8); 3.3490 (16.0); 2.5340 (1.8); 2.5280 (4.0); 2.5219 (5.5); 2.5158 (3.9); 2.5099 (1.8); 0.0177 (5.7)

I-083: $^1$H-NMR (300.2 MHz, d$_6$-DMSO):
δ=8.3722 (2.4); 7.8167 (1.3); 7.7900 (1.8); 7.7617 (1.2); 7.7352 (1.4); 7.7321 (1.4); 7.6635 (0.8); 7.6415 (0.9); 7.6360 (1.3); 7.6141 (1.3); 7.6088 (0.8); 7.5962 (0.5); 7.5896 (0.8); 7.5868 (0.8); 7.5686 (1.9); 7.5620 (2.6); 7.5568 (1.3); 7.5398 (1.4); 7.5350 (1.3); 7.5122 (0.5); 7.5074 (0.5); 7.4462 (1.0); 7.4396 (1.0); 7.4248 (0.8); 7.4188 (1.4); 7.4129 (0.9); 7.3976 (0.7); 7.3912 (0.6); 7.2920 (3.6); 7.2857 (4.3); 7.2546 (1.5); 7.2512 (1.0); 7.2265 (0.8); 7.2232 (0.7); 6.3403 (3.6); 6.3339 (3.6); 5.7789 (0.4); 3.7021 (8.6); 3.6979 (8.5); 3.6426 (0.4); 3.3452 (16.0); 2.5344 (2.1); 2.5283 (4.5); 2.5219 (7.3); 2.5166 (17.0); 0.0204 (5.2)

I-084: $^1$H-NMR (300.2 MHz, d$_6$-DMSO):
δ=8.6753 (2.5); 7.6807 (0.3); 7.6749 (0.8); 7.6704 (0.7); 7.6577 (2.9); 7.6542 (1.9); 7.6480 (2.8); 7.6423 (2.1); 7.6360 (2.0); 7.6160 (1.3); 7.6116 (1.0); 7.6041 (0.8); 7.5893 (0.5); 7.5764 (0.6); 7.4344 (0.7); 7.4277 (0.8); 7.4178 (0.8); 7.4111 (0.8); 7.4032 (0.6); 7.3964 (0.6); 7.3865 (0.6); 7.3799 (0.5); 7.3260 (0.8); 7.3161 (0.7); 7.3042 (0.6); 7.2943 (1.4); 7.2886 (0.9); 7.2682 (0.8); 7.2626 (0.8); 7.2547 (3.6); 7.2484 (3.6); 6.2885 (3.7); 6.2822 (3.6); 5.7778 (0.6); 3.6876 (8.3); 3.6832 (8.3); 3.3436 (16.0); 2.5742 (12.5); 2.5342 (1.8); 2.5282 (3.7); 2.5221 (5.1); 2.5160 (3.7); 2.5100 (1.7); 0.0194 (5.3)

I-085: $^1$H-NMR (300.2 MHz, CDCl3):
δ=9.0273 (6.9); 8.1592 (1.6); 8.1550 (1.3); 8.1499 (1.1); 8.1348 (2.1); 8.1280 (1.8); 8.1266 (1.8); 8.1185 (1.5); 8.1113 (1.9); 8.0954 (1.1); 8.0902 (1.4); 8.0867 (1.8); 7.7309 (0.7); 7.7248 (1.1); 7.7175 (4.5); 7.7111 (4.8); 7.7081 (2.8); 7.7019 (1.9); 7.6913 (2.1); 7.6836 (3.8); 7.6751 (1.9); 7.6646 (1.6); 7.6592 (1.8); 7.6415 (0.7); 7.6361 (0.5); 7.3987 (0.8); 7.3772 (0.9); 7.3710 (1.8); 7.3497 (1.8); 7.3435 (1.1); 7.3222 (1.0); 7.2986 (13.1); 7.0689 (2.6); 7.0413 (2.2); 6.8837 (1.4); 6.8808 (1.3); 6.8538 (2.3); 6.8265 (1.2); 6.8236 (1.2); 6.5537 (4.9); 6.5473 (4.8); 6.1903 (2.1); 5.3368 (0.4); 3.8657 (16.0); 3.8627 (15.8); 1.6368 (7.2); 0.0480 (0.5); 0.0372 (14.4); 0.0262 (0.5)

I-086: $^1$H-NMR (300.2 MHz, CDCl3):
δ=8.7803 (4.7); 8.1405 (1.3); 8.1375 (1.4); 8.1124 (1.5); 8.1099 (1.5); 8.0417 (1.3); 8.0388 (1.4); 8.0141 (1.6); 8.0108 (1.6); 7.7518 (0.8); 7.7471 (0.9); 7.7288 (4.6); 7.7227 (4.4); 7.7012 (1.1); 7.6963 (1.0); 7.6542 (1.1); 7.6496 (1.2); 7.6311 (0.8); 7.6264 (1.6); 7.6220 (1.1); 7.6033 (0.7); 7.5990 (0.6); 7.2985 (4.8); 7.2530 (0.6); 7.2313 (0.8); 7.2254 (1.4); 7.2038 (1.4); 7.1979 (0.9); 7.1762 (0.8); 6.7156 (1.0); 6.7127 (1.1); 6.6854 (1.9); 6.6581 (1.0); 6.6552 (0.9); 6.5671 (3.8); 6.5607 (3.7); 6.4519 (2.0); 6.4241 (1.8); 5.6896 (1.8); 3.9020 (12.6); 3.8994 (12.2); 2.5471 (16.0); 1.7446 (2.6); 0.0365 (4.8)

I-087: $^1$H-NMR (300.2 MHz, CDCl3):
δ=7.9326 (2.6); 7.7541 (3.4); 7.7479 (3.3); 7.4726 (0.5); 7.4677 (0.4); 7.4553 (0.6); 7.4496 (0.5); 7.4420 (1.1); 7.4373 (1.2); 7.4246 (1.0); 7.4190 (1.2); 7.4141 (1.8); 7.3923 (1.7); 7.3862 (1.8); 7.3648 (1.7); 7.3595 (1.9); 7.3517 (0.5); 7.3374 (0.8); 7.3293 (0.5); 7.2983 (8.4); 6.9856 (2.1); 6.9579 (1.8); 6.8492 (1.1); 6.8463 (1.0);

6.8201 (1.9); 6.7924 (1.0); 6.7895 (0.9); 6.4629 (3.6); 6.4568 (3.5); 5.7425 (1.8); 5.3359 (9.2); 4.1298 (0.6); 4.1219 (0.6); 4.1059 (1.8); 4.0979 (1.8); 4.0817 (1.8); 4.0739 (1.8); 4.0574 (0.6); 4.0501 (0.7); 2.5943 (16.0); 1.6287 (4.9); 1.4423 (4.0); 1.4182 (8.4); 1.3941 (3.9); 0.0364 (8.8)

I-088: $^1$H-NMR (300.2 MHz, CDCl3):
δ=8.7640 (4.6); 8.7555 (4.6); 7.8296 (3.0); 7.8241 (3.6); 7.8166 (2.8); 7.7419 (6.4); 7.7357 (6.4); 7.5013 (0.7); 7.4834 (1.0); 7.4697 (6.2); 7.4498 (4.9); 7.4388 (2.7); 7.4311 (1.4); 7.4186 (2.5); 7.4090 (1.6); 7.4033 (2.7); 7.3875 (1.0); 7.3821 (2.8); 7.3757 (1.7); 7.3544 (1.6); 7.2983 (13.1); 7.1887 (4.1); 7.1611 (3.2); 6.8756 (2.1); 6.8726 (1.9); 6.8465 (3.6); 6.8189 (1.9); 6.8159 (1.6); 6.4480 (7.0); 6.4418 (6.9); 5.9132 (3.4); 5.3352 (0.5); 4.1124 (1.6); 4.0883 (4.9); 4.0639 (5.2); 4.0396 (1.9); 1.6370 (6.3); 1.4418 (7.7); 1.4178 (16.0); 1.3936 (7.5); 0.0466 (0.5); 0.0434 (0.3); 0.0358 (14.6); 0.0281 (0.4); 0.0265 (0.4); 0.0249 (0.5)

I-089: $^1$H-NMR (300.2 MHz, CDCl3):
δ=9.0239 (10.3); 8.1550 (2.3); 8.1509 (2.0); 8.1459 (1.7); 8.1305 (3.3); 8.1237 (2.8); 8.1177 (2.5); 8.1103 (2.9); 8.0940 (1.6); 8.0889 (2.3); 8.0856 (2.7); 7.7573 (6.4); 7.7511 (6.4); 7.7295 (0.9); 7.7235 (1.3); 7.7064 (3.0); 7.7004 (2.6); 7.6887 (2.9); 7.6819 (5.0); 7.6736 (2.7); 7.6619 (2.3); 7.6567 (2.5); 7.6388 (1.0); 7.6335 (0.7); 7.3979 (1.2); 7.3764 (1.3); 7.3702 (2.6); 7.3489 (2.7); 7.3426 (1.7); 7.3212 (1.5); 7.2984 (17.6); 7.0592 (3.9); 7.0316 (3.2); 6.8754 (2.0); 6.8726 (1.9); 6.8465 (3.5); 6.8187 (1.8); 6.8158 (1.7); 6.5189 (6.9); 6.5127 (6.8); 6.1248 (3.3); 5.3362 (2.5); 4.1543 (1.3); 4.1495 (1.3); 4.1302 (3.8); 4.1254 (3.7); 4.1059 (3.9); 4.1014 (3.8); 4.0815 (1.4); 4.0775 (1.4); 1.6338 (10.0); 1.4606 (7.7); 1.4365 (16.0); 1.4124 (7.5); 0.0484 (0.6); 0.0376 (19.1); 0.0266 (0.7)

I-090: $^1$H-NMR (300.2 MHz, CDCl3):
δ=8.7661 (4.7); 8.1350 (1.3); 8.1319 (1.4); 8.1070 (1.5); 8.1043 (1.5); 8.0339 (1.3); 8.0310 (1.4); 8.0062 (1.5); 8.0030 (1.5); 7.7638 (3.5); 7.7576 (3.6); 7.7455 (0.8); 7.7408 (0.8); 7.7226 (1.3); 7.7179 (1.7); 7.7130 (0.8); 7.6949 (1.1); 7.6900 (1.0); 7.6482 (1.1); 7.6436 (1.2); 7.6252 (0.8); 7.6204 (1.6); 7.6159 (1.0); 7.5973 (0.7); 7.5929 (0.6); 7.2985 (3.0); 7.2540 (0.7); 7.2322 (0.7); 7.2263 (1.4); 7.2047 (1.4); 7.1987 (0.8); 7.1771 (0.8); 6.7108 (1.0); 6.7078 (1.1); 6.6810 (1.8); 6.6537 (1.0); 6.6507 (1.0); 6.5283 (3.8); 6.5221 (3.8); 6.4497 (2.0); 6.4220 (1.8); 5.6293 (1.8); 5.3297 (6.3); 4.1955 (1.1); 4.1714 (3.4); 4.1472 (3.5); 4.1232 (1.2); 2.5367 (16.0); 1.8207 (2.2); 1.5053 (4.1); 1.4812 (8.5); 1.4571 (3.9); 0.0359 (3.1)

I-091: $^1$H-NMR (300.2 MHz, CDCl3):
δ=9.0163 (1.8); 8.9881 (1.9); 7.9140 (1.4); 7.9084 (2.1); 7.9030 (1.4); 7.8877 (1.6); 7.8811 (2.4); 7.8755 (1.8); 7.8258 (3.3); 7.8197 (3.3); 7.6769 (0.8); 7.6720 (0.8); 7.6534 (1.2); 7.6492 (1.5); 7.6446 (0.8); 7.6261 (1.6); 7.6212 (1.0); 7.6045 (0.8); 7.5985 (1.5); 7.5765 (1.5); 7.5705 (0.8); 7.5572 (1.2); 7.5524 (1.3); 7.5487 (0.9); 7.5337 (1.0); 7.5296 (1.6); 7.5253 (1.1); 7.5068 (0.7); 7.5019 (0.7); 7.2983 (8.5); 7.0178 (1.4); 6.9887 (1.1); 6.9857 (1.1); 6.9594 (1.8); 6.9578 (1.8); 6.9315 (1.0); 6.9285 (0.9); 6.5330 (3.6); 6.5269 (3.5); 4.0957 (0.6); 4.0869 (0.6); 4.0720 (1.8); 4.0630 (1.7); 4.0478 (1.8); 4.0390 (1.8); 4.0235 (0.6); 4.0154 (0.7); 2.9117 (0.4); 2.3702 (16.0); 1.6209 (5.3); 1.4041 (4.1); 1.3801 (8.4); 1.3559 (4.0); 0.0378 (9.1)

I-092: $^1$H-NMR (300.2 MHz, CDCl3):
δ=8.9225 (1.9); 8.8944 (2.0); 7.8303 (3.6); 7.8242 (3.7); 7.6701 (0.7); 7.6635 (0.7); 7.6541 (0.7); 7.6473 (0.8); 7.6391 (1.1); 7.6324 (1.2); 7.6234 (1.3); 7.6163 (1.1); 7.6039 (0.9); 7.5977 (0.9); 7.5759 (1.6); 7.5698 (0.9); 7.5447 (1.1); 7.5184 (1.0); 7.5115 (1.3); 7.4858 (1.2); 7.4801 (0.7); 7.4540 (0.6); 7.2986 (12.2); 7.0918 (1.6); 7.0173 (1.2); 7.0142 (1.2); 6.9884 (1.9); 6.9860 (1.9); 6.9602 (1.0); 6.9572 (1.0); 6.5298 (3.9); 6.5237 (3.9); 5.3370 (0.9); 4.0905 (0.7); 4.0822 (0.6); 4.0666 (2.0); 4.0581 (1.8); 4.0425 (2.0); 4.0342 (1.9); 4.0181 (0.7); 4.0107 (0.8); 2.4127 (16.0); 1.6038 (9.1); 1.4045 (4.3); 1.3804 (8.9); 1.3563 (4.1); 0.0483 (0.4); 0.0375 (12.7); 0.0266 (0.4)

I-093: $^1$H-NMR (300.2 MHz, CDCl3):
δ=8.7282 (3.6); 8.7000 (3.7); 8.2796 (9.7); 7.8107 (6.5); 7.8046 (6.5); 7.6829 (1.1); 7.6772 (0.9); 7.6668 (1.2); 7.6606 (1.1); 7.6517 (2.2); 7.6460 (2.5); 7.6355 (2.1); 7.6294 (2.2); 7.6139 (2.2); 7.6069 (1.5); 7.5889 (2.3); 7.5800 (3.8); 7.5570 (5.1); 7.5507 (2.6); 7.5289 (1.6); 7.2986 (15.6); 7.0231 (2.1); 7.0201 (2.1); 6.9918 (4.9); 6.9847 (3.3); 6.9660 (2.2); 6.9631 (2.0); 6.4934 (7.0); 6.4873 (6.9); 5.3365 (0.4); 4.0865 (2.1); 4.0624 (6.6); 4.0383 (6.8); 4.0142 (2.3); 1.6111 (10.6); 1.4398 (7.8); 1.4157 (16.0); 1.3916 (7.6); 0.0477 (0.6); 0.0370 (16.4); 0.0262 (0.6)

I-094: $^1$H-NMR (499.9 MHz, CDCl3):
δ=8.5812 (3.0); 8.5794 (2.6); 8.5765 (3.1); 8.3783 (3.9); 8.3734 (3.8); 8.1045 (3.8); 8.0998 (3.9); 7.6695 (4.3); 7.6658 (4.4); 7.3037 (0.8); 7.2906 (1.1); 7.2871 (1.9); 7.2742 (2.0); 7.2705 (1.6); 7.2621 (12.6); 6.7493 (1.6); 6.7375 (3.5); 6.7329 (3.6); 6.7271 (3.5); 6.7255 (3.7); 6.7209 (5.7); 6.7167 (2.3); 6.4657 (4.6); 6.4620 (4.7); 5.6033 (2.6); 5.3000 (0.5); 3.8153 (16.0); 3.8138 (15.6); 1.5944 (11.2); 0.0061 (0.7); −0.0002 (12.3)

I-095: $^1$H-NMR (300.2 MHz, CDCl3):
δ=8.6089 (3.4); 8.6059 (2.6); 8.6007 (3.6); 8.3979 (5.1); 8.3897 (4.7); 8.1423 (4.9); 8.1343 (4.9); 7.7475 (5.6); 7.7413 (5.6); 7.3577 (1.1); 7.3365 (1.2); 7.3300 (2.4); 7.3087 (2.6); 7.2983 (24.8); 7.2813 (1.9); 7.2598 (0.5); 7.2449 (0.4); 7.2388 (0.4); 7.2347 (0.4); 7.0071 (0.3); 6.7954 (1.7); 6.7926 (1.9); 6.7698 (5.2); 6.7651 (7.3); 6.7565 (3.8); 6.7538 (3.4); 6.7423 (3.9); 6.7389 (3.3); 6.4678 (6.1); 6.4617 (6.0); 5.5385 (2.8); 5.3365 (0.7); 4.1705 (0.3); 4.1468 (0.4); 4.1371 (1.8); 4.1130 (5.7); 4.0889 (5.9); 4.0649 (2.0); 2.0818 (1.5); 1.6834 (1.9); 1.6140 (16.0); 1.4778 (6.7); 1.4537 (13.9); 1.4295 (6.6); 1.3201 (0.5); 1.2963 (0.9); 1.2725 (0.4); 0.1068 (0.4); 0.0477 (0.8); 0.0370 (25.7); 0.0261 (0.9)

I-096: $^1$H-NMR (300.2 MHz, CDCl3):
δ=8.4443 (4.5); 8.4356 (4.5); 7.7167 (5.6); 7.7106 (5.6); 7.5514 (2.6); 7.5457 (3.2); 7.5376 (2.5); 7.4682 (0.6); 7.4533 (0.6); 7.4451 (0.7); 7.4406 (1.9); 7.4257 (4.4); 7.4180 (8.2); 7.4067 (10.6); 7.4024 (7.3); 7.3902 (1.3); 7.2984 (3.7); 7.2867 (2.0); 7.2840 (2.2); 7.2713 (1.8); 7.2637 (3.5); 7.2601 (3.8); 7.2486 (1.4); 7.2414 (1.3); 7.2360 (1.6); 7.2249 (1.2); 7.2172 (1.2); 7.2059 (1.3); 7.2020 (1.0); 7.1928 (1.0); 7.1877 (0.7); 7.1728 (4.1); 7.1676 (2.1); 7.1633 (1.4); 7.1486 (6.1); 7.1385 (2.5); 7.1236 (3.3); 7.1144 (1.7); 7.1046 (1.7); 7.0979 (2.1); 7.0957 (1.9); 7.0879 (1.2); 7.0804 (1.1); 7.0699 (1.1); 7.0336 (3.9); 7.0273 (3.9); 7.0070 (3.1); 6.4262 (5.9); 6.4201 (5.8); 5.5704 (3.2); 5.3271 (2.7); 5.2572 (12.3); 2.0654 (1.3); 1.7890 (2.6); 1.2760 (16.0); 0.0369 (3.5)

I-097: $^1$H-NMR (300.2 MHz, CDCl3):
δ=7.7249 (3.5); 7.7188 (3.4); 7.5983 (2.8); 7.5944 (2.7); 7.4609 (0.6); 7.4557 (0.7); 7.4321 (1.3); 7.4091 (1.0);

7.4039 (1.0); 7.3458 (2.6); 7.3402 (1.9); 7.3346 (1.7); 7.3206 (5.6); 7.2987 (3.1); 7.2959 (2.0); 7.2741 (2.3); 7.2490 (1.5); 7.1376 (1.6); 7.1345 (1.6); 7.1304 (1.2); 7.1246 (0.6); 7.1127 (2.6); 7.1090 (4.1); 7.1023 (1.8); 7.0879 (2.2); 7.0835 (3.7); 7.0665 (0.8); 7.0614 (1.6); 7.0563 (1.1); 7.0467 (0.4); 7.0382 (1.5); 7.0266 (0.3); 7.0134 (0.4); 6.9905 (2.6); 6.9853 (3.0); 6.9633 (2.2); 6.4288 (3.6); 6.4227 (3.6); 5.4596 (2.1); 5.3269 (2.2); 5.2749 (7.6); 2.4283 (16.0); 1.8337 (0.7); 0.0375 (1.6)

I-098: ¹H-NMR (499.9 MHz, d₆-DMSO):

δ=8.6901 (6.3); 8.6851 (6.4); 8.1150 (8.2); 7.6050 (1.2); 7.5930 (1.6); 7.5862 (3.5); 7.5746 (4.7); 7.5608 (1.9); 7.5546 (2.3); 7.5406 (2.4); 7.5293 (5.6); 7.4803 (7.8); 7.4768 (8.2); 7.4559 (9.6); 7.4484 (9.6); 7.4301 (0.3); 7.2506 (3.8); 7.2356 (5.2); 7.1761 (0.5); 7.1674 (3.6); 7.1633 (3.1); 7.1591 (4.7); 7.1504 (10.0); 7.1354 (9.2); 7.1289 (5.1); 7.1152 (3.1); 7.1074 (0.6); 7.1006 (0.8); 6.9117 (7.2); 6.8982 (6.5); 6.4244 (7.9); 6.4209 (8.2); 5.7642 (0.5); 5.1635 (16.0); 3.3347 (113.3); 2.6436 (0.5); 2.5120 (63.2); 2.5087 (82.7); 2.5054 (64.4); 2.3696 (0.5); 1.0762 (0.5)

I-099: ¹H-NMR (300.2 MHz, CDCl3):

δ=8.7222 (5.4); 8.7136 (5.4); 7.8336 (3.2); 7.8276 (4.0); 7.8201 (3.1); 7.7857 (5.5); 7.7798 (5.6); 7.5226 (0.5); 7.5154 (1.2); 7.4994 (6.7); 7.4950 (4.1); 7.4880 (6.9); 7.4814 (3.8); 7.4676 (2.8); 7.4538 (0.6); 7.4396 (1.1); 7.4359 (1.3); 7.4143 (1.4); 7.4081 (2.9); 7.3869 (3.0); 7.3806 (2.0); 7.3592 (1.8); 7.3511 (0.5); 7.3351 (2.0); 7.3234 (1.7); 7.3169 (1.5); 7.3046 (2.1); 7.2984 (20.1); 7.2933 (2.5); 7.2772 (1.5); 7.2700 (1.4); 7.2272 (4.5); 7.1995 (3.4); 6.8765 (2.2); 6.8737 (2.0); 6.8478 (3.8); 6.8201 (2.0); 6.8172 (1.8); 6.4283 (7.6); 6.4222 (7.5); 5.8923 (3.7); 5.3355 (15.2); 4.3592 (0.6); 4.3372 (1.6); 4.3151 (2.2); 4.2931 (1.7); 4.2713 (0.7); 1.9873 (0.6); 1.6630 (0.6); 1.6249 (16.0); 1.5555 (14.7); 1.5335 (14.6); 1.4317 (0.5); 1.4017 (15.5); 1.3797 (15.2); 1.2942 (0.4); 0.1074 (0.5); 0.0474 (0.7); 0.0366 (19.2); 0.0257 (0.6)

I-100: ¹H-NMR (300.2 MHz, CDCl3):

δ=8.7555 (3.8); 8.7472 (3.8); 7.8176 (2.8); 7.8128 (3.4); 7.7798 (4.3); 7.7741 (4.2); 7.5002 (0.6); 7.4819 (0.9); 7.4686 (5.1); 7.4501 (3.9); 7.4375 (2.1); 7.4294 (1.2); 7.4174 (2.0); 7.4066 (1.5); 7.4017 (2.2); 7.3803 (2.2); 7.3742 (1.4); 7.3528 (1.3); 7.2976 (7.5); 7.1794 (3.5); 7.1518 (2.7); 6.8738 (1.9); 6.8457 (3.3); 6.8174 (1.7); 6.4218 (5.2); 6.4159 (4.7); 5.8728 (3.6); 5.3339 (16.0); 4.3544 (0.5); 4.3328 (1.3); 4.3108 (1.8); 4.2887 (1.4); 4.2667 (0.6); 1.6410 (6.4); 1.5555 (10.9); 1.5335 (10.7); 1.4019 (11.3); 1.3798 (11.0); 0.0452 (0.4); 0.0346 (7.6)

I-101: ¹H-NMR (300.2 MHz, CDCl3):

δ=9.0251 (6.2); 8.1527 (1.4); 8.1486 (1.2); 8.1437 (1.0); 8.1281 (2.0); 8.1194 (2.3); 8.1106 (1.8); 8.0943 (1.0); 8.0892 (1.4); 8.0859 (1.7); 7.7940 (3.0); 7.7887 (3.0); 7.7292 (0.5); 7.7233 (0.8); 7.7062 (1.8); 7.7002 (1.6); 7.6882 (1.8); 7.6816 (3.0); 7.6734 (1.7); 7.6615 (1.4); 7.6562 (1.6); 7.6384 (0.6); 7.6331 (0.4); 7.3979 (0.7); 7.3765 (0.8); 7.3704 (1.6); 7.3490 (1.6); 7.3430 (1.1); 7.3213 (1.0); 7.2986 (18.6); 7.0538 (2.4); 7.0263 (2.0); 6.8750 (1.2); 6.8722 (1.2); 6.8464 (2.2); 6.8184 (1.1); 6.8157 (1.0); 6.4890 (4.3); 6.4829 (4.3); 6.0903 (2.1); 5.3372 (6.4); 4.3951 (0.4); 4.3731 (0.9); 4.3511 (1.2); 4.3289 (1.0); 4.3067 (0.4); 1.6090 (16.0); 1.5765 (8.2); 1.5545 (8.0); 1.4410 (8.5); 1.4189 (8.5); 1.4021 (0.4); 0.1079 (0.7); 0.0487 (0.7); 0.0379 (18.6); 0.0270 (0.7)

I-102: ¹H-NMR (300.2 MHz, CDCl3):

δ=8.7621 (4.7); 8.1358 (1.4); 8.1083 (1.5); 8.0385 (1.3); 8.0347 (1.3); 8.0107 (1.6); 8.0065 (1.5); 7.8040 (2.7); 7.7981 (2.8); 7.7516 (0.7); 7.7471 (0.8); 7.7287 (1.2); 7.7241 (1.6); 7.7195 (0.7); 7.7011 (1.0); 7.6963 (1.0); 7.6537 (1.1); 7.6492 (1.2); 7.6305 (0.8); 7.6260 (1.5); 7.6216 (1.0); 7.6028 (0.6); 7.5986 (0.6); 7.2988 (9.6); 7.2568 (0.6); 7.2353 (0.7); 7.2293 (1.4); 7.2077 (1.4); 7.2017 (0.8); 7.1801 (0.5); 6.7111 (0.5); 6.6836 (1.5); 6.6563 (0.9); 6.6543 (0.9); 6.5026 (3.5); 6.4966 (3.5); 6.4430 (2.0); 6.4153 (1.8); 5.6023 (1.9); 5.3364 (7.8); 4.4375 (0.8); 4.4155 (1.1); 4.3935 (0.8); 4.3718 (0.3); 2.5402 (16.0); 1.6398 (6.5); 1.5982 (7.0); 1.5762 (6.9); 1.5204 (7.4); 1.4983 (7.2); 0.0380 (9.6); 0.0274 (0.4)

I-103: ¹H-NMR (300.2 MHz, CDCl3):

δ=9.0232 (1.8); 8.9949 (1.9); 7.9109 (2.5); 7.8807 (3.1); 7.8588 (2.6); 7.8530 (2.7); 7.6781 (0.8); 7.6732 (0.8); 7.6547 (1.2); 7.6506 (1.5); 7.6460 (0.9); 7.6277 (1.4); 7.6224 (1.0); 7.6064 (0.8); 7.6005 (1.5); 7.5785 (1.5); 7.5725 (0.9); 7.5567 (1.3); 7.5517 (1.7); 7.5332 (1.1); 7.5288 (1.5); 7.5248 (1.2); 7.5064 (0.7); 7.5014 (0.8); 7.2985 (11.6); 6.9876 (2.5); 6.9847 (2.2); 6.9589 (1.9); 6.9562 (1.9); 6.9307 (1.0); 6.9276 (1.0); 6.5011 (3.8); 6.4951 (3.8); 5.3367 (0.9); 4.2908 (0.8); 4.2689 (1.1); 4.2468 (0.8); 4.2248 (0.3); 2.3411 (16.0); 1.6051 (4.8); 1.5625 (7.2); 1.5405 (7.0); 1.3648 (7.6); 1.3428 (7.5); 0.0490 (0.5); 0.0382 (13.1); 0.0273 (0.5)

I-104: ¹H-NMR (300.2 MHz, CDCl3):

δ=8.9240 (2.0); 8.8959 (2.0); 7.8603 (2.8); 7.8545 (2.9); 7.6645 (0.7); 7.6578 (0.7); 7.6484 (0.7); 7.6416 (0.8); 7.6334 (1.1); 7.6264 (1.4); 7.6173 (1.1); 7.6106 (1.1); 7.6020 (0.9); 7.5958 (1.6); 7.5739 (1.6); 7.5678 (0.9); 7.5458 (0.9); 7.5367 (1.0); 7.5107 (1.1); 7.5040 (1.2); 7.4783 (1.3); 7.4725 (0.7); 7.4464 (0.6); 7.2983 (3.4); 7.0571 (1.7); 7.0120 (1.2); 7.0089 (1.2); 6.9999 (0.4); 6.9835 (2.2); 6.9808 (2.1); 6.9552 (1.1); 6.9522 (1.1); 6.4965 (4.1); 6.4906 (4.0); 5.3323 (2.3); 4.2969 (0.3); 4.2749 (0.8); 4.2529 (1.1); 4.2309 (0.9); 4.2091 (0.4); 2.3764 (16.0); 1.6736 (1.8); 1.5763 (0.4); 1.5634 (7.5); 1.5414 (7.4); 1.5271 (0.5); 1.3586 (7.9); 1.3365 (7.8); 1.3213 (0.5); 1.2989 (0.4); 0.0347 (3.6)

I-105: ¹H-NMR (300.2 MHz, CDCl3):

δ=8.7182 (3.9); 8.6900 (4.1); 8.2595 (10.7); 7.8424 (5.5); 7.8372 (5.6); 7.6823 (1.3); 7.6766 (1.1); 7.6662 (1.4); 7.6600 (1.3); 7.6511 (2.5); 7.6454 (2.9); 7.6350 (2.4); 7.6288 (2.5); 7.6129 (2.5); 7.6060 (1.7); 7.5879 (2.6); 7.5792 (4.4); 7.5560 (5.6); 7.5497 (2.9); 7.5282 (1.7); 7.5242 (1.4); 7.2986 (10.7); 7.0219 (2.2); 7.0188 (2.3); 6.9933 (3.9); 6.9905 (4.0); 6.9650 (2.2); 6.9620 (2.2); 6.9364 (3.4); 6.4649 (8.3); 6.4589 (8.2); 5.3351 (0.6); 4.3070 (0.6); 4.2848 (1.6); 4.2628 (2.2); 4.2409 (1.7); 4.2189 (0.7); 1.6289 (5.7); 1.5554 (14.9); 1.5334 (14.6); 1.3838 (16.0); 1.3618 (15.7); 0.0468 (0.4); 0.0359 (11.8); 0.0249 (0.4)

I-106: ¹H-NMR (300.2 MHz, CDCl3):

δ=8.5946 (4.5); 8.5916 (3.5); 8.5889 (3.8); 8.5865 (4.7); 8.3794 (6.7); 8.3712 (6.1); 8.1293 (6.4); 8.1214 (6.4); 7.7723 (5.8); 7.7664 (5.8); 7.3502 (1.4); 7.3289 (1.6); 7.3225 (3.1); 7.2983 (6.6); 7.2736 (1.6); 6.7877 (2.3); 6.7849 (2.5); 6.7589 (10.4); 6.7522 (5.6); 6.7494 (5.0); 6.7441 (5.1); 6.7414 (4.5); 6.7309 (8.1); 6.4309 (8.0); 6.4249 (7.8); 5.5166 (4.1); 5.3286 (7.7); 4.3680 (0.7); 4.3458 (1.7); 4.3238 (2.3); 4.3017 (1.8); 4.2798 (0.7); 1.7559 (1.1); 1.5694 (15.2); 1.5474 (14.9); 1.4723 (16.0); 1.4502 (15.7); 1.2887 (0.4); 0.0311 (5.8)

I-107: ¹H-NMR (400.2 MHz, d₆-DMSO):

δ=7.6516 (0.6); 7.6477 (0.7); 7.6344 (3.9); 7.6149 (0.9); 7.6117 (0.9); 7.5517 (0.7); 7.5335 (0.8); 7.5262 (0.9); 7.5083 (0.9); 7.4791 (3.3); 7.4423 (0.7); 7.4218 (1.5); 7.4050 (1.6); 7.3844 (0.8); 6.9733 (1.2); 6.9519 (1.9); 6.9292 (1.0); 6.8837 (2.3); 6.8633 (2.1); 6.0776 (6.0);

3.5450 (14.0); 3.3259 (37.0); 2.8931 (1.6); 2.7341 (1.4); 2.5583 (16.5); 2.5261 (0.9); 2.5127 (17.8); 2.5084 (35.4); 2.5039 (45.8); 2.4993 (32.9); 2.4950 (16.0); 1.9760 (16.0); 1.2390 (0.6); −0.0002 (0.5)

I-108: $^1$H-NMR (499.9 MHz, CDCl3):

δ=8.3214 (9.8); 8.3162 (9.9); 7.7705 (12.0); 7.7671 (12.6); 7.3886 (7.6); 7.3732 (10.2); 7.3670 (6.4); 7.3593 (5.3); 7.3550 (5.6); 7.3504 (6.1); 7.3438 (3.8); 7.3339 (3.3); 7.2926 (8.3); 7.2771 (13.8); 7.2631 (12.0); 7.2233 (8.6); 7.1973 (7.6); 7.1951 (10.7); 7.1804 (16.2); 7.1788 (15.6); 7.1683 (3.8); 7.1662 (4.0); 7.1624 (4.2); 7.1603 (4.2); 7.1470 (3.1); 7.1450 (3.3); 7.1312 (4.2); 7.1294 (4.6); 7.1166 (13.9); 7.1017 (16.0); 7.0859 (7.6); 7.0213 (4.8); 7.0065 (6.8); 6.9918 (2.6); 6.5459 (12.6); 6.5424 (13.1); 5.5553 (8.5); 1.9974 (8.0); 1.7218 (0.6); 1.2836 (0.4); 1.2551 (2.4); 0.8789 (0.5); −0.0002 (5.9)

I-109: $^1$H-NMR (400.1 MHz, d$_6$-DMSO):

δ=7.5867 (2.0); 7.5675 (2.9); 7.5493 (2.4); 7.5114 (1.4); 7.4884 (2.2); 7.4756 (2.0); 7.4428 (1.4); 7.4179 (1.8); 7.3996 (1.7); 7.3757 (0.7); 7.3186 (2.2); 7.2963 (3.7); 7.2742 (1.9); 7.2238 (8.3); 6.7484 (5.7); 6.1273 (1.3); 4.1021 (0.8); 3.6525 (0.4); 3.5743 (11.7); 3.5407 (0.5); 3.3136 (23.1); 3.1714 (0.3); 2.5536 (21.8); 2.5091 (20.3); 2.2820 (0.3); 2.2272 (16.0); 2.0802 (1.2); 1.2423 (0.5)

I-110: $^1$H-NMR (499.9 MHz, d$_6$-DMSO):

δ=7.4945 (1.4); 7.4828 (1.7); 7.4764 (2.2); 7.4605 (3.7); 7.4429 (3.2); 7.4213 (1.2); 7.4017 (1.7); 7.3869 (1.6); 7.3679 (0.7); 7.2281 (6.0); 7.2248 (6.0); 7.1893 (6.2); 6.6939 (6.7); 6.1148 (0.6); 3.5695 (7.6); 3.3238 (12.2); 2.5621 (0.4); 2.5375 (25.9); 2.5078 (8.4); 2.3282 (15.8); 2.1852 (16.0); 2.0798 (3.9)

I-111: $^1$H-NMR (499.9 MHz, d$_6$-DMSO):

δ=8.2284 (1.1); 7.8679 (0.7); 7.6387 (1.0); 7.6248 (1.2); 7.6218 (1.2); 7.6084 (1.0); 7.4342 (2.1); 7.4221 (2.4); 7.4146 (1.0); 7.4019 (0.8); 7.3162 (7.2); 7.3113 (2.0); 7.2934 (2.3); 7.2759 (1.2); 6.7752 (1.3); 3.7224 (1.5); 3.6977 (1.0); 3.6461 (4.3); 2.9759 (1.4); 2.6257 (16.0); 2.5153 (2.0); 2.5117 (4.5); 2.5080 (6.3); 2.5044 (4.6); 2.5008 (2.2); 2.2878 (9.5); 2.0800 (0.4)

I-112: $^1$H-NMR (499.9 MHz, d$_6$-DMSO):

δ=7.9493 (0.8); 7.9419 (0.7); 7.9327 (0.7); 7.9227 (0.6); 7.7567 (8.4); 7.7082 (0.6); 7.6930 (0.7); 7.6884 (0.9); 7.6734 (1.0); 7.6545 (0.6); 7.5332 (0.4); 7.0973 (0.9); 7.0800 (1.7); 7.0627 (0.8); 6.9625 (2.7); 5.7790 (1.6); 5.7622 (1.6); 3.7702 (16.0); 3.3195 (55.4); 2.6427 (1.0); 2.6393 (0.3); 2.6357 (0.4); 2.5789 (0.8); 2.5473 (1.2); 2.5117 (44.2); 2.5079 (56.6); 2.5043 (43.0); 2.5008 (30.5); 2.3691 (0.4); 2.2906 (0.4); 2.1437 (7.3); 2.1417 (7.3); 2.0802 (0.4); 1.2442 (2.6); 0.8613 (0.5)

I-113: $^1$H-NMR (499.9 MHz, d$_6$-DMSO):

δ=7.5317 (0.4); 7.4840 (0.4); 7.4640 (3.0); 7.4466 (3.5); 7.4391 (2.2); 7.4281 (1.7); 7.4132 (1.3); 7.3993 (1.3); 7.3931 (1.6); 7.3790 (1.2); 7.3600 (0.6); 7.2023 (4.8); 7.1810 (0.4); 7.1548 (0.7); 7.0788 (0.4); 7.0416 (0.4); 6.9931 (6.0); 6.9766 (0.4); 6.6873 (0.8); 6.6669 (4.0); 3.5937 (1.4); 3.5330 (10.4); 3.4567 (1.0); 3.3215 (198.3); 2.6464 (0.6); 2.6428 (0.8); 2.6391 (0.6); 2.6240 (0.3); 2.5687 (2.8); 2.5605 (24.1); 2.5475 (6.1); 2.5356 (1.7); 2.5150 (34.4); 2.5115 (70.5); 2.5079 (96.6); 2.5043 (70.1); 2.5008 (33.2); 2.3689 (0.6); 2.3652 (0.5); 2.3222 (12.6); 2.2822 (0.7); 2.2371 (16.0); 2.1659 (1.8); 1.9475 (2.8); 1.8451 (1.2); 1.7556 (7.0); 1.2425 (1.0); 0.7893 (0.4)

I-114: $^1$H-NMR (499.9 MHz, d$_6$-DMSO):

δ=7.9387 (0.7); 7.9354 (0.7); 7.9248 (0.7); 7.9197 (0.8); 7.9089 (0.7); 7.6980 (0.7); 7.6832 (0.7); 7.6783 (0.9); 7.6634 (0.9); 7.6442 (0.5); 7.5996 (4.3); 7.5959 (4.2); 7.0766 (0.4); 7.0529 (0.9); 7.0358 (1.6); 7.0182 (0.8); 6.7454 (2.8); 6.4544 (3.7); 6.4507 (3.4); 5.7901 (1.7); 5.7732 (1.6); 3.7434 (16.0); 3.3178 (335.4); 2.6496 (0.4); 2.6458 (0.6); 2.6421 (0.8); 2.6384 (0.6); 2.6347 (0.4); 2.6148 (0.8); 2.5466 (4.1); 2.5145 (41.8); 2.5109 (76.9); 2.5072 (99.3); 2.5036 (68.4); 2.4999 (30.7); 2.4916 (13.5); 2.4744 (12.8); 2.3718 (0.4); 2.3681 (0.5); 2.3645 (0.4); 2.1377 (7.0); 2.1353 (6.5); 1.8383 (0.4); 1.2422 (1.6); 0.8605 (0.4)

I-115: $^1$H-NMR (499.9 MHz, d$_6$-DMSO):

δ=8.1763 (1.3); 7.5195 (1.9); 7.5023 (1.9); 7.4190 (2.2); 7.4069 (2.1); 7.3989 (1.2); 7.3861 (1.0); 7.3674 (0.3); 7.3295 (4.4); 7.2516 (1.9); 6.7201 (2.0); 3.6438 (4.5); 2.6111 (16.0); 2.5116 (2.8); 2.5081 (4.0); 2.5048 (3.2); 2.3287 (9.4); 2.2428 (11.2); 2.0802 (7.1)

I-117: $^1$H-NMR (300.2 MHz, CDCl3):

δ=8.8341 (0.6); 8.8235 (4.7); 8.1404 (1.3); 8.1369 (1.4); 8.1123 (1.5); 8.1096 (1.5); 8.0554 (1.3); 8.0523 (1.4); 8.0282 (1.5); 8.0243 (1.5); 7.7486 (0.7); 7.7439 (0.8); 7.7257 (1.3); 7.7211 (1.6); 7.7162 (0.8); 7.6982 (1.2); 7.6932 (1.2); 7.6646 (1.3); 7.6599 (1.3); 7.6417 (0.9); 7.6370 (1.6); 7.6325 (1.1); 7.6141 (0.8); 7.6098 (0.7); 7.5457 (3.3); 7.5394 (3.3); 7.4430 (0.4); 7.4354 (0.4); 7.2989 (3.2); 6.6881 (0.7); 6.6785 (0.8); 6.6670 (0.7); 6.6574 (0.8); 6.6492 (0.7); 6.6396 (0.8); 6.6282 (0.7); 6.6186 (0.7); 6.4986 (0.9); 6.4925 (1.0); 6.4891 (1.0); 6.4828 (1.5); 6.4766 (1.1); 6.4732 (0.9); 6.4671 (0.8); 6.3349 (3.0); 6.3286 (3.0); 5.8587 (1.8); 5.3302 (4.7); 3.9656 (2.0); 3.8600 (10.2); 3.8550 (10.1); 3.7675 (0.3); 2.9866 (0.5); 2.9139 (0.4); 2.6531 (0.4); 2.6457 (0.4); 2.6266 (16.0); 2.5965 (1.9); 2.4676 (0.7); 1.8480 (2.6); 1.6723 (0.3); 0.0354 (3.3)

I-118: $^1$H-NMR (400.1 MHz, d$_6$-DMSO):

δ=9.0639 (9.2); 8.6017 (16.0); 7.9562 (6.3); 7.9355 (6.8); 7.7652 (1.6); 7.7416 (3.1); 7.7184 (3.0); 7.6948 (1.9); 7.6150 (2.2); 7.5982 (2.8); 7.5943 (4.6); 7.5776 (5.0); 7.5713 (12.3); 7.5667 (12.0); 7.5571 (2.8); 7.4670 (2.4); 7.4625 (2.6); 7.4548 (2.6); 7.4503 (2.7); 7.4435 (2.4); 7.4391 (2.4); 7.4313 (2.3); 7.4271 (2.2); 7.2027 (3.3); 7.1811 (5.8); 7.1596 (3.1); 7.1308 (3.5); 7.1138 (10.2); 7.0953 (9.8); 7.0766 (5.4); 7.0652 (1.9); 7.0590 (5.4); 7.0515 (1.4); 7.0407 (1.6); 6.9333 (10.3); 6.9161 (8.9); 6.4075 (10.7); 6.4030 (11.1); 4.0987 (0.5); 4.0821 (0.8); 4.0754 (0.8); 4.0646 (2.4); 4.0481 (2.6); 4.0404 (4.1); 4.0236 (4.3); 4.0162 (2.9); 3.9997 (2.7); 3.9892 (1.0); 3.9820 (1.0); 3.9657 (0.7); 3.3129 (61.6); 3.0416 (0.6); 3.0238 (0.8); 3.0187 (0.9); 3.0076 (2.2); 2.9859 (2.6); 2.9698 (3.6); 2.9537 (2.6); 2.9478 (2.4); 2.9313 (2.3); 2.9205 (1.1); 2.9133 (1.0); 2.8983 (7.6); 2.7397 (6.2); 2.5134 (17.8); 2.5090 (24.7); 2.5047 (18.9)

I-119: $^1$H-NMR (499.9 MHz, CDCl3):

δ=8.6552 (4.8); 8.0905 (1.4); 8.0892 (1.5); 8.0738 (1.6); 8.0725 (1.6); 8.0136 (0.7); 7.9784 (1.4); 7.9768 (1.5); 7.9616 (1.6); 7.9599 (1.6); 7.7609 (3.9); 7.7573 (3.8); 7.7278 (0.8); 7.6951 (0.9); 7.6925 (0.9); 7.6814 (1.2); 7.6786 (1.8); 7.6758 (1.0); 7.6647 (1.1); 7.6620 (1.1); 7.6324 (0.6); 7.6240 (0.7); 7.6172 (0.8); 7.6133 (0.7); 7.5981 (1.2); 7.5956 (1.2); 7.5843 (1.0); 7.5815 (1.7); 7.5788 (1.2); 7.5675 (0.9); 7.5650 (0.9); 7.4239 (0.9); 7.4205 (0.9); 7.4143 (1.4); 7.4101 (1.4); 7.4058 (0.3); 7.2588 (5.5); 7.2083 (1.5); 7.2051 (0.8); 7.1935 (3.8); 7.1786 (3.8); 7.1663 (1.7); 7.1627 (1.1); 7.1497 (0.9); 7.1059 (1.7); 7.1036 (1.4); 7.1012 (1.0); 7.0886 (1.8); 7.0734 (3.7); 7.0703 (3.5); 7.0562 (2.7); 7.0278 (0.3); 6.6567 (1.0); 6.6553 (1.0); 6.6388 (1.9); 6.6224 (1.0); 6.6209 (1.0); 6.4867 (3.7); 6.4830 (3.8); 6.3960 (2.0); 6.3793 (2.0); 5.4526 (2.2); 4.3441 (0.4); 4.3333 (0.4); 4.3251 (0.4); 4.3169 (0.9); 4.3063 (0.9); 4.2981 (1.0);

4.2873 (0.9); 4.2746 (0.7); 4.2601 (0.9); 4.2565 (0.9); 4.2474 (0.5); 4.2420 (0.8); 4.2331 (0.4); 4.2294 (0.5); 4.2150 (0.4); 3.2950 (0.4); 3.2807 (0.5); 3.2760 (0.5); 3.2680 (0.7); 3.2619 (0.5); 3.2538 (0.8); 3.2492 (0.7); 3.2349 (0.6); 3.1673 (0.6); 3.1565 (0.7); 3.1490 (0.7); 3.1389 (0.8); 3.1298 (0.5); 3.1220 (0.5); 3.1114 (0.5); 2.9505 (5.7); 2.8799 (4.8); 2.4515 (16.0); 1.6897 (2.0); −0.0002 (5.5)

I-120: $^1$H-NMR (400.1 MHz, $d_6$-DMSO):

δ=8.6757 (4.6); 8.6690 (4.9); 8.3397 (5.3); 8.3329 (5.3); 7.9606 (2.4); 7.8110 (6.2); 7.8080 (6.7); 7.6499 (6.2); 7.6470 (6.3); 7.5556 (6.0); 7.5511 (6.2); 7.3832 (1.0); 7.3626 (2.3); 7.3457 (2.4); 7.3250 (1.2); 7.2845 (5.6); 7.2128 (2.1); 7.1956 (5.8); 7.1770 (5.0); 7.1527 (2.7); 7.1406 (0.9); 7.1348 (2.9); 7.1277 (0.7); 7.1166 (0.8); 7.0122 (5.8); 6.9948 (4.8); 6.9044 (3.6); 6.8836 (3.3); 6.8263 (1.8); 6.8049 (3.2); 6.7831 (1.6); 6.3995 (6.0); 6.3950 (6.2); 4.1399 (2.2); 4.1252 (3.7); 4.1192 (3.7); 4.1022 (2.3); 3.3146 (20.4); 3.0321 (2.8); 3.0129 (4.0); 2.9940 (2.5); 2.8983 (16.0); 2.7395 (14.2); 2.5132 (8.4); 2.5089 (11.6); 2.5045 (8.8)

I-121: $^1$H-NMR (400.1 MHz, $d_6$-DMSO):

δ=8.7433 (6.1); 8.7371 (6.2); 8.0301 (7.5); 7.9606 (2.4); 7.7482 (4.9); 7.6682 (1.1); 7.6514 (1.4); 7.6428 (2.7); 7.6289 (2.5); 7.6213 (2.5); 7.6037 (1.9); 7.5961 (2.2); 7.5785 (2.0); 7.5549 (0.9); 7.5165 (8.8); 7.5119 (8.7); 7.4982 (3.2); 7.4815 (3.2); 7.4610 (1.7); 7.2845 (4.9); 7.2640 (4.1); 7.1723 (1.4); 7.1672 (2.1); 7.1507 (7.1); 7.1327 (7.5); 7.1236 (4.7); 7.1199 (3.0); 7.1137 (1.3); 7.1066 (3.2); 7.0969 (0.6); 7.0883 (0.8); 7.0371 (2.3); 7.0156 (4.2); 6.9936 (2.2); 6.9603 (5.8); 6.9565 (7.0); 6.9403 (6.1); 6.3978 (7.8); 6.3932 (8.0); 4.0896 (3.1); 4.0705 (6.4); 4.0512 (3.7); 3.3132 (50.8); 3.0122 (0.6); 2.9977 (1.7); 2.9791 (4.3); 2.9600 (4.0); 2.9414 (1.7); 2.9273 (0.6); 2.8981 (16.0); 2.7393 (14.0); 2.5132 (13.5); 2.5088 (18.5); 2.5044 (13.8)

I-122: $^1$H-NMR (300.2 MHz, CDCl3):

δ=8.0555 (0.4); 7.8036 (2.6); 7.8000 (2.6); 7.7833 (3.5); 7.7772 (3.6); 7.4450 (0.4); 7.4272 (0.5); 7.4230 (0.5); 7.4129 (2.5); 7.4066 (1.7); 7.3964 (1.4); 7.3923 (2.1); 7.3864 (2.4); 7.3764 (1.4); 7.3642 (1.6); 7.3565 (1.7); 7.3460 (0.4); 7.3366 (0.8); 7.3247 (0.5); 7.2986 (10.9); 7.1516 (1.2); 7.1465 (0.6); 7.1267 (2.8); 7.1085 (0.9); 7.1023 (2.6); 7.0259 (3.6); 7.0027 (2.7); 6.9980 (3.0); 6.9842 (1.7); 6.9673 (1.9); 6.9603 (0.8); 6.8549 (1.0); 6.8521 (1.0); 6.8251 (1.8); 6.7978 (1.0); 6.7949 (0.9); 6.4195 (3.8); 6.4133 (3.8); 5.5601 (2.1); 4.3745 (0.3); 4.3572 (0.4); 4.3451 (0.4); 4.3289 (1.0); 4.3120 (0.8); 4.3000 (0.8); 4.2825 (0.8); 4.2533 (0.5); 4.2272 (1.1); 4.2075 (0.4); 4.2014 (0.6); 4.1820 (0.6); 3.3127 (0.3); 3.2848 (0.5); 3.2672 (0.7); 3.2578 (0.4); 3.2400 (1.0); 3.2123 (0.6); 3.1603 (0.6); 3.1429 (0.6); 3.1322 (0.7); 3.1148 (0.9); 3.0981 (0.4); 3.0868 (0.4); 2.9945 (4.0); 2.9224 (3.4); 2.9211 (3.3); 2.5266 (16.0); 1.6352 (4.1); 0.0481 (0.4); 0.0373 (11.6); 0.0264 (0.4)

I-123: $^1$H-NMR (400.1 MHz, $d_6$-DMSO):

δ=8.7322 (6.9); 8.7268 (7.2); 8.4065 (9.5); 8.4005 (9.2); 8.1099 (10.0); 8.1040 (10.1); 7.9607 (2.4); 7.8806 (0.5); 7.8606 (0.5); 7.5759 (10.4); 7.5714 (10.6); 7.5039 (0.4); 7.4907 (0.7); 7.4826 (0.7); 7.4717 (0.5); 7.3999 (3.5); 7.3869 (3.1); 7.3813 (2.8); 7.3701 (3.2); 7.3605 (4.3); 7.3435 (4.1); 7.3230 (2.1); 7.2908 (9.6); 7.2089 (3.6); 7.1915 (10.1); 7.1729 (8.6); 7.1455 (4.4); 7.1276 (5.0); 7.1209 (1.2); 7.1095 (1.4); 7.0249 (9.8); 7.0075 (8.2); 6.8986 (6.3); 6.8778 (5.7); 6.8288 (3.1); 6.8072 (5.4); 6.7857 (2.8); 6.6779 (7.4); 6.6736 (7.2); 6.5368 (0.4); 6.4025 (10.4); 6.3980 (10.4); 4.1605 (4.2); 4.1438 (6.5); 4.1395 (6.4); 4.1225 (4.7); 3.3126 (57.5); 3.0472 (4.4); 3.0301 (6.1); 3.0261 (6.2); 3.0090 (3.9); 2.8982 (16.0); 2.7395 (14.2); 2.5131 (17.3); 2.5087 (23.4); 2.5044 (17.2); 1.6552 (3.8)

I-124: $^1$H-NMR (499.9 MHz, $d_6$-DMSO):

δ=8.6948 (5.7); 8.6897 (5.6); 8.0343 (7.3); 7.9556 (2.5); 7.8219 (1.3); 7.8142 (1.3); 7.8096 (1.2); 7.7985 (1.5); 7.7954 (1.3); 7.7899 (1.6); 7.6925 (4.6); 7.6748 (0.5); 7.6586 (0.6); 7.6082 (0.9); 7.6046 (0.9); 7.5670 (3.5); 7.5505 (4.5); 7.5424 (0.5); 7.5217 (7.0); 7.5181 (6.8); 7.4985 (2.9); 7.4851 (3.3); 7.4816 (2.4); 7.4680 (3.4); 7.4528 (1.6); 7.4424 (1.7); 7.4369 (2.6); 7.4268 (2.5); 7.4208 (1.8); 7.4106 (1.3); 7.4033 (0.6); 7.3957 (0.4); 7.3829 (1.9); 7.3721 (0.3); 7.3505 (1.5); 7.3045 (4.8); 7.2986 (2.5); 7.2880 (4.3); 7.2763 (2.4); 7.2609 (1.9); 7.2130 (0.4); 7.1996 (0.9); 7.1846 (0.9); 7.1722 (0.6); 7.1575 (1.8); 7.1542 (2.2); 7.1409 (6.4); 7.1261 (6.4); 7.1151 (3.6); 7.1063 (1.1); 7.1015 (3.1); 7.0944 (0.6); 7.0867 (0.8); 7.0361 (2.2); 7.0183 (3.8); 7.0012 (2.1); 6.9882 (0.8); 6.9744 (0.8); 6.9465 (6.2); 6.9328 (5.9); 6.3987 (6.9); 6.3952 (6.3); 6.3681 (0.8); 6.3646 (0.7); 4.0956 (0.5); 4.0852 (2.3); 4.0814 (2.5); 4.0682 (4.4); 4.0539 (2.6); 4.0509 (2.3); 4.0328 (0.5); 3.3269 (61.9); 3.0201 (0.4); 3.0036 (1.0); 2.9929 (1.9); 2.9774 (2.5); 2.9689 (1.8); 2.9618 (1.6); 2.9539 (2.2); 2.9379 (1.5); 2.9266 (0.7); 2.9107 (0.4); 2.8914 (16.0); 2.7336 (14.4); 2.5074 (6.7); 2.5042 (8.5); 2.5009 (6.0); 1.6487 (0.4); −0.0002 (2.7)

I-125: $^1$H-NMR (300.2 MHz, CDCl3):

δ=8.5572 (4.9); 8.5498 (5.0); 8.1046 (2.6); 8.0771 (3.1); 8.0748 (3.0); 7.7228 (3.0); 7.7182 (2.6); 7.7131 (1.6); 7.6973 (5.0); 7.6941 (6.2); 7.6850 (1.8); 7.6769 (0.5); 7.6668 (2.4); 7.6618 (1.8); 7.6507 (7.0); 7.6445 (7.2); 7.6363 (0.8); 7.5627 (2.5); 7.5589 (2.5); 7.5473 (0.5); 7.5364 (3.6); 7.5294 (4.3); 7.5270 (4.4); 7.5223 (4.2); 7.5131 (2.0); 7.5090 (1.6); 7.4925 (0.3); 7.4475 (1.2); 7.4427 (1.3); 7.4360 (0.4); 7.4225 (3.4); 7.4176 (3.4); 7.3975 (2.5); 7.3925 (2.5); 7.3780 (0.4); 7.3651 (0.3); 7.3402 (1.6); 7.3357 (2.1); 7.3153 (3.0); 7.3108 (3.9); 7.2986 (4.7); 7.2856 (5.8); 7.2739 (1.5); 7.2605 (11.1); 7.2549 (6.9); 7.2507 (8.8); 7.2391 (7.7); 7.2259 (1.0); 7.2098 (3.6); 7.2057 (3.7); 7.1850 (2.4); 7.1805 (2.3); 7.0119 (0.3); 6.9949 (0.7); 6.9816 (3.7); 6.9734 (3.5); 6.9668 (3.1); 6.9621 (3.7); 6.9542 (2.3); 6.9498 (2.8); 6.9371 (0.4); 6.2843 (0.5); 6.2780 (0.5); 6.2280 (7.1); 6.2219 (7.1); 5.3886 (0.6); 5.3245 (2.9); 5.0680 (1.1); 4.9533 (16.0); 3.8396 (13.5); 3.7380 (1.3); 2.0033 (3.1); 1.2977 (0.4); 0.0406 (4.0)

I-126: $^1$H-NMR (300.2 MHz, CDCl3):

δ=8.7062 (6.1); 8.6990 (6.1); 8.2871 (1.0); 8.0737 (3.4); 8.0461 (4.1); 7.7203 (5.0); 7.7165 (5.0); 7.6785 (3.6); 7.6727 (2.9); 7.6676 (2.0); 7.6490 (7.0); 7.6399 (2.0); 7.6213 (2.7); 7.6164 (1.9); 7.5780 (0.3); 7.5607 (3.0); 7.5501 (9.6); 7.5428 (8.9); 7.5309 (4.1); 7.5157 (3.2); 7.5125 (3.1); 7.5015 (0.5); 7.4900 (4.0); 7.4657 (1.7); 7.4623 (1.7); 7.4176 (0.6); 7.4107 (0.9); 7.3930 (2.8); 7.3862 (3.1); 7.3822 (3.4); 7.3727 (8.8); 7.3631 (4.6); 7.3584 (3.4); 7.3514 (4.0); 7.3295 (4.8); 7.3206 (3.2); 7.3103 (1.5); 7.3050 (1.7); 7.2985 (7.5); 6.7607 (1.5); 6.6305 (0.4); 6.6230 (0.4); 6.3374 (7.7); 6.3302 (7.5); 5.3295 (9.6); 4.7906 (0.5); 4.6645 (0.7); 4.3809 (16.0); 3.7411 (0.3); 3.7380 (0.4); 1.2963 (1.2); 1.2682 (0.7); 1.2448 (0.4); 0.1147 (0.6); 0.0399 (5.5)

I-127: $^1$H-NMR (300.2 MHz, CDCl3):

δ=8.7395 (3.3); 8.7309 (3.4); 7.7742 (2.2); 7.7688 (2.6); 7.7664 (2.6); 7.7610 (2.0); 7.7166 (3.5); 7.7111 (3.6); 7.4786 (0.4); 7.4642 (5.0); 7.4610 (5.2); 7.4514 (4.0);

7.4478 (3.3); 7.4405 (6.3); 7.4251 (2.2); 7.4192 (3.0); 7.4138 (2.4); 7.3943 (1.7); 7.3635 (0.5); 7.3318 (2.2); 7.3074 (2.7); 7.2986 (16.9); 7.1742 (1.4); 7.1630 (1.2); 7.1572 (1.2); 7.1485 (1.4); 7.1461 (1.4); 7.1389 (0.9); 7.1306 (0.9); 7.1206 (0.9); 6.3589 (4.8); 6.3529 (4.8); 5.8091 (2.6); 5.3372 (1.0); 4.4149 (0.5); 4.3930 (1.2); 4.3709 (1.7); 4.3488 (1.3); 4.3270 (0.5); 1.6117 (12.1); 1.4303 (16.0); 1.4082 (15.8); 1.3768 (0.5); 0.0476 (0.6); 0.0368 (17.3); 0.0259 (0.6)

I-128: $^1$H-NMR (300.2 MHz, CDCl3):
δ=8.7021 (3.6); 8.6933 (3.6); 7.7907 (2.2); 7.7849 (2.7); 7.7827 (2.7); 7.7770 (2.2); 7.7167 (3.6); 7.7112 (3.6); 7.5228 (1.0); 7.5187 (1.2); 7.4956 (3.2); 7.4914 (3.2); 7.4791 (2.0); 7.4709 (4.8); 7.4652 (3.2); 7.4622 (3.3); 7.4578 (5.6); 7.4538 (4.1); 7.4401 (2.0); 7.4283 (0.8); 7.4238 (0.9); 7.4124 (0.6); 7.3342 (1.8); 7.3300 (1.8); 7.3092 (2.8); 7.3040 (2.7); 7.2987 (10.0); 7.2935 (1.8); 7.2804 (1.2); 7.2762 (1.0); 7.2632 (1.1); 7.2578 (1.4); 7.2501 (1.3); 7.2356 (1.0); 7.2280 (1.0); 7.1741 (1.5); 7.1691 (1.5); 7.1493 (1.8); 7.1456 (2.0); 7.1255 (1.0); 7.1207 (1.0); 6.3610 (5.1); 6.3551 (5.1); 5.8371 (2.5); 5.3352 (1.4); 4.4177 (0.5); 4.3955 (1.2); 4.3735 (1.7); 4.3514 (1.3); 4.3294 (0.5); 1.6564 (9.0); 1.4258 (16.0); 1.4037 (15.9); 1.2902 (0.5); 1.2786 (1.3); 0.0467 (0.3); 0.0358 (10.0); 0.0249 (0.3)

I-129: $^1$H-NMR (300.2 MHz, CDCl3):
δ=7.8836 (2.8); 7.8802 (2.7); 7.7210 (2.7); 7.7152 (2.8); 7.4824 (0.6); 7.4773 (0.6); 7.4541 (1.4); 7.4306 (1.3); 7.4257 (1.2); 7.4173 (0.6); 7.4121 (0.5); 7.4037 (1.3); 7.4002 (1.4); 7.3856 (2.2); 7.3642 (1.1); 7.3540 (1.4); 7.3450 (1.6); 7.3385 (2.8); 7.3337 (3.1); 7.3206 (2.1); 7.3150 (1.9); 7.3097 (1.7); 7.2984 (9.5); 7.1617 (1.2); 7.1584 (1.1); 7.1369 (1.8); 7.1336 (1.6); 7.1122 (0.8); 7.1085 (0.7); 6.3700 (3.6); 6.3640 (3.5); 5.6507 (1.9); 5.3365 (7.9); 4.4146 (0.4); 4.3926 (1.0); 4.3705 (1.3); 4.3485 (1.0); 4.3264 (0.4); 2.5698 (16.0); 1.6285 (4.3); 1.4232 (8.8); 1.4012 (8.6); 1.3765 (0.4); 1.2917 (0.5); 0.0472 (0.4); 0.0364 (9.6)

I-130: $^1$H-NMR (499.9 MHz, d$_6$-DMSO):
δ=8.6132 (4.8); 7.6117 (0.7); 7.5929 (1.5); 7.5744 (1.5); 7.5555 (0.9); 7.5028 (0.6); 7.4861 (2.6); 7.4750 (8.0); 7.4617 (0.7); 7.3745 (1.1); 7.3716 (1.3); 7.3648 (1.2); 7.3619 (1.3); 7.3558 (1.1); 7.3529 (1.2); 7.3460 (1.0); 7.3434 (1.0); 7.3353 (0.4); 7.3273 (0.7); 7.2267 (4.9); 7.2231 (5.4); 6.2301 (5.1); 6.2264 (5.5); 3.6560 (16.0); 3.6300 (0.3); 3.3235 (12.0); 2.6559 (0.9); 2.5594 (0.6); 2.5451 (21.3); 2.5122 (4.9); 2.5087 (6.9); 2.5052 (5.4); 2.3406 (10.7); 2.3377 (12.1); 2.3268 (1.2); 1.7097 (0.5)

I-131: $^1$H-NMR (499.9 MHz, d$_6$-DMSO):
δ=8.5620 (3.6); 7.5586 (0.9); 7.5397 (1.7); 7.5223 (1.7); 7.5024 (1.0); 7.4678 (3.0); 7.4506 (3.0); 7.3207 (13.0); 7.3085 (1.6); 7.2965 (1.3); 7.2892 (1.2); 4.0902 (0.5); 4.0797 (0.5); 3.6316 (13.4); 3.3155 (43.4); 3.1756 (2.2); 3.1651 (2.2); 2.6301 (15.1); 2.5093 (5.1); 2.5058 (11.0); 2.5021 (15.3); 2.4985 (11.1); 2.4950 (5.3); 2.3304 (14.1); 2.3290 (14.1); 2.2728 (16.0); 2.0743 (1.6); 1.2335 (0.4); 0.0063 (0.3); −0.0002 (9.5); −0.0068 (0.4); −0.0138 (0.7)

I-132: $^1$H-NMR (499.9 MHz, d$_6$-DMSO):
δ=8.9283 (3.3); 7.6067 (0.6); 7.5879 (1.1); 7.5707 (1.1); 7.5554 (1.2); 7.5508 (0.8); 7.5388 (2.0); 7.5220 (1.0); 7.3918 (1.2); 7.3886 (1.3); 7.3808 (3.5); 7.3732 (1.1); 7.3697 (1.1); 7.3642 (2.8); 7.3084 (7.6); 3.7323 (12.8); 3.3141 (34.3); 2.6370 (16.0); 2.5532 (0.3); 2.5085 (4.9); 2.5050 (8.8); 2.5014 (11.2); 2.4978 (7.7); 2.4944 (3.5); 2.3415 (8.1); 2.0737 (0.6); 0.0062 (0.5); −0.0002 (7.0)

I-133: $^1$H-NMR (499.9 MHz, d$_6$-DMSO):
δ=8.3680 (4.2); 7.4885 (2.4); 7.4715 (4.0); 7.4515 (1.2); 7.4452 (1.2); 7.4286 (0.9); 3.5692 (0.5); 3.5286 (0.4); 3.5102 (0.4); 3.4850 (0.3); 3.4670 (0.3); 3.4509 (0.3); 3.3147 (46.3); 3.1753 (1.0); 3.1648 (1.0); 2.5246 (5.1); 2.5092 (6.1); 2.5056 (11.8); 2.5021 (16.3); 2.4985 (12.4); 2.4951 (6.5); 2.3319 (11.4); 2.2269 (9.5); 2.1972 (16.0); 2.0744 (0.6); 1.2340 (0.4); 0.0062 (0.3); −0.0002 (9.8); −0.0065 (0.5)

I-134: $^1$H-NMR (499.9 MHz, d$_6$-DMSO):
δ=8.5032 (2.7); 8.3097 (0.7); 7.9525 (0.6); 7.5551 (0.9); 7.5363 (1.8); 7.5181 (1.8); 7.4993 (1.0); 7.4085 (3.4); 7.3914 (3.5); 7.2705 (1.5); 7.2621 (1.4); 7.2329 (0.5); 7.2292 (0.5); 7.1899 (8.0); 7.1862 (8.4); 6.2665 (0.4); 6.2628 (0.4); 4.0934 (0.4); 3.6648 (1.0); 3.6626 (1.1); 3.6563 (0.6); 3.6325 (0.3); 3.5634 (4.0); 3.4785 (0.5); 3.3891 (2.0); 3.3190 (31.2); 3.1684 (0.5); 2.8903 (4.2); 2.8834 (0.4); 2.7308 (3.5); 2.6399 (0.4); 2.6360 (0.4); 2.5536 (2.0); 2.5347 (10.3); 2.5082 (20.9); 2.5047 (44.9); 2.5011 (63.6); 2.4975 (48.8); 2.4939 (25.8); 2.3621 (0.4); 2.3585 (0.3); 2.3228 (16.0); 2.2066 (8.1); 2.0732 (0.8); 1.2343 (1.3); 0.0063 (0.9); −0.0002 (29.3); −0.0067 (1.7)

I-135: $^1$H-NMR (400.0 MHz, d$_6$-DMSO):
δ=9.2930 (5.5); 8.5430 (9.3); 7.9093 (2.1); 7.8955 (2.2); 7.8869 (2.3); 7.8733 (2.2); 7.7169 (1.0); 7.6934 (1.8); 7.6697 (1.8); 7.6463 (1.1); 7.4304 (7.0); 7.4259 (7.2); 7.4169 (1.7); 7.4090 (2.9); 7.4038 (1.9); 7.3957 (4.0); 7.3876 (3.4); 7.3803 (1.8); 7.3736 (2.5); 7.3670 (2.5); 7.3021 (3.0); 7.2945 (2.6); 7.2793 (3.1); 7.2718 (2.5); 6.3036 (7.1); 6.2990 (7.3); 3.9523 (2.1); 3.9343 (6.9); 3.9163 (7.0); 3.8983 (2.2); 3.3515 (53.7); 3.3453 (67.5); 2.8944 (1.3); 2.7357 (1.2); 2.5295 (0.5); 2.5160 (13.2); 2.5117 (27.9); 2.5073 (37.5); 2.5028 (27.5); 2.4987 (13.7); 1.2253 (7.5); 1.2073 (16.0); 1.1892 (7.3); −0.0002 (2.6)

I-136: $^1$H-NMR (400.0 MHz, d$_6$-DMSO):
δ=9.1844 (8.9); 8.5698 (16.0); 7.9417 (5.4); 7.9215 (6.0); 7.7563 (0.4); 7.7526 (0.4); 7.7364 (0.5); 7.7333 (0.5); 7.7228 (1.7); 7.6993 (3.0); 7.6754 (2.9); 7.6523 (1.8); 7.5752 (0.8); 7.5707 (0.8); 7.5072 (14.4); 7.5027 (12.7); 7.4891 (5.0); 7.4723 (2.8); 7.4687 (2.8); 7.4006 (2.6); 7.3960 (2.9); 7.3882 (2.7); 7.3837 (3.0); 7.3771 (2.6); 7.3725 (2.5); 7.3643 (2.4); 7.3606 (2.4); 7.3511 (0.5); 7.3359 (0.5); 7.3326 (0.5); 7.3176 (0.3); 7.2963 (0.4); 7.2192 (3.1); 7.2022 (5.8); 7.2005 (5.9); 7.1838 (3.7); 7.1812 (3.9); 7.1737 (1.4); 7.1294 (0.3); 7.1073 (11.8); 7.0988 (14.6); 7.0915 (15.3); 7.0821 (2.0); 6.9638 (5.2); 6.9606 (5.6); 6.9447 (4.7); 6.9414 (4.7); 6.8671 (1.3); 6.8581 (6.7); 6.8492 (7.3); 6.8408 (6.1); 6.8347 (5.6); 6.8028 (0.4); 6.7980 (0.4); 6.2904 (12.0); 6.2859 (12.2); 6.2370 (0.8); 6.2325 (0.8); 4.0543 (5.7); 4.0360 (8.4); 4.0166 (6.1); 3.3512 (77.7); 3.3442 (81.3); 3.0043 (5.3); 2.9850 (7.6); 2.9666 (5.0); 2.8927 (0.8); 2.7346 (0.7); 2.6753 (0.4); 2.5285 (0.8); 2.5147 (25.0); 2.5107 (52.1); 2.5062 (69.6); 2.5018 (51.0); 2.3331 (0.4); 2.3286 (0.3); 1.2350 (0.7); −0.0002 (5.4)

I-137: $^1$H-NMR (400.0 MHz, d$_6$-DMSO):
δ=8.4874 (2.3); 8.4815 (2.6); 8.4046 (3.2); 8.3985 (2.8); 8.0219 (3.5); 8.0160 (3.6); 7.4608 (3.4); 7.4170 (3.3); 7.4127 (3.4); 7.2462 (3.0); 7.2422 (3.5); 7.2294 (3.2); 7.1990 (1.1); 7.1950 (1.6); 7.1912 (0.9); 7.1760 (1.1); 7.1727 (1.4); 6.6179 (2.6); 6.6122 (2.6); 6.3651 (3.6); 6.3606 (3.6); 3.7109 (16.0); 3.3587 (34.0); 2.8929 (0.7); 2.7342 (0.6); 2.5105 (8.9); 2.5063 (11.8); 2.5020 (8.8); −0.0002 (0.5)

I-138: $^1$H-NMR (400.0 MHz, d$_6$-DMSO):
δ=8.5442 (7.0); 8.5387 (7.6); 8.3948 (9.9); 8.3887 (9.1); 8.0499 (10.9); 8.0439 (11.0); 7.9533 (2.4); 7.8728 (0.3);

7.5151 (10.9); 7.5107 (11.0); 7.4885 (0.4); 7.4782 (0.4); 7.4668 (0.4); 7.3963 (1.7); 7.3843 (1.6); 7.3668 (1.4); 7.3464 (0.4); 7.3367 (2.2); 7.3329 (2.4); 7.3152 (4.8); 7.3010 (10.5); 7.1828 (1.4); 7.1741 (2.4); 7.1694 (2.2); 7.1608 (8.4); 7.1438 (16.0); 7.1350 (8.6); 7.1146 (5.8); 6.9294 (3.0); 6.9276 (3.0); 6.9145 (8.8); 6.9095 (12.8); 6.8922 (9.3); 6.8107 (5.4); 6.8072 (5.7); 6.7917 (4.1); 6.7882 (3.9); 6.6371 (7.6); 6.6323 (7.7); 6.2836 (11.2); 6.2792 (11.1); 4.1536 (5.2); 4.1357 (8.8); 4.1170 (5.5); 3.3585 (168.0); 3.0320 (5.1); 3.0137 (8.7); 2.9956 (4.8); 2.8916 (15.5); 2.7335 (14.0); 2.6741 (0.4); 2.5276 (0.8); 2.5139 (22.6); 2.5098 (46.7); 2.5054 (62.2); 2.5010 (45.2); 2.3319 (0.4); 1.6481 (1.9); 1.2386 (0.6); −0.0003 (1.3)

I-139: $^1$H-NMR (400.0 MHz, $d_6$-DMSO):

δ=8.6017 (4.3); 8.5962 (4.7); 8.4499 (6.2); 8.4438 (5.8); 8.0564 (6.5); 8.0505 (6.6); 7.9533 (0.9); 7.4853 (6.7); 7.4809 (6.8); 7.3697 (1.3); 7.3660 (1.4); 7.3480 (2.9); 7.3317 (7.3); 7.2380 (2.8); 7.2344 (2.9); 7.2191 (3.5); 7.2155 (3.3); 7.1548 (4.0); 7.1349 (3.3); 7.0455 (2.1); 7.0438 (2.1); 7.0269 (3.6); 7.0253 (3.6); 7.0086 (1.6); 7.0064 (1.6); 6.6449 (4.7); 6.6400 (4.7); 6.3212 (6.9); 6.3167 (6.9); 4.0009 (2.2); 3.9829 (7.0); 3.9649 (7.1); 3.9469 (2.3); 3.3680 (81.2); 3.3635 (73.5); 3.3615 (72.0); 2.8927 (6.0); 2.7340 (5.5); 2.5281 (0.3); 2.5107 (21.0); 2.5063 (27.9); 2.5019 (20.3); 1.2650 (7.5); 1.2471 (16.0); 1.2291 (7.3)

I-140: $^1$H-NMR (400.0 MHz, $d_6$-DMSO):

δ=8.5952 (2.3); 8.5894 (2.5); 8.4473 (3.1); 8.4413 (2.8); 8.0521 (3.6); 8.0461 (3.6); 7.4313 (3.7); 7.4265 (4.6); 7.4230 (3.4); 7.3728 (0.7); 7.3690 (0.8); 7.3511 (1.5); 7.3341 (1.0); 7.3302 (1.0); 7.2651 (1.5); 7.2614 (1.5); 7.2461 (1.9); 7.2424 (1.7); 7.1652 (2.2); 7.1451 (1.8); 7.0495 (1.2); 7.0473 (1.2); 7.0308 (1.9); 7.0287 (1.9); 7.0123 (0.9); 7.0100 (0.9); 6.6409 (2.6); 6.6351 (2.5); 6.3398 (3.6); 6.3354 (3.6); 3.6915 (16.0); 3.3710 (39.3); 3.3673 (39.0); 2.8929 (1.1); 2.7344 (1.1); 2.5152 (5.1); 2.5112 (10.5); 2.5068 (14.0); 2.5025 (10.2)

I-141: $^1$H-NMR (400.0 MHz, $d_6$-DMSO):

δ=8.4362 (7.6); 8.4303 (8.7); 8.3556 (11.0); 8.3495 (9.7); 8.0217 (11.9); 8.0157 (12.2); 7.5038 (11.5); 7.4994 (12.1); 7.4776 (0.4); 7.3953 (1.5); 7.3838 (1.5); 7.3658 (1.3); 7.3413 (11.1); 7.1819 (10.8); 7.1779 (10.8); 7.1649 (12.6); 7.1594 (9.0); 7.1547 (13.4); 7.1460 (15.3); 7.1391 (16.0); 7.1295 (2.1); 6.8868 (1.0); 6.8763 (6.6); 6.8677 (7.7); 6.8588 (6.5); 6.8531 (5.8); 6.6145 (9.0); 6.6086 (8.9); 6.4273 (4.6); 6.4048 (3.9); 6.2655 (11.9); 6.2611 (12.2); 4.1612 (5.6); 4.1437 (11.9); 4.1262 (6.0); 3.3623 (187.7); 3.3595 (173.8); 3.3570 (158.8); 3.0249 (5.6); 3.0075 (11.3); 2.9900 (5.4); 2.8917 (2.0); 2.7331 (1.9); 2.6746 (0.4); 2.5273 (0.9); 2.5138 (24.9); 2.5098 (52.2); 2.5054 (70.6); 2.5010 (52.0); 2.4968 (26.1); 2.3321 (0.4); 2.3281 (0.3); 1.6487 (1.6); 1.2382 (1.0); −0.0001 (1.0)

I-142: $^1$H-NMR (400.0 MHz, $d_6$-DMSO):

δ=8.4920 (4.8); 8.4863 (5.3); 8.4084 (6.6); 8.4023 (5.8); 8.0267 (7.0); 8.0208 (7.1); 7.4710 (6.8); 7.4665 (7.0); 7.3782 (6.9); 7.2370 (7.0); 7.2241 (6.4); 7.2202 (6.6); 7.1549 (2.6); 7.1371 (2.1); 7.1331 (3.3); 6.6219 (5.5); 6.6160 (5.3); 6.3457 (7.2); 6.3413 (7.3); 4.0149 (2.2); 3.9970 (7.2); 3.9790 (7.2); 3.9609 (2.3); 3.3585 (113.6); 3.3573 (115.4); 2.8929 (1.0); 2.7337 (0.9); 2.5102 (24.7); 2.5059 (32.6); 2.5017 (24.3); 1.2649 (7.6); 1.2469 (16.0); 1.2289 (7.4); −0.0002 (0.8)

I-143: $^1$H-NMR (400.0 MHz, $d_6$-DMSO):

δ=8.6088 (2.7); 8.6024 (2.7); 8.2409 (3.5); 7.5223 (1.1); 7.5089 (1.3); 7.5003 (1.6); 7.4856 (2.2); 7.4620 (2.4); 7.3974 (0.9); 7.3841 (1.6); 7.3769 (2.2); 7.3638 (2.2); 7.3553 (2.2); 7.3400 (5.5); 7.3357 (4.6); 7.3161 (4.3); 7.2161 (1.1); 7.1971 (1.0); 7.1882 (1.2); 7.1693 (0.9); 6.3225 (3.7); 6.3179 (3.6); 3.6777 (16.0); 3.6435 (0.5); 3.3565 (37.8); 2.8926 (0.8); 2.7347 (0.7); 2.5110 (11.9); 2.5069 (15.4); 2.5027 (11.2); −0.0002 (0.5)

I-144: $^1$H-NMR (400.0 MHz, $d_6$-DMSO):

δ=7.9542 (1.0); 7.5103 (0.6); 7.4936 (0.7); 7.4849 (1.3); 7.4710 (1.2); 7.4588 (1.0); 7.4404 (4.0); 7.4157 (1.0); 7.4114 (0.9); 7.4050 (0.5); 7.3896 (1.6); 7.3828 (1.8); 7.3752 (2.4); 7.3698 (1.9); 7.3623 (3.1); 7.3398 (0.3); 7.2952 (1.5); 7.2889 (1.4); 7.2721 (1.4); 7.2667 (1.2); 7.2441 (3.9); 7.2396 (4.1); 7.0947 (3.3); 6.2870 (4.0); 6.2825 (4.1); 4.0011 (1.2); 3.9831 (3.9); 3.9650 (4.0); 3.9470 (1.3); 3.3545 (38.2); 3.3514 (44.0); 3.3487 (43.6); 2.8926 (6.5); 2.7338 (5.9); 2.5718 (16.0); 2.5281 (0.3); 2.5146 (8.2); 2.5104 (17.4); 2.5059 (23.5); 2.5014 (17.1); 2.4971 (8.3); 1.2329 (0.3); 1.2109 (4.3); 1.1930 (9.0); 1.1749 (4.2); −0.0002 (0.5)

I-145: $^1$H-NMR (400.0 MHz, $d_6$-DMSO):

δ=7.9541 (2.5); 7.7746 (0.4); 7.7612 (0.4); 7.7522 (0.4); 7.7388 (0.4); 7.5999 (1.0); 7.5954 (1.0); 7.4918 (1.5); 7.4767 (1.9); 7.4679 (4.3); 7.4528 (5.7); 7.4354 (2.5); 7.4273 (3.0); 7.4101 (2.7); 7.3800 (9.5); 7.3456 (0.4); 7.3402 (0.5); 7.3124 (9.5); 7.2989 (9.3); 7.2952 (9.2); 7.2824 (10.3); 7.2780 (10.8); 7.2645 (0.7); 7.2564 (0.5); 7.2431 (0.3); 7.2030 (0.6); 7.1884 (3.1); 7.1800 (9.0); 7.1766 (9.8); 7.1686 (15.3); 7.1635 (14.9); 7.0686 (9.2); 6.8746 (6.3); 6.8656 (7.0); 6.8564 (6.4); 6.8520 (5.2); 6.8425 (1.2); 6.8285 (0.7); 6.8190 (0.5); 6.4903 (3.4); 6.4689 (3.8); 6.4117 (0.3); 6.2400 (0.9); 6.2356 (1.0); 6.1992 (9.9); 6.1949 (10.1); 4.1308 (4.8); 4.1133 (10.4); 4.0958 (5.2); 4.0715 (0.4); 4.0554 (0.6); 3.3539 (145.9); 3.0162 (0.5); 2.9992 (1.1); 2.9813 (0.8); 2.9702 (4.8); 2.9529 (9.7); 2.9354 (4.6); 2.8920 (16.0); 2.7335 (14.8); 2.6793 (0.3); 2.6747 (0.4); 2.5515 (40.7); 2.5278 (1.2); 2.5100 (57.2); 2.5056 (76.9); 2.5012 (56.7); 2.3324 (0.5); 2.3277 (0.4); 1.2369 (0.7); −0.0003 (1.9)

I-146: $^1$H-NMR (400.0 MHz, $d_6$-DMSO):

δ=7.9540 (2.6); 7.7557 (0.3); 7.7526 (0.4); 7.7335 (0.4); 7.5746 (0.8); 7.5701 (0.8); 7.5342 (2.2); 7.5190 (2.6); 7.5104 (4.6); 7.4970 (4.2); 7.4802 (3.4); 7.4610 (5.4); 7.4562 (6.3); 7.4376 (9.6); 7.4218 (4.2); 7.4182 (4.6); 7.4006 (0.4); 7.3964 (0.4); 7.3817 (0.6); 7.3764 (0.5); 7.3627 (0.5); 7.3552 (0.5); 7.3504 (0.5); 7.3456 (0.4); 7.3359 (0.6); 7.3325 (0.6); 7.3112 (13.9); 7.3068 (15.6); 7.2980 (12.4); 7.2847 (12.9); 7.2550 (8.5); 7.2351 (7.0); 7.1957 (2.5); 7.1898 (4.1); 7.1740 (13.0); 7.1555 (15.7); 7.1503 (10.0); 7.1414 (2.5); 7.1334 (5.2); 7.1199 (4.7); 7.1013 (7.7); 7.0825 (4.2); 6.9135 (11.4); 6.8974 (10.5); 6.8799 (7.4); 6.8610 (6.3); 6.8199 (0.4); 6.8150 (0.3); 6.8020 (0.3); 6.7970 (0.3); 6.2358 (1.1); 6.2285 (13.2); 6.2241 (13.7); 4.1267 (6.6); 4.1086 (11.7); 4.0903 (7.2); 4.0357 (0.5); 3.3507 (151.8); 3.3480 (151.4); 3.0078 (0.5); 2.9905 (1.0); 2.9737 (6.9); 2.9555 (11.4); 2.9375 (6.2); 2.8915 (16.0); 2.7331 (15.0); 2.7005 (0.3); 2.6740 (0.6); 2.6700 (0.5); 2.5432 (54.6); 2.5276 (2.0); 2.5093 (70.9); 2.5050 (95.4); 2.5007 (71.0); 2.3817 (0.3); 2.3361 (0.4); 2.3315 (0.6); 1.2364 (0.9); −0.0002 (3.0)

I-147: $^1$H-NMR (400.0 MHz, $d_6$-DMSO):

δ=7.9542 (1.1); 7.5248 (2.9); 7.5065 (0.6); 7.4890 (0.6); 7.4805 (1.1); 7.4667 (1.0); 7.4523 (0.8); 7.4346 (0.8); 7.4269 (0.9); 7.4092 (1.0); 7.3821 (3.5); 7.3686 (3.6); 7.3649 (4.8); 7.3459 (1.3); 7.3414 (1.3); 7.1756 (3.6); 7.1709 (3.6); 7.0704 (2.9); 6.2572 (3.6); 6.2525 (3.5); 3.6987 (16.0); 3.3927 (0.4); 3.3535 (36.0); 3.3516 (35.9); 3.3478 (32.7); 2.8926 (7.5); 2.7342 (6.6); 2.5882 (14.1); 2.5144 (7.4); 2.5102 (15.2); 2.5057 (20.2); 2.5012 (14.5); 2.4970 (7.0); −0.0002 (1.1)

I-148: $^1$H-NMR (400.0 MHz, d$_6$-DMSO):
δ=7.9540 (1.0); 7.5366 (0.6); 7.5338 (0.6); 7.5192 (0.7); 7.5104 (1.2); 7.4960 (3.8); 7.4853 (1.7); 7.4827 (1.7); 7.4717 (1.0); 7.4667 (1.2); 7.4628 (1.2); 7.4540 (0.8); 7.4464 (1.0); 7.4283 (0.9); 7.4235 (0.6); 7.4022 (1.5); 7.3985 (1.5); 7.3830 (1.9); 7.3795 (1.7); 7.2969 (2.1); 7.2771 (1.7); 7.2690 (1.3); 7.2666 (1.2); 7.2501 (2.0); 7.2478 (1.9); 7.2390 (3.0); 7.1909 (3.3); 7.1864 (3.4); 6.2415 (3.5); 6.2369 (3.6); 3.6752 (16.0); 3.3682 (58.8); 2.8929 (6.3); 2.7343 (5.8); 2.5966 (14.4); 2.5114 (13.0); 2.5070 (17.6); 2.5025 (13.0); 2.4983 (6.5)

I-149: $^1$H-NMR (400.0 MHz, d$_6$-DMSO):
δ=7.9540 (0.8); 7.5491 (0.7); 7.5345 (0.9); 7.5265 (1.4); 7.5127 (1.3); 7.5006 (1.0); 7.4980 (1.0); 7.4822 (2.6); 7.4591 (2.4); 7.4404 (1.2); 7.4169 (0.6); 7.3735 (3.7); 7.3553 (1.8); 7.3371 (2.4); 7.2942 (3.8); 7.2771 (2.9); 7.2689 (4.0); 7.2644 (4.9); 7.2622 (4.8); 7.2421 (2.4); 7.2233 (1.0); 6.2679 (3.7); 6.2659 (3.6); 6.2635 (4.1); 3.9824 (1.2); 3.9646 (3.8); 3.9466 (3.9); 3.9286 (1.3); 3.3563 (24.7); 3.3464 (55.5); 2.8922 (4.1); 2.7333 (4.1); 2.5733 (16.0); 2.5056 (23.4); 2.5015 (18.2); 1.2196 (4.1); 1.2018 (8.6); 1.1837 (4.0); −0.0002 (1.2); −0.0023 (0.9)

I-150: $^1$H-NMR (400.0 MHz, d$_6$-DMSO):
δ=8.6203 (5.4); 8.6138 (5.4); 8.1637 (5.7); 7.5403 (0.4); 7.5358 (0.5); 7.5281 (2.1); 7.5148 (2.9); 7.5058 (2.9); 7.4923 (5.3); 7.4703 (4.1); 7.4146 (0.3); 7.4025 (7.6); 7.3984 (7.6); 7.3870 (2.8); 7.3801 (3.3); 7.3663 (3.4); 7.3576 (3.2); 7.3444 (5.4); 7.2837 (2.9); 7.2762 (2.5); 7.2609 (3.0); 7.2534 (2.4); 7.2183 (1.9); 7.1992 (1.7); 7.1905 (2.0); 7.1713 (1.6); 6.3245 (7.4); 6.3200 (7.4); 3.9629 (2.2); 3.9450 (7.0); 3.9269 (7.2); 3.9088 (2.4); 3.8880 (0.5); 3.3555 (96.8); 2.8924 (1.0); 2.7339 (0.9); 2.5279 (0.5); 2.5105 (28.6); 2.5061 (38.1); 2.5017 (27.8); 1.2573 (0.6); 1.2389 (1.2); 1.2206 (0.8); 1.2120 (7.6); 1.1941 (16.0); 1.1760 (7.4); −0.0002 (0.5)

I-151: $^1$H-NMR (400.0 MHz, d$_6$-DMSO):
δ=8.7281 (5.2); 8.7217 (5.2); 8.1315 (6.3); 7.6130 (0.9); 7.5967 (1.2); 7.5883 (2.6); 7.5722 (3.3); 7.5540 (5.9); 7.5289 (1.8); 7.5233 (0.9); 7.5047 (1.0); 7.4826 (3.5); 7.4787 (5.9); 7.4694 (8.6); 7.4573 (0.9); 7.4133 (7.0); 7.4089 (7.2); 7.3967 (1.1); 7.3849 (1.0); 7.3671 (1.0); 7.3579 (3.1); 7.3391 (4.6); 7.2461 (2.0); 7.2380 (2.0); 7.2331 (1.8); 7.2254 (2.3); 7.2175 (1.6); 7.2152 (1.6); 7.2057 (1.3); 6.2985 (7.4); 6.2941 (7.3); 3.9393 (2.2); 3.9213 (7.0); 3.9033 (7.1); 3.8853 (2.3); 3.3608 (78.7); 3.3583 (84.6); 2.8940 (1.2); 2.7354 (1.1); 2.5164 (12.6); 2.5123 (25.6); 2.5079 (33.8); 2.5034 (24.4); 2.4992 (11.9); 1.6502 (1.1); 1.2354 (0.3); 1.2090 (7.5); 1.1911 (16.0); 1.1731 (7.3); −0.0002 (1.1)

I-152: $^1$H-NMR (400.0 MHz, d$_6$-DMSO):
δ=8.7160 (2.7); 8.7096 (2.6); 8.2260 (3.0); 7.6008 (0.6); 7.5844 (0.7); 7.5767 (1.6); 7.5651 (2.0); 7.5494 (1.2); 7.5413 (1.3); 7.5231 (2.6); 7.5185 (2.6); 7.5006 (0.9); 7.4822 (1.9); 7.4787 (2.1); 7.4734 (2.7); 7.4675 (4.2); 7.4656 (4.0); 7.4535 (0.7); 7.4383 (0.3); 7.3946 (1.5); 7.3927 (1.5); 7.3745 (2.3); 7.3491 (3.7); 7.3445 (3.6); 7.2480 (1.0); 7.2411 (1.0); 7.2337 (1.0); 7.2283 (1.2); 7.2211 (0.8); 7.2155 (0.8); 7.2076 (0.7); 6.3025 (3.7); 6.2978 (3.5); 3.6450 (16.0); 3.6268 (0.5); 3.6156 (0.7); 3.3581 (39.2); 3.3557 (42.3); 3.3360 (4.2); 2.8944 (1.7); 2.7362 (1.5); 2.5166 (6.5); 2.5125 (11.6); 2.5081 (14.5); 2.5036 (10.5); 2.4995 (5.3); 2.4797 (1.1); −0.0002 (0.6)

I-153: $^1$H-NMR (300.2 MHz, CDCl3):
δ=8.6938 (1.9); 8.6851 (2.0); 7.6535 (1.3); 7.6483 (1.5); 7.6452 (1.5); 7.6402 (1.5); 7.6015 (2.6); 7.5953 (2.6); 7.4660 (1.0); 7.4498 (1.0); 7.4362 (1.2); 7.4200 (2.4); 7.4130 (1.6); 7.4104 (1.5); 7.3948 (3.0); 7.3802 (1.0); 7.2985 (3.0); 7.2196 (0.6); 7.2096 (0.7); 7.1934 (0.7); 7.1901 (0.6); 7.1835 (0.8); 7.1803 (0.7); 7.1638 (0.5); 7.1539 (0.6); 7.1118 (1.2); 7.1019 (1.0); 7.0835 (1.2); 7.0736 (1.0); 6.3707 (2.8); 6.3645 (2.7); 5.7645 (1.4); 5.3330 (2.5); 3.7920 (16.0); 1.6898 (2.0); 0.0336 (3.0)

I-154: $^1$H-NMR (400.0 MHz, d$_6$-DMSO):
δ=8.7126 (5.6); 8.7064 (5.7); 8.1042 (7.3); 7.9556 (0.4); 7.8268 (0.6); 7.8173 (0.6); 7.8112 (0.5); 7.7982 (0.7); 7.7939 (0.6); 7.7866 (0.8); 7.7545 (0.4); 7.7352 (0.4); 7.5969 (0.9); 7.5816 (1.3); 7.5732 (5.0); 7.5584 (3.8); 7.5377 (5.5); 7.5048 (0.8); 7.4921 (0.3); 7.4802 (0.9); 7.4748 (0.8); 7.4670 (1.7); 7.4568 (9.1); 7.4525 (16.0); 7.4423 (8.6); 7.4187 (0.8); 7.3878 (0.9); 7.3782 (0.4); 7.3641 (0.3); 7.3574 (0.4); 7.3477 (0.8); 7.3369 (0.5); 7.3340 (0.5); 7.1899 (0.7); 7.1807 (1.0); 7.1742 (1.0); 7.1281 (9.0); 7.1210 (12.0); 7.1128 (12.3); 7.0924 (1.9); 6.9700 (4.6); 6.9512 (3.6); 6.8613 (4.6); 6.8532 (5.0); 6.8470 (4.6); 6.8385 (3.9); 6.8234 (0.5); 6.2869 (7.4); 6.2830 (7.6); 6.2377 (0.6); 6.2336 (0.6); 4.0757 (3.8); 4.0576 (5.9); 4.0382 (4.5); 4.0189 (0.4); 3.3474 (50.4); 3.3447 (57.1); 3.3416 (88.8); 3.0097 (0.4); 2.9919 (0.8); 2.9771 (3.9); 2.9580 (5.6); 2.9398 (3.6); 2.8928 (2.6); 2.7345 (2.5); 2.6753 (0.3); 2.5103 (44.7); 2.5061 (59.9); 2.5019 (44.7); 2.3328 (0.4); 1.2373 (0.4); 0.0012 (2.5); −0.0001 (2.6)

I-155: $^1$H-NMR (400.0 MHz, d$_6$-DMSO):
δ=8.5527 (4.5); 8.0574 (1.6); 8.0555 (1.6); 8.0372 (1.8); 8.0342 (1.8); 7.9434 (1.8); 7.9234 (2.0); 7.6591 (0.7); 7.6558 (0.8); 7.6420 (1.5); 7.6388 (1.8); 7.6219 (1.4); 7.6181 (1.3); 7.6081 (1.4); 7.6044 (1.5); 7.5873 (1.7); 7.5843 (1.4); 7.5702 (0.7); 7.5669 (0.7); 7.4830 (3.8); 7.4786 (3.9); 7.2654 (0.8); 7.2616 (0.9); 7.2435 (1.7); 7.2266 (1.0); 7.2228 (1.1); 7.2080 (1.8); 7.2044 (1.7); 7.1892 (2.2); 7.1856 (1.9); 7.0976 (3.3); 6.9465 (1.2); 6.9444 (1.3); 6.9279 (2.1); 6.9258 (2.2); 6.9095 (1.0); 6.9072 (1.0); 6.5981 (2.2); 6.5781 (2.1); 6.3665 (3.9); 6.3621 (4.0); 4.0648 (1.2); 4.0468 (3.8); 4.0288 (3.9); 4.0108 (1.3); 3.3570 (28.1); 3.3524 (34.0); 3.3493 (28.0); 2.8911 (0.8); 2.7329 (0.8); 2.5094 (14.4); 2.5050 (19.2); 2.5005 (14.1); 2.4964 (7.0); 2.4405 (16.0); 1.3047 (4.0); 1.2867 (8.6); 1.2687 (4.0); −0.0002 (0.8)

I-156: $^1$H-NMR (400.0 MHz, d$_6$-DMSO):
δ=8.5409 (4.8); 8.0535 (1.7); 8.0331 (1.9); 7.9375 (1.8); 7.9172 (2.0); 7.6484 (0.8); 7.6315 (1.7); 7.6122 (1.4); 7.6082 (1.3); 7.6023 (1.5); 7.5818 (1.5); 7.5649 (0.7); 7.4216 (3.5); 7.4203 (3.5); 7.4174 (3.3); 7.2687 (0.9); 7.2498 (1.9); 7.2342 (2.7); 7.2171 (5.4); 6.9547 (1.4); 6.9361 (2.3); 6.9175 (1.1); 6.6323 (2.4); 6.6120 (2.3); 6.3640 (3.6); 6.3597 (3.3); 3.7474 (16.0); 3.3459 (45.5); 2.8907 (1.2); 2.7333 (1.2); 2.5040 (19.9); 2.4509 (14.5); −0.0002 (1.2)

I-157: $^1$H-NMR (400.0 MHz, d$_6$-DMSO):
δ=8.4613 (4.7); 8.0269 (1.3); 8.0243 (1.2); 8.0213 (1.0); 8.0078 (1.6); 8.0029 (1.5); 7.9527 (0.8); 7.9084 (1.3); 7.9040 (1.5); 7.8848 (1.6); 7.6155 (0.5); 7.6115 (0.6); 7.5985 (1.4); 7.5946 (1.4); 7.5800 (2.1); 7.5775 (2.1); 7.5624 (1.2); 7.5587 (1.3); 7.5453 (0.6); 7.5416 (0.4); 7.3821 (3.3); 7.3776 (3.3); 7.2487 (2.8); 7.1748 (3.0); 7.1533 (3.7); 7.1337 (1.0); 7.1261 (0.5); 6.7598 (0.9); 6.7475 (0.9); 6.7374 (0.9); 6.7244 (0.8); 6.3729 (3.5); 6.3683 (3.5); 3.7574 (16.0); 3.3718 (59.9); 2.8915 (5.2); 2.7331 (4.8); 2.5101 (13.4); 2.5058 (17.9); 2.5014 (13.2); 2.4359 (14.5)

I-158: $^1$H-NMR (400.0 MHz, d$_6$-DMSO):
δ=8.3041 (2.4); 7.9092 (1.5); 7.8892 (1.7); 7.7225 (2.0); 7.7023 (2.1); 7.5559 (0.8); 7.5521 (0.9); 7.5333 (1.7); 7.5173 (1.0); 7.5135 (1.1); 7.5053 (0.4); 7.4945 (4.4);

7.4839 (3.7); 7.4625 (1.6); 7.4591 (1.6); 7.4522 (0.6); 7.4435 (2.1); 7.4400 (1.9); 7.3842 (1.0); 7.3751 (1.1); 7.3726 (1.0); 7.3632 (2.0); 7.3580 (1.6); 7.3514 (1.0); 7.3424 (2.3); 7.3233 (0.7); 7.3208 (0.8); 7.2413 (3.0); 7.2369 (3.1); 6.3204 (0.4); 6.3158 (0.4); 6.2802 (3.2); 6.2758 (3.2); 3.7169 (16.0); 3.6144 (2.0); 3.3467 (22.4); 3.3420 (26.2); 2.8895 (0.6); 2.7319 (0.5); 2.5125 (22.4); 2.5080 (16.7); 2.5033 (20.0); 2.4989 (14.5); −0.0002 (1.4)

I-159: $^1$H-NMR (400.0 MHz, d$_6$-DMSO):
δ=8.1110 (5.8); 8.0559 (3.6); 8.0359 (3.9); 7.9546 (0.5); 7.8544 (0.3); 7.7372 (4.2); 7.7172 (4.6); 7.5756 (1.8); 7.5556 (3.6); 7.5340 (2.8); 7.5174 (9.0); 7.5026 (4.4); 7.4817 (1.4); 7.4656 (0.4); 7.4148 (2.8); 7.3941 (7.9); 7.3798 (4.8); 7.3737 (2.9); 7.3639 (11.3); 7.3616 (11.0); 7.3413 (4.4); 7.3226 (1.6); 6.3462 (7.5); 6.3440 (6.5); 3.9783 (2.3); 3.9603 (7.2); 3.9423 (7.3); 3.9244 (2.4); 3.3417 (79.3); 2.8899 (2.8); 2.7323 (2.6); 2.5038 (40.5); 2.4669 (30.3); 1.6473 (1.9); 1.2345 (8.3); 1.2164 (16.0); 1.1984 (7.5); −0.0002 (2.5)

I-160: $^1$H-NMR (400.0 MHz, d$_6$-DMSO):
δ=8.2417 (4.5); 7.8798 (2.0); 7.8661 (2.0); 7.8577 (2.3); 7.8440 (2.1); 7.7219 (3.2); 7.7020 (3.9); 7.5407 (0.3); 7.5361 (0.3); 7.5088 (0.6); 7.5059 (0.6); 7.4879 (2.7); 7.4851 (3.0); 7.4708 (8.4); 7.4557 (1.1); 7.4345 (1.4); 7.4270 (1.5); 7.4131 (2.5); 7.4055 (2.7); 7.3981 (0.7); 7.3910 (2.1); 7.3821 (3.2); 7.3759 (2.4); 7.3670 (2.0); 7.3612 (3.6); 7.3549 (1.9); 7.3472 (1.7); 7.3403 (1.8); 7.3351 (3.1); 7.3242 (7.4); 7.3196 (7.2); 7.3124 (3.1); 7.3048 (2.4); 6.3301 (6.8); 6.3256 (6.9); 3.9955 (2.1); 3.9774 (6.8); 3.9594 (6.9); 3.9414 (2.2); 3.9051 (0.4); 3.8870 (0.4); 3.3751 (113.7); 3.3694 (153.2); 2.8913 (1.1); 2.7333 (1.0); 2.5104 (27.8); 2.5060 (36.5); 2.5016 (26.5); 2.4834 (27.6); 1.6493 (1.0); 1.2558 (0.5); 1.2376 (1.5); 1.2247 (7.6); 1.2067 (16.0); 1.1886 (7.3); −0.0002 (0.3)

I-161: $^1$H-NMR (400.0 MHz, d$_6$-DMSO):
δ=8.0168 (3.0); 7.9650 (1.1); 7.9518 (1.5); 7.9430 (1.2); 7.9291 (1.1); 7.7369 (2.0); 7.7167 (2.2); 7.5989 (0.4); 7.5945 (0.4); 7.5112 (0.4); 7.4932 (1.4); 7.4903 (1.5); 7.4764 (4.2); 7.4560 (0.8); 7.4243 (3.6); 7.4199 (3.8); 7.3959 (1.2); 7.3906 (1.1); 7.3756 (2.1); 7.3705 (1.8); 7.3564 (1.9); 7.3493 (1.5); 7.3354 (0.9); 7.3279 (0.8); 7.1869 (0.5); 7.1813 (0.6); 7.1709 (0.4); 7.1420 (1.4); 7.1247 (3.9); 7.1059 (3.2); 7.0793 (1.7); 7.0614 (2.0); 7.0546 (0.4); 7.0431 (0.6); 6.8895 (3.7); 6.8719 (3.2); 6.5907 (1.4); 6.5833 (1.4); 6.5679 (1.4); 6.5605 (1.3); 6.3219 (3.6); 6.3175 (3.7); 6.2392 (0.4); 6.2348 (0.4); 4.1378 (1.8); 4.1204 (4.0); 4.1030 (2.0); 3.3436 (52.1); 3.0066 (1.8); 2.9893 (3.8); 2.9719 (1.7); 2.8901 (2.6); 2.7323 (2.5); 2.5081 (19.9); 2.5039 (26.4); 2.4996 (19.4); 2.4166 (16.0); −0.0002 (1.0)

I-162: $^1$H-NMR (400.0 MHz, d$_6$-DMSO):
δ=8.6634 (2.6); 8.6569 (2.7); 8.2257 (2.9); 7.9538 (0.6); 7.5050 (1.5); 7.4849 (5.8); 7.4756 (4.1); 7.4582 (2.2); 7.4091 (0.8); 7.3967 (2.4); 7.3895 (1.4); 7.3774 (3.0); 7.3695 (0.8); 7.3535 (3.4); 7.3489 (3.4); 7.2520 (1.0); 7.2413 (1.4); 7.2328 (1.9); 7.2219 (1.2); 7.2119 (1.1); 7.2080 (1.1); 7.2057 (1.0); 7.1863 (0.8); 6.3023 (3.4); 6.2977 (3.5); 3.6470 (16.0); 3.6157 (0.8); 3.3414 (54.9); 3.1834 (0.4); 2.8916 (3.6); 2.7330 (3.3); 2.5129 (8.4); 2.5089 (17.5); 2.5045 (23.5); 2.5001 (17.3); −0.0002 (2.3)

I-163: $^1$H-NMR (300.2 MHz, CDCl3):
δ=8.6820 (4.1); 8.6733 (4.1); 7.6622 (2.7); 7.6570 (3.2); 7.6538 (3.3); 7.6449 (6.2); 7.6387 (5.7); 7.4570 (2.0); 7.4408 (2.2); 7.4290 (3.4); 7.4216 (4.2); 7.4158 (3.3); 7.4107 (5.0); 7.3966 (7.0); 7.3802 (2.2); 7.3497 (0.4); 7.2986 (5.0); 7.2169 (1.2); 7.2069 (1.4); 7.1906 (1.4); 7.1874 (1.2); 7.1807 (1.7); 7.1776 (1.5); 7.1610 (1.0); 7.1511 (1.2); 7.1030 (2.6); 7.0931 (2.2); 7.0747 (2.7); 7.0649 (2.1); 6.3526 (6.0); 6.3464 (6.0); 5.7308 (3.1); 4.1022 (2.2); 4.0781 (7.1); 4.0540 (7.2); 4.0299 (2.3); 2.2026 (1.0); 2.0403 (2.9); 1.7083 (1.4); 1.3871 (7.5); 1.3630 (16.0); 1.3389 (7.3); 0.0324 (5.5)

I-164: $^1$H-NMR (400.0 MHz, d$_6$-DMSO):
δ=8.4916 (8.6); 8.0368 (2.7); 8.0330 (3.1); 8.0130 (3.2); 7.9549 (0.7); 7.9410 (2.8); 7.9217 (3.3); 7.9182 (3.1); 7.6758 (6.0); 7.6633 (3.1); 7.6601 (3.0); 7.6435 (3.1); 7.6395 (4.8); 7.6352 (3.3); 7.6192 (2.6); 7.6158 (2.7); 7.6021 (1.2); 7.5984 (1.1); 7.4566 (1.4); 7.4527 (1.6); 7.4368 (2.8); 7.4334 (3.1); 7.4180 (2.0); 7.4141 (2.1); 7.3578 (6.5); 7.3534 (6.6); 7.3392 (2.8); 7.3356 (2.9); 7.3203 (3.8); 7.3166 (3.5); 7.2174 (2.6); 7.1987 (4.2); 7.1883 (4.4); 7.1800 (2.1); 7.1683 (3.6); 6.2970 (6.8); 6.2925 (6.8); 4.0287 (2.2); 4.0107 (6.9); 3.9927 (7.0); 3.9746 (2.2); 3.3642 (62.0); 3.3619 (75.5); 3.3592 (78.6); 3.3566 (74.8); 2.8925 (4.2); 2.7344 (3.8); 2.5290 (0.5); 2.5155 (13.4); 2.5113 (28.0); 2.5069 (37.6); 2.5024 (27.3); 2.4981 (13.4); 1.2508 (7.5); 1.2329 (16.0); 1.2148 (7.2); −0.0002 (0.7)

I-165: $^1$H-NMR (400.0 MHz, d$_6$-DMSO):
δ=8.4370 (4.5); 8.0321 (1.3); 8.0289 (1.6); 8.0110 (1.5); 8.0087 (1.6); 7.9547 (0.7); 7.9276 (1.4); 7.9095 (1.6); 7.9067 (1.6); 7.8239 (2.4); 7.6737 (0.6); 7.6708 (0.7); 7.6565 (1.3); 7.6536 (1.4); 7.6366 (1.2); 7.6327 (1.2); 7.6273 (1.3); 7.6231 (1.4); 7.6065 (1.4); 7.6034 (1.3); 7.5895 (0.6); 7.5859 (0.6); 7.4626 (0.7); 7.4589 (0.8); 7.4426 (1.4); 7.4241 (0.9); 7.4204 (1.0); 7.3949 (0.6); 7.3829 (0.6); 7.3755 (1.4); 7.3714 (1.6); 7.3556 (1.9); 7.3521 (1.7); 7.2791 (3.2); 7.2746 (3.4); 7.2267 (1.3); 7.2136 (2.3); 7.2098 (2.3); 7.1929 (2.1); 6.2781 (3.4); 6.2735 (3.5); 3.7096 (16.0); 3.3560 (30.0); 3.3514 (42.2); 2.8918 (4.3); 2.7339 (3.8); 2.5102 (14.1); 2.5058 (19.0); 2.5013 (14.1); 1.6485 (0.6); −0.0002 (0.7)

I-166: $^1$H-NMR (400.0 MHz, d$_6$-DMSO):
δ=8.3244 (4.8); 7.9957 (1.6); 7.9768 (1.7); 7.9750 (1.8); 7.9544 (0.9); 7.8949 (3.2); 7.8786 (1.9); 7.6535 (0.7); 7.6505 (0.8); 7.6361 (1.3); 7.6331 (1.7); 7.6156 (1.2); 7.6123 (1.1); 7.5909 (1.2); 7.5874 (1.3); 7.5702 (1.6); 7.5671 (1.3); 7.5530 (0.7); 7.5497 (0.7); 7.3955 (0.7); 7.3835 (0.6); 7.3664 (0.8); 7.3609 (0.5); 7.3437 (1.1); 7.3379 (1.8); 7.3264 (3.7); 7.3185 (2.9); 7.3133 (2.4); 7.3035 (1.8); 7.2980 (1.3); 7.2906 (0.5); 7.2460 (3.3); 7.2415 (3.4); 6.2896 (3.5); 6.2850 (3.5); 3.7271 (16.0); 3.7022 (0.5); 3.3927 (0.5); 3.3496 (30.9); 3.3451 (30.0); 3.3429 (30.2); 2.8916 (5.6); 2.7335 (5.1); 2.5139 (7.8); 2.5096 (16.4); 2.5052 (22.1); 2.5007 (16.1); 2.4965 (7.9); 1.6485 (0.7); −0.0001 (1.1)

I-167: $^1$H-NMR (400.0 MHz, d$_6$-DMSO):
δ=8.4540 (16.0); 8.0212 (4.3); 8.0175 (5.0); 8.0004 (4.6); 7.9973 (5.1); 7.9544 (2.0); 7.9334 (4.4); 7.9156 (5.0); 7.9122 (4.9); 7.6752 (1.7); 7.6720 (2.2); 7.6577 (4.2); 7.6549 (4.4); 7.6380 (4.8); 7.6343 (7.3); 7.6303 (5.5); 7.6149 (11.0); 7.5971 (2.0); 7.5935 (1.8); 7.5722 (0.3); 7.4872 (0.3); 7.4673 (0.4); 7.4627 (0.4); 7.4477 (0.5); 7.4216 (2.4); 7.4182 (2.6); 7.3997 (5.1); 7.3862 (11.9); 7.3818 (14.2); 7.3508 (0.6); 7.3438 (0.6); 7.3250 (0.6); 7.3148 (0.6); 7.3069 (0.6); 7.2951 (0.7); 7.2664 (0.5); 7.2520 (0.4); 7.2347 (0.4); 7.2250 (0.5); 7.2204 (0.6); 7.1927 (2.4); 7.1880 (3.7); 7.1717 (16.0); 7.1529 (15.0); 7.1460 (4.4); 7.1413 (6.0); 7.1307 (2.0); 7.1240 (5.0); 7.1151 (1.1); 7.1059 (1.5); 7.0955 (3.1); 7.0766 (5.9); 7.0580 (3.2); 6.9331 (7.7); 6.9296 (9.8); 6.9105 (12.5); 6.8912 (4.6); 6.8877 (4.6); 6.2536 (10.6); 6.2492 (11.1); 4.6974 (0.4); 4.6782 (0.4); 4.6052 (0.3); 4.1835 (5.3); 4.1656 (8.8); 4.1468 (5.7); 3.3734 (250.3); 3.3708 (245.8);

3.0015 (5.2); 2.9829 (8.7); 2.9650 (5.0); 2.8918 (12.5); 2.7538 (0.3); 2.7339 (11.4); 2.6801 (0.3); 2.6763 (0.4); 2.6715 (0.3); 2.5292 (0.9); 2.5114 (54.2); 2.5070 (73.7); 2.5026 (54.8); 2.4177 (0.4); 2.3379 (0.3); 2.3338 (0.4); 2.3293 (0.4); 1.2348 (1.3); −0.0001 (0.9)

I-168: $^1$H-NMR (400.0 MHz, $d_6$-DMSO):

δ=8.3187 (15.1); 7.9865 (5.0); 7.9659 (5.7); 7.9547 (2.5); 7.8981 (5.1); 7.8778 (5.7); 7.7751 (0.3); 7.7614 (0.4); 7.7527 (0.4); 7.7253 (9.3); 7.6501 (2.4); 7.6327 (5.0); 7.6151 (3.8); 7.6120 (3.6); 7.5959 (4.4); 7.5927 (4.3); 7.5753 (4.9); 7.5583 (2.2); 7.5551 (2.0); 7.4652 (0.3); 7.4450 (0.3); 7.4286 (0.4); 7.4068 (0.4); 7.3863 (0.4); 7.3464 (10.4); 7.3421 (10.8); 7.3151 (0.9); 7.3076 (0.7); 7.2958 (2.7); 7.2887 (1.8); 7.2737 (4.1); 7.2666 (4.3); 7.2528 (9.1); 7.2472 (5.2); 7.2383 (6.8); 7.2304 (2.7); 7.2166 (2.0); 7.1992 (1.4); 7.1875 (3.2); 7.1763 (8.9); 7.1633 (15.6); 7.1593 (16.0); 7.1523 (4.2); 7.1313 (1.2); 7.1080 (0.4); 7.0822 (0.4); 7.0617 (0.5); 7.0492 (0.4); 7.0261 (0.4); 7.0082 (0.4); 6.9982 (0.4); 6.9859 (0.6); 6.8955 (7.2); 6.8888 (6.7); 6.8767 (7.1); 6.8374 (0.5); 6.8283 (0.5); 6.8189 (0.4); 6.5317 (3.6); 6.5249 (3.7); 6.5088 (3.7); 6.5025 (3.6); 6.2398 (0.6); 6.2353 (0.7); 6.2218 (10.3); 6.2174 (10.5); 4.1826 (5.1); 4.1650 (10.8); 4.1475 (5.6); 4.0554 (0.4); 3.3417 (112.0); 3.0581 (0.4); 3.0167 (0.6); 2.9971 (5.6); 2.9794 (10.4); 2.9619 (5.0); 2.8913 (14.2); 2.7527 (0.3); 2.7335 (13.2); 2.6783 (0.4); 2.6739 (0.5); 2.6697 (0.4); 2.5266 (1.0); 2.5090 (62.8); 2.5048 (82.8); 2.5005 (60.9); 2.3317 (0.5); 1.2371 (1.1); −0.0001 (6.4)

I-169: $^1$H-NMR (400.0 MHz, $d_6$-DMSO):

δ=8.3679 (9.5); 7.9997 (3.3); 7.9803 (3.7); 7.9552 (1.1); 7.9076 (3.4); 7.8874 (3.8); 7.7792 (5.6); 7.6558 (1.6); 7.6384 (3.2); 7.6205 (2.4); 7.6176 (2.3); 7.6013 (2.4); 7.5982 (2.7); 7.5807 (3.2); 7.5635 (1.4); 7.5607 (1.3); 7.4714 (0.3); 7.3938 (0.4); 7.3831 (0.4); 7.3622 (1.1); 7.3548 (1.1); 7.3401 (2.5); 7.3328 (2.9); 7.3198 (8.5); 7.3157 (7.7); 7.3036 (3.8); 7.2901 (3.9); 7.2816 (1.8); 7.2680 (4.4); 7.2609 (2.7); 7.2454 (3.0); 7.2384 (2.5); 6.3126 (6.7); 6.3083 (6.8); 4.0405 (2.2); 4.0225 (7.0); 4.0045 (7.1); 3.9865 (2.3); 3.3513 (59.5); 2.8926 (6.2); 2.7345 (6.0); 2.5104 (31.4); 2.5063 (41.5); 2.5022 (31.2); 1.6513 (0.4); 1.2520 (7.6); 1.2339 (16.0); 1.2160 (7.4); −0.0002 (2.4)

I-170: $^1$H-NMR (400.0 MHz, $d_6$-DMSO):

δ=8.4800 (5.3); 8.0315 (1.5); 8.0117 (1.8); 8.0075 (1.7); 7.9536 (0.6); 7.9169 (1.5); 7.9131 (1.6); 7.8935 (1.8); 7.6257 (0.6); 7.6222 (0.8); 7.6087 (1.6); 7.6054 (1.5); 7.5887 (2.5); 7.5839 (2.5); 7.5671 (1.4); 7.5642 (1.4); 7.5503 (0.6); 7.5467 (0.5); 7.4478 (3.6); 7.4435 (3.6); 7.1689 (0.6); 7.1611 (0.9); 7.1475 (1.2); 7.1382 (4.8); 7.1363 (4.9); 7.1273 (1.6); 7.1186 (1.4); 7.1121 (2.2); 7.1050 (1.0); 6.7149 (1.3); 6.7023 (1.4); 6.6932 (1.3); 6.6805 (1.2); 6.3765 (3.6); 6.3721 (3.7); 4.0739 (1.2); 4.0559 (3.7); 4.0378 (3.8); 4.0198 (1.2); 3.3458 (31.0); 3.3424 (31.3); 3.3409 (30.7); 2.8910 (3.8); 2.7326 (3.6); 2.5086 (16.9); 2.5042 (22.6); 2.4999 (16.6); 2.4257 (16.0); 2.3298 (0.7); 1.3008 (4.1); 1.2828 (8.5); 1.2648 (4.0); −0.0007 (1.6)

I-171: $^1$H-NMR (400.0 MHz, $d_6$-DMSO):

δ=8.1907 (1.7); 8.1704 (1.8); 7.9541 (0.4); 7.8631 (2.9); 7.7571 (2.1); 7.7371 (2.2); 7.5439 (1.0); 7.5405 (1.4); 7.5257 (5.5); 7.5206 (4.5); 7.5145 (2.4); 7.5053 (1.2); 7.5016 (1.1); 7.4936 (0.4); 7.4907 (0.4); 7.4692 (3.7); 7.4648 (3.8); 7.4194 (1.2); 7.4120 (1.1); 7.4058 (1.0); 7.3988 (1.7); 7.3922 (1.0); 7.3850 (0.9); 7.3780 (0.8); 7.2214 (1.0); 7.2191 (1.1); 7.2026 (2.1); 7.2003 (2.1); 7.1840 (1.2); 7.1815 (1.2); 7.1089 (1.6); 7.0908 (4.1); 7.0719 (3.0); 7.0149 (1.4); 6.9966 (2.0); 6.9780 (0.8); 6.9715 (1.9); 6.9685 (1.9); 6.9524 (1.6); 6.9494 (1.6); 6.9041 (3.7); 6.8864 (3.2); 6.3787 (3.7); 6.3743 (3.7); 4.1542 (1.9); 4.1364 (3.6); 4.1183 (2.0); 3.3553 (37.2); 3.3512 (38.4); 3.3477 (33.7); 3.0076 (1.8); 2.9898 (3.5); 2.9718 (1.8); 2.8901 (2.6); 2.7329 (2.3); 2.5132 (8.5); 2.5089 (17.9); 2.5045 (23.9); 2.5000 (17.4); 2.4959 (8.6); 2.3818 (16.0); 1.2355 (0.3); −0.0002 (1.4)

I-172: $^1$H-NMR (400.0 MHz, $d_6$-DMSO):

δ=8.1948 (3.0); 7.9966 (1.9); 7.9765 (2.1); 7.9548 (1.0); 7.6258 (0.6); 7.6025 (1.1); 7.5779 (1.1); 7.5555 (0.7); 7.5415 (1.0); 7.5380 (1.1); 7.5190 (1.8); 7.5027 (1.0); 7.4992 (1.1); 7.4268 (4.0); 7.4224 (4.2); 7.3447 (1.0); 7.3406 (1.1); 7.3325 (1.0); 7.3285 (1.1); 7.3213 (0.9); 7.3171 (1.0); 7.3090 (0.9); 7.3054 (0.9); 7.2509 (1.2); 7.2321 (2.3); 7.2156 (1.2); 7.2132 (1.2); 7.1346 (1.7); 7.1168 (4.3); 7.0978 (3.3); 7.0540 (1.6); 7.0357 (2.1); 7.0175 (0.7); 6.9566 (1.9); 6.9538 (2.0); 6.9377 (1.8); 6.9348 (1.8); 6.9098 (3.9); 6.8921 (3.4); 6.3276 (3.9); 6.3232 (4.0); 4.1278 (2.0); 4.1099 (3.7); 4.0920 (2.1); 3.3442 (41.4); 3.0057 (1.9); 2.9877 (3.6); 2.9698 (1.8); 2.8918 (6.5); 2.7336 (6.0); 2.5137 (10.4); 2.5095 (21.8); 2.5051 (29.3); 2.5007 (21.6); 2.4574 (16.0); 1.2357 (0.5); −0.0002 (2.4)

I-173: $^1$H-NMR (400.0 MHz, $d_6$-DMSO):

δ=8.3469 (11.5); 7.9549 (0.5); 7.8131 (4.6); 7.7994 (4.9); 7.7909 (5.3); 7.7772 (5.0); 7.7601 (0.6); 7.7512 (0.6); 7.7378 (0.6); 7.6050 (2.3); 7.6007 (1.8); 7.5959 (1.6); 7.5816 (4.3); 7.5585 (4.2); 7.5347 (2.5); 7.5105 (0.3); 7.5035 (0.3); 7.4878 (0.4); 7.4269 (0.4); 7.3944 (15.2); 7.3899 (16.0); 7.3760 (4.1); 7.3684 (3.9); 7.3544 (6.5); 7.3469 (6.0); 7.3331 (3.6); 7.3255 (3.4); 7.2985 (4.0); 7.2947 (4.5); 7.2861 (4.3); 7.2826 (4.4); 7.2756 (3.8); 7.2712 (3.8); 7.2630 (3.9); 7.2593 (3.6); 7.2417 (0.9); 7.2341 (0.9); 7.2254 (0.8); 7.2099 (0.7); 7.1879 (2.1); 7.1824 (2.2); 7.1710 (1.8); 7.1648 (3.7); 7.1608 (5.4); 7.1438 (14.7); 7.1253 (13.8); 7.1099 (8.1); 7.0988 (2.9); 7.0924 (7.4); 7.0843 (1.9); 7.0742 (2.2); 7.0266 (0.4); 7.0098 (0.4); 6.9856 (0.4); 6.8844 (14.3); 6.8674 (12.8); 6.8413 (0.8); 6.8364 (1.0); 6.8277 (0.9); 6.8182 (0.7); 6.5524 (5.1); 6.5451 (5.2); 6.5296 (5.4); 6.5223 (5.0); 6.4083 (0.4); 6.4004 (0.4); 6.3857 (0.4); 6.3779 (0.4); 6.2797 (15.0); 6.2752 (15.4); 6.2397 (1.1); 6.2351 (1.2); 5.8248 (0.3); 5.8062 (0.6); 4.6961 (0.6); 4.6766 (0.6); 4.6224 (0.4); 4.6038 (0.7); 4.5851 (0.4); 4.1136 (7.2); 4.0962 (15.4); 4.0788 (7.8); 4.0563 (0.8); 4.0383 (0.5); 3.4472 (0.4); 3.3655 (308.4); 3.0036 (7.5); 2.9865 (14.7); 2.9691 (6.8); 2.8928 (3.0); 2.7535 (0.4); 2.7345 (2.6); 2.6803 (0.6); 2.6762 (0.7); 2.6715 (0.6); 2.6460 (0.4); 2.5114 (84.0); 2.5070 (112.5); 2.5026 (83.9); 2.4872 (60.3); 2.4431 (0.4); 2.4279 (0.7); 2.4177 (0.5); 2.3336 (0.7); 2.3288 (0.6); 2.3247 (0.6); 1.2584 (0.3); 1.2354 (1.7); 0.8512 (0.4); −0.0002 (3.2)

I-174: $^1$H-NMR (400.0 MHz, $d_6$-DMSO):

δ=9.3738 (2.6); 8.5384 (5.0); 7.9522 (0.5); 7.8867 (1.8); 7.8664 (2.0); 7.7141 (0.6); 7.6906 (1.0); 7.6660 (1.0); 7.6434 (0.6); 7.5386 (0.9); 7.5347 (1.0); 7.5165 (1.7); 7.4995 (1.1); 7.4963 (1.2); 7.4529 (0.4); 7.4480 (0.4); 7.4382 (1.6); 7.4346 (1.7); 7.4192 (2.2); 7.4156 (2.0); 7.4085 (1.0); 7.4039 (1.0); 7.3961 (1.1); 7.3917 (1.2); 7.3848 (0.9); 7.3803 (1.1); 7.3726 (0.8); 7.3685 (0.8); 7.3447 (1.6); 7.3366 (3.4); 7.3321 (3.5); 7.3073 (0.8); 6.2484 (3.3); 6.2440 (3.3); 3.6818 (16.0); 3.6143 (0.8); 3.3392 (161.8); 2.8913 (3.0); 2.7320 (2.8); 2.6762 (0.4); 2.6721 (0.6); 2.6677 (0.4); 2.5249 (1.4); 2.5074 (75.8); 2.5031 (101.5); 2.4987 (74.6); 2.3341 (0.4); 2.3300 (0.6); 2.3256 (0.4); 1.2395 (0.9); −0.0007 (7.5)

I-175: $^1$H-NMR (300.2 MHz, CDCl3):

δ=8.7860 (3.1); 8.7583 (3.2); 8.3024 (9.0); 7.7357 (5.6); 7.7298 (5.6); 7.6469 (0.8); 7.6358 (1.1); 7.6300 (1.1); 7.6208 (2.2); 7.6152 (2.3); 7.6055 (3.0); 7.5989 (2.3); 7.5888 (3.5); 7.5832 (2.7); 7.5647 (2.2); 7.5577 (3.4); 7.5326 (2.2); 7.5262 (1.0); 7.5008 (0.9); 7.3607 (2.0); 7.3551 (2.2); 7.3354 (3.7); 7.3298 (3.3); 7.2983 (6.5); 7.2790 (2.5); 7.2761 (2.4); 7.2543 (3.2); 7.2514 (3.1); 7.2293 (1.3); 7.2264 (1.2); 6.9441 (2.9); 6.4367 (5.9); 6.4307 (5.8); 5.3340 (1.5); 4.0989 (2.3); 4.0748 (7.3); 4.0507 (7.4); 4.0267 (2.4); 1.6615 (2.0); 1.3987 (7.8); 1.3747 (16.0); 1.3506 (7.5); 1.2908 (0.4); 0.0354 (6.5)

I-176: $^1$H-NMR (499.9 MHz, d$_6$-DMSO):

δ=8.7078 (0.6); 8.3169 (5.9); 7.6921 (2.9); 7.6758 (3.2); 7.6320 (0.3); 7.6140 (0.6); 7.5928 (0.4); 7.5766 (0.4); 7.5361 (3.2); 7.5225 (3.7); 7.5190 (3.9); 7.5060 (3.6); 7.4852 (0.5); 7.4591 (1.4); 7.4431 (3.6); 7.4275 (3.8); 7.4138 (4.6); 7.3992 (2.0); 7.3777 (0.3); 7.3601 (0.3); 7.3397 (2.3); 7.3371 (2.3); 7.3236 (3.6); 7.3143 (4.8); 7.2965 (6.8); 7.2788 (3.5); 7.1825 (9.9); 7.1788 (10.2); 4.4893 (0.6); 4.4679 (0.7); 3.7598 (0.3); 3.6307 (1.0); 3.5858 (10.2); 3.5087 (0.4); 3.3944 (0.7); 3.3887 (0.5); 3.3834 (0.8); 3.3139 (666.0); 2.8902 (0.5); 2.8162 (1.7); 2.7309 (0.4); 2.6391 (0.6); 2.6356 (1.0); 2.6318 (0.7); 2.5515 (0.6); 2.5457 (0.8); 2.5077 (50.6); 2.5041 (114.8); 2.5007 (161.6); 2.4970 (112.4); 2.4935 (56.5); 2.3652 (0.7); 2.3616 (0.9); 2.3579 (0.7); 2.2476 (16.0); 2.1645 (0.4); 2.0728 (3.5); 1.2589 (0.4); 1.2357 (2.2); 0.8624 (0.3); 0.8535 (0.5); 0.1164 (0.3); 0.0063 (2.6); −0.0002 (87.3); −0.0068 (4.5); −0.1202 (0.4)

I-177: $^1$H-NMR (499.9 MHz, d$_6$-DMSO):

δ=8.6430 (4.1); 7.7012 (2.4); 7.6850 (2.5); 7.5378 (2.5); 7.5234 (4.3); 7.5099 (2.0); 7.4977 (2.0); 7.4837 (2.4); 7.4674 (1.2); 7.4391 (3.5); 7.4226 (2.5); 7.3794 (1.7); 7.3656 (2.4); 7.3496 (1.2); 7.3091 (6.5); 3.7501 (16.0); 3.3169 (25.2); 2.5867 (17.9); 2.5012 (9.8); 2.4063 (0.4); 2.3373 (11.0); −0.0002 (4.1)

I-178: $^1$H-NMR (499.9 MHz, d$_6$-DMSO):

δ=8.3052 (4.5); 7.7192 (2.4); 7.7040 (2.6); 7.7024 (2.6); 7.6070 (2.8); 7.5907 (3.6); 7.5340 (0.9); 7.5309 (1.2); 7.5175 (3.6); 7.5144 (3.6); 7.5100 (2.4); 7.5075 (2.2); 7.4968 (2.3); 7.4941 (2.4); 7.4856 (1.7); 7.4804 (1.2); 7.4776 (1.1); 7.4687 (2.7); 7.4518 (1.3); 7.3892 (1.6); 7.3856 (1.6); 7.3760 (1.4); 7.3727 (2.5); 7.3694 (1.6); 7.3597 (1.2); 7.3562 (1.2); 7.2571 (5.3); 7.2534 (5.5); 6.2746 (5.6); 6.2709 (5.6); 3.8048 (0.4); 3.7126 (0.4); 3.6694 (16.0); 3.3329 (9.9); 2.8818 (0.4); 2.8755 (0.4); 2.5074 (1.5); 2.5038 (2.1); 2.5003 (1.6); 2.4966 (1.0); 2.4851 (22.7); 2.3313 (10.7); 2.3288 (10.8); 2.0750 (1.6); −0.0002 (1.2)

I-179: $^1$H-NMR (300.2 MHz, CDCl3):

δ=8.5805 (3.0); 8.5731 (3.0); 8.1010 (1.8); 8.0736 (1.7); 8.0709 (1.6); 7.7241 (3.3); 7.6988 (5.0); 7.6736 (1.5); 7.6686 (0.9); 7.6417 (4.1); 7.6356 (4.1); 7.5696 (1.5); 7.5658 (1.5); 7.5429 (1.8); 7.5393 (1.4); 7.5156 (3.0); 7.5095 (2.4); 7.4732 (0.7); 7.4683 (0.7); 7.4479 (1.6); 7.4443 (1.5); 7.4231 (1.5); 7.4183 (1.5); 7.3498 (1.8); 7.3436 (2.4); 7.3392 (2.3); 7.3278 (2.3); 7.3239 (1.8); 7.3189 (1.7); 7.3143 (1.5); 7.2987 (14.5); 7.1778 (2.0); 7.1723 (1.9); 7.1620 (0.4); 7.1505 (1.6); 7.1473 (1.5); 6.9324 (16.0); 6.9090 (13.8); 6.2266 (4.2); 6.2204 (4.3); 4.8700 (8.6); 3.8747 (8.0); 1.6840 (9.1); 1.2917 (1.4); 0.1078 (4.3); 0.0479 (0.3); 0.0371 (10.8); 0.0262 (0.5)

I-180: $^1$H-NMR (300.2 MHz, d$_6$-DMSO):

δ=8.6394 (2.8); 7.7858 (1.4); 7.7828 (1.4); 7.7592 (1.8); 7.7563 (1.7); 7.6336 (0.5); 7.6023 (0.9); 7.5851 (0.9); 7.5793 (1.2); 7.5747 (1.0); 7.5705 (1.0); 7.5671 (1.0); 7.5606 (1.4); 7.5551 (1.5); 7.5393 (0.8); 7.5345 (0.9); 7.5287 (1.0); 7.5078 (1.1); 7.5026 (1.2); 7.4823 (2.0); 7.4772 (1.6); 7.4191 (0.3); 7.4152 (1.3); 7.3943 (1.6); 7.3908 (1.5); 7.3694 (0.7); 7.3654 (0.7); 7.3587 (0.8); 7.3521 (0.8); 7.3421 (0.8); 7.3355 (0.9); 7.3276 (0.7); 7.3208 (0.7); 7.3110 (0.6); 7.3044 (0.6); 7.2209 (3.5); 7.2147 (3.5); 6.2493 (3.6); 6.2431 (3.5); 3.7262 (16.0); 3.3500 (13.4); 2.5909 (13.1); 2.5342 (2.0); 2.5284 (4.1); 2.5224 (5.5); 2.5164 (4.0); 2.5106 (1.9); 2.0961 (0.6); 0.0193 (4.4)

I-181: $^1$H-NMR (400.0 MHz, d$_6$-DMSO):

δ=8.6791 (3.1); 7.9544 (0.5); 7.8746 (1.2); 7.8573 (1.2); 7.6854 (1.2); 7.6718 (1.3); 7.6637 (1.5); 7.6500 (1.3); 7.5898 (0.7); 7.5664 (1.2); 7.5421 (1.2); 7.5194 (0.8); 7.4924 (1.0); 7.4776 (1.6); 7.4696 (1.6); 7.4601 (1.2); 7.4435 (1.7); 7.4363 (2.0); 7.4203 (1.8); 7.4136 (3.1); 7.4068 (1.2); 7.3925 (3.1); 7.3819 (7.6); 7.3692 (6.5); 7.3522 (5.9); 7.3100 (1.0); 7.3055 (1.1); 7.2973 (1.1); 7.2933 (1.1); 7.2864 (1.0); 7.2824 (1.0); 7.2742 (1.0); 7.1889 (3.9); 7.1848 (3.6); 7.1734 (1.3); 7.1695 (1.2); 7.1543 (0.7); 7.1502 (0.6); 6.9316 (0.4); 6.9137 (0.4); 6.8982 (0.4); 6.2319 (3.6); 6.2275 (3.6); 3.7312 (15.6); 3.7025 (0.7); 3.3927 (0.9); 3.3482 (53.2); 2.8913 (2.7); 2.7332 (2.6); 2.5727 (16.0); 2.5096 (25.3); 2.5053 (32.7); 2.5009 (23.7); 1.6406 (8.1); 1.2361 (0.7); −0.0002 (2.0)

I-182: $^1$H-NMR (400.0 MHz, d$_6$-DMSO):

δ=8.6013 (7.7); 8.5948 (7.9); 8.1176 (8.5); 7.9525 (0.5); 7.4756 (6.8); 7.4623 (4.0); 7.4520 (16.0); 7.4471 (11.2); 7.4405 (4.4); 7.4006 (2.0); 7.3880 (2.2); 7.3810 (3.3); 7.3682 (3.2); 7.3609 (1.8); 7.3482 (1.7); 7.3241 (7.4); 7.3019 (3.4); 7.2943 (3.3); 7.2804 (1.7); 7.2728 (1.6); 7.2202 (2.7); 7.2011 (2.4); 7.1925 (2.9); 7.1741 (2.4); 7.1593 (0.4); 7.1377 (12.1); 7.1330 (14.0); 7.1248 (7.8); 7.1205 (8.4); 7.1102 (2.3); 7.0976 (0.8); 6.8377 (5.7); 6.8333 (7.1); 6.8239 (5.8); 6.8146 (5.8); 6.5986 (3.8); 6.5910 (3.8); 6.5758 (4.0); 6.5682 (3.7); 6.2773 (9.4); 6.2730 (9.7); 4.0880 (4.7); 4.0700 (8.9); 4.0521 (5.2); 3.4236 (0.5); 3.3628 (506.5); 2.9985 (0.4); 2.9779 (4.6); 2.9599 (8.4); 2.9421 (4.4); 2.8917 (2.9); 2.7329 (2.7); 2.6787 (0.4); 2.6744 (0.5); 2.6700 (0.4); 2.5271 (1.3); 2.5096 (71.0); 2.5053 (95.4); 2.5010 (71.2); 2.3363 (0.4); 2.3320 (0.5); 2.3275 (0.4); 1.2378 (1.1); −0.0002 (6.3)

I-183: $^1$H-NMR (400.0 MHz, d$_6$-DMSO):

δ=8.6496 (8.6); 8.6432 (8.8); 8.1175 (9.6); 7.9534 (0.6); 7.5993 (0.5); 7.5947 (0.5); 7.5694 (0.5); 7.5475 (9.3); 7.5305 (7.0); 7.5119 (2.8); 7.4884 (0.8); 7.4594 (3.4); 7.4446 (13.7); 7.4398 (13.8); 7.4241 (4.4); 7.3789 (6.8); 7.3183 (2.4); 7.3108 (2.4); 7.2971 (3.7); 7.2896 (3.6); 7.2758 (2.0); 7.2682 (1.8); 7.1879 (0.7); 7.1821 (0.7); 7.1715 (0.5); 7.1598 (0.4); 7.1397 (14.4); 7.1345 (16.0); 7.1265 (10.1); 7.1230 (10.0); 7.1132 (2.7); 7.0995 (0.7); 6.8390 (6.6); 6.8342 (8.1); 6.8255 (7.5); 6.8158 (6.4); 6.5935 (4.3); 6.5859 (4.2); 6.5707 (4.5); 6.5632 (4.2); 6.2740 (11.1); 6.2695 (11.4); 6.2388 (0.5); 6.2344 (0.5); 4.0837 (5.4); 4.0658 (10.3); 4.0478 (5.9); 3.3609 (514.3); 2.9990 (0.6); 2.9770 (5.3); 2.9590 (9.7); 2.9412 (5.0); 2.8927 (3.5); 2.7337 (3.2); 2.6796 (0.4); 2.6750 (0.6); 2.6707 (0.4); 2.5280 (1.5); 2.5104 (79.0); 2.5060 (105.1); 2.5016 (77.5); 2.3370 (0.5); 2.3328 (0.6); 2.3284 (0.4); 1.2374 (1.1); −0.0002 (5.9)

I-184: $^1$H-NMR (400.0 MHz, d$_6$-DMSO):

δ=8.6616 (5.9); 8.6552 (6.1); 8.1026 (6.2); 7.9532 (2.1); 7.4999 (3.1); 7.4781 (10.2); 7.4626 (16.0); 7.4581 (13.8); 7.4491 (3.8); 7.4461 (3.4); 7.4254 (0.9); 7.4145 (1.6); 7.4016 (1.7); 7.3948 (2.5); 7.3819 (2.4); 7.3748 (1.4); 7.3619 (1.3); 7.2408 (2.1); 7.2216 (1.8); 7.2128 (2.2);

7.1939 (1.7); 7.1377 (1.8); 7.1246 (10.1); 7.1177 (12.3); 7.1090 (9.4); 7.1037 (4.4); 7.0979 (2.8); 6.9735 (4.5); 6.9554 (3.2); 6.8570 (4.3); 6.8513 (4.7); 6.8425 (5.0); 6.8337 (3.8); 6.2884 (7.4); 6.2840 (7.6); 4.0775 (3.7); 4.0594 (5.5); 4.0400 (4.1); 3.3602 (423.1); 2.9756 (3.6); 2.9564 (5.3); 2.9382 (3.5); 2.8919 (13.2); 2.7332 (12.2); 2.6747 (0.4); 2.6701 (0.3); 2.5098 (57.0); 2.5054 (75.6); 2.5010 (55.6); 2.3321 (0.4); 2.3275 (0.3); 1.2377 (1.0); −0.0002 (6.6)

I-185: $^1$H-NMR (400.0 MHz, $d_6$-DMSO):
δ=8.3956 (2.2); 7.7727 (0.9); 7.7590 (0.9); 7.7515 (1.1); 7.7379 (1.0); 7.7088 (1.5); 7.6892 (1.8); 7.4752 (1.2); 7.4720 (1.3); 7.4610 (3.1); 7.4574 (4.0); 7.4420 (0.6); 7.4215 (0.8); 7.4143 (1.7); 7.4099 (1.4); 7.3985 (0.9); 7.3888 (2.6); 7.3809 (0.9); 7.3697 (1.2); 7.3677 (1.2); 7.3641 (1.1); 7.3601 (0.7); 7.3553 (0.9); 7.3495 (1.4); 7.3433 (0.8); 7.3353 (0.7); 7.3288 (0.7); 7.2073 (3.2); 7.2026 (3.4); 6.2616 (3.3); 6.2570 (3.5); 3.7378 (16.0); 3.3585 (66.9); 3.3555 (61.4); 3.3527 (68.0); 2.8908 (1.6); 2.7324 (1.4); 2.5166 (16.2); 2.5086 (18.6); 2.5042 (24.4); 2.4997 (18.2); 2.4955 (9.4); −0.0002 (1.4)

I-186: $^1$H-NMR (400.0 MHz, $d_6$-DMSO):
δ=8.4183 (5.6); 8.0113 (1.5); 7.9915 (1.8); 7.9872 (1.7); 7.9524 (0.8); 7.9025 (1.5); 7.8985 (1.7); 7.8788 (1.9); 7.6143 (0.6); 7.6107 (0.7); 7.5973 (1.5); 7.5942 (1.5); 7.5781 (2.8); 7.5732 (2.8); 7.5570 (1.4); 7.5541 (1.4); 7.5401 (0.6); 7.5369 (0.5); 7.4739 (3.7); 7.4699 (3.8); 7.2197 (0.3); 7.2089 (0.7); 7.1971 (3.0); 7.1836 (5.4); 7.1795 (5.6); 7.1724 (1.4); 7.1106 (0.7); 7.1028 (0.8); 7.0874 (4.3); 7.0677 (0.9); 7.0600 (0.8); 6.9135 (2.7); 6.9070 (2.4); 6.8947 (2.6); 6.8907 (2.1); 6.6897 (1.5); 6.6770 (1.6); 6.6673 (1.4); 6.6546 (1.4); 6.3861 (1.4); 6.3786 (1.4); 6.3634 (1.5); 6.3559 (1.4); 6.2850 (3.8); 6.2809 (3.9); 4.2104 (1.8); 4.1928 (4.0); 4.1753 (2.0); 3.3617 (100.0); 3.0516 (1.9); 3.0342 (3.8); 3.0168 (1.8); 2.8911 (4.8); 2.7325 (4.5); 2.5265 (0.4); 2.5086 (28.8); 2.5044 (38.0); 2.5000 (27.9); 2.3870 (16.0); 1.2380 (0.6); −0.0002 (3.0)

I-187: $^1$H-NMR (400.0 MHz, $d_6$-DMSO):
δ=8.5038 (5.7); 8.0368 (1.6); 8.0177 (1.9); 8.0146 (1.8); 7.9522 (0.6); 7.9324 (1.8); 7.9122 (2.0); 7.6499 (0.7); 7.6469 (0.8); 7.6300 (1.7); 7.6129 (1.4); 7.6092 (1.3); 7.5990 (1.3); 7.5955 (1.4); 7.5783 (1.7); 7.5612 (0.7); 7.5582 (0.7); 7.5122 (3.9); 7.5079 (4.0); 7.2370 (0.8); 7.2328 (0.9); 7.2250 (0.8); 7.2191 (2.2); 7.2158 (2.2); 7.2036 (3.7); 7.1992 (2.8); 7.1852 (3.9); 7.1772 (2.4); 7.1674 (0.6); 7.1601 (1.6); 7.1421 (0.4); 7.0397 (3.2); 6.9565 (3.4); 6.9402 (3.1); 6.8307 (0.8); 6.8122 (2.2); 6.7941 (1.6); 6.7744 (2.3); 6.7703 (2.5); 6.7556 (1.2); 6.7515 (1.1); 6.5914 (2.4); 6.5711 (2.3); 6.3287 (4.0); 6.3242 (4.1); 4.2165 (1.9); 4.1985 (3.2); 4.1798 (2.1); 3.3625 (155.4); 3.0631 (1.9); 3.0447 (3.2); 3.0266 (1.8); 2.8914 (3.9); 2.7331 (3.6); 2.5091 (26.6); 2.5049 (35.1); 2.5006 (25.8); 2.3961 (16.0); 1.2375 (0.5); −0.0002 (4.6)

I-188: $^1$H-NMR (400.0 MHz, $d_6$-DMSO):
δ=9.2141 (8.2); 8.5320 (16.0); 7.8766 (3.6); 7.8630 (3.8); 7.8541 (4.0); 7.8405 (3.8); 7.7168 (1.5); 7.6935 (2.8); 7.6702 (2.7); 7.6463 (1.6); 7.5076 (11.8); 7.5030 (12.1); 7.3817 (2.2); 7.3771 (2.5); 7.3694 (2.5); 7.3649 (2.6); 7.3574 (4.1); 7.3494 (3.3); 7.3415 (2.4); 7.3355 (3.8); 7.3279 (3.5); 7.3142 (2.2); 7.3066 (2.1); 7.1307 (1.5); 7.1211 (15.0); 7.1154 (15.2); 7.1074 (9.8); 7.1046 (10.0); 7.0959 (2.5); 7.0833 (0.5); 7.0804 (0.5); 6.8406 (0.9); 6.8315 (6.0); 6.8264 (7.1); 6.8175 (6.9); 6.8080 (5.5); 6.5767 (4.3); 6.5691 (4.2); 6.5538 (4.5); 6.5463 (4.1); 6.2853 (12.0); 6.2807 (12.1); 4.0559 (5.1); 4.0380 (9.0); 4.0196 (5.5); 3.3414 (248.9); 2.9998 (4.8); 2.9816 (8.4); 2.9637 (4.6); 2.8924 (0.9); 2.7333 (0.8); 2.6785 (0.4); 2.6739 (0.6); 2.6695 (0.4); 2.5272 (1.4); 2.5137 (35.5); 2.5094 (73.7); 2.5049 (98.2); 2.5004 (70.8); 2.4960 (34.4); 2.3362 (0.4); 2.3315 (0.6); 2.3272 (0.4); 1.2364 (0.8); 0.0079 (0.3); −0.0002 (10.6); −0.0084 (0.4)

I-189: $^1$H-NMR (400.0 MHz, $d_6$-DMSO):
δ=9.4002 (2.7); 8.5074 (4.9); 7.8488 (0.7); 7.8348 (0.9); 7.8315 (0.9); 7.8255 (0.9); 7.8123 (0.8); 7.7070 (0.5); 7.6837 (1.0); 7.6596 (0.9); 7.6365 (0.5); 7.4053 (0.5); 7.3978 (1.0); 7.3837 (2.3); 7.3785 (4.1); 7.3571 (3.2); 7.3329 (3.4); 7.3283 (3.5); 6.2694 (3.5); 6.2648 (3.5); 3.7088 (16.0); 3.3361 (44.2); 2.8933 (1.7); 2.7344 (1.6); 2.5274 (0.3); 2.5096 (19.0); 2.5053 (24.9); 2.5010 (18.4); −0.0002 (4.3)

I-190: $^1$H-NMR (400.0 MHz, $d_6$-DMSO):
δ=8.5538 (4.7); 8.3150 (1.1); 7.9535 (1.1); 7.7579 (2.3); 7.7441 (2.5); 7.7358 (2.7); 7.7220 (2.6); 7.5990 (1.0); 7.5757 (1.9); 7.5517 (1.8); 7.5285 (1.2); 7.4562 (0.4); 7.4339 (1.8); 7.4266 (1.9); 7.4124 (2.7); 7.4049 (3.0); 7.3911 (1.4); 7.3835 (1.6); 7.3481 (3.2); 7.3407 (2.7); 7.3253 (3.4); 7.3178 (2.8); 7.3106 (1.7); 7.3068 (1.8); 7.2928 (8.4); 7.2882 (8.6); 7.2704 (1.9); 7.2482 (1.5); 7.1898 (1.7); 7.1698 (0.5); 7.1606 (1.0); 7.1418 (1.4); 7.1224 (0.8); 7.0999 (0.3); 7.0280 (0.6); 7.0202 (0.7); 7.0118 (1.0); 7.0064 (1.7); 6.9875 (1.4); 6.9719 (0.4); 6.5983 (1.2); 6.5816 (1.0); 6.2880 (6.4); 6.2838 (6.6); 4.5746 (0.3); 4.5620 (0.3); 4.5478 (0.4); 4.5356 (0.4); 3.9822 (2.7); 3.9642 (7.9); 3.9461 (7.6); 3.9282 (2.5); 3.3398 (283.4); 3.2885 (0.5); 3.2722 (0.4); 2.8917 (6.6); 2.8646 (0.3); 2.8589 (0.4); 2.8267 (0.4); 2.8122 (0.3); 2.7502 (0.3); 2.7327 (6.4); 2.7176 (0.4); 2.6780 (0.6); 2.6734 (0.6); 2.6691 (0.4); 2.5421 (27.1); 2.5264 (1.6); 2.5085 (63.6); 2.5042 (84.4); 2.4998 (61.9); 2.3353 (0.3); 2.3312 (0.5); 2.3267 (0.4); 1.2277 (7.8); 1.2097 (16.0); 1.1917 (7.4); 0.0076 (0.4); −0.0002 (10.7); −0.0082 (0.5)

I-191: $^1$H-NMR (400.0 MHz, $d_6$-DMSO):
δ=8.4527 (4.9); 7.8711 (3.3); 7.8511 (3.8); 7.6133 (1.0); 7.5898 (2.0); 7.5775 (1.8); 7.5722 (2.4); 7.5695 (2.3); 7.5598 (2.9); 7.5552 (3.0); 7.5403 (2.2); 7.5352 (1.9); 7.4317 (1.4); 7.4271 (1.9); 7.4127 (4.9); 7.4081 (4.3); 7.3976 (3.4); 7.3799 (3.3); 7.3605 (1.2); 7.3496 (1.6); 7.3454 (1.8); 7.3374 (1.8); 7.3331 (1.8); 7.3263 (1.6); 7.3217 (1.9); 7.3154 (7.5); 7.3116 (7.9); 6.2912 (6.5); 6.2870 (6.7); 3.9644 (2.2); 3.9464 (7.0); 3.9284 (7.1); 3.9104 (2.3); 3.3620 (98.2); 3.3588 (111.2); 3.3528 (124.9); 2.8925 (0.4); 2.7337 (0.4); 2.6745 (0.3); 2.5338 (28.8); 2.5100 (42.4); 2.5057 (55.9); 2.5013 (41.5); 2.3319 (0.3); 1.2396 (7.9); 1.2216 (16.0); 1.2036 (7.4); −0.0002 (2.7)

I-192: $^1$H-NMR (499.9 MHz, $d_6$-DMSO):
δ=8.3654 (3.2); 7.6678 (1.7); 7.6663 (1.7); 7.6518 (2.0); 7.6497 (2.0); 7.6437 (1.8); 7.6277 (2.4); 7.5734 (0.9); 7.5603 (1.1); 7.5570 (1.6); 7.5439 (1.5); 7.5408 (0.9); 7.5275 (0.7); 7.4951 (0.8); 7.4923 (1.0); 7.4785 (2.5); 7.4758 (2.5); 7.4672 (1.5); 7.4646 (1.5); 7.4539 (1.6); 7.4511 (1.8); 7.4373 (0.7); 7.4346 (0.7); 7.3507 (1.1); 7.3474 (1.2); 7.3373 (1.1); 7.3343 (1.9); 7.3312 (1.2); 7.3211 (0.9); 7.3178 (0.9); 7.1865 (1.0); 7.1696 (1.8); 7.1526 (0.9); 7.0047 (5.1); 3.5907 (13.8); 3.2833 (0.5); 3.2563 (193.9); 2.4471 (41.0); 2.4433 (36.4); 2.4396 (26.4); 2.4361 (13.5); 1.7750 (16.0); 1.1770 (0.6); −0.0002 (0.3)

I-193: $^1$H-NMR (499.9 MHz, $d_6$-DMSO):
δ=8.4040 (3.2); 7.7138 (2.1); 7.6981 (2.1); 7.5330 (2.3); 7.5250 (1.4); 7.5164 (4.6); 7.5126 (3.6); 7.5087 (4.6); 7.4934 (3.2); 7.4766 (2.5); 7.4598 (0.8); 7.3888 (1.3); 7.3847 (1.2); 7.3762 (1.2); 7.3724 (1.9); 7.3686 (1.1); 7.3598 (0.9); 7.3558 (0.8); 7.0503 (5.4); 3.6456 (14.6);

3.3263 (23.6); 2.5109 (4.5); 2.5073 (6.2); 2.5015 (18.5); 2.3717 (0.4); 2.3354 (8.6); 2.3328 (8.0); 1.8533 (0.5); 1.8303 (16.0)

I-194: $^1$H-NMR (499.9 MHz, d$_6$-DMSO):

δ=8.4118 (0.4); 7.7086 (0.5); 7.6919 (1.4); 7.6811 (1.4); 7.6656 (0.9); 7.5666 (0.5); 7.5587 (0.7); 7.5449 (1.3); 7.5392 (1.2); 7.5319 (1.0); 7.5248 (1.3); 7.5119 (0.5); 7.5048 (0.5); 7.3627 (1.1); 7.3478 (1.7); 7.3338 (1.5); 7.3225 (0.9); 7.0412 (2.3); 7.0144 (2.9); 6.8439 (2.6); 6.8404 (2.8); 6.8240 (3.6); 6.8204 (3.6); 6.8005 (1.8); 6.7834 (3.2); 6.7659 (1.6); 5.8214 (2.7); 5.8178 (2.8); 5.7686 (3.6); 5.7649 (3.6); 3.3884 (0.4); 3.3334 (13.2); 3.3129 (39.5); 3.2826 (15.4); 2.6390 (0.4); 2.6355 (0.5); 2.6317 (0.4); 2.5222 (0.5); 2.5077 (27.3); 2.5041 (59.5); 2.5005 (83.8); 2.4968 (61.6); 2.4933 (29.2); 2.4173 (15.0); 2.3651 (0.4); 2.3616 (0.7); 2.3580 (0.5); 2.3293 (10.8); 2.3065 (16.0); 2.2562 (8.5); 2.2427 (14.0); 2.0729 (0.7); 1.2586 (0.4); 1.2352 (1.8); 0.8536 (0.4); 0.0063 (1.5); −0.0002 (45.4); −0.0068 (1.7)

I-195: $^1$H-NMR (499.9 MHz, d$_6$-DMSO):

δ=8.5877 (5.3); 7.8881 (0.6); 7.8847 (0.7); 7.8775 (0.7); 7.8742 (0.7); 7.8692 (0.8); 7.8657 (0.8); 7.8585 (0.7); 7.8554 (0.7); 7.6765 (0.6); 7.6614 (0.7); 7.6657 (1.0); 7.6417 (1.0); 7.6373 (0.6); 7.6221 (0.5); 7.4045 (4.4); 7.4006 (6.0); 7.2398 (2.0); 7.2261 (0.9); 7.2233 (1.5); 7.2097 (1.5); 7.2070 (0.9); 7.1932 (0.8); 6.7366 (1.1); 6.7196 (1.9); 6.7027 (1.0); 6.7015 (1.0); 6.3479 (5.3); 6.3443 (5.9); 6.3290 (2.1); 3.6485 (16.0); 3.2577 (98.0); 3.1148 (1.0); 3.1044 (1.0); 2.4490 (4.2); 2.4454 (9.1); 2.4418 (12.7); 2.4381 (9.1); 2.4345 (4.2); 2.3902 (15.9); 2.2301 (0.4); 2.0140 (0.4); 1.1748 (0.3)

I-196: $^1$H-NMR (499.9 MHz, d$_6$-DMSO):

δ=7.9492 (4.8); 7.8972 (1.5); 7.8951 (1.6); 7.8802 (1.7); 7.8787 (1.7); 7.7903 (1.6); 7.7884 (1.6); 7.7743 (1.9); 7.7719 (1.8); 7.4946 (0.7); 7.4919 (0.8); 7.4810 (1.4); 7.4783 (1.7); 7.4646 (1.4); 7.4616 (1.3); 7.4525 (1.4); 7.4496 (1.5); 7.4360 (1.7); 7.4336 (1.4); 7.4226 (0.8); 7.4199 (0.8); 7.3937 (1.8); 7.3762 (1.8); 7.1469 (4.1); 7.1431 (4.2); 7.0285 (3.0); 6.0620 (1.0); 3.7366 (0.3); 3.5790 (0.3); 3.5483 (8.1); 3.3974 (0.4); 3.3275 (18.2); 3.2047 (4.5); 3.1763 (0.5); 2.6355 (6.8); 2.5152 (4.6); 2.5117 (10.0); 2.5080 (14.0); 2.5044 (10.7); 2.5009 (5.7); 2.3710 (16.0); 2.3509 (0.4); 2.2969 (8.0); 2.2944 (8.1); 2.1835 (10.2); 2.0800 (0.6); 1.2419 (0.6)

I-197: $^1$H-NMR (499.9 MHz, d$_6$-DMSO):

δ=8.5592 (5.2); 8.1476 (3.5); 8.0487 (1.7); 8.0338 (1.8); 8.0320 (1.8); 7.9496 (1.8); 7.9344 (1.9); 7.9332 (1.9); 7.6602 (0.8); 7.6578 (0.9); 7.6465 (1.4); 7.6440 (1.8); 7.6302 (1.2); 7.6275 (1.2); 7.6039 (1.2); 7.6014 (1.3); 7.5874 (1.8); 7.5850 (1.4); 7.5736 (0.8); 7.5712 (0.8); 7.4758 (3.9); 7.4721 (4.1); 7.1652 (3.6); 7.1435 (2.0); 7.1262 (1.0); 6.4033 (4.0); 6.3996 (4.2); 6.3296 (2.2); 6.3129 (2.2); 3.7168 (16.0); 3.6773 (0.4); 3.6617 (0.3); 3.6606 (0.3); 3.3510 (0.5); 3.1978 (0.9); 2.6338 (1.3); 2.5150 (0.6); 2.5115 (1.2); 2.5080 (1.7); 2.5044 (1.3); 2.4646 (0.4); 2.4302 (15.7); 2.2968 (0.3); 2.1808 (7.8); 2.1784 (8.2); 1.9473 (0.4)

I-198: $^1$H-NMR (499.9 MHz, d$_6$-DMSO):

δ=8.5120 (5.5); 8.0516 (1.5); 8.0499 (1.5); 8.0351 (1.6); 8.0331 (1.6); 7.9453 (1.5); 7.9434 (1.6); 7.9287 (1.7); 7.9270 (1.7); 7.6609 (0.8); 7.6583 (0.8); 7.6472 (1.3); 7.6446 (1.7); 7.6308 (1.2); 7.6280 (1.1); 7.6080 (1.2); 7.6053 (1.2); 7.5940 (0.9); 7.5914 (1.6); 7.5889 (1.2); 7.5776 (0.7); 7.5751 (0.7); 7.2751 (4.8); 7.2284 (0.5); 7.2168 (3.1); 7.1776 (0.9); 7.1603 (1.7); 7.1431 (0.9); 6.3467 (2.1); 6.3299 (2.1); 6.3563 (16.0); 6.6441 (0.6); 3.3927 (0.5); 3.3861 (0.6); 3.3290 (4.7); 2.5150 (3.1); 2.5115 (6.5); 2.5078 (8.9); 2.5042 (6.5); 2.5007 (3.1); 2.4463 (15.2); 2.1887 (7.2); 2.1863 (7.3); 2.0800 (0.4); 1.9242 (14.9); 1.2404 (0.4); 0.9968 (0.6); 0.9837 (0.6)

I-199: $^1$H-NMR (499.9 MHz, d$_6$-DMSO):

δ=12.8210 (1.2); 9.4946 (1.0); 9.0756 (16.0); 8.8365 (0.6); 8.8321 (0.6); 8.4845 (5.8); 8.4801 (6.0); 8.0648 (0.4); 7.9740 (0.3); 7.9568 (0.4); 7.9470 (3.3); 7.9301 (3.7); 7.8929 (0.3); 7.8763 (0.4); 7.8084 (3.0); 7.7920 (3.4); 7.7640 (4.3); 7.7613 (4.4); 7.6954 (2.0); 7.6927 (2.0); 7.6817 (2.6); 7.6788 (3.9); 7.6759 (2.0); 7.6648 (2.2); 7.6620 (2.1); 7.5704 (0.3); 7.5681 (0.4); 7.5636 (2.3); 7.5615 (2.3); 7.5543 (0.6); 7.5475 (3.7); 7.5409 (0.4); 7.5383 (0.4); 7.5336 (1.7); 7.5314 (1.7); 7.4457 (1.0); 7.4421 (1.1); 7.4301 (2.5); 7.4266 (2.4); 7.4169 (2.6); 7.4131 (2.9); 7.3934 (4.5); 7.3797 (2.1); 7.3452 (1.2); 7.3424 (1.1); 7.3299 (3.2); 7.3271 (3.0); 7.3164 (3.0); 7.3122 (5.5); 7.3084 (4.8); 7.2966 (1.6); 7.2933 (1.1); 7.1505 (0.3); 6.8318 (0.4); 6.8301 (0.4); 6.8159 (0.4); 6.8140 (0.4); 6.7518 (0.4); 6.7496 (0.4); 4.0725 (14.1); 3.3184 (33.3); 3.1694 (5.2); 2.5406 (0.6); 2.5084 (9.0); 2.5049 (19.5); 2.5012 (27.3); 2.4976 (19.8); 2.4941 (9.4); 0.0063 (0.8); −0.0002 (26.4); −0.0068 (1.0)

I-200: $^1$H-NMR (499.9 MHz, CDCl3):

δ=8.5927 (3.3); 8.2783 (1.2); 8.2613 (1.2); 8.1409 (1.7); 8.1241 (1.8); 7.7589 (0.9); 7.7444 (1.6); 7.7284 (1.0); 7.6433 (1.1); 7.6286 (1.6); 7.6139 (0.8); 7.6124 (0.8); 7.5794 (3.0); 7.5761 (3.1); 7.3677 (0.4); 7.3584 (2.2); 7.3527 (1.9); 7.3496 (2.2); 7.3459 (2.0); 7.3404 (3.2); 7.3311 (0.5); 7.3141 (0.3); 7.3078 (1.8); 7.2981 (1.2); 7.2897 (0.9); 7.2611 (5.4); 7.1883 (1.1); 7.0816 (2.1); 7.0348 (1.1); 7.0268 (1.2); 7.0170 (1.1); 6.9749 (1.1); 6.2973 (3.1); 6.2938 (3.3); 5.2973 (3.0); 4.1894 (6.2); 3.6265 (16.0); 3.3339 (0.5); 1.6719 (0.5); −0.0002 (4.8)

I-201: $^1$H-NMR (499.9 MHz, CDCl3):

δ=8.1036 (1.1); 8.0868 (1.2); 7.7364 (0.6); 7.7336 (0.7); 7.7227 (0.7); 7.7197 (1.2); 7.7167 (0.7); 7.7057 (0.6); 7.7028 (0.9); 7.6991 (1.0); 7.6825 (1.3); 7.6200 (2.2); 7.5897 (0.8); 7.5882 (0.8); 7.5741 (1.1); 7.5597 (0.5); 7.5583 (0.5); 7.4608 (2.6); 7.4571 (2.6); 7.4291 (0.4); 7.4178 (1.0); 7.4142 (1.2); 7.4041 (1.7); 7.4000 (1.6); 7.3903 (1.2); 7.3870 (1.2); 7.3755 (0.5); 7.3721 (0.4); 7.3299 (1.3); 7.3269 (1.0); 7.3157 (1.0); 7.3119 (0.8); 7.2602 (8.4); 7.2209 (1.0); 7.2173 (1.1); 7.2058 (0.7); 7.2033 (0.9); 6.8709 (1.0); 6.7617 (2.0); 6.6525 (1.0); 6.1050 (2.8); 6.1013 (2.8); 4.2729 (4.0); 3.6204 (16.0); 3.3512 (0.6); 1.6026 (5.3); −0.0002 (7.2)

I-202: $^1$H-NMR (300.2 MHz, CDCl3):

δ=8.7605 (5.7); 8.7537 (5.8); 8.1001 (3.1); 8.0726 (3.6); 8.0700 (3.6); 7.7082 (5.6); 7.7048 (5.8); 7.6913 (2.8); 7.6684 (6.4); 7.6645 (6.2); 7.6413 (7.3); 7.6379 (6.5); 7.6295 (3.7); 7.6188 (2.9); 7.6148 (3.2); 7.6054 (2.6); 7.5990 (3.2); 7.5262 (2.8); 7.5222 (2.8); 7.5035 (3.0); 7.4995 (3.6); 7.4946 (2.5); 7.4764 (1.6); 7.4723 (1.5); 7.3966 (0.7); 7.3877 (1.2); 7.3679 (10.4); 7.3641 (9.0); 7.3605 (10.3); 7.3484 (6.5); 7.3425 (7.1); 7.3403 (6.8); 7.3245 (4.1); 7.3200 (5.4); 7.3125 (3.6); 7.2988 (9.4); 7.2940 (3.7); 7.1799 (3.3); 7.1729 (2.6); 7.1621 (4.3); 7.1509 (4.9); 7.1403 (3.0); 7.1333 (4.2); 6.9812 (4.8); 6.9751 (2.6); 6.9524 (8.1); 6.9474 (3.9); 6.9299 (2.2); 6.9234 (3.6); 6.3626 (7.6); 6.3551 (7.4); 6.3504 (2.4); 5.2933 (16.0); 4.5061 (15.0); 1.7660 (10.4); 1.3472 (0.4); 1.2957 (1.4); 0.1131 (3.0); 0.1084 (1.1); 0.0402 (5.9); 0.0354 (1.9)

I-203: $^1$H-NMR (499.9 MHz, CDCl3):

δ=8.5792 (1.5); 8.0362 (1.3); 8.0194 (1.4); 7.6585 (1.4); 7.6443 (3.8); 7.6310 (1.2); 7.6283 (1.3); 7.6142 (0.8); 7.6118 (0.7); 7.4927 (1.0); 7.4912 (1.0); 7.4770 (1.5);

7.4627 (0.7); 7.3615 (1.4); 7.3580 (2.2); 7.3521 (4.3); 7.3482 (3.2); 7.3394 (0.7); 7.3327 (1.8); 7.3247 (1.1); 7.3227 (1.2); 7.3142 (2.3); 7.3096 (0.9); 7.3018 (0.7); 7.2986 (0.5); 7.2966 (0.4); 7.2823 (2.7); 7.2777 (2.6); 7.2603 (3.9); 6.1489 (2.6); 6.1443 (2.4); 4.2426 (6.4); 3.1049 (0.4); 3.0910 (0.9); 3.0771 (1.2); 3.0632 (0.9); 3.0494 (0.4); 1.3275 (16.0); 1.3136 (15.7); −0.0002 (1.7)

I-204: $^1$H-NMR (499.9 MHz, CDCl3):

δ=8.6510 (8.5); 8.6467 (8.7); 8.0654 (5.6); 8.0486 (6.1); 7.7185 (5.2); 7.7023 (6.2); 7.6867 (7.7); 7.6770 (3.2); 7.6747 (3.0); 7.6605 (5.4); 7.6463 (3.3); 7.6439 (2.9); 7.5592 (0.4); 7.5443 (0.3); 7.5276 (3.9); 7.5115 (16.0); 7.5085 (12.4); 7.4977 (3.2); 7.4672 (0.8); 7.3858 (2.0); 7.3830 (2.2); 7.3707 (4.8); 7.3681 (5.4); 7.3559 (3.3); 7.3531 (4.2); 7.3468 (3.8); 7.3442 (3.9); 7.3316 (7.5); 7.3101 (0.3); 7.3002 (4.6); 7.2867 (5.3); 7.2703 (2.2); 7.2606 (112.4); 7.2425 (6.8); 7.2271 (5.3); 7.0489 (0.6); 6.0474 (10.9); 6.0441 (10.8); 5.3461 (0.4); 5.3426 (0.3); 4.6254 (0.5); 4.0241 (4.0); 3.9930 (8.7); 3.9413 (9.0); 3.9103 (4.2); 3.6576 (0.8); 2.2344 (0.9); 2.2194 (1.5); 2.2039 (1.0); 2.0153 (0.4); 2.0055 (0.4); 1.6502 (0.9); 1.6327 (1.3); 1.6213 (1.3); 1.5749 (51.1); 1.5169 (1.8); 1.4722 (0.4); 1.4635 (0.4); 1.4228 (179.7); 1.3958 (1.3); 1.3645 (1.2); 1.3519 (1.3); 1.3286 (1.9); 1.3140 (2.3); 1.2934 (2.7); 1.2846 (2.4); 1.2546 (8.3); 1.2056 (4.0); 1.1729 (0.4); 1.1002 (1.6); 1.0462 (0.3); 1.0260 (1.3); 1.0179 (1.6); 0.8938 (1.3); 0.8806 (2.6); 0.8668 (1.4); 0.8398 (0.6); 0.1164 (0.5); 0.0870 (0.9); 0.0696 (38.8); 0.0452 (0.6); 0.0061 (3.6); −0.0002 (110.0); −0.0063 (5.7); −0.1200 (0.6)

I-205: $^1$H-NMR (499.9 MHz, CDCl3):

δ=8.8342 (0.4); 8.8298 (0.4); 8.7525 (5.4); 8.7481 (5.7); 8.0589 (0.4); 8.0408 (3.4); 8.0239 (3.8); 7.8451 (0.4); 7.7690 (4.6); 7.7670 (4.7); 7.7216 (0.4); 7.7057 (0.4); 7.6570 (3.5); 7.6407 (4.1); 7.6270 (2.2); 7.6242 (2.0); 7.6132 (2.8); 7.6103 (3.7); 7.6074 (2.2); 7.5963 (2.4); 7.5936 (2.1); 7.5815 (3.0); 7.5784 (3.6); 7.5645 (3.8); 7.5443 (0.8); 7.5137 (0.4); 7.4996 (0.5); 7.4973 (0.4); 7.4880 (8.1); 7.4833 (8.4); 7.4704 (2.8); 7.4683 (2.8); 7.4544 (4.1); 7.4404 (2.0); 7.4384 (1.9); 7.3946 (0.4); 7.3675 (0.4); 7.3526 (0.3); 7.3212 (1.1); 7.3166 (1.4); 7.3077 (2.5); 7.3032 (3.0); 7.2936 (2.2); 7.2883 (3.8); 7.2752 (4.4); 7.2721 (4.8); 7.2601 (73.6); 7.2488 (3.0); 7.2443 (2.0); 7.0484 (0.4); 6.2836 (7.5); 6.2789 (7.6); 4.6254 (1.1); 4.5237 (16.0); 4.4626 (0.4); 3.6566 (0.6); 3.6508 (0.6); 2.2335 (0.8); 2.2185 (1.3); 2.2030 (1.0); 2.0155 (0.4); 2.0046 (0.4); 1.6787 (2.3); 1.6351 (1.2); 1.5841 (12.6); 1.5539 (137.6); 1.5279 (3.2); 1.5032 (1.5); 1.4537 (0.5); 1.4228 (2.2); 1.4053 (0.4); 1.3926 (0.4); 1.3127 (1.9); 1.3026 (1.8); 1.2843 (2.0); 1.2544 (6.5); 1.2055 (9.6); 1.1726 (0.4); 1.0177 (2.2); 0.8940 (1.0); 0.8806 (2.2); 0.8666 (1.2); 0.8398 (0.7); 0.0870 (0.5); 0.0768 (0.8); 0.0696 (22.1); 0.0452 (0.6); 0.0063 (2.0); −0.0002 (66.9); −0.0067 (4.2); −0.0500 (0.4); −0.1200 (0.3)

I-206: $^1$H-NMR (499.9 MHz, d$_6$-DMSO):

δ=8.6273 (3.4); 8.6221 (3.3); 8.1127 (3.7); 7.5236 (1.9); 7.5075 (2.4); 7.4917 (2.5); 7.4163 (1.9); 7.4058 (1.4); 7.3999 (3.5); 7.3906 (5.7); 7.3868 (5.0); 7.3742 (0.8); 7.2450 (1.2); 7.2433 (1.2); 7.2270 (3.4); 7.2098 (2.4); 6.2953 (4.3); 6.2916 (4.1); 3.6326 (16.0); 3.3195 (18.8); 2.9441 (0.4); 2.7850 (0.3); 2.5094 (2.4); 2.5061 (4.4); 2.5025 (5.7); 2.4989 (4.1); 2.4956 (1.9); 2.2792 (8.4); 2.2766 (8.2); 1.9576 (0.4); −0.0002 (3.3)

I-207: $^1$H-NMR (499.9 MHz, d$_6$-DMSO):

δ=8.6091 (5.5); 7.8776 (2.0); 7.8607 (2.2); 7.5950 (0.8); 7.5843 (0.9); 7.5791 (1.3); 7.5685 (1.3); 7.5626 (0.9); 7.5520 (0.8); 7.4890 (1.5); 7.4710 (5.1); 7.4673 (5.3); 7.4565 (3.8); 7.3025 (0.9); 7.2859 (1.8); 7.2722 (1.6); 7.2558 (0.7); 7.2023 (0.4); 6.7997 (1.3); 6.7819 (2.0); 6.7648 (1.1); 6.4203 (3.1); 6.4165 (4.5); 6.4127 (4.0); 6.4042 (2.3); 3.7148 (16.0); 3.6080 (1.1); 3.3185 (18.5); 2.9443 (0.7); 2.7851 (0.6); 2.5059 (4.4); 2.5025 (5.4); 2.4990 (3.8); 2.4449 (15.8); 1.9576 (0.6); 1.8213 (1.1); −0.0002 (2.7)

I-208: $^1$H-NMR (499.9 MHz, d$_6$-DMSO):

δ=8.6186 (0.3); 8.5660 (5.4); 8.1097 (0.3); 7.8734 (1.8); 7.8563 (2.1); 7.5948 (0.7); 7.5841 (0.8); 7.5787 (1.2); 7.5681 (1.2); 7.5624 (0.8); 7.5517 (0.7); 7.5062 (3.4); 7.4858 (1.3); 7.4698 (1.0); 7.4647 (1.2); 7.4489 (0.8); 7.3998 (0.4); 7.3887 (0.5); 7.3848 (0.5); 7.3139 (0.7); 7.2975 (1.5); 7.2789 (5.3); 7.2674 (0.8); 6.7957 (1.1); 6.7784 (1.9); 6.7610 (1.0); 6.4343 (2.2); 6.4177 (2.2); 6.2931 (0.4); 6.2895 (0.4); 3.6575 (16.0); 3.6304 (1.6); 3.3176 (118.2); 2.8905 (0.6); 2.7312 (0.5); 2.5048 (14.9); 2.5013 (20.2); 2.4978 (15.1); 2.4583 (15.3); 2.2761 (0.9); 1.9202 (15.0); 1.9083 (1.1); 1.2359 (1.1); −0.0002 (10.5)

I-209: $^1$H-NMR (499.9 MHz, d$_6$-DMSO):

δ=8.5540 (5.6); 7.8415 (2.0); 7.8245 (2.2); 7.5679 (0.7); 7.5571 (0.8); 7.5518 (1.3); 7.5412 (1.2); 7.5355 (0.9); 7.5248 (0.7); 7.4445 (1.2); 7.4290 (4.8); 7.4254 (4.8); 7.4077 (1.0); 7.3280 (3.6); 7.2080 (1.1); 7.1909 (2.0); 7.1815 (0.4); 7.1738 (1.1); 6.4484 (2.4); 6.4317 (2.3); 6.3673 (3.9); 6.3637 (3.8); 3.6958 (16.0); 3.5950 (0.5); 3.3229 (17.8); 3.1779 (1.1); 3.1674 (1.1); 2.5067 (3.1); 2.5034 (4.1); 2.5001 (3.1); 2.4200 (15.8); 2.1973 (8.8); 2.1960 (8.8); 2.0759 (0.5); 1.8052 (0.5); 1.2329 (0.3); −0.0002 (1.3)

I-210: $^1$H-NMR (400.0 MHz, d$_6$-DMSO):

δ=8.4411 (1.9); 8.4352 (2.5); 8.4038 (3.3); 8.3976 (2.4); 8.0083 (3.2); 8.0024 (3.2); 7.3989 (3.3); 7.3944 (3.6); 7.3865 (3.0); 7.2067 (0.8); 7.2020 (0.9); 7.1858 (1.4); 7.1812 (1.5); 7.1324 (2.9); 7.1118 (1.7); 7.0976 (2.3); 7.0935 (2.2); 6.6078 (2.3); 6.6021 (2.3); 6.3032 (3.3); 6.2987 (3.4); 3.6723 (16.0); 3.3574 (78.1); 2.8919 (1.3); 2.7330 (1.2); 2.5137 (5.6); 2.5095 (11.4); 2.5051 (15.2); 2.5007 (11.1); 2.4965 (5.5); 2.2944 (10.7); −0.0002 (0.4)

I-211: $^1$H-NMR (400.0 MHz, d$_6$-DMSO):

δ=8.6828 (2.1); 8.6778 (2.1); 8.4441 (3.1); 8.4380 (3.0); 8.0734 (3.3); 8.0675 (3.2); 7.5092 (2.8); 7.4433 (3.6); 7.4386 (3.5); 7.3803 (1.2); 7.3739 (1.3); 7.3584 (1.4); 7.3520 (1.6); 7.2892 (3.2); 7.2828 (2.7); 7.1515 (2.7); 7.1295 (2.3); 6.6538 (2.2); 6.6517 (2.3); 6.6479 (2.3); 6.6459 (2.0); 6.3822 (3.6); 6.3776 (3.5); 3.7066 (16.0); 3.3517 (76.9); 2.8921 (1.1); 2.7325 (1.0); 2.5132 (7.5); 2.5091 (14.8); 2.5046 (19.2); 2.5001 (14.0); 2.4958 (6.9)

I-212: $^1$H-NMR (300.2 MHz, CDCl3):

δ=8.9531 (4.3); 8.1003 (0.9); 8.0892 (1.0); 8.0816 (0.6); 8.0771 (0.9); 8.0668 (1.8); 8.0563 (0.9); 8.0445 (1.1); 8.0337 (1.0); 7.6499 (0.3); 7.6475 (0.4); 7.6371 (2.7); 7.6272 (1.5); 7.6244 (1.4); 7.6145 (1.7); 7.6097 (2.9); 7.6040 (4.6); 7.5921 (0.4); 7.2989 (2.3); 7.2740 (2.9); 7.2552 (1.3); 7.2492 (1.5); 7.2270 (0.4); 7.2213 (0.5); 7.1809 (1.8); 6.4084 (2.8); 6.4021 (2.8); 5.9951 (1.5); 5.3308 (0.6); 3.8128 (16.0); 2.4145 (9.7); 1.8419 (1.8); 0.0357 (2.0)

I-213: $^1$H-NMR (300.2 MHz, d$_6$-DMSO):

δ=8.5943 (1.3); 7.5976 (1.0); 7.5843 (0.5); 7.5708 (1.3); 7.5564 (0.4); 7.5523 (0.4); 7.3703 (0.5); 7.3654 (0.6); 7.3432 (0.4); 7.3384 (0.6); 7.3257 (0.4); 7.3157 (0.4); 7.3023 (1.3); 7.2028 (1.7); 7.1966 (1.7); 6.2066 (1.8); 6.2004 (1.7); 5.7798 (0.5); 3.7120 (7.5); 3.3516 (16.0); 2.5764 (6.1); 2.5345 (1.0); 2.5285 (2.2); 2.5225 (3.0); 2.5165 (2.2); 2.5106 (1.0); 2.4167 (4.7); 0.0194 (2.8)

I-214: $^1$H-NMR (400.0 MHz, d$_6$-DMSO):

δ=8.6728 (2.8); 7.7679 (1.5); 7.7459 (2.0); 7.6143 (0.7); 7.6094 (1.6); 7.6031 (2.5); 7.5838 (6.9); 7.5703 (1.1); 7.5442 (0.6); 7.3557 (0.8); 7.3512 (0.9); 7.3434 (0.9); 7.3389 (0.9); 7.3323 (0.8); 7.3278 (0.8); 7.3199 (0.7); 7.3158 (0.7); 7.2052 (3.5); 7.2006 (3.8); 6.2600 (3.6); 6.2553 (3.8); 3.7281 (16.0); 3.3448 (43.7); 2.5714 (14.3); 2.5104 (12.8); 2.5060 (17.4); 2.5015 (13.2); −0.0002 (0.7)

I-215: $^1$H-NMR (400.0 MHz, d$_6$-DMSO):

δ=8.6268 (2.6); 8.6199 (2.7); 7.9091 (2.7); 7.4828 (0.9); 7.4773 (1.1); 7.4636 (1.0); 7.4590 (1.2); 7.3509 (1.7); 7.3454 (3.7); 7.3408 (3.8); 7.3305 (3.1); 7.3239 (2.7); 7.3170 (2.6); 7.3072 (0.8); 7.2895 (2.6); 7.2809 (1.8); 7.2714 (4.0); 7.2596 (1.2); 7.1879 (2.2); 7.1839 (2.1); 6.2807 (3.7); 6.2760 (3.7); 3.6354 (16.0); 3.3486 (62.2); 2.8902 (2.1); 2.7320 (1.9); 2.6210 (11.1); 2.5127 (6.9); 2.5083 (14.6); 2.5038 (19.8); 2.4993 (14.5); 2.4949 (7.1); 2.3438 (10.3); −0.0002 (0.5)

I-216: $^1$H-NMR (400.0 MHz, d$_6$-DMSO):

δ=8.4682 (4.5); 8.0173 (1.1); 8.0143 (1.0); 8.0106 (0.8); 7.9985 (1.3); 7.9934 (1.2); 7.9528 (0.7); 7.9010 (1.2); 7.8962 (1.4); 7.8838 (0.8); 7.8805 (1.1); 7.8772 (1.3); 7.6052 (0.4); 7.6009 (0.6); 7.5881 (1.3); 7.5838 (1.2); 7.5747 (1.3); 7.5694 (2.2); 7.5639 (1.7); 7.5546 (1.0); 7.5506 (1.1); 7.5376 (0.4); 7.5336 (0.3); 7.3690 (3.4); 7.3644 (3.4); 7.1264 (2.4); 7.1142 (1.0); 7.1093 (1.1); 7.0930 (0.9); 7.0887 (1.2); 7.0669 (2.2); 7.0630 (1.8); 6.6544 (2.2); 6.6339 (2.1); 6.3120 (3.4); 6.3074 (3.4); 3.7274 (16.0); 3.6578 (0.3); 3.3534 (39.8); 3.2576 (0.4); 2.8909 (4.5); 2.7319 (4.0); 2.5260 (0.4); 2.5126 (10.0); 2.5082 (20.7); 2.5037 (27.6); 2.4992 (20.0); 2.4949 (9.6); 2.4282 (12.9); 2.2730 (9.8); −0.0002 (0.4)

I-217: $^1$H-NMR (300.2 MHz, CDCl3):

δ=8.7514 (3.1); 8.1319 (1.0); 8.1287 (1.0); 8.1038 (1.2); 8.1012 (1.2); 8.0317 (1.0); 8.0287 (1.0); 8.0041 (1.2); 8.0006 (1.2); 7.7404 (0.6); 7.7356 (0.6); 7.7175 (1.0); 7.7128 (1.2); 7.7079 (0.6); 7.6899 (0.9); 7.6849 (0.8); 7.6727 (2.6); 7.6665 (2.7); 7.6501 (0.9); 7.6455 (1.0); 7.6271 (0.6); 7.6224 (1.2); 7.6179 (0.8); 7.5993 (0.5); 7.5949 (0.5); 7.2989 (2.0); 7.2497 (1.6); 7.2423 (2.7); 7.2310 (1.5); 7.2227 (0.7); 7.2022 (1.3); 7.1940 (1.0); 6.6212 (2.1); 6.5923 (1.9); 6.4969 (2.8); 6.4906 (2.8); 5.5492 (1.5); 3.9270 (0.5); 3.9047 (16.0); 2.9882 (0.5); 2.9141 (0.4); 2.9127 (0.4); 2.5303 (12.1); 1.2886 (1.3); 0.0324 (1.5)

I-218: $^1$H-NMR (400.0 MHz, d$_6$-DMSO):

δ=9.3079 (2.4); 8.5010 (4.5); 7.7122 (1.9); 7.6919 (2.3); 7.6712 (0.8); 7.6501 (0.8); 7.6475 (0.8); 7.6239 (0.5); 7.3795 (0.8); 7.3746 (0.8); 7.3670 (0.9); 7.3626 (0.8); 7.3559 (0.6); 7.3511 (0.7); 7.3435 (0.6); 7.3350 (1.2); 7.3299 (1.3); 7.3228 (3.4); 7.3182 (3.7); 7.3095 (1.2); 7.2425 (2.1); 7.2385 (2.0); 6.2219 (3.5); 6.2173 (3.5); 3.6662 (16.0); 3.3435 (31.0); 2.8930 (1.5); 2.7342 (1.3); 2.5233 (0.5); 2.5149 (6.3); 2.5104 (13.2); 2.5059 (17.6); 2.5014 (12.6); 2.4969 (6.0); 2.3761 (9.8); 1.6497 (0.3); −0.0002 (0.8)

I-219: $^1$H-NMR (400.0 MHz, d$_6$-DMSO):

δ=8.4812 (5.3); 8.0539 (1.2); 8.0490 (1.5); 8.0366 (0.9); 8.0331 (1.2); 8.0299 (1.4); 7.9512 (3.7); 7.9438 (1.2); 7.9312 (1.6); 7.9264 (1.4); 7.6905 (0.4); 7.6865 (0.6); 7.6732 (1.3); 7.6692 (1.2); 7.6593 (1.4); 7.6538 (2.2); 7.6491 (1.3); 7.6394 (1.1); 7.6352 (1.4); 7.6221 (0.5); 7.6178 (0.4); 7.4680 (1.2); 7.4617 (1.4); 7.4465 (1.3); 7.4401 (1.7); 7.4008 (3.1); 7.3945 (2.6); 7.2927 (3.4); 7.2880 (3.6); 7.1389 (2.6); 7.1172 (2.4); 6.3212 (3.6); 6.3165 (3.7); 3.7285 (16.0); 3.6664 (0.7); 3.3654 (64.1); 2.8930 (6.0); 2.7345 (5.0); 2.5248 (0.4); 2.5162 (5.1); 2.5118 (10.8); 2.5073 (14.6); 2.5027 (10.6); 2.4983 (5.2)

I-220: $^1$H-NMR (400.0 MHz, d$_6$-DMSO):

δ=9.4203 (2.3); 8.5651 (4.4); 7.9705 (2.0); 7.9487 (2.3); 7.7345 (0.4); 7.7110 (0.8); 7.6874 (0.8); 7.6640 (0.5); 7.5870 (1.5); 7.5807 (1.8); 7.5653 (1.3); 7.5589 (1.7); 7.5169 (3.2); 7.5106 (2.6); 7.4351 (0.7); 7.4303 (0.7); 7.4228 (0.7); 7.4181 (0.8); 7.4117 (0.6); 7.4068 (0.6); 7.3993 (0.6); 7.3948 (0.6); 7.3707 (3.4); 7.3660 (3.5); 6.3120 (3.6); 6.3072 (3.7); 3.6953 (16.0); 3.3460 (26.2); 2.5173 (4.3); 2.5128 (9.3); 2.5083 (12.6); 2.5037 (9.2); 2.4992 (4.5); −0.0002 (0.7)

I-221: $^1$H-NMR (400.0 MHz, d$_6$-DMSO):

δ=8.7190 (2.6); 8.7120 (2.7); 8.2435 (2.7); 7.9605 (1.4); 7.9404 (1.5); 7.8270 (0.7); 7.8172 (0.6); 7.8105 (0.6); 7.7977 (0.9); 7.7875 (2.1); 7.7711 (1.6); 7.5304 (1.0); 7.5109 (1.6); 7.4915 (1.1); 7.4803 (0.9); 7.4747 (0.7); 7.4670 (1.4); 7.4626 (1.4); 7.4010 (1.8); 7.3912 (2.9); 7.3839 (3.4); 7.3811 (3.6); 7.3477 (0.9); 7.3336 (3.6); 7.3289 (4.5); 7.3227 (1.7); 7.3059 (0.8); 7.3019 (1.0); 7.2341 (2.3); 7.2303 (2.2); 6.2899 (3.5); 6.2853 (3.5); 3.6408 (16.0); 3.3523 (73.3); 2.8926 (0.6); 2.7344 (0.5); 2.5152 (7.4); 2.5108 (15.4); 2.5064 (20.6); 2.5019 (15.0); 2.4976 (7.4); 2.3655 (10.5); −0.0002 (0.6)

I-222: $^1$H-NMR (400.0 MHz, d$_6$-DMSO):

δ=8.7688 (2.6); 8.7619 (2.7); 8.3730 (2.9); 8.3147 (0.4); 8.0092 (1.3); 7.9891 (1.4); 7.8472 (1.3); 7.8294 (1.5); 7.5862 (2.6); 7.5792 (2.6); 7.5735 (1.2); 7.5536 (1.5); 7.5399 (0.6); 7.5344 (1.2); 7.5183 (2.4); 7.5128 (3.3); 7.5081 (4.0); 7.4869 (0.6); 7.4580 (2.7); 7.4527 (2.4); 7.3679 (3.5); 7.3632 (3.6); 6.3726 (3.6); 6.3679 (3.5); 3.6679 (16.0); 3.3652 (82.0); 2.8936 (1.6); 2.7353 (1.4); 2.5167 (5.9); 2.5123 (12.5); 2.5078 (16.7); 2.5033 (12.1); 2.4989 (5.8)

I-223: $^1$H-NMR (300.2 MHz, CDCl3):

δ=8.9211 (1.9); 8.8928 (2.0); 7.8880 (1.1); 7.8846 (1.1); 7.8607 (2.3); 7.8567 (2.3); 7.8318 (1.3); 7.8289 (1.4); 7.7083 (2.6); 7.7022 (2.6); 7.6382 (0.6); 7.6335 (0.6); 7.6146 (1.0); 7.6103 (1.2); 7.5874 (0.7); 7.5826 (0.7); 7.5093 (0.9); 7.5045 (0.9); 7.4819 (1.2); 7.4775 (0.9); 7.4588 (0.6); 7.4541 (0.5); 7.4198 (0.9); 7.4133 (0.9); 7.3914 (0.8); 7.3850 (0.9); 7.2987 (1.6); 7.1520 (1.8); 7.1463 (1.6); 6.8688 (1.4); 6.4667 (2.8); 6.4605 (2.8); 3.7751 (16.0); 3.7438 (0.5); 2.4388 (9.8); 2.3987 (12.2); 2.3776 (0.3); 1.8251 (1.5); 0.0353 (1.2)

I-224: $^1$H-NMR (400.0 MHz, d$_6$-DMSO):

δ=8.3748 (2.2); 7.9533 (0.8); 7.9011 (1.9); 7.8797 (2.2); 7.7287 (1.7); 7.7086 (1.7); 7.6047 (1.5); 7.5984 (2.0); 7.5834 (1.1); 7.5770 (2.0); 7.5628 (3.4); 7.5566 (2.3); 7.5092 (3.2); 7.5070 (3.5); 7.5012 (2.3); 7.4964 (2.0); 7.4932 (1.7); 7.3998 (1.0); 7.3921 (1.0); 7.3867 (0.8); 7.3792 (1.4); 7.3723 (0.8); 7.3658 (0.8); 7.3585 (0.7); 7.2378 (3.4); 7.2331 (3.6); 6.3027 (3.6); 6.2980 (3.6); 3.7364 (16.0); 3.7269 (0.8); 3.3410 (26.7); 2.8903 (6.2); 2.7321 (5.2); 2.7253 (0.5); 2.5138 (18.3); 2.5082 (13.8); 2.5036 (17.7); 2.4990 (12.7); 2.4945 (6.2); −0.0002 (0.6)

I-225: $^1$H-NMR (400.0 MHz, d$_6$-DMSO):

δ=8.6769 (2.7); 8.6701 (2.8); 8.3152 (0.3); 8.0552 (2.6); 7.9528 (0.4); 7.5440 (0.8); 7.5328 (1.7); 7.5253 (2.8); 7.5186 (3.4); 7.4851 (0.9); 7.4789 (1.0); 7.4633 (1.9); 7.4571 (2.3); 7.4303 (3.4); 7.4086 (1.5); 7.3977 (3.2); 7.3916 (2.9); 7.3865 (3.7); 7.3818 (3.8); 7.3350 (3.3); 7.3213 (4.2); 6.3671 (3.6); 6.3624 (3.6); 3.6818 (0.8); 3.6646 (16.0); 3.3462 (46.2); 2.8910 (2.4); 2.7322 (2.1); 2.6736 (0.7); 2.6378 (11.4); 2.5264 (0.3); 2.5130 (7.9); 2.5085 (16.7); 2.5040 (22.4); 2.4994 (16.2); 2.4950 (7.9); −0.0002 (1.0)

I-226: ¹H-NMR (400.0 MHz, d₆-DMSO):
δ=8.6653 (2.6); 8.6589 (2.7); 8.2998 (3.1); 7.9542 (1.5); 7.5223 (3.9); 7.5060 (3.7); 7.5008 (4.4); 7.4867 (4.0); 7.4651 (1.2); 7.4419 (3.2); 7.4361 (2.9); 7.4279 (0.8); 7.4151 (0.8); 7.4081 (1.2); 7.3953 (1.1); 7.3879 (0.7); 7.3751 (0.7); 7.3617 (3.4); 7.3570 (3.6); 7.2614 (0.9); 7.2591 (1.0); 7.2424 (0.8); 7.2399 (0.8); 7.2335 (1.0); 7.2312 (1.0); 7.2144 (0.8); 7.2118 (0.8); 6.3569 (3.7); 6.3523 (3.7); 3.6882 (0.6); 3.6595 (16.0); 3.3567 (70.0); 2.8929 (10.0); 2.7343 (9.0); 2.5148 (7.0); 2.5106 (14.4); 2.5062 (19.3); 2.5018 (14.2); 2.4977 (7.2); −0.0002 (0.4)

I-227: ¹H-NMR (400.0 MHz, d₆-DMSO):
δ=8.6670 (2.4); 8.6605 (2.4); 8.1661 (2.6); 7.5647 (0.3); 7.5491 (0.4); 7.5409 (1.9); 7.5253 (1.4); 7.5133 (0.9); 7.4969 (0.8); 7.4900 (0.3); 7.3953 (0.4); 7.3822 (1.7); 7.3764 (1.9); 7.3702 (2.3); 7.3491 (2.9); 7.3213 (3.6); 7.3166 (4.1); 7.3089 (1.6); 7.2926 (0.7); 7.2879 (0.8); 7.2161 (2.1); 7.2121 (2.0); 6.2731 (3.6); 6.2684 (3.7); 3.6271 (16.0); 3.3559 (71.0); 2.8929 (0.8); 2.7340 (0.7); 2.5243 (0.4); 2.5155 (6.3); 2.5111 (13.3); 2.5065 (18.0); 2.5020 (13.1); 2.4975 (6.4); 2.3563 (9.9); 1.6497 (0.4); −0.0002 (0.3)

I-228: ¹H-NMR (400.0 MHz, d₆-DMSO):
δ=8.7148 (2.4); 8.7084 (2.5); 8.2982 (2.9); 7.6147 (0.4); 7.5986 (0.5); 7.5907 (1.7); 7.5822 (2.3); 7.5763 (3.1); 7.5597 (1.0); 7.5430 (0.8); 7.5368 (0.3); 7.5222 (1.0); 7.5163 (1.1); 7.5006 (2.2); 7.4945 (2.6); 7.4697 (3.6); 7.4481 (1.6); 7.4379 (3.3); 7.4318 (2.8); 7.3550 (3.6); 7.3503 (3.7); 6.3537 (3.8); 6.3490 (3.8); 3.6856 (0.3); 3.6551 (16.0); 3.3523 (47.0); 3.3510 (47.2); 2.8939 (1.5); 2.7345 (1.3); 2.5159 (6.2); 2.5115 (12.9); 2.5070 (17.1); 2.5025 (12.3); 2.4981 (5.9); −0.0002 (0.6)

I-229: ¹H-NMR (400.0 MHz, d₆-DMSO):
δ=7.4983 (0.5); 7.4809 (0.7); 7.4729 (1.1); 7.4614 (1.0); 7.4371 (3.3); 7.4214 (0.9); 7.4139 (0.9); 7.3962 (1.0); 7.3725 (0.5); 7.3331 (0.9); 7.3296 (1.0); 7.3127 (1.5); 7.3093 (1.6); 7.2496 (2.9); 7.2295 (4.2); 7.1632 (3.5); 7.1586 (3.6); 7.0717 (3.0); 6.2116 (3.7); 6.2070 (3.7); 3.6620 (16.0); 3.3613 (99.7); 2.8927 (1.8); 2.7346 (1.5); 2.7337 (1.5); 2.5860 (13.4); 2.5285 (0.4); 2.5107 (15.7); 2.5062 (20.5); 2.5018 (15.3); 2.3736 (10.9); −0.0002 (0.4)

I-230: ¹H-NMR (400.0 MHz, d₆-DMSO):
δ=7.9543 (1.2); 7.6089 (2.5); 7.5668 (0.5); 7.5631 (0.5); 7.5529 (0.5); 7.5490 (0.6); 7.5436 (0.9); 7.5400 (0.9); 7.5288 (2.1); 7.5224 (1.7); 7.5072 (1.6); 7.5008 (1.9); 7.4936 (0.7); 7.4755 (0.7); 7.4678 (0.8); 7.4477 (3.6); 7.4414 (2.8); 7.4266 (0.4); 7.3224 (2.5); 7.2602 (2.8); 7.2386 (2.4); 7.1874 (3.8); 7.1827 (3.8); 6.2776 (3.8); 6.2729 (3.8); 3.6901 (16.0); 3.6814 (1.1); 3.3621 (85.3); 2.8933 (8.5); 2.7350 (7.0); 2.7341 (7.2); 2.6839 (0.6); 2.5920 (13.1); 2.5158 (6.3); 2.5113 (13.3); 2.5068 (17.8); 2.5022 (12.7); 2.4977 (6.0); −0.0002 (0.4)

I-231: ¹H-NMR (300.2 MHz, d₆-DMSO):
δ=8.6358 (2.0); 8.6270 (1.9); 8.1925 (2.1); 7.4949 (0.9); 7.4702 (1.4); 7.4076 (1.3); 7.3952 (0.8); 7.3803 (2.6); 7.3694 (1.0); 7.3591 (0.8); 7.3487 (3.9); 7.3424 (5.3); 7.3351 (2.3); 7.3124 (0.5); 7.3068 (0.6); 7.2411 (1.7); 7.2352 (1.6); 7.2261 (0.8); 7.2047 (0.6); 7.2006 (0.6); 7.1926 (0.7); 7.1888 (0.7); 7.1672 (0.5); 7.1633 (0.5); 6.2944 (2.7); 6.2882 (2.7); 5.7803 (1.0); 3.6483 (11.8); 3.3507 (16.0); 2.5341 (2.0); 2.5282 (4.1); 2.5221 (5.5); 2.5161 (4.0); 2.5102 (1.9); 2.3775 (7.4); 0.0193 (3.0)

I-232: ¹H-NMR (300.2 MHz, CDCl3):
δ=8.1528 (0.8); 8.1435 (0.8); 8.1303 (0.8); 8.1210 (0.8); 8.1128 (0.8); 8.1035 (0.8); 8.0902 (0.7); 8.0810 (0.7); 7.6259 (3.9); 7.6195 (3.9); 7.6075 (0.8); 7.6013 (0.7); 7.5926 (1.2); 7.5869 (1.3); 7.5764 (1.2); 7.5703 (1.2); 7.5539 (1.1); 7.5290 (1.1); 7.5216 (1.3); 7.4966 (1.3); 7.4904 (0.6); 7.4649 (1.4); 7.4585 (1.2); 7.4489 (1.5); 7.4413 (1.2); 7.4325 (0.8); 7.2987 (13.9); 6.8193 (1.8); 6.4513 (3.0); 6.4451 (2.9); 5.3372 (3.6); 3.9532 (11.5); 3.9484 (11.0); 2.8361 (16.0); 1.6178 (11.3); 0.1074 (0.4); 0.0477 (0.6); 0.0370 (15.0); 0.0260 (0.5)

I-233: ¹H-NMR (300.2 MHz, CDCl3):
δ=7.8618 (2.4); 7.6565 (2.7); 7.6503 (2.7); 7.4525 (0.4); 7.4484 (0.4); 7.4351 (0.5); 7.4298 (0.5); 7.4218 (1.1); 7.4177 (1.2); 7.4044 (1.0); 7.3987 (1.8); 7.3765 (0.9); 7.3666 (1.1); 7.3446 (1.0); 7.3360 (0.4); 7.3136 (0.8); 7.2988 (1.8); 7.2749 (1.5); 7.2491 (3.3); 7.2313 (1.8); 7.2225 (1.9); 6.4490 (3.1); 6.4428 (3.0); 5.7010 (1.9); 5.3283 (2.0); 3.8330 (16.0); 2.6890 (0.7); 2.6133 (13.6); 1.8173 (0.8); 0.0297 (1.6)

I-234: ¹H-NMR (300.2 MHz, CDCl3):
δ=7.7811 (2.8); 7.7774 (2.7); 7.5923 (3.4); 7.5860 (3.4); 7.4456 (0.5); 7.4282 (0.6); 7.4236 (0.6); 7.4133 (2.0); 7.4074 (1.7); 7.3974 (1.4); 7.3934 (1.6); 7.3879 (1.4); 7.3771 (1.5); 7.3561 (1.3); 7.3466 (0.5); 7.3254 (0.6); 7.2989 (12.3); 7.0913 (0.8); 7.0821 (0.9); 7.0700 (0.8); 7.0607 (0.9); 7.0540 (0.8); 7.0446 (0.8); 7.0327 (0.7); 7.0232 (0.8); 6.8350 (0.9); 6.8287 (1.1); 6.8191 (1.5); 6.8121 (1.1); 6.8033 (0.8); 6.3940 (3.0); 6.3877 (3.0); 5.6976 (1.8); 5.3370 (2.5); 3.9962 (10.8); 3.9117 (10.7); 3.9064 (10.7); 3.8045 (0.4); 2.7996 (16.0); 2.7849 (0.7); 1.6325 (10.9); 1.2928 (0.7); 0.1074 (0.4); 0.0477 (0.6); 0.0369 (13.0); 0.0260 (0.5)

I-235: ¹H-NMR (300.2 MHz, CDCl3):
δ=9.1021 (2.2); 9.0715 (2.3); 7.7558 (2.6); 7.7496 (2.6); 7.6441 (0.5); 7.6377 (0.5); 7.6280 (0.5); 7.6214 (0.5); 7.6130 (0.8); 7.6066 (0.8); 7.5969 (0.7); 7.5903 (0.8); 7.5401 (0.7); 7.5144 (0.7); 7.5075 (0.9); 7.4814 (1.5); 7.4565 (0.7); 7.4500 (1.0); 7.2990 (2.6); 7.2463 (1.4); 7.2388 (1.2); 7.0854 (1.4); 6.5424 (2.8); 6.5361 (2.8); 5.3342 (0.5); 3.8052 (16.0); 2.4672 (11.5); 1.6652 (2.4); 0.0349 (2.8)

I-236: ¹H-NMR (300.2 MHz, CDCl3):
δ=8.7718 (3.6); 8.7630 (3.6); 7.7686 (2.2); 7.7632 (2.6); 7.7601 (2.5); 7.7548 (2.0); 7.5973 (4.5); 7.5909 (4.4); 7.5122 (0.7); 7.4985 (3.8); 7.4919 (3.6); 7.4847 (4.6); 7.4689 (1.9); 7.4412 (0.5); 7.3185 (1.3); 7.2987 (11.2); 7.2885 (1.2); 7.2834 (1.4); 7.2750 (1.2); 7.2616 (1.0); 7.2534 (0.9); 7.1849 (0.9); 7.1755 (1.0); 7.1636 (1.0); 7.1541 (1.1); 7.1475 (1.0); 7.1380 (1.0); 7.1262 (0.9); 7.1168 (0.9); 6.9200 (1.1); 6.9137 (1.4); 6.9111 (1.4); 6.9042 (1.9); 6.8972 (1.4); 6.8883 (1.0); 6.4010 (3.9); 6.3947 (3.8); 6.1917 (2.4); 3.9129 (14.4); 3.9078 (14.0); 1.6589 (16.0); 0.1065 (0.5); 0.0464 (0.6); 0.0356 (11.7); 0.0247 (0.5)

I-237: ¹H-NMR (300.2 MHz, CDCl3):
δ=8.9542 (7.9); 8.1703 (1.8); 8.1593 (1.5); 8.1569 (1.3); 8.1485 (1.9); 8.1376 (2.1); 8.1250 (0.6); 8.1096 (1.8); 8.0978 (1.9); 8.0892 (1.4); 8.0863 (1.3); 8.0774 (2.1); 8.0659 (0.4); 7.7080 (1.0); 7.6960 (5.3); 7.6850 (4.1); 7.6750 (3.7); 7.6635 (4.7); 7.6520 (0.8); 7.5805 (4.9); 7.5741 (4.9); 7.2985 (7.7); 7.1324 (1.0); 7.1231 (1.1); 7.1112 (1.1); 7.1018 (1.2); 7.0957 (1.1); 7.0862 (1.2); 7.0743 (1.0); 7.0649 (1.1); 6.9243 (1.2); 6.9174 (1.6); 6.9083 (2.1); 6.9010 (1.6); 6.8926 (1.1); 6.3940 (4.4); 6.3876 (4.4); 6.2518 (2.8); 5.3339 (3.4); 3.9833 (0.4); 3.9049 (16.0); 3.8999 (15.4); 3.7952 (0.5); 2.6984 (0.5); 2.6903 (0.5); 1.7040 (7.8); 1.2919 (0.5); 0.0360 (8.0)

I-238: ¹H-NMR (300.2 MHz, CDCl3):
δ=8.8090 (1.1); 8.8004 (1.2); 7.7552 (0.8); 7.7504 (1.0); 7.5999 (1.4); 7.5936 (1.4); 7.4721 (1.8); 7.4565 (0.8); 7.4512 (1.0); 7.4455 (0.7); 7.4261 (0.6); 7.2986 (13.4);

7.1616 (0.3); 7.1519 (0.3); 7.1401 (0.3); 7.1307 (0.4); 7.1246 (0.3); 7.1151 (0.3); 7.0937 (0.3); 6.9020 (0.4); 6.8954 (0.5); 6.8862 (0.7); 6.8789 (0.5); 6.8707 (0.3); 6.3992 (1.4); 6.3929 (1.3); 6.0501 (0.9); 3.9140 (4.8); 3.9091 (4.5); 1.6003 (16.0); 0.1061 (0.6); 0.0470 (0.6); 0.0365 (14.3); 0.0257 (0.5)

I-239: $^1$H-NMR (300.2 MHz, CDCl3):
δ=8.6228 (3.1); 8.6147 (3.4); 8.4776 (4.8); 8.4693 (4.3); 8.1414 (4.4); 8.1334 (4.5); 7.5742 (5.0); 7.5678 (5.1); 7.2990 (9.0); 6.8771 (1.1); 6.8675 (1.2); 6.8563 (1.1); 6.8467 (1.2); 6.8396 (1.2); 6.8299 (1.2); 6.8187 (1.1); 6.8091 (1.1); 6.7755 (3.1); 6.7732 (3.1); 6.7676 (3.2); 6.7654 (3.0); 6.6381 (1.3); 6.6318 (1.6); 6.6288 (1.5); 6.6224 (2.4); 6.6159 (1.6); 6.6067 (1.2); 6.3609 (4.8); 6.3546 (4.8); 5.7027 (2.8); 3.8785 (15.8); 3.8733 (16.0); 2.0454 (1.5); 1.7007 (3.8); 0.1048 (0.4); 0.0338 (8.9)

I-240: $^1$H-NMR (300.2 MHz, CDCl3):
δ=8.7845 (3.6); 8.7753 (3.6); 7.7776 (3.4); 7.7684 (3.3); 7.5902 (4.9); 7.5839 (4.7); 7.5719 (1.7); 7.5636 (1.7); 7.4915 (0.7); 7.4707 (5.4); 7.4470 (2.6); 7.4235 (0.7); 7.2986 (14.2); 7.1291 (0.8); 7.1196 (0.9); 7.1078 (0.9); 7.0983 (0.9); 7.0910 (0.9); 7.0815 (0.9); 7.0697 (0.8); 7.0603 (0.8); 6.8610 (1.0); 6.8546 (1.2); 6.8451 (1.8); 6.8383 (1.3); 6.8293 (0.9); 6.3916 (3.6); 6.3853 (3.6); 6.0237 (2.2); 5.3373 (1.3); 3.9097 (13.0); 3.9045 (13.0); 2.8269 (16.0); 1.6453 (3.9); 1.2916 (0.6); 0.1071 (1.1); 0.0475 (0.5); 0.0367 (14.2); 0.0258 (0.5)

I-241: $^1$H-NMR (300.2 MHz, d$_6$-DMSO):
δ=9.1996 (1.9); 8.8614 (1.8); 8.8519 (1.8); 8.1958 (0.9); 8.1696 (1.0); 8.1102 (1.8); 8.1008 (1.7); 7.9409 (0.9); 7.9173 (1.0); 7.6705 (0.7); 7.6447 (1.0); 7.6188 (0.6); 7.5820 (2.6); 7.5757 (2.6); 7.5138 (0.4); 7.5047 (0.5); 7.4918 (0.4); 7.4825 (0.4); 7.4727 (0.4); 7.4635 (0.4); 7.4505 (0.4); 7.4415 (0.4); 7.1235 (0.5); 7.1174 (0.7); 7.1075 (0.8); 7.1000 (0.7); 6.5381 (1.7); 6.5338 (1.7); 5.7803 (0.7); 3.8450 (6.8); 3.8413 (6.8); 3.3500 (16.0); 2.5344 (3.0); 2.5284 (6.2); 2.5223 (8.4); 2.5163 (6.0); 2.5103 (2.9); 0.0302 (0.4); 0.0193 (10.2); 0.0083 (0.4)

I-242: $^1$H-NMR (300.2 MHz, CDCl3):
δ=8.7584 (5.0); 8.7497 (5.0); 8.0528 (1.5); 7.7692 (3.2); 7.7638 (4.0); 7.7611 (3.8); 7.7559 (3.0); 7.6252 (6.9); 7.6190 (6.9); 7.4947 (0.9); 7.4813 (5.3); 7.4745 (5.6); 7.4671 (7.2); 7.4520 (2.8); 7.4371 (0.4); 7.4243 (0.7); 7.3088 (0.5); 7.2983 (5.3); 7.2943 (2.1); 7.2794 (2.4); 7.2640 (1.6); 7.2588 (1.9); 7.2503 (1.8); 7.2372 (1.4); 7.2289 (1.4); 7.1910 (1.3); 7.1817 (1.4); 7.1697 (1.4); 7.1603 (1.5); 7.1533 (1.4); 7.1440 (1.4); 7.1320 (1.3); 7.1227 (1.3); 6.9042 (1.6); 6.8979 (2.1); 6.8886 (2.7); 6.8815 (2.2); 6.8729 (1.4); 6.6397 (3.7); 6.3607 (6.2); 6.3545 (6.1); 5.3275 (0.6); 4.1835 (2.0); 4.1595 (6.2); 4.1355 (6.3); 4.1114 (2.1); 2.9917 (11.3); 2.9155 (10.0); 1.8893 (3.7); 1.4802 (7.7); 1.4562 (16.0); 1.4321 (7.4); 1.2843 (0.4); 0.1038 (1.0); 0.0280 (5.0)

I-243: $^1$H-NMR (300.2 MHz, CDCl3):
δ=7.7809 (2.8); 7.7770 (2.8); 7.6269 (3.6); 7.6207 (3.6); 7.4377 (0.5); 7.4196 (0.6); 7.4162 (0.5); 7.4060 (2.7); 7.3850 (2.4); 7.3732 (1.4); 7.3527 (1.3); 7.3428 (0.4); 7.3220 (0.5); 7.2987 (6.7); 7.0950 (0.9); 7.0854 (0.8); 7.0734 (0.8); 7.0641 (0.8); 7.0574 (0.8); 7.0480 (0.8); 7.0360 (0.7); 7.0267 (0.7); 6.8169 (0.9); 6.8105 (1.0); 6.8011 (1.4); 6.7941 (1.1); 6.7854 (0.8); 6.3607 (3.3); 6.3546 (3.2); 5.7297 (1.8); 5.3357 (1.7); 4.1900 (1.0); 4.1660 (3.2); 4.1420 (3.2); 4.1179 (1.1); 2.7951 (16.0); 2.6995 (0.4); 1.6835 (3.1); 1.4907 (4.0); 1.4667 (8.4); 1.4426 (3.9); 1.2890 (0.5); 0.0344 (7.0)

I-244: $^1$H-NMR (499.9 MHz, d$_6$-DMSO):
δ=8.6150 (15.8); 8.6095 (16.0); 7.9855 (15.8); 7.8290 (0.8); 7.8229 (5.6); 7.8138 (5.2); 7.8037 (6.4); 7.7944 (0.4); 7.6840 (0.4); 7.6781 (1.1); 7.6733 (6.1); 7.6689 (4.2); 7.6631 (6.1); 7.6600 (4.8); 7.6541 (7.2); 7.6478 (1.2); 7.6448 (0.6); 7.6033 (12.4); 7.4757 (5.9); 7.4650 (6.2); 7.4580 (7.2); 7.4473 (7.0); 7.4425 (1.1); 7.4371 (2.6); 7.4273 (11.9); 7.4234 (8.6); 7.4188 (10.3); 7.4173 (10.5); 7.4127 (8.0); 7.4085 (13.2); 7.3991 (2.0); 7.3943 (0.6); 7.3641 (12.0); 7.3588 (11.9); 7.3028 (3.6); 7.2967 (4.5); 7.2859 (5.5); 7.2796 (7.0); 7.2687 (3.0); 7.2625 (4.2); 7.2564 (8.6); 7.2504 (6.1); 7.2379 (8.7); 7.2318 (5.9); 6.9733 (11.9); 5.7568 (0.6); 3.6405 (0.6); 3.6239 (0.4); 3.4859 (82.0); 3.3321 (10.4); 2.5100 (4.9); 2.5065 (10.6); 2.5028 (14.7); 2.4992 (10.6); 2.4956 (4.9); 1.2323 (0.3); 1.1600 (0.6); −0.0002 (1.0)

I-245: $^1$H-NMR (300.2 MHz, CDCl3):
δ=8.8017 (4.7); 8.7932 (4.8); 7.7560 (3.4); 7.7507 (4.0); 7.7483 (4.0); 7.7435 (3.2); 7.6339 (6.6); 7.6277 (6.6); 7.4931 (0.6); 7.4742 (1.2); 7.4645 (7.3); 7.4503 (3.0); 7.4426 (4.8); 7.4195 (2.6); 7.4078 (0.4); 7.3888 (0.8); 7.2988 (12.8); 7.1639 (1.4); 7.1546 (1.5); 7.1427 (1.4); 7.1333 (1.5); 7.1267 (1.5); 7.1172 (1.5); 7.1053 (1.3); 7.0960 (1.4); 6.8840 (1.6); 6.8772 (2.2); 6.8684 (2.8); 6.8612 (2.2); 6.8529 (1.5); 6.3658 (6.2); 6.3597 (6.1); 6.1853 (2.7); 5.3357 (3.3); 4.1890 (2.1); 4.1651 (6.5); 4.1410 (6.6); 4.1168 (2.2); 1.6741 (4.9); 1.4933 (7.8); 1.4693 (16.0); 1.4452 (7.4); 1.2892 (1.0); 0.0454 (0.6); 0.0346 (13.2); 0.0238 (0.4)

I-246: $^1$H-NMR (300.2 MHz, CDCl3):
δ=8.9510 (10.9); 8.1751 (0.4); 8.1654 (2.3); 8.1643 (2.3); 8.1547 (1.9); 8.1524 (1.8); 8.1435 (2.5); 8.1327 (2.6); 8.1202 (0.7); 8.1049 (2.2); 8.0934 (2.5); 8.0849 (1.8); 8.0819 (1.7); 8.0728 (2.6); 8.0615 (0.5); 7.7035 (1.3); 7.6915 (7.2); 7.6804 (5.6); 7.6703 (5.0); 7.6590 (6.4); 7.6473 (1.0); 7.6159 (6.7); 7.6097 (6.8); 7.2987 (5.0); 7.1292 (1.3); 7.1197 (1.4); 7.1080 (1.3); 7.0985 (1.5); 7.0923 (1.4); 7.0828 (1.4); 7.0710 (1.3); 7.0616 (1.3); 6.9078 (1.5); 6.9011 (2.0); 6.8919 (2.7); 6.8848 (2.0); 6.8763 (1.4); 6.3566 (6.1); 6.3504 (6.1); 6.2743 (3.8); 5.3308 (0.6); 4.1841 (2.0); 4.1603 (6.0); 4.1362 (6.2); 4.1120 (2.0); 1.8013 (5.2); 1.4874 (7.7); 1.4634 (16.0); 1.4393 (7.4); 0.0338 (5.2)

I-247: $^1$H-NMR (499.9 MHz, d$_6$-DMSO):
δ=8.1798 (3.0); 7.6897 (0.7); 7.6801 (0.8); 7.6670 (2.4); 7.6513 (1.9); 7.6309 (0.8); 7.6129 (1.4); 7.5929 (1.2); 7.5748 (0.4); 7.4729 (0.4); 7.4691 (0.7); 7.4565 (4.0); 7.4534 (3.6); 7.4443 (1.8); 7.4419 (1.5); 7.4277 (0.4); 7.4252 (0.4); 7.3410 (1.2); 7.3362 (1.2); 7.3260 (4.6); 7.3225 (4.2); 7.3125 (0.9); 7.3080 (0.8); 6.3076 (3.9); 6.3039 (3.6); 3.9113 (0.4); 3.8975 (0.6); 3.8837 (0.9); 3.8694 (0.8); 3.8002 (0.8); 3.7859 (0.9); 3.7722 (0.6); 3.7583 (0.4); 3.2513 (15.9); 2.4399 (1.4); 2.4365 (2.6); 2.4329 (3.4); 2.4294 (2.4); 2.4260 (1.1); 2.3911 (16.0); 2.0046 (1.7); 1.1577 (4.2); 1.1433 (8.3); 1.1289 (3.8)

I-248: $^1$H-NMR (300.2 MHz, CDCl3):
δ=8.7331 (2.8); 8.7239 (2.8); 7.7604 (1.9); 7.6774 (2.8); 7.6683 (2.8); 7.5467 (0.8); 7.5371 (0.7); 7.5246 (1.3); 7.5146 (1.4); 7.4995 (0.3); 7.4553 (1.5); 7.4368 (6.2); 7.4261 (2.8); 7.4139 (2.3); 7.4095 (1.8); 7.3907 (0.4); 7.2986 (5.1); 7.2148 (1.9); 7.1867 (0.9); 7.1767 (1.0); 7.1604 (1.0); 7.1570 (0.8); 7.1504 (1.1); 7.1470 (1.0); 7.1307 (0.7); 7.1207 (0.8); 7.0756 (1.5); 7.0657 (1.3); 7.0472 (1.6); 7.0373 (1.2); 5.8287 (0.4); 5.4253 (0.4); 3.5669 (16.0); 2.8022 (13.2); 2.0421 (0.6); 1.2982 (0.4); 0.0345 (5.4)

I-249: ¹H-NMR (300.2 MHz, CDCl3):

δ=8.8449 (3.2); 8.2780 (0.4); 8.2558 (0.4); 7.9234 (3.8); 7.8995 (4.3); 7.8598 (3.5); 7.8327 (4.3); 7.7710 (1.2); 7.6638 (5.1); 7.5810 (2.8); 7.5554 (4.1); 7.5244 (3.1); 7.5072 (2.7); 7.4937 (3.1); 7.4775 (2.9); 7.2983 (32.1); 7.2291 (2.3); 7.2194 (3.2); 7.2031 (4.2); 7.1938 (3.7); 7.1736 (1.7); 7.1643 (1.8); 7.1088 (3.0); 7.0991 (2.6); 7.0805 (3.1); 7.0710 (2.4); 6.0002 (1.6); 3.9169 (2.4); 3.7892 (0.8); 3.7526 (0.4); 3.5584 (16.0); 3.0018 (0.9); 2.9249 (0.8); 1.3036 (0.4); 0.0451 (1.2); 0.0344 (31.4); 0.0252 (1.0); 0.0235 (1.2)

I-250: ¹H-NMR (300.2 MHz, d₆-DMSO):

δ=10.4987 (0.5); 8.6402 (1.0); 7.6757 (0.4); 7.6689 (0.3); 7.6483 (0.8); 7.6421 (0.9); 6.5152 (0.5); 6.5094 (0.5); 4.1418 (0.6); 4.1179 (0.6); 3.3546 (16.0); 2.5342 (1.2); 2.5283 (2.6); 2.5222 (3.6); 2.5162 (2.6); 2.5104 (1.2); 1.3960 (0.7); 1.3722 (1.7); 1.3482 (0.7); 0.0189 (4.7)

I-251: ¹H-NMR (300.2 MHz, d₆-DMSO):

δ=9.0937 (0.4); 7.6398 (0.5); 7.6337 (0.5); 6.5058 (0.4); 6.5006 (0.4); 4.1624 (0.4); 4.1385 (0.4); 3.3520 (16.0); 2.7834 (1.9); 2.5339 (1.8); 2.5281 (3.6); 2.5222 (4.8); 2.5162 (3.5); 2.5105 (1.7); 1.3658 (0.5); 1.3420 (1.2); 1.3181 (0.5); 0.0197 (6.3)

I-252: ¹H-NMR (300.2 MHz, CDCl3):

δ=8.6399 (2.7); 8.6349 (3.1); 7.5751 (3.3); 7.5693 (3.9); 7.5647 (2.4); 7.5050 (5.6); 7.5005 (6.8); 7.4948 (7.1); 7.4729 (1.5); 7.4685 (1.3); 7.4593 (0.7); 7.4452 (1.0); 7.4404 (1.0); 7.4249 (2.0); 7.4135 (2.2); 7.4080 (2.6); 7.4023 (2.7); 7.3973 (2.8); 7.3787 (2.6); 7.3557 (0.8); 7.3502 (0.8); 7.3442 (0.6); 7.2991 (4.3); 7.2947 (3.5); 7.2167 (1.2); 7.2123 (1.2); 7.2077 (1.3); 7.2033 (1.2); 7.1890 (1.5); 7.1848 (1.5); 7.1803 (1.6); 7.1611 (0.7); 7.1567 (0.6); 7.1522 (0.7); 7.0429 (1.7); 7.0385 (1.7); 7.0343 (1.6); 7.0135 (1.5); 7.0093 (1.4); 6.2096 (3.4); 6.2037 (3.9); 6.1991 (2.3); 4.0574 (7.4); 3.4277 (16.0); 3.4233 (12.7); 2.0446 (2.1); 2.0401 (1.6); 1.6882 (2.0); 1.2896 (1.3); 0.9108 (0.3); 0.0344 (4.2); 0.0300 (3.3)

I-253: ¹H-NMR (300.2 MHz, CDCl3):

δ=8.7211 (2.1); 8.7123 (2.1); 7.8141 (1.2); 7.8085 (1.4); 7.8004 (1.2); 7.6628 (2.6); 7.6565 (2.6); 7.4931 (2.9); 7.4844 (3.0); 7.4705 (1.4); 7.4658 (2.6); 7.3317 (1.1); 7.3172 (1.8); 7.2988 (12.2); 7.2881 (1.4); 7.2758 (0.6); 7.2669 (0.5); 7.2277 (1.4); 7.2205 (1.2); 6.4500 (2.8); 6.4437 (2.8); 5.8869 (1.5); 3.8297 (16.0); 1.6228 (6.2); 0.0467 (0.4); 0.0358 (12.0); 0.0248 (0.4)

I-254: ¹H-NMR (300.2 MHz, CDCl3):

δ=9.1997 (2.2); 9.1691 (2.3); 7.9140 (1.0); 7.9102 (1.1); 7.8865 (1.3); 7.8817 (2.0); 7.8767 (1.2); 7.8536 (1.2); 7.8522 (1.3); 7.8491 (1.3); 7.7511 (2.6); 7.7449 (2.6); 7.6723 (0.6); 7.6675 (0.6); 7.6488 (1.0); 7.6444 (1.2); 7.6215 (0.7); 7.6166 (0.7); 7.5533 (0.9); 7.5485 (0.9); 7.5297 (0.8); 7.5258 (1.3); 7.5215 (0.9); 7.5027 (0.6); 7.4978 (0.8); 7.4908 (0.7); 7.4832 (0.7); 7.4600 (0.6); 7.4527 (0.7); 7.2986 (1.5); 7.2321 (1.3); 7.2304 (1.3); 7.2230 (1.2); 7.0104 (1.4); 6.5433 (2.9); 6.5371 (2.8); 3.8037 (16.0); 2.4182 (11.9); 1.7886 (0.6); 0.1116 (0.3); 0.0341 (1.5)

I-255: ¹H-NMR (300.2 MHz, CDCl3):

δ=8.7510 (2.0); 8.7424 (2.0); 7.7977 (1.3); 7.7925 (1.5); 7.7901 (1.5); 7.7850 (1.2); 7.6361 (2.7); 7.6298 (2.6); 7.4732 (0.4); 7.4616 (3.3); 7.4528 (2.0); 7.4450 (1.6); 7.4424 (1.6); 7.4341 (1.2); 7.4230 (2.7); 7.4146 (1.1); 7.3179 (0.8); 7.3106 (0.9); 7.2983 (3.1); 7.2905 (0.5); 7.2809 (0.6); 7.2231 (1.5); 7.2146 (1.2); 6.4361 (2.9); 6.4298 (2.8); 5.9473 (1.7); 5.3332 (3.8); 3.8178 (16.0); 1.7032 (2.4); 0.0321 (3.1)

I-256: ¹H-NMR (300.2 MHz, CDCl3):

δ=8.9723 (4.2); 8.1521 (0.9); 8.1472 (0.7); 8.1406 (0.6); 8.1298 (0.8); 8.1274 (0.8); 8.1204 (1.1); 8.1193 (1.1); 8.1146 (1.0); 8.1073 (0.8); 8.1048 (0.8); 8.0932 (0.6); 8.0865 (0.8); 8.0824 (1.1); 7.7190 (0.5); 7.7025 (1.3); 7.6956 (1.2); 7.6919 (1.4); 7.6810 (2.6); 7.6664 (3.5); 7.6600 (3.6); 7.6425 (0.4); 7.2987 (4.1); 7.2751 (3.3); 7.2705 (4.3); 7.2387 (1.5); 7.2363 (1.6); 6.5083 (2.8); 6.5020 (2.8); 6.0667 (1.6); 5.3352 (0.7); 3.8666 (16.0); 1.6952 (4.4); 0.0356 (4.0)

I-257: ¹H-NMR (300.2 MHz, CDCl3):

δ=8.7472 (3.9); 8.1245 (1.1); 8.1215 (1.2); 8.0964 (1.3); 8.0940 (1.3); 8.0285 (1.1); 8.0256 (1.1); 8.0011 (1.2); 7.9976 (1.3); 7.7337 (0.6); 7.7291 (0.6); 7.7108 (1.0); 7.7062 (1.3); 7.7015 (0.7); 7.6832 (1.0); 7.6783 (1.0); 7.6716 (2.8); 7.6654 (2.8); 7.6424 (0.9); 7.6379 (1.0); 7.6192 (0.7); 7.6147 (1.2); 7.6103 (0.9); 7.5916 (0.5); 7.5873 (0.5); 7.2988 (0.9); 7.1483 (1.7); 7.1372 (1.0); 7.1072 (0.8); 7.0992 (0.6); 6.6471 (2.3); 6.6177 (2.0); 6.5269 (3.0); 6.5206 (2.9); 5.6447 (1.8); 5.3155 (0.9); 3.9035 (16.0); 2.5377 (12.5); 2.1505 (0.6); 1.6783 (0.9); 0.0307 (0.8)

I-258: ¹H-NMR (300.2 MHz, CDCl3):

δ=8.9365 (2.2); 8.9059 (2.3); 8.3029 (4.1); 7.7329 (2.6); 7.7267 (2.7); 7.6699 (0.4); 7.6537 (0.5); 7.6482 (0.4); 7.6386 (1.0); 7.6344 (1.2); 7.6222 (1.0); 7.6175 (1.8); 7.5942 (0.8); 7.5864 (1.1); 7.5620 (1.0); 7.5552 (0.4); 7.5303 (0.4); 7.4728 (0.7); 7.4658 (0.8); 7.4428 (0.7); 7.4346 (0.7); 7.2991 (10.8); 7.2319 (1.4); 7.2241 (1.3); 6.9954 (1.5); 6.5070 (2.8); 6.5007 (2.8); 5.3379 (0.6); 3.8192 (16.0); 1.6010 (11.6); 0.0485 (0.4); 0.0376 (11.2); 0.0270 (0.4)

I-259: ¹H-NMR (300.2 MHz, CDCl3):

δ=8.5949 (1.6); 8.5925 (1.2); 8.5868 (1.7); 8.4146 (2.4); 8.4064 (2.2); 8.1308 (2.4); 8.1228 (2.4); 7.6477 (2.6); 7.6414 (2.6); 7.2988 (2.6); 7.2442 (0.5); 7.2361 (0.6); 7.2145 (0.6); 7.2066 (0.8); 7.1700 (1.4); 7.1632 (1.1); 7.0127 (2.4); 6.9830 (1.8); 6.7602 (1.6); 6.7575 (1.6); 6.7522 (1.6); 6.7495 (1.5); 6.4684 (2.8); 6.4621 (2.8); 5.6184 (1.5); 3.8522 (16.0); 2.0749 (0.8); 1.7400 (3.0); 1.2907 (0.5); 0.0324 (2.6)

I-260: ¹H-NMR (499.9 MHz, CDCl3):

δ=8.4285 (2.9); 8.4236 (3.0); 8.0101 (2.2); 7.9936 (2.4); 7.9120 (2.1); 7.8954 (2.4); 7.6028 (1.1); 7.5888 (2.3); 7.5742 (1.8); 7.5499 (1.8); 7.5277 (4.3); 7.5247 (4.5); 7.4665 (0.4); 7.2598 (24.7); 7.1660 (0.7); 7.1457 (1.4); 7.1310 (1.4); 7.1258 (1.1); 7.1109 (0.8); 6.3035 (3.7); 6.3005 (3.8); 5.2984 (0.6); 5.1512 (2.3); 4.0232 (0.7); 4.0084 (1.8); 3.9931 (2.6); 3.9779 (2.0); 3.9639 (0.9); 2.5010 (0.4); 2.4753 (16.0); 2.0048 (0.6); 1.5957 (1.3); 1.4137 (0.7); 1.3684 (4.3); 1.3540 (8.9); 1.3395 (5.2); 1.2561 (2.7); 1.1069 (2.1); 0.8801 (0.5); 0.8664 (0.4); 0.0762 (0.5); −0.0002 (25.1)

I-261: ¹H-NMR (499.9 MHz, CDCl3):

δ=8.6974 (4.7); 8.0900 (1.6); 8.0739 (1.7); 7.9876 (1.6); 7.9721 (1.7); 7.7372 (3.3); 7.7335 (3.3); 7.7021 (0.9); 7.6997 (0.9); 7.6884 (1.2); 7.6858 (1.7); 7.6717 (1.0); 7.6692 (1.0); 7.6083 (1.1); 7.6060 (1.2); 7.5918 (1.7); 7.5777 (0.8); 7.5755 (0.8); 7.2597 (45.3); 7.0827 (0.6); 7.0643 (1.5); 7.0462 (1.5); 7.0277 (0.6); 6.5028 (3.4); 6.4992 (3.5); 6.3272 (0.8); 6.3237 (0.9); 6.3196 (0.9); 6.3161 (0.9); 6.3088 (0.8); 6.3053 (0.8); 6.3012 (0.8); 6.2979 (0.7); 5.3976 (2.1); 4.1514 (1.0); 4.1369 (3.0); 4.1224 (3.1); 4.1080 (1.1); 2.5539 (0.4); 2.5251 (0.5); 2.4912 (16.0); 1.5511 (7.0); 1.4694 (4.2); 1.4549 (8.5); 1.4404 (4.1); 1.3254 (0.4); 1.3215 (0.4); 1.3067 (0.3);

1.2554 (3.3); 1.1069 (0.3); 0.8938 (0.3); 0.8803 (0.6); 0.0761 (0.4); 0.0713 (0.5); 0.0063 (1.8); −0.0002 (46.4)

I-262: $^1$H-NMR (499.9 MHz, CDCl3):

δ=8.4983 (2.9); 8.4928 (2.8); 8.0225 (2.2); 8.0060 (2.3); 7.9228 (2.1); 7.9062 (2.3); 7.6120 (1.1); 7.5972 (2.1); 7.5824 (1.5); 7.5523 (1.7); 7.5365 (2.3); 7.5250 (4.2); 7.5223 (4.4); 7.2603 (8.4); 7.1804 (0.8); 7.1703 (0.8); 7.1614 (1.1); 7.1516 (1.1); 7.1406 (0.8); 7.1306 (0.7); 6.8045 (0.9); 6.7971 (0.9); 6.7874 (1.4); 6.7803 (1.4); 6.7702 (0.8); 6.7628 (0.7); 6.3064 (3.8); 6.3034 (3.6); 5.3542 (2.1); 4.0509 (0.4); 4.0377 (0.9); 4.0234 (2.2); 4.0087 (3.1); 3.9940 (2.2); 3.9798 (0.8); 3.9668 (0.3); 2.5008 (16.0); 2.0963 (0.3); 1.6788 (0.3); 1.6007 (0.5); 1.4145 (0.4); 1.3714 (4.7); 1.3569 (8.9); 1.3424 (4.6); 1.2557 (4.4); 1.1079 (0.6); 0.8927 (0.5); 0.8801 (0.7); 0.8669 (0.5); 0.8541 (0.5); 0.8440 (0.5); −0.0002 (8.4)

I-263: $^1$H-NMR (499.9 MHz, CDCl3):

δ=8.4533 (0.8); 8.0341 (0.5); 8.0183 (0.5); 7.9311 (0.7); 7.9157 (0.8); 7.6192 (0.4); 7.6053 (0.7); 7.5913 (0.5); 7.5611 (0.6); 7.5466 (0.7); 7.5320 (0.4); 7.2597 (27.4); 7.2423 (0.4); 7.2322 (0.4); 7.2238 (0.5); 7.2212 (0.5); 7.2137 (0.6); 7.2088 (1.5); 7.1996 (1.4); 7.1928 (0.4); 6.8244 (0.3); 6.8147 (0.5); 6.8076 (0.5); 5.4585 (0.6); 4.0542 (0.4); 3.9423 (0.4); 3.9284 (0.8); 3.9175 (0.9); 3.9141 (0.9); 3.9032 (0.4); 3.8893 (0.3); 2.5566 (6.0); 2.3658 (0.6); 2.3511 (0.8); 2.3361 (0.5); 2.3131 (0.3); 2.2982 (0.4); 2.0864 (0.4); 2.0680 (0.5); 2.0512 (0.6); 2.0359 (0.6); 2.0159 (0.9); 2.0037 (0.8); 1.9879 (0.7); 1.9721 (0.5); 1.7475 (0.4); 1.6792 (1.4); 1.6695 (0.7); 1.6535 (0.9); 1.6396 (1.1); 1.6254 (1.1); 1.6002 (2.7); 1.5755 (0.8); 1.5590 (0.8); 1.5438 (0.7); 1.5299 (0.7); 1.5141 (0.7); 1.5010 (0.6); 1.4698 (0.6); 1.4458 (0.7); 1.4394 (0.7); 1.4207 (1.0); 1.4057 (1.2); 1.3911 (1.0); 1.3766 (1.0); 1.3719 (1.0); 1.3572 (1.4); 1.3544 (1.4); 1.3402 (3.7); 1.3329 (2.5); 1.3257 (5.8); 1.3112 (4.1); 1.2842 (3.9); 1.2554 (16.0); 1.1590 (0.5); 1.1401 (0.5); 1.1056 (0.8); 1.0905 (0.5); 1.0187 (0.3); 1.0087 (0.3); 0.9956 (0.8); 0.9890 (0.4); 0.9822 (0.9); 0.9689 (0.3); 0.9539 (0.4); 0.9393 (0.4); 0.9211 (0.4); 0.9164 (0.4); 0.8938 (2.0); 0.8802 (4.0); 0.8664 (2.5); 0.8549 (1.7); 0.8441 (1.4); 0.8382 (1.1); 0.8314 (1.0); 0.0709 (0.4); 0.0063 (1.6); −0.0002 (28.1); −0.0067 (1.4)

I-264: $^1$H-NMR (499.9 MHz, d$_6$-DMSO):

δ=8.6083 (3.7); 8.5882 (3.6); 8.2395 (5.6); 7.6997 (1.0); 7.6883 (1.4); 7.6803 (3.0); 7.6698 (4.0); 7.6572 (1.6); 7.6505 (2.0); 7.6374 (1.8); 7.6183 (0.6); 7.4492 (1.2); 7.4389 (1.3); 7.4284 (1.7); 7.4200 (1.8); 7.4183 (1.9); 7.4096 (1.4); 7.3994 (1.2); 7.2248 (6.8); 7.2212 (7.2); 7.1179 (1.3); 7.1099 (1.4); 7.1001 (2.2); 7.0923 (2.3); 7.0822 (1.2); 7.0743 (1.1); 6.1693 (6.6); 6.1657 (6.9); 5.6880 (0.7); 3.8403 (0.3); 3.8285 (1.2); 3.8143 (3.0); 3.8044 (3.2); 3.8001 (3.3); 3.7902 (3.0); 3.7760 (1.2); 3.2643 (43.0); 2.4416 (3.2); 2.4381 (4.4); 2.4346 (3.5); 1.2710 (0.3); 1.1778 (0.6); 1.1622 (8.2); 1.1478 (16.0); 1.1334 (7.6)

I-265: $^1$H-NMR (499.9 MHz, d$_6$-DMSO):

δ=8.6442 (4.9); 8.6390 (5.0); 8.3213 (5.9); 7.6226 (1.0); 7.6112 (1.2); 7.6039 (2.1); 7.5942 (2.9); 7.5838 (1.5); 7.5803 (1.8); 7.5748 (2.0); 7.5655 (2.9); 7.5556 (1.7); 7.5454 (2.5); 7.5271 (0.6); 7.3994 (6.7); 7.3957 (6.9); 7.3215 (1.2); 7.3134 (1.3); 7.3035 (2.3); 7.2952 (5.2); 7.2777 (1.0); 6.2690 (6.9); 6.2653 (6.9); 3.9239 (0.3); 3.9125 (0.8); 3.8983 (1.7); 3.8843 (1.9); 3.8725 (1.9); 3.8584 (1.7); 3.8444 (0.8); 3.8314 (0.3); 3.3252 (293.0); 2.5144 (8.6); 2.5109 (18.8); 2.5073 (26.4); 2.5037 (19.9); 2.5003 (10.0); 2.0790 (0.6); 1.2426 (1.3); 1.2213 (7.6); 1.2069 (16.0); 1.1925 (7.5); 0.8591 (0.3)

I-266: $^1$H-NMR (499.9 MHz, d$_6$-DMSO):

δ=8.0571 (5.1); 8.0039 (0.9); 7.9946 (0.9); 7.9912 (1.0); 7.9835 (1.0); 7.9801 (1.1); 7.9762 (1.1); 7.9728 (1.0); 7.9650 (1.0); 7.9622 (0.9); 7.6780 (5.6); 7.6743 (5.6); 7.4151 (0.7); 7.3997 (1.7); 7.3965 (1.3); 7.3828 (2.9); 7.3693 (2.1); 7.3528 (1.0); 7.2220 (0.3); 7.2071 (0.4); 6.8849 (2.7); 6.8682 (2.5); 6.8010 (1.5); 6.7831 (2.6); 6.7663 (1.4); 6.5653 (0.6); 6.5069 (4.4); 6.4693 (5.7); 6.4657 (5.6); 4.0475 (0.6); 4.0338 (1.1); 4.0199 (2.3); 4.0132 (0.8); 4.0055 (2.2); 3.9987 (2.1); 3.9911 (0.8); 3.9843 (2.3); 3.9705 (1.1); 3.9567 (0.6); 3.4627 (0.5); 3.4203 (0.8); 3.3712 (784.2); 2.9420 (6.5); 2.7990 (0.7); 2.7828 (5.4); 2.6876 (0.4); 2.5743 (0.4); 2.5599 (25.4); 2.5563 (55.0); 2.5527 (76.6); 2.5490 (55.5); 2.5455 (26.3); 2.4136 (0.4); 1.3496 (0.7); 1.3354 (0.6); 1.3102 (1.1); 1.3015 (6.6); 1.2870 (16.0); 1.2726 (6.4); 1.2408 (0.4); 1.2270 (0.5); 1.2124 (0.4); 0.9171 (0.4); 0.9052 (0.7); 0.8913 (0.4); −0.0002 (0.5)

I-267: $^1$H-NMR (499.9 MHz, d$_6$-DMSO):

δ=11.8276 (0.4); 7.8360 (1.2); 7.8328 (1.3); 7.8250 (1.3); 7.8218 (1.4); 7.8176 (1.4); 7.8144 (1.4); 7.8066 (1.3); 7.8037 (1.3); 7.3311 (3.8); 7.3201 (8.5); 7.3164 (7.7); 7.3096 (1.5); 7.3017 (1.4); 7.2976 (1.4); 7.2913 (1.4); 7.2871 (1.4); 7.2793 (1.2); 7.2689 (1.2); 7.2568 (1.0); 7.2424 (1.1); 7.2374 (1.6); 7.2232 (1.6); 7.2182 (1.1); 7.2038 (0.8); 6.8799 (1.2); 6.8722 (1.3); 6.8622 (2.1); 6.8547 (2.2); 6.8444 (1.2); 6.8368 (1.1); 6.6421 (3.9); 6.1532 (7.6); 6.1495 (7.6); 5.6860 (0.7); 3.8305 (0.4); 3.8172 (1.0); 3.8031 (1.9); 3.7885 (2.3); 3.7735 (2.3); 3.7590 (2.0); 3.7448 (1.0); 3.7315 (0.4); 3.2545 (72.5); 2.4412 (4.5); 2.4377 (9.9); 2.4340 (13.9); 2.4304 (10.3); 2.4268 (5.0); 2.0054 (5.8); 1.1685 (0.7); 1.1072 (7.4); 1.0928 (16.0); 1.0784 (7.4)

I-268: $^1$H-NMR (499.9 MHz, d$_6$-DMSO):

δ=9.5134 (0.8); 8.7538 (2.8); 8.7343 (2.8); 8.5624 (0.9); 8.1643 (4.5); 8.1209 (0.3); 8.1069 (0.4); 7.8305 (0.9); 7.8169 (0.9); 7.8064 (1.0); 7.7981 (1.4); 7.7883 (1.3); 7.7421 (0.9); 7.7280 (1.0); 7.7222 (1.4); 7.7081 (1.5); 7.7033 (1.1); 7.6889 (0.8); 7.5739 (0.4); 7.5582 (0.4); 7.4289 (3.8); 7.4199 (3.9); 7.3824 (0.9); 7.3658 (2.0); 7.3523 (2.0); 7.3357 (1.0); 6.8848 (1.5); 6.8676 (2.7); 6.8498 (1.4); 6.7668 (1.6); 6.7633 (1.6); 6.7502 (1.5); 6.7471 (1.6); 4.8392 (0.6); 4.8318 (0.4); 4.8251 (0.5); 4.8176 (0.7); 3.8452 (1.5); 3.8308 (4.8); 3.8163 (4.8); 3.8019 (1.6); 3.2514 (504.6); 2.4405 (14.3); 2.4372 (31.7); 2.4337 (45.4); 2.4302 (35.4); 2.1113 (0.5); 1.4834 (0.7); 1.4671 (1.3); 1.4529 (2.7); 1.4389 (1.5); 1.4234 (0.3); 1.4077 (0.3); 1.2673 (1.0); 1.2305 (0.8); 1.1912 (2.1); 1.1767 (8.0); 1.1673 (9.7); 1.1625 (16.0); 1.1479 (6.5); 1.1050 (0.4); 1.0923 (0.4); 0.7988 (0.7); 0.7859 (1.5); 0.7715 (1.0); 0.7579 (0.5); 0.7434 (0.4)

I-269: $^1$H-NMR (499.9 MHz, d$_6$-DMSO):

δ=12.1381 (1.0); 7.9508 (1.2); 7.9476 (1.3); 7.9398 (1.4); 7.9364 (1.6); 7.9275 (7.2); 7.6471 (0.4); 7.6363 (6.5); 7.6327 (6.6); 7.4119 (0.9); 7.3933 (2.2); 7.3739 (2.5); 7.3617 (1.2); 7.3556 (2.1); 7.3425 (1.4); 7.3376 (1.0); 7.3232 (0.7); 6.7530 (1.3); 6.7477 (1.3); 6.7452 (1.3); 6.7346 (1.3); 6.7293 (1.2); 6.4588 (6.5); 6.4551 (6.5); 6.4309 (5.4); 5.7592 (5.0); 4.0339 (0.6); 4.0203 (1.2); 4.0063 (2.5); 3.9979 (1.0); 3.9919 (2.5); 3.9836 (2.4); 3.9776 (1.0); 3.9692 (2.5); 3.9553 (1.2); 3.9417 (0.6); 3.3268 (257.6); 2.8963 (1.3); 2.7371 (1.1); 2.5143 (7.2); 2.5108 (15.5); 2.5072 (21.6); 2.5036 (15.9); 2.5001 (7.8); 2.0786 (0.7); 1.2576 (7.0); 1.2432 (16.0); 1.2288 (7.1); 1.0615 (0.4); 0.8588 (0.3); 0.2816 (0.9)

I-270: $^1$H-NMR (499.9 MHz, d$_6$-DMSO):

δ=12.0867 (0.3); 7.9109 (3.4); 7.8847 (0.7); 7.8814 (0.7); 7.8738 (0.7); 7.8704 (0.8); 7.8664 (0.8); 7.8630 (0.8); 7.8553 (0.7); 7.8523 (0.7); 7.5058 (4.1); 7.5020 (4.1); 7.3098 (0.5); 7.2953 (0.6); 7.2904 (0.5); 7.2760 (0.9); 7.2713 (1.2); 7.2550 (1.7); 7.2411 (1.4); 7.2246 (0.7); 6.7388 (1.8); 6.7222 (1.7); 6.6829 (1.1); 6.6648 (1.9); 6.6478 (1.0); 6.4963 (3.1); 6.3680 (4.0); 6.3643 (4.0); 5.6859 (0.4); 3.6108 (16.0); 3.2531 (346.0); 2.4408 (8.5); 2.4373 (18.6); 2.4336 (26.1); 2.4300 (19.1); 2.4265 (9.3); 2.0051 (4.8); 1.1680 (1.1)

I-271: $^1$H-NMR (499.9 MHz, d$_6$-DMSO):

δ=8.5590 (3.3); 8.5538 (3.3); 8.3385 (4.0); 7.5397 (0.7); 7.5269 (1.0); 7.5193 (2.1); 7.5083 (2.1); 7.5038 (1.5); 7.4991 (1.5); 7.4894 (2.1); 7.4839 (1.5); 7.4795 (1.2); 7.4694 (1.8); 7.4509 (0.5); 7.2490 (4.5); 7.2452 (4.7); 7.2405 (1.2); 7.2320 (1.0); 7.2221 (1.5); 7.2136 (2.5); 7.2051 (2.8); 7.1962 (0.9); 7.0961 (1.0); 7.0471 (0.6); 7.0383 (0.4); 6.3948 (0.4); 6.1732 (4.4); 6.1694 (4.4); 5.6860 (4.8); 3.9304 (0.4); 3.9126 (0.4); 3.8962 (1.0); 3.8791 (1.0); 3.8484 (0.3); 3.8317 (0.3); 3.5688 (16.0); 3.2537 (134.8); 2.8224 (0.5); 2.6634 (0.4); 2.4407 (4.7); 2.4374 (9.8); 2.4339 (13.6); 2.4303 (10.2); 2.4269 (5.2); 2.0055 (6.1); 1.7535 (0.4); 1.1901 (0.3); 1.1664 (1.3); 1.1434 (0.4)

I-272: $^1$H-NMR (499.9 MHz, d$_6$-DMSO):

δ=7.9583 (0.6); 7.9036 (0.7); 7.9002 (0.8); 7.8924 (0.8); 7.8893 (0.8); 7.8852 (0.8); 7.8819 (0.8); 7.8741 (0.8); 7.8711 (0.7); 7.4081 (2.4); 7.3859 (0.7); 7.3754 (0.7); 7.3675 (0.8); 7.3636 (0.8); 7.3571 (0.8); 7.3531 (0.8); 7.3454 (0.7); 7.3349 (0.7); 7.3212 (0.6); 7.3067 (0.7); 7.3018 (1.0); 7.2904 (4.7); 7.2867 (5.2); 7.2684 (0.5); 6.9338 (0.8); 6.9260 (0.8); 6.9160 (1.3); 6.9083 (1.4); 6.8981 (0.7); 6.8904 (0.7); 6.8690 (2.2); 6.1812 (4.5); 6.1775 (4.4); 5.7596 (3.8); 3.5764 (16.0); 3.3875 (0.5); 3.3254 (223.4); 2.8964 (4.3); 2.7536 (0.5); 2.7373 (3.5); 2.5143 (9.0); 2.5108 (19.4); 2.5071 (27.0); 2.5035 (19.5); 2.5000 (9.2); 1.2645 (0.5); 1.2415 (1.8); 1.1798 (0.6); 0.8596 (0.4)

I-273: $^1$H-NMR (499.9 MHz, d$_6$-DMSO):

δ=8.7574 (2.0); 8.7376 (2.0); 8.0671 (3.0); 7.8340 (0.6); 7.8316 (0.6); 7.8236 (0.6); 7.8211 (0.6); 7.8152 (1.0); 7.8129 (1.0); 7.8048 (0.9); 7.8027 (0.9); 7.7739 (0.7); 7.7599 (0.7); 7.7540 (1.0); 7.7402 (0.7); 7.7351 (0.5); 7.7209 (0.4); 7.5136 (0.6); 7.4951 (1.3); 7.4755 (1.3); 7.4570 (0.6); 7.3897 (3.8); 7.3860 (3.8); 6.9400 (0.7); 6.9360 (0.7); 6.9320 (0.8); 6.9218 (0.7); 6.9179 (0.7); 6.9140 (0.7); 6.3787 (3.8); 6.3749 (3.8); 5.7589 (5.2); 3.6817 (16.0); 3.3273 (62.6); 2.5142 (2.0); 2.5108 (4.3); 2.5073 (6.0); 2.5037 (4.5); 2.5003 (2.2); 2.0789 (3.9); 1.2393 (0.4)

I-274: $^1$H-NMR (499.9 MHz, d$_6$-DMSO):

δ=12.0492 (0.5); 7.8803 (0.7); 7.8770 (0.7); 7.8693 (0.7); 7.8660 (0.7); 7.8620 (0.8); 7.8586 (0.7); 7.8508 (0.7); 7.8479 (0.7); 7.8245 (3.3); 7.5023 (3.8); 7.4985 (3.8); 7.3292 (0.5); 7.3106 (1.3); 7.3023 (0.6); 7.2905 (1.5); 7.2830 (0.9); 7.2714 (0.9); 7.2695 (0.9); 7.2638 (0.6); 7.2494 (0.4); 6.6623 (0.7); 6.6569 (0.7); 6.6544 (0.7); 6.6438 (0.7); 6.6387 (0.6); 6.4607 (3.0); 6.3937 (3.8); 6.3900 (3.6); 5.6860 (1.4); 3.6378 (16.0); 3.5775 (0.5); 3.2515 (272.3); 2.4408 (7.9); 2.4372 (17.0); 2.4336 (23.7); 2.4300 (17.3); 2.4265 (8.3); 2.0052 (1.7); 1.1680 (1.1)

I-275: $^1$H-NMR (499.9 MHz, d$_6$-DMSO):

δ=8.8154 (2.1); 8.7958 (2.1); 7.9852 (3.4); 7.8502 (0.6); 7.8473 (0.6); 7.8398 (0.7); 7.8369 (0.7); 7.8315 (0.9); 7.8286 (1.0); 7.8210 (0.9); 7.8185 (0.9); 7.7717 (0.7); 7.7576 (0.8); 7.7519 (1.0); 7.7380 (1.0); 7.7327 (0.6); 7.7185 (0.5); 7.4075 (0.8); 7.4016 (4.2); 7.3978 (4.4); 7.3943 (1.2); 7.3911 (1.6); 7.3777 (1.6); 7.3748 (1.0); 7.3612 (0.8); 6.9428 (1.1); 6.9423 (1.1); 6.9249 (2.0); 6.9079 (1.0); 6.8474 (1.2); 6.8451 (1.2); 6.8311 (1.2); 6.8287 (1.2); 6.3445 (4.2); 6.3407 (4.2); 5.7540 (0.6); 4.5067 (0.6); 4.4861 (0.6); 3.6684 (16.0); 3.6575 (0.6); 3.3438 (17.5); 2.5141 (0.4); 2.5106 (0.8); 2.5070 (1.1); 2.5034 (0.8); 2.5000 (0.4); 2.0784 (2.1)

I-277: $^1$H-NMR (400.2 MHz, d$_6$-DMSO):

δ=7.9560 (0.4); 7.7070 (3.6); 7.6972 (1.1); 7.6930 (1.0); 7.6829 (0.9); 7.6795 (0.9); 7.6166 (0.8); 7.5985 (0.9); 7.5910 (1.0); 7.5733 (0.9); 7.5682 (0.6); 7.5497 (0.5); 7.4738 (3.6); 7.4695 (3.5); 7.4624 (1.7); 7.4582 (1.8); 7.4442 (1.7); 7.4395 (2.5); 7.4353 (1.5); 7.4209 (1.7); 7.4173 (1.8); 7.4025 (0.8); 7.3988 (0.7); 7.3498 (2.1); 7.3462 (1.9); 7.3317 (1.5); 7.3276 (1.3); 7.2624 (1.7); 7.2590 (1.8); 7.2435 (1.4); 7.2410 (1.4); 6.2109 (3.5); 6.2065 (3.4); 4.0320 (5.6); 3.7411 (0.9); 3.7232 (2.7); 3.7051 (2.7); 3.6872 (0.9); 3.3445 (39.6); 2.8968 (2.8); 2.7383 (2.5); 2.5309 (0.6); 2.5174 (9.3); 2.5132 (18.5); 2.5087 (24.0); 2.5042 (17.2); 2.4999 (8.3); 2.4453 (16.0); 1.2357 (0.5); 1.1329 (3.5); 1.1150 (7.3); 1.0970 (3.4); −0.0002 (1.7)

I-279: $^1$H-NMR (400.2 MHz, d$_6$-DMSO):

δ=7.5484 (0.9); 7.3724 (1.2); 7.3681 (1.3); 7.3249 (0.4); 7.3173 (0.5); 7.2961 (0.3); 7.2733 (0.5); 7.2659 (0.4); 7.2506 (0.6); 7.2472 (0.7); 7.2441 (0.5); 7.2340 (0.6); 7.2249 (0.4); 6.7000 (0.9); 6.2153 (1.3); 6.2110 (1.3); 3.3360 (10.4); 2.8954 (2.1); 2.7367 (1.9); 2.5157 (2.8); 2.5114 (5.7); 2.5069 (7.4); 2.5024 (5.4); 2.4979 (2.6); 2.4551 (4.6); 1.4110 (16.0); −0.0002 (0.6)

I-281: $^1$H-NMR (400.2 MHz, d$_6$-DMSO):

δ=9.3762 (3.6); 8.3109 (0.3); 8.0111 (3.6); 8.0049 (3.7); 7.9550 (1.7); 7.9325 (3.6); 7.7500 (1.6); 7.7425 (1.6); 7.7247 (1.7); 7.7173 (1.6); 7.6370 (0.7); 7.6339 (0.7); 7.6195 (0.8); 7.6138 (1.1); 7.6107 (1.1); 7.5998 (1.0); 7.5536 (1.5); 7.5410 (2.0); 7.5309 (1.9); 7.5251 (1.2); 7.5181 (2.6); 7.5000 (1.0); 7.4765 (0.6); 7.2190 (1.0); 7.2116 (0.9); 7.1985 (1.3); 7.1911 (1.2); 7.1767 (0.9); 7.1692 (0.8); 7.0366 (3.9); 7.0303 (3.8); 5.3135 (0.8); 5.2910 (2.7); 5.2684 (2.8); 5.2456 (1.0); 3.6667 (0.5); 3.6153 (0.9); 3.3309 (29.3); 2.8953 (10.2); 2.7836 (16.0); 2.7368 (9.4); 2.5286 (0.6); 2.5111 (32.6); 2.5067 (43.4); 2.5023 (32.5); 1.2359 (1.2); −0.0002 (3.6)

I-282: $^1$H-NMR (400.2 MHz, d$_6$-DMSO):

δ=7.9538 (1.5); 7.8939 (2.7); 7.8609 (0.4); 7.8578 (0.4); 7.8416 (0.4); 7.8381 (0.4); 7.8339 (0.4); 7.8303 (0.4); 7.8219 (1.1); 7.8125 (2.8); 7.7921 (1.0); 7.7876 (0.9); 7.7822 (1.1); 7.7046 (0.4); 7.7005 (0.4); 7.6906 (0.5); 7.6867 (0.5); 7.6816 (0.6); 7.6775 (0.6); 7.6674 (0.6); 7.6643 (0.6); 7.6290 (2.1); 7.6149 (0.4); 7.6070 (0.7); 7.5891 (0.7); 7.5817 (0.6); 7.5635 (0.6); 7.5583 (0.4); 7.5400 (0.4); 7.4911 (0.4); 7.4877 (0.5); 7.4761 (1.6); 7.4728 (1.6); 7.4626 (2.1); 7.4584 (2.5); 7.4544 (1.1); 7.4427 (0.7); 7.4391 (1.1); 7.4288 (0.8); 7.4222 (1.3); 7.4186 (1.2); 7.4138 (0.9); 7.4101 (1.0); 7.4060 (0.8); 7.4015 (0.8); 7.3951 (0.3); 7.3912 (0.5); 7.3810 (1.3); 7.3409 (1.4); 7.3226 (1.6); 7.3018 (0.9); 7.0439 (0.5); 7.0406 (0.5); 7.0345 (0.5); 7.0315 (0.5); 7.0251 (0.5); 7.0222 (0.5); 7.0153 (0.6); 6.9225 (0.8); 6.9012 (1.3); 6.8790 (0.9); 6.7041 (3.2); 6.6831 (3.0); 6.6669 (1.4); 6.6462 (1.3); 3.7411 (9.2); 3.6657 (1.0); 3.6150 (16.0); 3.3348 (37.8); 3.0038 (0.3); 2.8943 (10.7); 2.7358 (9.3); 2.6862 (0.4); 2.5399 (9.8); 2.5280 (0.8); 2.5231 (1.0); 2.5144 (14.2); 2.5100 (28.8); 2.5055 (37.8); 2.5009 (27.2);

2.4965 (13.2); 1.6420 (1.2); 1.6106 (1.4); 1.5556 (1.4); 1.4232 (0.7); 1.2607 (0.7); 1.2393 (2.0); 1.0538 (2.3); 0.8537 (0.4); −0.0002 (3.2)

I-284: $^1$H-NMR (400.2 MHz, $d_6$-DMSO):

δ=8.3097 (0.5); 7.9527 (2.0); 7.5964 (0.6); 7.5819 (0.8); 7.5734 (1.2); 7.5601 (1.1); 7.5306 (0.9); 7.5129 (0.9); 7.5054 (1.1); 7.4869 (1.3); 7.4779 (3.5); 7.4646 (0.7); 7.3318 (0.7); 7.3217 (0.4); 7.3113 (1.6); 7.2947 (1.6); 7.2675 (3.1); 6.9194 (1.2); 6.8977 (2.0); 6.8755 (1.1); 6.8651 (2.2); 6.8447 (2.1); 6.7037 (0.5); 6.6825 (0.4); 3.6654 (1.7); 3.6519 (0.9); 3.6250 (0.5); 3.6141 (2.5); 3.5711 (0.6); 3.5084 (14.7); 3.3260 (54.4); 2.8935 (13.6); 2.7345 (12.0); 2.6732 (0.4); 2.6685 (0.4); 2.6636 (0.4); 2.5643 (16.0); 2.5265 (1.0); 2.5130 (24.9); 2.5086 (52.5); 2.5041 (70.6); 2.4996 (52.5); 2.4952 (26.8); 2.3354 (0.4); 2.3309 (0.5); 2.3265 (0.4); 2.0603 (14.8); 1.9676 (14.2); 1.8039 (0.4); 1.6406 (0.4); 1.5967 (0.5); 1.5552 (0.5); 1.2607 (0.4); 1.2393 (1.7); 1.1347 (0.3); 1.1128 (0.3); 1.0910 (0.4); 1.0558 (0.6); 0.8539 (0.4); −0.0002 (6.3)

I-285: $^1$H-NMR (400.2 MHz, $d_6$-DMSO):

δ=9.7021 (3.1); 8.3116 (0.5); 8.1499 (3.1); 8.0670 (3.6); 8.0608 (3.6); 7.9542 (1.2); 7.7147 (0.7); 7.7102 (0.8); 7.7010 (0.8); 7.6965 (0.8); 7.6915 (1.0); 7.6873 (1.0); 7.6776 (1.0); 7.6740 (0.9); 7.5943 (0.8); 7.5759 (0.9); 7.5686 (1.0); 7.5505 (0.9); 7.5456 (0.6); 7.5271 (0.5); 7.3491 (0.6); 7.3333 (0.7); 7.3285 (1.4); 7.3127 (1.5); 7.3081 (1.2); 7.2927 (1.1); 7.2660 (2.7); 7.2473 (1.3); 6.9024 (1.0); 6.9001 (1.0); 6.8824 (1.0); 6.8799 (1.0); 6.8740 (1.1); 6.8711 (1.0); 6.8542 (0.9); 6.8513 (0.9); 6.8282 (1.8); 6.8220 (1.9); 6.8151 (2.0); 6.8089 (1.8); 6.6841 (0.3); 5.3582 (0.8); 5.3357 (2.6); 5.3129 (2.8); 5.2901 (1.0); 3.6658 (0.6); 3.6201 (0.4); 3.6146 (1.6); 3.3329 (54.3); 2.8944 (9.1); 2.7479 (16.0); 2.7354 (7.8); 2.6744 (0.4); 2.5281 (1.1); 2.5234 (1.7); 2.5147 (22.8); 2.5102 (46.4); 2.5057 (60.5); 2.5011 (42.8); 2.4965 (20.2); 2.3325 (0.4); 1.9611 (0.6); 1.2378 (1.3); 0.8531 (0.3); −0.0002 (5.1)

I-287: $^1$H-NMR (400.2 MHz, $d_6$-DMSO):

δ=8.3098 (0.4); 7.6221 (0.6); 7.6182 (0.6); 7.6083 (0.7); 7.6042 (0.8); 7.5990 (1.1); 7.5947 (1.4); 7.5860 (3.3); 7.5311 (3.1); 7.5193 (0.9); 7.5117 (1.0); 7.4907 (1.2); 7.4735 (1.1); 7.4701 (2.0); 7.4533 (1.6); 7.4496 (1.0); 7.4327 (0.8); 7.0908 (4.2); 7.0103 (1.0); 6.9889 (1.8); 6.9663 (1.0); 6.9342 (2.0); 6.9138 (1.9); 3.6134 (12.6); 3.3314 (22.2); 2.8947 (0.8); 2.7362 (0.7); 2.5769 (16.0); 2.5281 (0.4); 2.5234 (0.7); 2.5148 (9.2); 2.5104 (18.8); 2.5059 (24.8); 2.5013 (17.8); 2.4968 (8.6); 1.8697 (13.9); 1.2385 (0.4); −0.0002 (2.1)

I-288: $^1$H-NMR (400.2 MHz, $d_6$-DMSO):

δ=7.9551 (0.4); 7.7190 (0.6); 7.7152 (0.6); 7.7053 (0.7); 7.7011 (0.8); 7.6962 (1.0); 7.6923 (1.0); 7.6823 (0.9); 7.6788 (0.9); 7.6515 (3.0); 7.6114 (0.7); 7.5934 (0.8); 7.5858 (0.9); 7.5679 (0.9); 7.5629 (0.6); 7.5446 (0.6); 7.5344 (4.4); 7.5299 (4.6); 7.4482 (0.7); 7.4446 (0.7); 7.4296 (1.8); 7.4259 (1.8); 7.4108 (1.4); 7.4070 (1.4); 7.3845 (1.0); 7.3812 (1.1); 7.3657 (1.8); 7.3626 (1.9); 7.3471 (0.9); 7.3440 (0.8); 7.2685 (2.1); 7.2652 (2.2); 7.2501 (2.2); 7.2463 (2.1); 7.2409 (3.3); 7.2368 (3.4); 7.2289 (5.6); 7.2238 (6.2); 7.2151 (0.7); 7.1303 (1.8); 7.1130 (1.6); 6.9086 (2.3); 6.8987 (2.4); 6.8900 (2.3); 6.8851 (2.0); 6.2319 (4.2); 6.2274 (4.2); 5.0511 (7.6); 3.8255 (6.2); 3.3380 (43.9); 2.8953 (3.1); 2.7374 (2.6); 2.5294 (0.5); 2.5248 (0.7); 2.5160 (10.3); 2.5117 (21.4); 2.5071 (28.2); 2.5026 (20.6); 2.4982 (10.2); 2.3695 (16.0); 1.2366 (0.6); −0.0002 (2.4)

I-289: $^1$H-NMR (400.2 MHz, $d_6$-DMSO):

δ=7.7678 (2.9); 7.7332 (0.6); 7.7297 (0.6); 7.7193 (0.7); 7.7154 (0.7); 7.7103 (0.9); 7.7067 (0.9); 7.6965 (0.9); 7.6933 (0.9); 7.6220 (0.7); 7.6038 (0.8); 7.5967 (0.9); 7.5787 (0.9); 7.5553 (0.4); 7.4716 (4.8); 7.4671 (4.8); 7.4538 (1.6); 7.4495 (1.8); 7.4357 (2.3); 7.4305 (2.6); 7.4158 (1.7); 7.4119 (1.8); 7.3973 (0.8); 7.3934 (0.6); 7.3326 (2.1); 7.3290 (1.7); 7.3147 (1.6); 7.3102 (1.3); 7.2154 (1.6); 7.2114 (1.8); 7.1964 (1.3); 7.1935 (1.4); 6.1586 (3.7); 6.1542 (3.7); 3.9970 (4.3); 3.5692 (2.9); 3.5508 (2.9); 3.3320 (17.7); 2.8971 (1.6); 2.7387 (1.4); 2.5307 (0.4); 2.5173 (8.8); 2.5129 (18.0); 2.5083 (23.5); 2.5038 (16.8); 2.4993 (8.1); 2.4361 (16.0); 2.0294 (0.4); 2.0122 (0.7); 1.9950 (0.9); 1.9778 (0.7); 1.9608 (0.4); 1.2356 (0.5); 0.6586 (13.6); 0.6418 (13.2); −0.0002 (2.1)

I-290: $^1$H-NMR (400.2 MHz, $d_6$-DMSO):

δ=7.9558 (0.4); 7.7222 (0.6); 7.7180 (0.7); 7.6990 (3.8); 7.6857 (1.0); 7.6816 (0.9); 7.6172 (0.8); 7.5991 (0.8); 7.5916 (0.9); 7.5735 (0.9); 7.5686 (0.6); 7.5502 (0.5); 7.4781 (0.5); 7.4739 (0.6); 7.4599 (1.5); 7.4555 (1.8); 7.4418 (1.8); 7.4370 (2.5); 7.4314 (4.9); 7.4268 (4.6); 7.4202 (1.9); 7.4162 (2.0); 7.4017 (0.9); 7.3978 (0.8); 7.3707 (2.2); 7.3671 (1.9); 7.3527 (1.4); 7.3483 (1.1); 7.2704 (1.6); 7.2668 (1.7); 7.2516 (1.3); 7.2489 (1.4); 6.2300 (4.2); 6.2254 (4.2); 4.0151 (6.3); 3.4502 (20.0); 3.3408 (35.3); 2.8966 (3.1); 2.7378 (2.6); 2.5308 (0.5); 2.5259 (0.7); 2.5173 (8.0); 2.5129 (16.0); 2.5084 (20.8); 2.5038 (15.0); 2.4994 (7.4); 2.4454 (16.0); 1.2359 (0.4); −0.0002 (1.7)

I-291: $^1$H-NMR (400.2 MHz, $d_6$-DMSO):

δ=7.9541 (1.3); 7.5142 (0.6); 7.5001 (0.8); 7.4912 (1.4); 7.4776 (1.2); 7.4549 (1.0); 7.4370 (1.0); 7.4296 (1.2); 7.4132 (1.3); 7.4071 (1.0); 7.3915 (1.8); 7.3851 (2.0); 7.3783 (2.8); 7.3720 (2.0); 7.3649 (3.7); 7.3419 (0.5); 7.3300 (4.9); 7.3254 (7.0); 7.2514 (1.7); 7.2450 (1.6); 7.2288 (1.6); 7.2230 (1.5); 7.1237 (3.9); 6.3344 (5.2); 6.3299 (5.2); 4.3974 (0.4); 4.3810 (1.1); 4.3647 (1.6); 4.3484 (1.2); 4.3320 (0.4); 3.3302 (23.0); 2.8946 (8.6); 2.7361 (7.7); 2.5589 (19.2); 2.5283 (0.6); 2.5237 (0.8); 2.5148 (11.3); 2.5105 (23.6); 2.5060 (31.4); 2.5014 (23.0); 2.4971 (11.4); 1.2378 (0.9); 1.2120 (16.0); 1.1956 (15.8); −0.0002 (3.0)

I-292: $^1$H-NMR (400.2 MHz, $d_6$-DMSO):

δ=7.6901 (3.9); 7.6764 (0.9); 7.6710 (1.2); 7.6677 (1.2); 7.6569 (1.1); 7.6543 (1.0); 7.6199 (0.9); 7.6021 (1.0); 7.5945 (1.1); 7.5767 (1.0); 7.5717 (0.6); 7.5533 (0.5); 7.4905 (0.6); 7.4873 (0.7); 7.4720 (1.8); 7.4686 (1.8); 7.4535 (1.5); 7.4498 (1.5); 7.4349 (1.2); 7.4319 (1.3); 7.4163 (1.8); 7.4136 (2.0); 7.3979 (0.8); 7.3951 (0.8); 7.3162 (2.1); 7.2978 (1.7); 7.2733 (4.8); 7.2588 (2.2); 7.2558 (2.1); 7.2404 (1.8); 7.2372 (1.7); 4.0151 (1.2); 3.9753 (2.8); 3.9246 (2.8); 3.8847 (1.2); 3.3357 (27.1); 3.3275 (13.9); 2.8965 (1.8); 2.7380 (1.7); 2.5125 (18.4); 2.5082 (23.6); 2.5039 (17.1); 2.3837 (16.0); 1.6862 (15.6); 1.2355 (0.5); −0.0002 (1.6)

I-293: $^1$H-NMR (400.2 MHz, $d_6$-DMSO):

δ=7.8220 (1.4); 7.8111 (1.3); 7.8045 (1.1); 7.7917 (1.6); 7.7872 (1.5); 7.7820 (1.8); 7.7363 (3.2); 7.7273 (0.9); 7.7226 (0.8); 7.7127 (0.7); 7.7085 (0.8); 7.7036 (1.0); 7.6995 (1.0); 7.6898 (1.0); 7.6862 (1.0); 7.6294 (0.4); 7.6181 (0.9); 7.6001 (0.9); 7.5922 (1.1); 7.5745 (1.0); 7.5697 (0.7); 7.5512 (0.5); 7.4874 (0.5); 7.4758 (2.4); 7.4695 (5.6); 7.4647 (6.4); 7.4590 (4.4); 7.4471 (0.6); 7.4415 (1.8); 7.4370 (2.6); 7.4336 (1.8); 7.4189 (2.3); 7.4153 (2.3); 7.4057 (0.5); 7.4009 (1.0); 7.3970 (0.8); 7.3798 (2.0); 7.3558 (0.4); 7.3374 (3.0); 7.3334 (2.1); 7.3186 (1.6); 7.3143 (1.4); 7.2441 (1.7); 7.2406 (1.8);

7.2225 (1.5); 6.9189 (0.4); 6.7048 (0.5); 6.6838 (0.4); 6.5775 (0.3); 6.1867 (4.3); 6.1823 (4.2); 4.0157 (5.1); 3.6834 (2.4); 3.6655 (4.0); 3.6477 (2.4); 3.6165 (2.3); 3.3383 (40.0); 2.8961 (0.4); 2.7379 (0.3); 2.5301 (0.5); 2.5125 (21.7); 2.5081 (28.5); 2.5036 (20.8); 2.4996 (10.4); 2.4404 (16.0); 1.6035 (0.4); 1.5853 (1.2); 1.5669 (2.4); 1.5488 (2.4); 1.5308 (1.3); 1.2356 (0.6); 1.0557 (0.4); 0.6586 (4.0); 0.6403 (8.1); 0.6217 (3.7); −0.0002 (2.0)

I-294: $^1$H-NMR (400.2 MHz, $d_6$-DMSO):

δ=7.9551 (0.9); 7.7160 (3.0); 7.7055 (0.7); 7.7015 (0.6); 7.6915 (0.7); 7.6872 (0.7); 7.6823 (1.0); 7.6783 (1.0); 7.6684 (0.9); 7.6647 (0.9); 7.6232 (0.8); 7.6054 (0.9); 7.5974 (1.1); 7.5864 (8.4); 7.5748 (0.6); 7.5565 (0.5); 7.5467 (0.6); 7.5430 (0.7); 7.5279 (1.8); 7.5243 (1.7); 7.5089 (1.3); 7.5053 (1.4); 7.4785 (1.1); 7.4757 (1.3); 7.4598 (1.8); 7.4568 (2.1); 7.4414 (0.9); 7.4382 (0.9); 7.3573 (2.1); 7.3541 (2.1); 7.3394 (3.2); 7.3354 (1.7); 7.3245 (2.0); 7.3040 (0.3); 6.7067 (1.1); 6.6856 (1.1); 4.1063 (1.1); 4.0660 (2.5); 4.0112 (2.5); 3.9706 (1.1); 3.6163 (5.9); 3.3656 (20.2); 3.3441 (60.7); 2.8955 (6.3); 2.7368 (5.5); 2.5298 (0.5); 2.5165 (10.6); 2.5121 (21.1); 2.5076 (27.3); 2.5030 (19.4); 2.4986 (9.3); 2.4283 (16.0); 1.6404 (0.4); 1.6129 (0.5); 1.5561 (0.5); 1.2368 (0.6); 1.0536 (0.8); −0.0002 (1.9)

I-295: $^1$H-NMR (400.2 MHz, $d_6$-DMSO):

δ=7.9551 (1.5); 7.5591 (0.7); 7.5450 (0.8); 7.5391 (1.1); 7.5361 (1.2); 7.5228 (1.1); 7.5039 (3.6); 7.4822 (0.9); 7.4640 (0.9); 7.4566 (1.1); 7.4516 (0.9); 7.4430 (1.2); 7.4302 (1.6); 7.4223 (1.7); 7.4153 (0.7); 7.4088 (1.0); 7.4012 (1.1); 7.3720 (1.7); 7.3646 (1.4); 7.3484 (2.8); 7.3425 (1.7); 7.3340 (2.0); 7.3251 (1.2); 7.3118 (1.1); 7.2245 (3.5); 6.8100 (5.6); 4.4710 (0.4); 4.4547 (1.0); 4.4383 (1.4); 4.4220 (1.0); 4.4056 (0.4); 3.3302 (22.2); 2.8955 (9.4); 2.7371 (8.6); 2.5658 (16.0); 2.5290 (0.5); 2.5112 (23.0); 2.5068 (30.2); 2.5024 (22.2); 1.2334 (13.3); 1.2171 (12.8); −0.0002 (2.4)

I-296: $^1$H-NMR (400.2 MHz, $d_6$-DMSO):

δ=7.9539 (1.2); 7.4958 (0.5); 7.4790 (0.6); 7.4704 (1.3); 7.4560 (1.3); 7.4518 (1.3); 7.4374 (3.4); 7.4265 (1.2); 7.4107 (2.4); 7.3829 (5.4); 7.3784 (3.1); 7.3655 (4.3); 7.1846 (4.4); 7.1800 (4.6); 7.1023 (3.1); 6.2984 (4.6); 6.2937 (4.6); 3.6550 (0.4); 3.6454 (0.8); 3.6370 (0.9); 3.6275 (1.4); 3.6178 (1.1); 3.6092 (0.8); 3.5994 (0.4); 3.3298 (17.6); 2.8940 (8.5); 2.7355 (7.4); 2.6936 (0.3); 2.5882 (16.0); 2.5277 (0.5); 2.5228 (0.8); 2.5142 (10.2); 2.5098 (21.0); 2.5053 (27.6); 2.5007 (19.8); 2.4962 (9.6); 1.2381 (0.6); 0.9130 (0.5); 0.9082 (0.4); 0.9027 (0.7); 0.8915 (2.3); 0.8831 (2.9); 0.8736 (1.2); 0.8608 (0.5); 0.8492 (0.6); 0.8428 (1.2); 0.8333 (2.0); 0.8258 (1.8); 0.8145 (2.1); 0.8098 (1.6); 0.8019 (0.5); 0.7945 (0.5); −0.0002 (2.7)

I-297: $^1$H-NMR (400.2 MHz, $d_6$-DMSO):

δ=7.9536 (0.5); 7.5895 (3.0); 7.4777 (0.5); 7.4618 (0.6); 7.4539 (2.1); 7.4474 (1.5); 7.4393 (1.6); 7.4318 (1.1); 7.4231 (1.2); 7.4063 (1.1); 7.3821 (1.7); 7.3752 (1.8); 7.3704 (2.3); 7.3623 (1.8); 7.3563 (3.4); 7.2527 (1.3); 7.2466 (1.2); 7.2295 (1.3); 7.2248 (1.2); 7.0271 (3.3); 6.9709 (4.3); 3.6252 (14.4); 3.3300 (21.4); 2.8940 (3.5); 2.7355 (3.1); 2.5974 (16.0); 2.5276 (0.5); 2.5141 (10.6); 2.5098 (21.5); 2.5054 (28.1); 2.5008 (20.2); 2.4964 (9.8); 1.8780 (14.5); 1.2381 (0.6); −0.0002 (2.6)

I-298: $^1$H-NMR (400.2 MHz, $d_6$-DMSO):

δ=7.5112 (0.6); 7.4947 (0.7); 7.4864 (1.3); 7.4688 (3.5); 7.4602 (1.2); 7.4418 (0.8); 7.4342 (1.0); 7.4167 (0.9); 7.3932 (0.4); 7.3437 (1.3); 7.3371 (3.0); 7.3194 (3.2); 7.3012 (1.4); 7.2963 (1.1); 7.2753 (1.2); 7.1259 (3.1); 6.0451 (5.4); 3.5841 (16.0); 3.3430 (47.2); 2.8948 (1.9); 2.7364 (1.6); 2.5934 (14.8); 2.5288 (0.5); 2.5152 (9.4); 2.5110 (18.8); 2.5065 (24.4); 2.5021 (17.7); 1.9119 (14.2); 1.2375 (0.6); −0.0002 (1.5)

I-299: $^1$H-NMR (400.2 MHz, $d_6$-DMSO):

δ=8.3088 (1.2); 7.9537 (0.9); 7.8220 (1.4); 7.8110 (1.3); 7.8044 (1.1); 7.7917 (1.6); 7.7870 (1.4); 7.7820 (1.8); 7.6664 (2.1); 7.6627 (2.3); 7.6527 (2.4); 7.6488 (2.7); 7.6434 (3.4); 7.6395 (3.6); 7.6264 (14.3); 7.6046 (0.4); 7.5894 (0.4); 7.5587 (2.6); 7.5405 (3.0); 7.5333 (3.4); 7.5152 (3.2); 7.5103 (2.2); 7.4917 (1.8); 7.4758 (1.8); 7.4703 (1.4); 7.4626 (3.1); 7.4582 (3.2); 7.4478 (15.2); 7.4434 (14.2); 7.4296 (3.5); 7.4259 (5.6); 7.4187 (1.3); 7.4093 (5.6); 7.4055 (3.9); 7.3887 (2.9); 7.3802 (2.1); 7.3552 (0.5); 7.3398 (2.1); 7.2348 (9.5); 7.1783 (2.2); 7.1715 (2.9); 7.1674 (1.9); 7.1565 (11.2); 7.1380 (16.0); 7.1314 (6.7); 7.1199 (4.0); 7.1049 (0.8); 7.1009 (1.0); 7.0465 (0.3); 7.0146 (0.4); 6.9349 (13.6); 6.9155 (13.1); 6.8986 (8.2); 6.8933 (4.6); 6.8782 (7.7); 6.5771 (0.4); 6.5450 (0.4); 6.4556 (14.1); 6.4511 (13.9); 5.2501 (3.4); 5.2113 (7.5); 5.1301 (7.7); 5.0913 (3.6); 3.6151 (0.3); 3.3383 (178.2); 2.8937 (5.8); 2.7361 (5.2); 2.6791 (0.4); 2.6746 (0.6); 2.6700 (0.5); 2.6627 (0.3); 2.6116 (0.6); 2.5442 (0.6); 2.5276 (2.1); 2.5142 (41.3); 2.5100 (83.0); 2.5053 (140.5); 2.3426 (0.4); 2.3370 (0.5); 2.3323 (0.6); 2.3280 (0.4); 1.2604 (0.4); 1.2381 (2.1); 0.8534 (0.5); −0.0002 (7.5)

I-300: $^1$H-NMR (400.2 MHz, $d_6$-DMSO):

δ=7.9540 (2.2); 7.6569 (3.4); 7.5326 (0.6); 7.5187 (0.8); 7.5105 (1.2); 7.4962 (1.2); 7.4687 (1.0); 7.4506 (1.9); 7.4435 (3.2); 7.4214 (4.2); 7.4138 (1.5); 7.4004 (1.6); 7.3930 (1.0); 7.3734 (1.6); 7.3602 (1.6); 7.3522 (1.0); 7.3395 (0.8); 7.3226 (0.8); 7.3017 (0.4); 7.1793 (3.7); 6.7103 (5.1); 6.6835 (1.4); 3.7524 (14.5); 3.6162 (8.4); 3.3323 (36.0); 2.8949 (13.4); 2.7364 (12.5); 2.5904 (16.0); 2.5102 (28.2); 2.5059 (36.8); 2.5016 (27.8); 1.6403 (0.8); 1.6096 (0.9); 1.5567 (0.8); 1.4236 (0.4); 1.2397 (1.1); 1.0550 (1.5); −0.0002 (2.5)

I-301: $^1$H-NMR (400.2 MHz, $d_6$-DMSO):

δ=7.9545 (0.7); 7.5065 (0.6); 7.4896 (0.7); 7.4809 (1.3); 7.4690 (1.2); 7.4542 (1.0); 7.4366 (0.9); 7.4288 (1.2); 7.4130 (4.1); 7.3831 (1.6); 7.3757 (3.0); 7.3583 (3.5); 7.2668 (1.4); 7.2613 (1.3); 7.2471 (4.7); 7.2426 (5.4); 7.1141 (3.3); 6.3098 (4.1); 6.3053 (4.1); 3.9116 (2.3); 3.8939 (3.5); 3.8756 (2.4); 3.6156 (0.9); 3.3318 (23.8); 2.8945 (5.0); 2.7362 (4.4); 2.5719 (16.0); 2.5280 (0.6); 2.5146 (10.6); 2.5103 (20.8); 2.5059 (26.8); 2.5014 (19.3); 2.4971 (9.5); 1.6445 (0.4); 1.6259 (1.4); 1.6075 (2.5); 1.5895 (2.5); 1.5713 (1.4); 1.5529 (0.4); 1.2379 (0.6); 0.6723 (4.5); 0.6539 (9.3); 0.6353 (4.2); −0.0002 (2.2)

I-302: $^1$H-NMR (400.2 MHz, $d_6$-DMSO):

δ=8.3095 (1.7); 8.0574 (1.4); 7.9544 (2.3); 7.6819 (6.3); 7.6655 (1.3); 7.6614 (1.3); 7.6518 (1.3); 7.6476 (1.5); 7.6426 (1.9); 7.6384 (1.9); 7.6287 (1.8); 7.6250 (1.8); 7.5513 (1.7); 7.5331 (1.8); 7.5256 (2.1); 7.5075 (1.9); 7.5026 (1.3); 7.4843 (1.0); 7.4621 (1.5); 7.4453 (1.9); 7.4415 (3.2); 7.4248 (3.3); 7.4210 (2.1); 7.4042 (1.7); 7.3545 (5.5); 7.3362 (0.4); 7.3170 (8.4); 7.3124 (8.3); 7.2984 (0.7); 6.9923 (2.2); 6.9712 (4.3); 6.9502 (2.2); 6.9201 (0.5); 6.8969 (0.5); 6.8876 (4.6); 6.8672 (4.2); 6.7087 (0.4); 6.7029 (0.4); 6.3535 (9.0); 6.3489 (8.9); 3.4977 (0.6); 3.4884 (1.2); 3.4794 (1.7); 3.4705 (2.4); 3.4610 (1.8); 3.4522 (1.2); 3.4423 (0.6); 3.3343 (55.7); 3.3107 (0.7); 3.0039 (0.3); 2.8955 (16.0); 2.7371 (13.9); 2.6874 (5.4); 2.6756 (0.4); 2.5515 (32.6); 2.5291 (1.0); 2.5243 (1.5); 2.5156 (19.1); 2.5113 (38.9); 2.5067 (51.1); 2.5022 (36.6); 2.4977 (17.6); 1.2374 (1.0); 0.9670 (0.5); 0.9517 (1.2); 0.9442 (1.4); 0.9353 (1.9); 0.9266 (1.5);

0.9200 (1.6); 0.9095 (1.9); 0.9023 (1.5); 0.8964 (1.9); 0.8862 (1.4); 0.8690 (1.2); 0.8610 (0.8); 0.8480 (1.6); 0.8367 (1.8); 0.8324 (2.0); 0.8222 (2.1); 0.8145 (2.8); 0.8047 (2.5); 0.7971 (1.7); 0.7880 (1.2); 0.7805 (1.1); 0.7656 (0.3); 0.7603 (0.3); −0.0002 (4.3)

I-303: $^1$H-NMR (400.2 MHz, d$_6$-DMSO):

δ=8.3071 (0.4); 7.9539 (1.3); 7.8214 (0.4); 7.8110 (0.4); 7.7888 (3.1); 7.6526 (3.5); 7.6365 (1.0); 7.6322 (1.0); 7.6226 (1.0); 7.6192 (0.9); 7.5526 (0.7); 7.5345 (0.8); 7.5270 (1.0); 7.5159 (1.0); 7.5096 (1.0); 7.5036 (0.7); 7.4990 (1.2); 7.4954 (1.7); 7.4857 (0.7); 7.4784 (1.9); 7.4751 (1.5); 7.4629 (0.8); 7.4583 (1.5); 7.4138 (0.3); 7.3796 (0.5); 7.3393 (0.6); 7.0214 (1.1); 6.9989 (1.8); 6.9773 (1.0); 6.9126 (2.2); 6.8922 (2.0); 6.7648 (5.0); 6.7041 (0.3); 3.7271 (12.0); 3.6166 (1.6); 3.3372 (58.8); 2.8956 (8.7); 2.7372 (7.7); 2.5765 (16.0); 2.5289 (0.6); 2.5154 (12.2); 2.5111 (25.2); 2.5066 (33.5); 2.5020 (24.5); 2.4977 (12.1); 1.2393 (0.8); −0.0002 (2.4)

I-304: $^1$H-NMR (400.2 MHz, d$_6$-DMSO):

δ=8.3095 (0.4); 8.0569 (0.6); 7.9547 (2.0); 7.8449 (2.8); 7.6154 (1.1); 7.6121 (1.0); 7.6019 (0.8); 7.5981 (0.7); 7.5925 (1.0); 7.5889 (1.1); 7.5787 (1.0); 7.5753 (1.0); 7.5437 (1.1); 7.5290 (4.1); 7.5228 (2.7); 7.5059 (2.4); 7.5025 (1.9); 7.4854 (0.9); 7.4800 (0.5); 7.3781 (9.1); 7.0316 (1.1); 7.0101 (1.9); 6.9874 (1.0); 6.9488 (2.2); 6.9282 (2.1); 3.6735 (16.0); 3.6161 (0.5); 3.3376 (43.5); 2.9998 (2.2); 2.8955 (14.2); 2.7370 (12.3); 2.6868 (2.3); 2.6178 (16.0); 2.5294 (0.5); 2.5247 (0.8); 2.5160 (11.2); 2.5116 (22.9); 2.5070 (30.1); 2.5025 (21.5); 2.4980 (10.3); 1.2365 (0.6); −0.0002 (2.3)

I-305: $^1$H-NMR (400.2 MHz, d$_6$-DMSO):

δ=7.9549 (2.2); 7.8200 (6.1); 7.7319 (1.2); 7.7278 (1.3); 7.7181 (1.3); 7.7141 (1.5); 7.7089 (1.8); 7.7049 (1.8); 7.6951 (1.7); 7.6915 (1.7); 7.6000 (1.4); 7.5818 (1.5); 7.5745 (1.8); 7.5563 (1.8); 7.5511 (1.4); 7.5360 (6.6); 7.4658 (1.4); 7.4487 (1.8); 7.4451 (3.0); 7.4282 (3.1); 7.4247 (2.0); 7.4075 (1.6); 7.1765 (2.3); 6.9754 (2.3); 6.9543 (3.9); 6.9316 (2.0); 6.8708 (10.0); 6.7291 (4.4); 6.7084 (4.3); 4.3667 (0.6); 4.3609 (0.7); 4.3503 (1.0); 4.3446 (1.8); 4.3281 (2.5); 4.3117 (1.8); 4.2954 (0.7); 3.3320 (58.3); 2.8943 (16.0); 2.7350 (13.6); 2.6869 (0.5); 2.6747 (0.4); 2.5455 (31.5); 2.5282 (1.3); 2.5234 (1.8); 2.5147 (24.3); 2.5103 (50.5); 2.5057 (66.7); 2.5011 (48.2); 2.4966 (23.5); 2.3325 (0.4); 1.3991 (7.7); 1.3827 (7.7); 1.3510 (13.4); 1.3345 (13.3); 1.3166 (12.9); 1.3003 (12.7); 1.2603 (0.4); 1.2389 (1.6); 0.8530 (0.4); −0.0002 (6.7)

I-306: $^1$H-NMR (400.2 MHz, d$_6$-DMSO):

δ=8.3075 (0.7); 7.9545 (1.6); 7.8214 (1.2); 7.8107 (1.2); 7.8040 (1.0); 7.7912 (1.3); 7.7867 (1.2); 7.7814 (1.5); 7.7721 (0.4); 7.7076 (8.0); 7.6790 (2.1); 7.6692 (1.8); 7.6653 (2.0); 7.6601 (2.4); 7.6560 (2.4); 7.6461 (2.2); 7.6428 (2.2); 7.6292 (0.6); 7.6226 (0.4); 7.6140 (0.4); 7.5891 (0.5); 7.5577 (1.7); 7.5392 (2.2); 7.5325 (2.4); 7.5144 (2.2); 7.4904 (1.4); 7.4759 (1.6); 7.4705 (1.3); 7.4625 (2.6); 7.4579 (3.9); 7.4364 (3.8); 7.4196 (4.4); 7.4036 (10.0); 7.3991 (11.4); 7.3793 (1.7); 7.3552 (0.5); 7.3390 (1.9); 7.3224 (0.6); 7.3016 (0.4); 7.2694 (6.2); 7.0464 (0.4); 7.0146 (0.5); 6.9715 (2.7); 6.9496 (4.4); 6.9278 (2.4); 6.9179 (0.6); 6.8902 (5.3); 6.8767 (0.9); 6.8698 (5.0); 6.7038 (0.8); 6.6828 (0.8); 6.5765 (0.4); 6.5445 (0.4); 6.3875 (9.8); 6.3829 (9.7); 3.7296 (8.7); 3.7112 (9.5); 3.6635 (0.4); 3.6165 (4.3); 3.3400 (137.0); 2.8959 (11.9); 2.7375 (10.3); 2.6963 (0.3); 2.6806 (0.4); 2.6761 (0.5); 2.6717 (0.4); 2.6418 (1.8); 2.5739 (0.4); 2.5381 (41.6); 2.5248 (2.9); 2.5161 (29.7); 2.5117 (60.2); 2.5072 (78.9); 2.5026 (56.5); 2.4981 (27.1); 2.3386 (0.3); 2.3340 (0.4); 2.3294 (0.3); 2.0437 (0.9); 2.0266 (1.7); 2.0096 (2.2); 1.9925 (1.7); 1.9755 (0.9); 1.6464 (0.3); 1.6113 (0.4); 1.5560 (0.4); 1.2610 (0.4); 1.2382 (1.8); 1.0556 (0.6); 0.8537 (0.5); 0.7282 (16.0); 0.7114 (15.6); 0.6607 (15.1); 0.6441 (14.6); −0.0002 (6.4)

I-307: $^1$H-NMR (400.2 MHz, d$_6$-DMSO):

δ=7.7822 (0.9); 7.7100 (0.3); 7.4382 (1.3); 7.4341 (1.3); 7.4144 (0.4); 7.3956 (0.4); 7.3714 (1.6); 7.3559 (0.4); 7.3530 (0.4); 7.1294 (0.6); 7.1106 (0.5); 6.0269 (1.2); 6.0227 (1.2); 4.2673 (0.3); 4.0539 (0.4); 4.0133 (0.6); 3.8809 (0.6); 3.8402 (0.4); 3.3382 (9.1); 2.8959 (1.6); 2.7371 (1.4); 2.5314 (1.0); 2.5167 (3.1); 2.5124 (6.4); 2.5079 (8.4); 2.5034 (6.2); 2.4991 (3.1); 2.4710 (4.7); 1.4614 (3.3); 1.3220 (16.0); −0.0002 (0.6)

I-308: $^1$H-NMR (400.2 MHz, d$_6$-DMSO):

δ=12.3881 (0.3); 7.9557 (1.9); 7.7647 (0.3); 7.7278 (4.9); 7.5492 (3.3); 7.5164 (0.4); 7.4929 (1.4); 7.4811 (3.7); 7.4654 (2.6); 7.4472 (0.9); 7.4331 (1.5); 7.4257 (1.5); 7.4119 (1.1); 7.4043 (1.0); 7.3233 (1.6); 7.3161 (1.4); 7.3011 (1.7); 7.2938 (1.3); 7.2747 (1.6); 7.2618 (1.7); 7.2524 (1.4); 7.2393 (4.6); 6.7048 (0.6); 6.6838 (0.6); 3.7250 (15.4); 3.6162 (3.3); 3.3348 (26.0); 2.9837 (2.9); 2.8952 (12.2); 2.7373 (10.8); 2.7363 (10.4); 2.5694 (16.0); 2.5293 (0.6); 2.5115 (24.4); 2.5070 (30.9); 2.5026 (22.7); 1.6120 (0.3); 1.5576 (0.3); 1.2362 (0.9); 1.0553 (0.6); −0.0002 (2.6)

I-309: $^1$H-NMR (499.9 MHz, d$_6$-DMSO):

δ=8.5992 (2.2); 8.5792 (2.2); 8.3224 (3.2); 7.6980 (0.5); 7.6870 (0.7); 7.6785 (2.0); 7.6692 (1.9); 7.6588 (1.0); 7.6520 (1.1); 7.6391 (1.0); 7.6333 (0.3); 7.6199 (0.4); 7.4529 (0.7); 7.4426 (0.8); 7.4341 (1.0); 7.4320 (1.0); 7.4239 (1.0); 7.4218 (1.0); 7.4133 (0.8); 7.4031 (0.8); 7.1398 (4.5); 7.1360 (4.4); 7.1181 (0.8); 7.1100 (1.0); 7.1002 (1.4); 7.0922 (1.4); 7.0822 (0.8); 7.0742 (0.7); 6.1395 (4.3); 6.1357 (4.2); 3.6319 (0.7); 3.5912 (0.6); 3.5447 (16.0); 3.5030 (0.8); 3.2534 (305.8); 2.4409 (7.5); 2.4375 (15.2); 2.4339 (20.4); 2.4303 (14.5); 2.4268 (6.7); 2.0054 (6.6); 1.1670 (0.5); −0.0002 (0.4)

I-310: $^1$H-NMR (499.9 MHz, d$_6$-DMSO):

δ=8.4836 (7.5); 8.1880 (1.4); 7.9561 (0.4); 7.7448 (4.0); 7.7289 (4.4); 7.6104 (1.2); 7.6003 (1.4); 7.5921 (2.7); 7.5820 (2.7); 7.5739 (1.7); 7.5638 (1.5); 7.5034 (1.2); 7.5015 (1.2); 7.4873 (3.5); 7.4736 (3.7); 7.4717 (3.8); 7.4564 (7.2); 7.4436 (4.2); 7.4390 (3.8); 7.4275 (1.4); 7.4192 (1.3); 7.3982 (2.5); 7.3953 (2.4); 7.3819 (3.9); 7.3688 (1.9); 7.3657 (1.8); 7.3308 (8.1); 7.3273 (8.3); 6.2173 (5.5); 5.7559 (3.7); 3.9599 (0.4); 3.9463 (0.6); 3.9327 (1.4); 3.9192 (1.8); 3.9050 (1.6); 3.8910 (0.7); 3.8164 (0.7); 3.8024 (1.6); 3.7882 (1.8); 3.7746 (1.5); 3.7612 (1.1); 3.7475 (0.6); 3.5117 (0.6); 3.4678 (0.6); 3.4538 (0.6); 3.4399 (0.6); 3.4259 (0.5); 3.4007 (0.5); 2.8891 (2.3); 2.7329 (2.1); 2.5255 (32.7); 2.5118 (3.0); 2.5083 (5.0); 2.5048 (6.5); 2.5013 (5.0); 2.0751 (1.7); 1.2305 (0.4); 1.1661 (7.8); 1.1517 (16.0); 1.1373 (7.9)

I-311: $^1$H-NMR (499.9 MHz, d$_6$-DMSO):

δ=8.6795 (4.6); 8.0882 (16.0); 7.8882 (0.9); 7.6845 (2.9); 7.6685 (3.1); 7.5925 (0.9); 7.5822 (1.1); 7.5741 (1.9); 7.5640 (2.0); 7.5557 (1.2); 7.5456 (1.1); 7.4451 (1.2); 7.4301 (2.8); 7.4158 (2.5); 7.4008 (1.3); 7.3842 (5.6); 7.3749 (2.6); 7.3697 (3.0); 7.3573 (1.1); 7.3453 (1.9); 7.3295 (2.8); 7.3156 (1.4); 7.2720 (3.9); 7.2631 (3.8); 5.6860 (0.5); 3.9793 (0.3); 3.9659 (0.3); 3.9519 (0.3); 3.9374 (0.4); 3.9217 (0.4); 3.8561 (0.8); 3.8418 (1.6); 3.8277 (2.2); 3.8142 (2.6); 3.7999 (2.3); 3.7856 (1.0); 3.7417 (0.9); 3.7274 (2.0); 3.7131 (2.3); 3.6995 (1.9); 3.6855 (1.5); 3.6713 (0.8); 3.6577 (0.5); 3.6430 (0.5); 3.6290 (0.4); 3.5849 (0.4); 3.5710 (0.4); 3.5568 (0.4); 3.5425 (0.4); 3.4444 (0.3); 3.4005 (0.3); 3.3866 (0.4);

3.3726 (0.4); 2.8825 (0.4); 2.8229 (6.2); 2.6662 (5.3); 2.5113 (19.8); 2.4773 (0.8); 2.4618 (1.1); 2.4459 (2.3); 2.4424 (4.8); 2.4388 (6.7); 2.4353 (5.1); 2.4319 (2.7); 1.1628 (0.4); 1.0853 (0.7); 1.0745 (6.9); 1.0601 (14.3); 1.0458 (7.1)

I-312: $^1$H-NMR (499.9 MHz, $d_6$-DMSO):

δ=8.5860 (5.7); 7.6637 (3.3); 7.6482 (3.6); 7.6046 (1.3); 7.5882 (2.8); 7.5751 (2.8); 7.5719 (1.9); 7.5587 (1.6); 7.4916 (4.5); 7.4756 (3.3); 7.4575 (1.0); 7.4550 (1.0); 7.4410 (2.8); 7.4384 (2.8); 7.4254 (6.7); 7.4209 (5.0); 7.4081 (1.5); 7.4045 (0.8); 7.3436 (2.2); 7.3396 (2.0); 7.3308 (2.0); 7.3271 (3.2); 7.3232 (1.8); 7.3147 (1.6); 7.3106 (1.4); 7.2271 (2.2); 7.2100 (8.6); 7.2011 (5.7); 7.1920 (1.7); 3.8568 (0.5); 3.8425 (1.3); 3.8285 (1.9); 3.8149 (2.7); 3.8006 (2.4); 3.7861 (0.9); 3.7789 (0.9); 3.7645 (2.3); 3.7502 (2.6); 3.7366 (1.7); 3.7226 (1.1); 3.7081 (0.4); 3.2457 (80.8); 2.5689 (0.4); 2.5655 (0.3); 2.4832 (30.3); 2.4410 (13.1); 2.4376 (24.5); 2.4341 (31.9); 2.4305 (22.5); 2.4272 (10.4); 1.1682 (0.6); 1.1268 (8.0); 1.1124 (16.0); 1.0980 (7.4)

I-313: $^1$H-NMR (499.9 MHz, $d_6$-DMSO):

δ=8.5680 (6.9); 7.7928 (3.4); 7.7779 (3.6); 7.5592 (1.4); 7.5445 (3.3); 7.5414 (3.0); 7.5304 (3.6); 7.5222 (2.8); 7.5121 (2.7); 7.5037 (1.6); 7.4937 (1.5); 7.4610 (4.5); 7.4461 (3.0); 7.4443 (3.0); 7.4209 (2.5); 7.4182 (2.3); 7.4069 (2.5); 7.4045 (4.0); 7.4020 (2.5); 7.3910 (3.2); 7.3880 (2.3); 7.3832 (1.8); 7.3736 (2.5); 7.3653 (2.6); 7.3554 (1.2); 7.3471 (1.1); 7.2416 (8.3); 7.2379 (8.2); 6.1535 (5.0); 6.1503 (4.9); 5.6128 (8.6); 5.5192 (8.8); 3.8728 (0.6); 3.8594 (1.0); 3.8458 (1.3); 3.8316 (1.1); 3.8174 (0.4); 3.7511 (0.4); 3.7374 (1.1); 3.7232 (1.2); 3.7095 (0.9); 3.6961 (0.6); 3.2479 (65.9); 2.4402 (5.3); 2.4366 (11.1); 2.4330 (15.2); 2.4294 (10.8); 2.4258 (4.9); 2.0050 (0.4); 1.1659 (0.4); 1.0989 (7.8); 1.0845 (16.0); 1.0701 (7.5)

I-314: $^1$H-NMR (499.9 MHz, $d_6$-DMSO):

δ=8.7696 (6.6); 8.7208 (0.4); 7.6633 (1.2); 7.6528 (1.2); 7.6447 (2.3); 7.6346 (2.4); 7.6262 (1.3); 7.6160 (1.3); 7.5407 (2.5); 7.5352 (2.8); 7.5216 (2.8); 7.5155 (3.4); 7.5018 (2.1); 7.4952 (3.4); 7.4835 (3.3); 7.4703 (1.3); 7.4626 (1.4); 7.4528 (2.1); 7.4447 (2.4); 7.4388 (2.2); 7.4336 (2.7); 7.4215 (3.5); 7.4157 (2.6); 7.4039 (1.5); 7.3982 (1.2); 7.3341 (5.1); 7.3251 (5.2); 7.3033 (0.3); 6.5215 (0.4); 3.9108 (0.5); 3.8972 (1.5); 3.8836 (2.0); 3.8695 (2.5); 3.8553 (2.2); 3.8413 (0.8); 3.7962 (0.8); 3.7824 (1.8); 3.7674 (2.2); 3.7535 (1.7); 3.7398 (1.2); 3.7244 (0.5); 3.7187 (0.3); 3.3642 (1.4); 3.3156 (1318.0); 2.6913 (0.3); 2.6753 (0.4); 2.6432 (2.0); 2.6395 (2.7); 2.6357 (2.0); 2.5796 (30.0); 2.5117 (154.8); 2.5082 (306.8); 2.5046 (407.8); 2.5010 (284.2); 2.4975 (126.7); 2.3693 (1.5); 2.3658 (2.1); 2.3620 (1.6); 2.0769 (0.3); 1.5566 (0.5); 1.4268 (0.4); 1.3874 (0.4); 1.3387 (0.9); 1.3029 (1.0); 1.2628 (2.3); 1.2404 (7.9); 1.1604 (0.8); 1.1407 (8.0); 1.1263 (16.0); 1.1119 (7.5); 0.9724 (0.3); 0.9430 (0.4); 0.9269 (0.3); 0.8947 (0.3); 0.8802 (0.8); 0.8670 (1.2); 0.8579 (1.9); 0.8436 (1.1); 0.6939 (0.3); 0.0718 (0.7)

I-315: $^1$H-NMR (499.9 MHz, $d_6$-DMSO):

δ=8.3628 (7.4); 7.9861 (2.9); 7.9839 (3.0); 7.9693 (3.2); 7.9675 (3.2); 7.9169 (3.1); 7.9159 (3.1); 7.9008 (3.9); 7.8989 (4.0); 7.8928 (6.2); 7.6616 (1.4); 7.6593 (1.5); 7.6478 (2.5); 7.6454 (3.1); 7.6314 (2.3); 7.6288 (2.1); 7.6125 (2.4); 7.6096 (2.5); 7.5984 (1.8); 7.5959 (3.1); 7.5934 (2.4); 7.5822 (1.4); 7.5795 (1.3); 7.5695 (1.1); 7.5592 (1.2); 7.5502 (1.9); 7.5399 (1.8); 7.5309 (1.3); 7.5206 (1.2); 7.3017 (8.0); 7.2980 (7.5); 7.2849 (2.1); 7.2768 (2.1); 7.2669 (1.1); 7.2588 (1.0); 6.2669 (7.2); 6.2632 (7.1); 3.9490 (0.3); 3.9380 (0.7); 3.9239 (1.4); 3.9093 (1.6); 3.8913 (1.6); 3.8767 (1.5); 3.8626 (0.8); 3.8507 (0.4); 3.3226 (13.0); 2.5118 (3.0); 2.5083 (6.2); 2.5047 (8.6); 2.5011 (6.2); 2.4977 (3.0); 2.0770 (2.7); 1.2346 (8.0); 1.2202 (16.0); 1.2058 (7.5)

I-316: $^1$H-NMR (499.9 MHz, $d_6$-DMSO):

δ=8.4386 (10.9); 8.0653 (0.4); 8.0491 (0.3); 8.0270 (5.7); 8.0156 (0.6); 8.0089 (2.4); 8.0037 (1.7); 7.9998 (2.3); 7.9934 (1.8); 7.9894 (2.7); 7.9843 (0.6); 7.9257 (0.3); 7.9189 (0.5); 7.9135 (2.4); 7.9098 (1.7); 7.9033 (2.3); 7.8996 (1.7); 7.8944 (2.6); 7.8879 (0.5); 7.6410 (0.5); 7.6367 (1.0); 7.6272 (3.6); 7.6252 (4.0); 7.6231 (3.3); 7.6165 (4.5); 7.6104 (3.0); 7.6079 (3.6); 7.6061 (3.5); 7.5967 (0.9); 7.5921 (0.4); 7.5220 (1.0); 7.5034 (2.3); 7.4923 (0.6); 7.4808 (13.2); 7.4652 (1.1); 6.8446 (1.2); 6.8415 (1.4); 6.8362 (1.3); 6.8333 (1.4); 6.8261 (1.2); 6.8233 (1.3); 6.8177 (1.2); 6.8154 (1.2); 3.9673 (1.4); 3.9547 (4.0); 3.9524 (4.1); 3.9402 (4.0); 3.9380 (4.2); 3.9239 (1.6); 3.9100 (0.3); 3.2465 (91.1); 2.4414 (17.2); 2.4379 (36.2); 2.4343 (49.8); 2.4307 (36.1); 2.4272 (17.0); 2.0066 (0.7); 1.3979 (0.4); 1.3788 (0.3); 1.2292 (0.4); 1.2145 (0.8); 1.2059 (7.6); 1.1915 (16.0); 1.1771 (7.9); 1.1685 (2.7); 0.7954 (0.3); 0.7869 (0.6)

I-317: $^1$H-NMR (499.9 MHz, $d_6$-DMSO):

δ=8.2562 (7.8); 7.8936 (3.0); 7.8918 (3.1); 7.8834 (1.3); 7.8769 (3.6); 7.8752 (3.4); 7.8682 (1.3); 7.8627 (1.8); 7.8473 (1.8); 7.8419 (1.1); 7.8281 (3.6); 7.8130 (3.6); 7.7910 (6.1); 7.5808 (1.5); 7.5785 (1.6); 7.5669 (2.5); 7.5645 (3.2); 7.5504 (2.2); 7.5480 (2.0); 7.5166 (2.4); 7.5139 (2.4); 7.5026 (1.9); 7.5000 (3.3); 7.4974 (2.3); 7.4862 (1.5); 7.4835 (1.4); 7.2684 (6.8); 7.2647 (6.8); 6.2496 (7.0); 6.2459 (6.8); 3.9053 (0.6); 3.8918 (1.0); 3.8776 (1.1); 3.8633 (0.8); 3.8487 (1.1); 3.8343 (1.1); 3.8211 (0.7); 3.2836 (0.4); 3.2459 (238.4); 2.8225 (0.4); 2.6632 (0.3); 2.4402 (15.4); 2.4367 (31.3); 2.4332 (42.3); 2.4296 (30.0); 2.4261 (13.9); 2.0053 (0.4); 1.1665 (8.5); 1.1521 (16.0); 1.1377 (7.5); 1.1255 (0.4)

I-318: $^1$H-NMR (499.9 MHz, $d_6$-DMSO):

δ=8.3318 (7.8); 8.1758 (6.0); 8.1089 (5.7); 7.9442 (2.9); 7.9414 (3.1); 7.9273 (3.0); 7.9254 (3.0); 7.8856 (0.6); 7.8685 (3.0); 7.8527 (3.4); 7.8503 (3.0); 7.6104 (1.5); 7.6077 (1.6); 7.5965 (3.0); 7.5942 (3.1); 7.5806 (2.9); 7.5774 (2.7); 7.5735 (2.8); 7.5701 (2.8); 7.5570 (2.8); 7.5544 (2.4); 7.5433 (1.4); 7.5403 (1.4); 7.5373 (1.3); 7.5268 (1.3); 7.5179 (1.8); 7.5072 (1.6); 7.4981 (1.2); 7.4878 (1.1); 7.2217 (5.6); 7.2126 (5.4); 7.2048 (1.4); 7.1968 (1.3); 7.1870 (2.1); 7.1791 (2.0); 7.1690 (1.0); 7.1611 (0.9); 3.8671 (0.5); 3.8530 (1.1); 3.8391 (1.8); 3.8253 (3.1); 3.8182 (1.2); 3.8110 (3.0); 3.8039 (2.7); 3.7966 (1.2); 3.7896 (2.7); 3.7758 (1.4); 3.7619 (0.8); 3.4405 (0.5); 3.2454 (58.5); 2.8237 (2.8); 2.6643 (2.5); 2.5723 (1.2); 2.5689 (1.4); 2.5653 (1.2); 2.4411 (58.1); 2.4376 (111.4); 2.4340 (147.0); 2.4304 (104.1); 2.4271 (48.1); 2.2986 (0.6); 2.2950 (0.9); 2.2914 (0.6); 2.0063 (0.3); 1.2314 (0.4); 1.1916 (0.8); 1.1687 (3.5); 1.1467 (8.1); 1.1323 (16.0); 1.1179 (7.5); 0.7994 (0.4); 0.7870 (0.6); 0.7738 (0.4); −0.0002 (0.4)

I-319: $^1$H-NMR (499.9 MHz, $d_6$-DMSO):

δ=8.7604 (4.3); 8.6571 (1.2); 7.7444 (0.8); 7.7340 (0.9); 7.7259 (4.0); 7.7199 (1.2); 7.7088 (3.6); 7.6880 (0.8); 7.6620 (0.4); 7.6589 (0.7); 7.6459 (0.7); 7.6425 (0.5); 7.6293 (0.4); 7.5621 (1.0); 7.5463 (0.7); 7.5179 (0.9); 7.5152 (1.0); 7.5119 (0.8); 7.5090 (0.8); 7.5043 (1.2); 7.5014 (2.5); 7.4987 (2.6); 7.4963 (2.0); 7.4913 (1.5); 7.4879 (2.3); 7.4851 (2.2); 7.4783 (1.4); 7.4752 (1.4); 7.4644 (3.5); 7.4613 (4.0); 7.4478 (2.4); 7.4143 (0.5); 7.4103 (0.5); 7.4029 (1.8); 7.3998 (1.8); 7.3938 (0.6); 7.3894 (1.6); 7.3865 (2.8); 7.3837 (1.7); 7.3732 (1.2);

7.3700 (1.2); 7.2985 (4.8); 7.2895 (4.4); 7.2805 (2.1); 7.2715 (1.4); 7.2629 (0.4); 3.9397 (1.0); 3.9257 (1.4); 3.9122 (2.1); 3.8979 (2.0); 3.8848 (0.9); 3.8713 (0.6); 3.8628 (0.5); 3.8485 (1.7); 3.8343 (2.2); 3.8206 (1.8); 3.8066 (1.3); 3.7926 (0.5); 3.3173 (199.3); 2.5560 (24.8); 2.5121 (12.9); 2.5085 (27.4); 2.5049 (37.8); 2.5012 (27.0); 2.4977 (12.4); 2.0769 (12.0); 1.2390 (0.8); 1.1979 (7.6); 1.1834 (16.0); 1.1690 (7.5)

I-320: $^1$H-NMR (300.2 MHz, CDCl3):

δ=7.4904 (2.3); 7.4621 (0.5); 7.4563 (0.6); 7.4478 (0.6); 7.4447 (0.6); 7.4385 (0.6); 7.4310 (2.1); 7.4247 (2.6); 7.4125 (3.4); 7.4008 (3.0); 7.3935 (2.2); 7.3762 (0.6); 7.3692 (1.1); 7.3596 (1.0); 7.3346 (2.0); 7.3280 (1.3); 7.3214 (0.7); 7.3133 (1.0); 7.3040 (1.1); 7.2985 (3.4); 7.2080 (1.2); 7.1985 (1.0); 7.1897 (0.6); 7.1834 (0.6); 7.1780 (0.9); 5.8998 (4.4); 5.3319 (0.6); 4.0423 (6.0); 3.5103 (16.0); 2.5972 (13.9); 2.2808 (13.8); 0.0335 (3.7)

I-321: $^1$H-NMR (400.2 MHz, d$_6$-DMSO):

δ=7.6794 (3.8); 7.6737 (3.9); 7.6404 (4.3); 7.6361 (3.1); 7.6214 (2.6); 7.6172 (2.2); 7.6090 (1.0); 7.5695 (0.8); 7.5517 (0.8); 7.5439 (1.0); 7.5260 (0.9); 7.5210 (0.6); 7.5030 (0.5); 7.3794 (0.6); 7.3758 (0.7); 7.3610 (1.6); 7.3573 (1.8); 7.3427 (1.4); 7.3384 (1.4); 7.3348 (1.4); 7.3302 (1.4); 7.3159 (1.7); 7.3120 (1.8); 7.2975 (0.8); 7.2936 (0.7); 7.1735 (1.8); 7.1708 (1.7); 7.1552 (1.5); 7.1518 (1.4); 6.4392 (4.0); 6.4335 (4.1); 5.9567 (0.4); 5.9426 (0.9); 5.9289 (0.6); 5.9169 (1.0); 5.9000 (1.1); 5.8862 (0.6); 5.8743 (1.0); 5.8602 (0.5); 5.0725 (1.6); 5.0689 (1.7); 5.0469 (1.5); 5.0433 (1.6); 4.9554 (0.6); 4.9517 (1.6); 4.9478 (1.6); 4.9127 (0.5); 4.9090 (1.4); 4.9051 (1.5); 4.9014 (0.6); 4.7121 (2.2); 4.7085 (3.7); 4.7050 (2.3); 4.6981 (2.2); 4.6944 (3.6); 4.6910 (2.1); 4.4562 (6.1); 3.3319 (18.1); 2.5787 (16.0); 2.5283 (0.5); 2.5149 (9.8); 2.5106 (19.7); 2.5061 (25.7); 2.5015 (18.7); 2.4971 (9.2); 1.2352 (0.5)

I-322: $^1$H-NMR (400.2 MHz, d$_6$-DMSO):

δ=7.9541 (1.5); 7.7591 (2.6); 7.4694 (0.6); 7.4620 (0.6); 7.4473 (2.7); 7.4404 (1.7); 7.4313 (3.2); 7.4271 (1.6); 7.4195 (1.8); 7.4001 (1.6); 7.3867 (1.7); 7.3779 (0.8); 7.3645 (0.7); 7.3339 (1.3); 7.3265 (1.2); 7.3114 (1.4); 7.3040 (1.1); 7.2777 (7.4); 7.0502 (2.6); 7.0481 (2.6); 3.6789 (16.0); 3.3320 (17.7); 2.8938 (11.2); 2.7351 (9.3); 2.6332 (13.6); 2.5277 (0.4); 2.5229 (0.6); 2.5142 (8.6); 2.5098 (17.3); 2.5052 (22.6); 2.5006 (16.1); 2.4961 (7.8); 1.2380 (0.5)

I-323: $^1$H-NMR (400.2 MHz, d$_6$-DMSO):

δ=8.0089 (0.9); 7.5429 (1.3); 7.5385 (1.3); 7.3629 (0.4); 7.3460 (0.5); 6.8467 (0.3); 6.8259 (0.6); 6.7280 (1.2); 6.7052 (0.6); 6.3223 (1.3); 6.3180 (1.2); 3.3259 (16.7); 2.8926 (0.5); 2.7331 (0.4); 2.6388 (0.4); 2.5257 (0.4); 2.5122 (8.6); 2.5079 (17.0); 2.5034 (21.9); 2.4988 (15.7); 2.4944 (7.6); 2.4775 (4.8); 1.4664 (16.0)

I-324: $^1$H-NMR (400.2 MHz, d$_6$-DMSO):

δ=7.9545 (0.9); 7.6822 (5.3); 7.6710 (1.2); 7.6612 (1.1); 7.6570 (1.2); 7.6518 (1.6); 7.6478 (1.6); 7.6380 (1.5); 7.6343 (1.5); 7.5592 (1.2); 7.5410 (1.4); 7.5336 (1.6); 7.5156 (1.5); 7.5105 (1.1); 7.4921 (0.8); 7.4671 (1.3); 7.4503 (1.6); 7.4466 (2.7); 7.4299 (2.7); 7.4262 (1.8); 7.4093 (1.4); 7.3907 (7.3); 7.3862 (7.4); 7.3116 (5.2); 6.9935 (1.9); 6.9722 (3.3); 6.9498 (1.7); 6.9042 (3.8); 6.8837 (3.6); 6.3590 (7.3); 6.3544 (7.3); 3.8911 (0.6); 3.8756 (1.6); 3.8574 (2.8); 3.8518 (1.8); 3.8350 (2.4); 3.8166 (1.7); 3.8006 (0.5); 3.3312 (34.6); 3.0032 (0.6); 2.8939 (7.0); 2.7353 (5.9); 2.5362 (28.0); 2.5233 (1.5); 2.5144 (18.1); 2.5100 (36.9); 2.5054 (48.5); 2.5009 (34.9); 2.4964 (17.0); 1.7050 (0.4); 1.6892 (1.1); 1.6709 (1.9); 1.6646 (1.2); 1.6525 (2.0); 1.6465 (1.8); 1.6291 (1.8); 1.6108 (1.2); 1.5932 (0.5); 1.2375 (1.0); 0.7239 (7.7); 0.7055 (16.0); 0.6869 (7.1); −0.0002 (0.6)

I-325: $^1$H-NMR (400.2 MHz, d$_6$-DMSO):

δ=7.5149 (0.5); 7.5123 (0.5); 7.4979 (0.7); 7.4892 (1.2); 7.4757 (1.0); 7.4589 (0.9); 7.4412 (0.9); 7.4335 (1.1); 7.4142 (4.0); 7.3976 (0.4); 7.3925 (0.5); 7.3821 (1.4); 7.3754 (1.7); 7.3695 (2.3); 7.3625 (1.7); 7.3560 (3.3); 7.2569 (1.5); 7.2500 (5.4); 7.2454 (4.6); 7.2344 (1.3); 7.2289 (1.2); 7.1190 (3.2); 6.3346 (4.3); 6.3301 (4.2); 3.7682 (4.4); 3.7497 (4.4); 3.3311 (29.0); 2.8935 (0.3); 2.7343 (0.3); 2.5747 (15.8); 2.5274 (0.7); 2.5139 (12.4); 2.5096 (24.5); 2.5050 (31.7); 2.5005 (22.9); 2.4961 (11.2); 1.9807 (0.4); 1.9635 (0.8); 1.9465 (1.0); 1.9295 (0.8); 1.9124 (0.4); 1.2378 (0.6); 0.6269 (16.0); 0.6102 (15.4)

I-326: $^1$H-NMR (400.2 MHz, d$_6$-DMSO):

δ=7.5159 (0.6); 7.5014 (0.7); 7.4928 (1.3); 7.4790 (1.2); 7.4666 (1.0); 7.4493 (0.9); 7.4415 (1.1); 7.4237 (1.1); 7.4101 (3.5); 7.3669 (3.5); 7.3629 (3.5); 7.3497 (3.7); 7.3101 (4.1); 7.3055 (4.3); 7.1978 (0.5); 7.1934 (0.4); 7.1889 (0.7); 7.1845 (0.7); 7.1755 (3.0); 7.1582 (5.7); 7.1467 (1.0); 7.1433 (0.8); 7.1195 (3.5); 7.0807 (1.0); 7.0769 (1.8); 7.0550 (1.4); 6.9044 (2.7); 6.8988 (2.6); 6.8849 (2.6); 6.8814 (2.2); 6.3905 (4.2); 6.3859 (4.2); 5.2385 (7.5); 3.3340 (46.3); 2.8924 (1.5); 2.7344 (1.4); 2.5720 (16.0); 2.5266 (0.6); 2.5218 (12.3); 2.5131 (13.6); 2.5088 (27.5); 2.5043 (36.1); 2.4999 (26.5); 1.2387 (0.7)

I-327: $^1$H-NMR (400.2 MHz, d$_6$-DMSO):

δ=7.9557 (0.5); 7.7595 (3.0); 7.7421 (0.6); 7.7380 (0.7); 7.7284 (0.7); 7.7242 (0.8); 7.7193 (1.0); 7.7150 (1.0); 7.7053 (0.9); 7.7015 (0.9); 7.6206 (0.8); 7.6025 (0.8); 7.5950 (1.0); 7.5770 (0.9); 7.5719 (0.6); 7.5536 (0.5); 7.5045 (3.5); 7.5005 (3.5); 7.4853 (0.5); 7.4812 (0.6); 7.4668 (1.5); 7.4627 (1.7); 7.4492 (2.6); 7.4440 (2.9); 7.4304 (1.6); 7.4265 (1.7); 7.4119 (0.7); 7.4080 (0.6); 7.3383 (2.0); 7.3348 (1.7); 7.3206 (1.6); 7.3160 (1.3); 7.2449 (1.6); 7.2409 (1.8); 7.2261 (1.3); 7.2231 (1.4); 6.1942 (4.3); 6.1898 (4.3); 4.1074 (0.4); 4.0912 (1.1); 4.0748 (1.5); 4.0584 (1.2); 4.0416 (0.9); 4.0235 (1.0); 3.3312 (17.4); 2.8951 (3.4); 2.7361 (3.0); 2.5291 (0.5); 2.5156 (10.0); 2.5113 (20.0); 2.5068 (26.1); 2.5022 (18.9); 2.4978 (9.3); 2.4405 (16.0); 1.2355 (1.0); 1.1714 (1.4)

I-328: $^1$H-NMR (499.9 MHz, d$_6$-DMSO):

δ=8.4164 (9.4); 7.8892 (1.6); 7.8695 (2.7); 7.8540 (2.6); 7.8338 (1.4); 7.6779 (5.0); 7.6755 (5.0); 7.6609 (5.4); 7.4793 (0.4); 7.4608 (0.4); 7.4546 (0.6); 7.4420 (2.1); 7.4396 (2.0); 7.4257 (5.0); 7.4120 (4.7); 7.4095 (4.4); 7.3881 (7.3); 7.3744 (3.6); 7.3717 (3.1); 7.3349 (3.8); 7.3319 (3.4); 7.3185 (5.5); 7.3051 (3.2); 7.3018 (3.4); 7.2973 (10.3); 7.2937 (9.9); 7.2538 (0.4); 7.2502 (0.4); 6.1835 (4.3); 6.1326 (0.3); 3.8978 (1.1); 3.8850 (1.6); 3.8713 (2.0); 3.8571 (1.7); 3.8433 (0.8); 3.7495 (1.6); 3.7359 (1.8); 3.7225 (1.4); 3.7098 (1.0); 3.4361 (0.5); 3.4253 (0.5); 3.4150 (0.6); 3.2444 (271.0); 2.8227 (0.4); 2.6635 (0.6); 2.5681 (1.5); 2.4542 (6.7); 2.4417 (68.3); 2.4366 (71.3); 2.4331 (89.3); 2.4296 (62.4); 2.2977 (0.5); 2.2942 (0.6); 2.2904 (0.4); 2.1965 (0.6); 2.0052 (0.4); 1.2297 (0.4); 1.2150 (0.4); 1.1684 (1.9); 1.1386 (0.8); 1.1241 (0.7); 1.0893 (8.7); 1.0749 (16.0); 1.0606 (7.7); 0.7864 (0.4); −0.0002 (0.4)

I-329: $^1$H-NMR (499.9 MHz, d$_6$-DMSO):

δ=8.5394 (4.1); 7.8468 (2.1); 7.8307 (2.1); 7.6937 (0.4); 7.6562 (0.5); 7.6494 (0.7); 7.6380 (1.5); 7.6176 (2.4); 7.6056 (1.7); 7.5679 (0.4); 7.5218 (1.8); 7.5136 (1.9); 7.4948 (3.3); 7.4766 (3.0); 7.4597 (2.2); 7.4450 (1.4); 7.4259 (0.6); 7.3787 (1.5); 7.3475 (0.4); 7.3199 (0.6); 7.3024 (0.5); 7.2918 (0.6); 7.2828 (0.5); 7.2458 (8.1); 7.2423 (7.6); 7.1869 (0.4); 7.1385 (2.7); 7.0328 (1.4);

6.1490 (4.9); 4.0799 (0.5); 4.0692 (0.7); 4.0587 (0.5); 3.8873 (0.5); 3.8735 (1.0); 3.8593 (1.3); 3.8489 (1.5); 3.8351 (1.3); 3.8210 (0.6); 3.7484 (0.7); 3.7342 (1.3); 3.7201 (1.4); 3.7076 (1.1); 3.6929 (0.7); 3.2453 (461.7); 2.6557 (0.5); 2.5714 (0.6); 2.5678 (0.7); 2.5642 (0.6); 2.5100 (1.5); 2.4890 (2.2); 2.4857 (1.9); 2.4401 (36.6); 2.4365 (69.1); 2.4329 (90.7); 2.4293 (63.6); 2.4258 (29.0); 2.2976 (0.4); 2.2939 (0.5); 1.3009 (0.4); 1.2838 (0.4); 1.2723 (0.4); 1.2682 (0.4); 1.2532 (0.4); 1.2307 (0.7); 1.2143 (1.4); 1.2052 (1.1); 1.1912 (0.9); 1.1836 (1.1); 1.1703 (1.7); 1.1496 (0.5); 1.1347 (0.5); 1.1197 (0.9); 1.0932 (8.5); 1.0788 (16.0); 1.0644 (7.6); 0.8228 (1.0); 0.8080 (2.3); 0.7940 (1.8); 0.7864 (0.7); −0.0002 (0.6)

I-330: $^1$H-NMR (400.2 MHz, $d_6$-DMSO):
δ=7.9569 (1.2); 7.7393 (0.6); 7.7353 (0.7); 7.7254 (0.7); 7.7213 (0.8); 7.7165 (1.0); 7.7124 (1.0); 7.7024 (0.9); 7.6989 (0.9); 7.6507 (3.0); 7.6314 (1.0); 7.6134 (0.9); 7.6057 (1.1); 7.5931 (1.9); 7.5827 (0.8); 7.5757 (2.8); 7.5733 (2.7); 7.5648 (0.7); 7.5360 (2.2); 7.5167 (3.1); 7.4968 (1.5); 7.4790 (3.2); 7.4745 (3.2); 7.3044 (2.0); 7.2870 (1.7); 6.2484 (3.5); 6.2438 (3.5); 4.0995 (1.4); 4.0589 (2.2); 3.9300 (2.0); 3.8893 (1.3); 3.3423 (10.4); 3.2596 (13.1); 2.8960 (8.2); 2.7371 (7.0); 2.6049 (0.4); 2.5308 (0.5); 2.5173 (7.8); 2.5129 (15.2); 2.5084 (19.8); 2.5039 (14.5); 2.4995 (7.1); 2.4470 (16.0); 1.2351 (0.8)

I-331: $^1$H-NMR (400.2 MHz, $d_6$-DMSO):
δ=7.9569 (0.7); 7.7390 (0.6); 7.7348 (0.7); 7.7251 (0.7); 7.7208 (0.8); 7.7160 (1.0); 7.7116 (1.2); 7.7019 (3.8); 7.6305 (0.9); 7.6125 (0.9); 7.6047 (1.0); 7.5868 (0.9); 7.5818 (0.7); 7.5690 (0.9); 7.5637 (0.6); 7.5539 (1.0); 7.5488 (1.4); 7.5333 (5.4); 7.5287 (5.1); 7.5138 (1.0); 7.3411 (1.1); 7.3196 (1.9); 7.2968 (0.9); 7.1494 (2.1); 7.1304 (1.9); 6.2936 (4.2); 6.2890 (4.2); 4.1370 (1.4); 4.0961 (2.2); 3.9595 (2.0); 3.9187 (1.3); 3.7159 (0.8); 3.6983 (1.0); 3.6815 (1.4); 3.6637 (1.2); 3.6456 (0.4); 3.6014 (0.4); 3.5834 (1.1); 3.5656 (1.3); 3.5487 (1.0); 3.5311 (0.7); 3.3440 (34.5); 2.8961 (5.0); 2.7372 (4.2); 2.5310 (0.5); 2.5263 (0.7); 2.5177 (7.9); 2.5132 (15.6); 2.5087 (20.4); 2.5041 (14.9); 2.4996 (7.2); 2.4566 (16.0); 1.2353 (0.8); 1.0959 (4.1); 1.0779 (8.5); 1.0599 (4.0)

I-332: $^1$H-NMR (400.2 MHz, $d_6$-DMSO):
δ=7.9574 (2.5); 7.7390 (1.7); 7.7354 (1.7); 7.7252 (1.9); 7.7208 (2.1); 7.7162 (2.6); 7.7125 (2.6); 7.7023 (2.5); 7.6992 (2.4); 7.6797 (7.8); 7.6299 (2.3); 7.6115 (2.4); 7.6042 (2.7); 7.5865 (2.5); 7.5812 (1.8); 7.5728 (2.0); 7.5623 (1.8); 7.5573 (2.6); 7.5529 (3.7); 7.5377 (3.6); 7.5329 (2.6); 7.5176 (2.1); 7.4809 (8.7); 7.4765 (8.4); 7.3472 (3.0); 7.3247 (4.8); 7.3030 (2.4); 7.1696 (5.4); 7.1503 (4.9); 6.3245 (9.0); 6.3200 (8.6); 4.1704 (3.5); 4.1296 (5.3); 3.9822 (5.1); 3.9413 (3.3); 3.3721 (33.3); 3.3477 (85.9); 2.8963 (16.0); 2.7379 (14.6); 2.6749 (0.7); 2.6091 (0.5); 2.5307 (1.3); 2.5133 (39.1); 2.5090 (48.5); 2.5046 (35.2); 2.4618 (38.1); 1.2359 (2.0); 0.8526 (0.4); −0.0002 (0.5)

I-333: $^1$H-NMR (400.2 MHz, $d_6$-DMSO):
δ=7.9564 (0.7); 7.7367 (0.6); 7.7329 (0.7); 7.7229 (0.7); 7.7188 (0.8); 7.7139 (1.0); 7.7099 (1.1); 7.6905 (3.2); 7.6240 (0.8); 7.6057 (0.8); 7.5984 (1.0); 7.5802 (1.0); 7.5757 (0.7); 7.5570 (0.5); 7.4755 (4.3); 7.4709 (4.4); 7.3273 (3.8); 7.3129 (3.6); 7.3091 (3.7); 7.2718 (1.5); 7.2489 (1.7); 6.2417 (4.0); 6.2373 (4.1); 4.0079 (5.4); 3.7702 (1.3); 3.7522 (4.1); 3.7341 (4.2); 3.7161 (1.3); 3.3471 (40.4); 2.8964 (4.6); 2.7379 (3.9); 2.7370 (3.9); 2.5309 (0.5); 2.5174 (8.8); 2.5132 (17.0); 2.5086 (22.0); 2.5041 (16.5); 2.4998 (8.5); 2.4483 (16.0); 1.2351 (0.8); 1.1237 (4.8); 1.1057 (10.4); 1.0877 (4.7)

I-334: $^1$H-NMR (400.2 MHz, $d_6$-DMSO):
δ=7.9569 (0.9); 7.7536 (0.6); 7.7494 (0.7); 7.7399 (0.7); 7.7355 (0.8); 7.7306 (1.1); 7.7175 (3.7); 7.6346 (0.8); 7.6165 (0.8); 7.6089 (1.0); 7.5920 (2.4); 7.5860 (0.8); 7.5745 (2.7); 7.5718 (2.6); 7.5270 (6.5); 7.5223 (4.8); 7.5081 (3.2); 7.4881 (1.6); 7.2553 (2.0); 7.2532 (2.0); 7.2362 (1.8); 7.2341 (1.7); 6.1900 (4.5); 6.1855 (4.5); 4.0607 (1.4); 4.0198 (2.2); 3.8856 (2.1); 3.8448 (1.4); 3.6891 (1.1); 3.6712 (1.3); 3.6549 (1.6); 3.6369 (1.5); 3.6188 (0.5); 3.5315 (0.4); 3.5134 (1.5); 3.4954 (1.7); 3.4791 (1.3); 3.4612 (1.1); 3.4432 (0.3); 3.3402 (24.4); 2.8962 (6.3); 2.7377 (5.4); 2.7368 (5.1); 2.5307 (0.5); 2.5259 (0.7); 2.5173 (8.2); 2.5128 (16.3); 2.5083 (21.4); 2.5037 (15.7); 2.4992 (7.7); 2.4400 (16.0); 1.2353 (0.8); 1.1174 (4.9); 1.0994 (10.5); 1.0813 (4.8); −0.0002 (0.4)

I-335: $^1$H-NMR (400.2 MHz, $d_6$-DMSO):
δ=8.3135 (0.4); 7.9534 (0.4); 7.7405 (0.6); 7.7363 (0.7); 7.7268 (0.7); 7.7227 (0.7); 7.7179 (0.9); 7.7134 (0.9); 7.7039 (0.8); 7.6998 (0.8); 7.6785 (2.7); 7.6325 (0.3); 7.6244 (1.1); 7.6151 (0.5); 7.6065 (1.0); 7.5983 (1.3); 7.5805 (0.9); 7.5753 (0.8); 7.5656 (0.4); 7.5573 (0.7); 7.5505 (0.3); 7.5480 (0.3); 7.4253 (4.0); 7.4206 (4.0); 7.3269 (3.9); 7.3154 (2.6); 7.3105 (3.9); 7.2931 (1.5); 7.2878 (1.8); 6.2572 (4.0); 6.2525 (4.0); 4.0319 (5.6); 3.4759 (18.2); 3.3291 (68.8); 2.8930 (2.7); 2.7343 (2.3); 2.7331 (2.2); 2.6772 (0.6); 2.6728 (0.5); 2.6683 (0.4); 2.5262 (1.7); 2.5215 (2.6); 2.5129 (29.9); 2.5084 (59.2); 2.5038 (77.3); 2.4992 (55.9); 2.4947 (27.0); 2.4506 (16.0); 2.3352 (0.4); 2.3306 (0.5); 2.3260 (0.4); 1.5347 (1.0); 1.4994 (0.9); 1.4928 (0.4); 1.3023 (0.7); 1.2720 (0.8); 1.2391 (1.2); −0.0002 (1.3)

I-336: $^1$H-NMR (400.2 MHz, $d_6$-DMSO):
δ=8.6293 (5.4); 8.6237 (5.4); 8.3177 (0.4); 8.1569 (2.9); 8.1364 (3.1); 8.1092 (2.9); 8.0911 (3.2); 7.9584 (0.5); 7.8512 (4.5); 7.8458 (4.4); 7.7056 (2.2); 7.6863 (3.4); 7.6668 (1.9); 7.6503 (0.7); 7.6364 (0.8); 7.6309 (1.4); 7.6246 (0.6); 7.6208 (0.7); 7.6099 (0.6); 7.6035 (1.1); 7.5781 (0.7); 7.5765 (0.7); 7.5689 (0.8); 7.5594 (0.7); 7.5535 (0.9); 7.5510 (0.9); 7.5484 (0.7); 7.5379 (7.2); 7.5335 (7.2); 7.5275 (1.2); 7.5221 (1.5); 7.5071 (4.5); 7.5029 (6.8); 7.4859 (3.3); 7.4825 (3.3); 7.4668 (1.2); 7.4632 (1.3); 7.4228 (1.7); 7.4179 (1.5); 7.4041 (2.8); 7.3996 (2.6); 7.3867 (1.7); 7.3820 (1.6); 7.3394 (0.8); 7.3321 (0.4); 7.3245 (0.5); 7.3163 (3.9); 7.2981 (2.7); 7.2954 (2.4); 6.3135 (7.4); 6.3090 (7.3); 4.2206 (0.5); 4.1152 (8.6); 3.6169 (2.0); 3.5989 (6.4); 3.5808 (6.5); 3.5628 (2.1); 3.3486 (72.5); 2.8959 (3.8); 2.7375 (3.2); 2.5319 (0.9); 2.5271 (1.4); 2.5186 (15.9); 2.5142 (31.4); 2.5096 (41.0); 2.5050 (29.8); 2.5005 (14.5); 1.2367 (1.3); 0.9986 (7.6); 0.9806 (16.0); 0.9625 (7.4); 0.8522 (0.4); −0.0002 (0.5)

I-337: $^1$H-NMR (400.2 MHz, $d_6$-DMSO):
δ=8.6383 (6.6); 8.6327 (6.7); 8.1565 (3.5); 8.1358 (3.8); 8.1129 (3.4); 8.0951 (3.7); 7.8160 (5.4); 7.8106 (5.4); 7.7092 (2.6); 7.6898 (4.1); 7.6704 (2.2); 7.5089 (1.3); 7.4978 (13.7); 7.4936 (16.0); 7.4808 (4.5); 7.4774 (4.2); 7.4616 (1.1); 7.4581 (1.2); 7.4209 (1.9); 7.4145 (1.6); 7.4020 (3.0); 7.3962 (2.5); 7.3861 (2.1); 7.3801 (1.9); 7.3288 (5.3); 7.3109 (3.0); 7.3087 (2.8); 6.3082 (9.6); 6.3036 (9.5); 4.1224 (14.6); 3.3440 (64.4); 3.3109 (42.0); 2.8960 (0.5); 2.7378 (0.4); 2.5316 (1.0); 2.5268 (1.5); 2.5183 (16.3); 2.5138 (32.4); 2.5093 (42.6); 2.5047 (31.2); 2.5002 (15.4); 1.2361 (1.2); 0.8522 (0.3); −0.0002 (0.6)

I-338: $^1$H-NMR (400.2 MHz, $d_6$-DMSO):
δ=8.5784 (7.1); 8.5730 (7.2); 7.9565 (1.2); 7.8915 (4.1); 7.8884 (4.8); 7.8729 (4.6); 7.8698 (5.3); 7.8509 (4.0); 7.8480 (3.9); 7.8302 (4.9); 7.8273 (4.1); 7.7972 (5.5);

7.7920 (5.5); 7.5932 (9.4); 7.5887 (9.6); 7.5590 (4.7); 7.5390 (5.8); 7.5197 (3.7); 7.4600 (1.4); 7.4566 (1.5); 7.4412 (3.8); 7.4224 (2.9); 7.4189 (2.9); 7.3539 (3.0); 7.3447 (4.1); 7.3418 (5.4); 7.3373 (5.1); 7.3255 (3.0); 7.3219 (3.4); 7.3199 (3.4); 7.2245 (4.4); 7.2202 (5.0); 7.2093 (10.0); 7.2039 (9.3); 7.2011 (13.6); 7.1934 (11.6); 7.1836 (1.2); 6.8738 (0.6); 6.8641 (4.3); 6.8546 (4.6); 6.8510 (3.9); 6.8468 (3.8); 6.8404 (3.8); 6.3331 (9.5); 6.3285 (9.4); 4.9625 (16.0); 3.9448 (13.8); 3.3456 (91.1); 2.8935 (8.6); 2.7357 (7.3); 2.5297 (1.1); 2.5250 (1.7); 2.5163 (18.6); 2.5119 (36.8); 2.5074 (48.1); 2.5028 (34.9); 2.4983 (16.8); 1.2348 (1.5); 0.8515 (0.4); −0.0002 (1.0)

I-339: $^1$H-NMR (400.2 MHz, d$_6$-DMSO):
δ=7.8513 (0.8); 7.8319 (0.8); 7.8275 (1.7); 7.8085 (1.8); 7.8018 (1.5); 7.7830 (1.9); 7.7800 (2.2); 7.7759 (1.9); 7.7659 (2.2); 7.7630 (2.0); 7.7563 (0.8); 7.7522 (1.0); 7.7393 (0.8); 7.4506 (0.6); 7.4459 (0.8); 7.4321 (2.3); 7.4275 (2.7); 7.4231 (2.2); 7.4163 (5.5); 7.4095 (3.5); 7.4019 (8.9); 7.3975 (7.8); 7.3866 (1.2); 7.3818 (0.7); 7.3358 (3.2); 7.3318 (2.2); 7.3285 (1.7); 7.3191 (2.3); 7.3133 (1.9); 7.2699 (2.4); 7.2641 (2.5); 7.2514 (1.5); 7.2477 (2.0); 6.1792 (7.0); 6.1747 (7.0); 4.2877 (7.8); 3.7925 (1.8); 3.7745 (6.0); 3.7564 (6.1); 3.7384 (1.9); 3.3410 (75.0); 2.8954 (1.2); 2.7371 (1.0); 2.7359 (1.0); 2.5296 (1.0); 2.5248 (1.5); 2.5163 (15.6); 2.5118 (31.3); 2.5068 (50.6); 2.4982 (15.2); 1.2366 (1.0); 1.1731 (7.4); 1.1551 (16.0); 1.1370 (7.2); −0.0002 (0.9)

I-340: $^1$H-NMR (400.2 MHz, d$_6$-DMSO):
δ=8.5725 (7.3); 8.5670 (7.4); 7.9569 (1.0); 7.8779 (4.3); 7.8748 (5.0); 7.8593 (5.0); 7.8561 (5.4); 7.8346 (4.1); 7.8315 (3.9); 7.8138 (4.9); 7.8108 (4.1); 7.7542 (5.5); 7.7490 (5.4); 7.5528 (4.9); 7.5337 (5.7); 7.5136 (4.5); 7.4973 (15.2); 7.4927 (16.0); 7.4783 (4.4); 7.4748 (4.1); 7.4592 (1.4); 7.4556 (1.4); 7.4170 (2.1); 7.4114 (1.7); 7.3981 (3.1); 7.3930 (2.8); 7.3814 (2.2); 7.3762 (2.0); 7.3221 (4.9); 7.3041 (3.1); 7.3015 (2.7); 6.2973 (10.6); 6.2926 (10.4); 4.1115 (14.4); 3.3513 (89.4); 3.2922 (45.5); 2.8950 (7.6); 2.7374 (6.3); 2.7364 (6.1); 2.5311 (0.8); 2.5264 (1.2); 2.5177 (15.3); 2.5132 (30.6); 2.5086 (40.1); 2.5040 (29.0); 2.4995 (14.0); 1.2353 (1.4); 0.8520 (0.3); −0.0002 (1.1)

I-341: $^1$H-NMR (400.2 MHz, d$_6$-DMSO):
δ=8.6115 (8.0); 8.6061 (8.0); 7.9577 (1.3); 7.8714 (4.5); 7.8685 (5.5); 7.8499 (16.0); 7.8467 (10.8); 7.8290 (5.8); 7.8262 (4.4); 7.5574 (0.5); 7.5468 (10.9); 7.5441 (9.8); 7.5266 (6.3); 7.5066 (4.2); 7.4895 (9.2); 7.4799 (12.0); 7.4604 (0.4); 7.4577 (0.5); 7.4410 (0.6); 7.4315 (2.4); 7.4205 (3.0); 7.4126 (3.1); 7.4012 (3.4); 7.3905 (1.8); 7.3279 (0.4); 7.3170 (0.5); 7.3010 (5.8); 7.2825 (4.3); 6.2706 (10.7); 6.2662 (10.5); 4.2112 (0.4); 4.1059 (1.0); 4.0302 (0.6); 4.0143 (1.2); 3.9984 (2.6); 3.9820 (3.4); 3.9656 (2.6); 3.9493 (1.0); 3.3473 (73.0); 2.8953 (9.3); 2.7374 (7.8); 2.5313 (1.0); 2.5264 (1.5); 2.5178 (17.8); 2.5134 (35.0); 2.5089 (45.4); 2.5043 (32.9); 2.4999 (15.9); 1.3013 (0.4); 1.2585 (0.8); 1.2347 (2.2); 1.0978 (1.5); 0.8677 (0.4); 0.8515 (0.6); 0.8343 (0.4); −0.0002 (1.1)

I-342: $^1$H-NMR (400.2 MHz, d$_6$-DMSO):
δ=7.9554 (0.7); 7.8442 (0.4); 7.8203 (1.1); 7.8024 (1.2); 7.7948 (1.1); 7.7881 (1.6); 7.7862 (1.6); 7.7781 (1.4); 7.7731 (2.3); 7.7623 (0.6); 7.7490 (0.4); 7.4750 (4.2); 7.4705 (4.2); 7.4262 (0.7); 7.4227 (0.7); 7.4075 (1.8); 7.4040 (1.8); 7.3887 (1.3); 7.3851 (1.3); 7.3508 (1.0); 7.3478 (1.1); 7.3321 (1.8); 7.3291 (1.8); 7.3136 (0.8); 7.3104 (0.8); 7.2548 (0.4); 7.2506 (0.4); 7.2454 (0.8); 7.2412 (0.7); 7.2327 (2.9); 7.2173 (5.2); 7.2143 (6.0); 7.2012 (0.9); 7.1929 (3.6); 7.1907 (3.7); 7.1747 (1.6); 7.1716 (1.5); 6.9194 (2.6); 6.9135 (2.3); 6.9001 (2.4); 6.8962 (2.0); 6.2001 (4.2); 6.1956 (4.1); 5.0514 (7.1); 4.1475 (5.9); 3.3340 (15.7); 2.8940 (4.5); 2.7360 (3.9); 2.5285 (0.6); 2.5151 (9.8); 2.5108 (18.7); 2.5063 (24.0); 2.5017 (17.4); 2.4974 (8.4); 2.4388 (16.0); 1.2359 (0.8); −0.0002 (0.5)

I-343: $^1$H-NMR (400.2 MHz, d$_6$-DMSO):
δ=8.5456 (5.0); 8.5408 (5.1); 7.8067 (4.6); 7.7715 (1.0); 7.7680 (1.0); 7.7577 (1.1); 7.7537 (1.2); 7.7485 (2.0); 7.7448 (2.1); 7.7346 (1.8); 7.7310 (1.8); 7.7091 (1.6); 7.6914 (1.6); 7.6838 (2.0); 7.6659 (1.8); 7.6607 (1.0); 7.6425 (0.9); 7.5263 (7.0); 7.5219 (7.4); 7.5003 (6.6); 7.4848 (3.2); 7.4818 (3.2); 7.4657 (1.1); 7.4625 (1.1); 7.4210 (1.6); 7.4158 (1.4); 7.4023 (2.6); 7.3978 (2.5); 7.3851 (1.5); 7.3802 (1.4); 7.3091 (4.0); 7.2910 (2.8); 6.2848 (6.5); 6.2804 (6.6); 4.0901 (8.8); 3.5872 (2.2); 3.5692 (6.9); 3.5511 (7.0); 3.5331 (2.3); 3.3399 (23.0); 2.8970 (1.8); 2.7384 (1.6); 2.5140 (24.4); 2.5096 (31.6); 2.5051 (23.7); 1.2350 (1.1); 1.0139 (7.7); 0.9959 (16.0); 0.9778 (7.5); −0.0002 (0.6)

I-344: $^1$H-NMR (400.2 MHz, d$_6$-DMSO):
δ=7.8470 (0.4); 7.8232 (1.0); 7.8044 (1.2); 7.7976 (1.0); 7.7797 (2.1); 7.7660 (1.5); 7.7568 (0.5); 7.7533 (0.6); 7.7404 (0.5); 7.4463 (0.4); 7.4330 (1.3); 7.4275 (2.0); 7.4183 (2.9); 7.4100 (2.6); 7.4034 (2.0); 7.3900 (0.7); 7.3850 (0.4); 7.3624 (2.1); 7.3583 (1.4); 7.3544 (1.0); 7.3461 (1.3); 7.3356 (3.6); 7.3311 (3.5); 7.2942 (1.5); 7.2879 (1.4); 7.2759 (0.9); 7.2720 (1.2); 6.2140 (3.7); 6.2095 (3.6); 4.3309 (6.6); 3.5164 (16.0); 3.3427 (48.7); 2.8946 (1.4); 2.7357 (1.3); 2.5155 (25.2); 2.5113 (21.8); 2.5066 (25.4); 2.5022 (18.7); 1.2369 (0.7); −0.0002 (0.4)

I-345: $^1$H-NMR (400.2 MHz, d$_6$-DMSO):
δ=8.3148 (0.4); 7.9560 (2.2); 7.8617 (1.7); 7.8378 (4.1); 7.8190 (4.5); 7.8123 (3.8); 7.7945 (8.4); 7.7807 (6.0); 7.7715 (2.1); 7.7681 (2.4); 7.7552 (2.0); 7.4627 (13.5); 7.4586 (13.6); 7.4454 (1.2); 7.4403 (1.8); 7.4268 (5.9); 7.4214 (10.1); 7.4126 (13.2); 7.4040 (12.3); 7.3983 (7.7); 7.3849 (2.3); 7.3797 (1.2); 7.3280 (0.8); 7.3187 (7.4); 7.3145 (4.9); 7.3101 (3.8); 7.3029 (4.8); 7.2962 (4.9); 7.2854 (0.4); 7.2347 (0.8); 7.2239 (6.0); 7.2172 (5.4); 7.2101 (3.1); 7.2057 (3.7); 7.2015 (5.0); 6.1371 (15.8); 6.1328 (16.0); 4.2486 (5.4); 4.1907 (0.6); 4.1748 (1.6); 4.1584 (3.9); 4.1421 (5.4); 4.1257 (4.0); 4.1094 (1.6); 4.0934 (0.3); 3.3441 (156.9); 2.8959 (15.3); 2.8770 (0.3); 2.7554 (0.3); 2.7373 (12.9); 2.6816 (0.4); 2.6770 (0.5); 2.6726 (0.4); 2.6512 (0.4); 2.5304 (1.9); 2.5169 (33.2); 2.5126 (65.0); 2.5081 (84.6); 2.5036 (63.5); 2.4991 (34.8); 2.4927 (66.7); 2.3394 (0.4); 2.3348 (0.6); 2.3307 (0.7); 1.2356 (7.0); 1.2013 (5.9); 0.8680 (0.3); 0.8520 (0.8); 0.8343 (0.4); −0.0002 (1.5)

I-346: $^1$H-NMR (400.2 MHz, d$_6$-DMSO):
δ=8.5789 (5.3); 8.5734 (5.4); 7.9564 (0.4); 7.8729 (3.0); 7.8698 (3.5); 7.8542 (3.4); 7.8512 (3.8); 7.8319 (2.9); 7.8290 (2.9); 7.8113 (3.6); 7.8083 (3.1); 7.7800 (4.1); 7.7748 (4.1); 7.5496 (3.5); 7.5346 (7.3); 7.5301 (11.2); 7.5206 (0.9); 7.5161 (1.3); 7.5104 (3.0); 7.5014 (4.1); 7.4977 (5.6); 7.4816 (2.9); 7.4783 (2.9); 7.4625 (1.0); 7.4590 (1.0); 7.4191 (1.5); 7.4139 (1.3); 7.4004 (2.4); 7.3957 (2.2); 7.3832 (1.5); 7.3783 (1.4); 7.3093 (3.5); 7.2914 (2.4); 7.2885 (2.2); 6.2916 (7.0); 6.2871 (6.9); 4.1000 (7.8); 3.6020 (2.1); 3.5840 (6.8); 3.5659 (6.9); 3.5479 (2.2); 3.3736 (140.9); 3.3372 (0.4); 2.8967 (3.2); 2.7386 (2.7); 2.5331 (0.7); 2.5282 (1.0); 2.5198 (11.6); 2.5154 (23.2); 2.5108 (30.5); 2.5063 (22.2); 2.5018 (10.7); 1.2352 (1.0); 1.0136 (7.5); 0.9956 (16.0); 0.9775 (7.3); −0.0002 (0.8)

I-347: ¹H-NMR (400.2 MHz, d₆-DMSO):

δ=7.9552 (0.6); 7.8823 (1.8); 7.8614 (2.1); 7.7901 (1.6); 7.7699 (1.8); 7.6568 (4.6); 7.6436 (1.5); 7.6400 (1.9); 7.6365 (1.1); 7.6226 (1.1); 7.6191 (1.1); 7.5085 (3.5); 7.5044 (3.5); 7.4943 (1.3); 7.4918 (1.3); 7.4744 (2.2); 7.4573 (2.3); 7.4536 (2.4); 7.4399 (2.7); 7.4348 (2.9); 7.4212 (1.7); 7.4173 (1.7); 7.4028 (0.7); 7.3988 (0.6); 7.3355 (2.0); 7.3319 (1.6); 7.3177 (1.6); 7.3131 (1.3); 7.2311 (1.6); 7.2270 (1.7); 7.2123 (1.3); 7.2092 (1.4); 6.1938 (4.3); 6.1894 (4.3); 4.1154 (0.4); 4.0991 (1.0); 4.0827 (1.4); 4.0663 (1.1); 4.0498 (0.5); 4.0014 (1.1); 3.3448 (35.3); 2.8932 (4.0); 2.7353 (3.4); 2.5285 (0.5); 2.5152 (8.4); 2.5109 (16.4); 2.5064 (21.3); 2.5018 (15.7); 2.4974 (7.9); 2.3979 (16.0); 1.3062 (0.6); 1.2898 (0.6); 1.2362 (1.3); 1.1761 (1.4)

I-348: ¹H-NMR (400.2 MHz, d₆-DMSO):

δ=7.9555 (0.5); 7.8842 (1.7); 7.8632 (2.0); 7.7853 (1.6); 7.7649 (1.8); 7.6660 (1.0); 7.6625 (1.0); 7.6487 (1.3); 7.6451 (1.9); 7.6416 (1.0); 7.6278 (1.1); 7.6242 (1.1); 7.6110 (3.6); 7.4995 (1.2); 7.4970 (1.2); 7.4796 (2.0); 7.4678 (0.6); 7.4627 (1.3); 7.4596 (1.0); 7.4496 (1.8); 7.4455 (5.8); 7.4410 (4.6); 7.4316 (1.9); 7.4264 (2.2); 7.4108 (1.7); 7.4070 (1.9); 7.3924 (0.9); 7.3887 (0.8); 7.3704 (2.2); 7.3666 (1.8); 7.3524 (1.3); 7.3477 (1.0); 7.2520 (1.6); 7.2483 (1.7); 7.2331 (1.3); 7.2304 (1.4); 6.2348 (4.4); 6.2302 (4.4); 4.0291 (6.5); 3.7837 (0.5); 3.5926 (0.5); 3.4603 (19.7); 3.3454 (6.5); 2.8927 (3.5); 2.7354 (2.9); 2.5598 (0.4); 2.5286 (0.4); 2.5237 (0.6); 2.5152 (6.7); 2.5108 (13.2); 2.5062 (17.2); 2.5016 (12.5); 2.4972 (6.1); 2.4024 (16.0); 1.2358 (0.6)

I-349: ¹H-NMR (400.2 MHz, d₆-DMSO):

δ=7.8831 (1.9); 7.8623 (2.3); 7.7829 (1.7); 7.7639 (2.0); 7.6644 (1.1); 7.6611 (1.1); 7.6472 (1.6); 7.6437 (2.0); 7.6213 (4.4); 7.6023 (0.3); 7.4984 (1.4); 7.4959 (1.4); 7.4836 (5.3); 7.4792 (6.3); 7.4706 (1.2); 7.4661 (1.1); 7.4611 (1.3); 7.4583 (1.2); 7.4519 (1.9); 7.4477 (1.9); 7.4338 (2.0); 7.4294 (2.7); 7.4258 (1.8); 7.4114 (2.0); 7.4077 (1.9); 7.3930 (1.0); 7.3893 (0.8); 7.3494 (2.3); 7.3459 (2.0); 7.3313 (1.6); 7.3272 (1.4); 7.2427 (1.9); 7.2393 (1.9); 7.2238 (1.6); 7.2215 (1.6); 6.2146 (4.6); 6.2101 (4.4); 4.0272 (0.5); 4.0121 (6.4); 3.7548 (1.3); 3.7368 (4.1); 3.7187 (4.2); 3.7008 (1.4); 3.3371 (6.2); 2.8927 (1.0); 2.7351 (0.9); 2.5599 (0.3); 2.5098 (20.3); 2.5054 (25.4); 2.5009 (19.5); 2.4031 (16.0); 1.2716 (0.3); 1.2535 (0.6); 1.2360 (1.0); 1.1327 (4.3); 1.1147 (9.2); 1.0967 (4.4); −0.0002 (0.4)

I-350: ¹H-NMR (400.2 MHz, d₆-DMSO):

δ=7.9536 (0.4); 7.7534 (0.6); 7.7494 (0.7); 7.7396 (0.7); 7.7353 (0.8); 7.7306 (1.0); 7.7261 (1.0); 7.7131 (3.7); 7.6274 (1.0); 7.6091 (0.9); 7.6013 (1.0); 7.5836 (0.9); 7.5783 (0.7); 7.5602 (0.6); 7.5427 (1.6); 7.5368 (1.9); 7.5220 (1.8); 7.5161 (2.3); 7.4821 (3.7); 7.4764 (3.0); 7.4312 (4.0); 7.4266 (4.1); 7.3079 (2.9); 7.2870 (2.5); 6.2673 (4.1); 6.2627 (4.1); 4.0306 (5.9); 3.4781 (18.3); 3.3320 (59.3); 2.8937 (2.8); 2.7348 (2.4); 2.6737 (0.3); 2.5271 (1.2); 2.5222 (1.8); 2.5137 (20.2); 2.5093 (40.0); 2.5047 (52.3); 2.5001 (38.2); 2.4957 (18.8); 2.4447 (16.0); 2.3315 (0.3); 1.2383 (1.4); 0.8531 (0.3); −0.0002 (0.8)

I-351: ¹H-NMR (400.2 MHz, d₆-DMSO):

δ=7.9559 (0.8); 7.7526 (0.7); 7.7485 (0.7); 7.7387 (0.8); 7.7256 (3.8); 7.7163 (1.0); 7.7121 (0.9); 7.6285 (0.9); 7.6103 (0.9); 7.6026 (1.0); 7.5847 (0.9); 7.5796 (0.7); 7.5613 (0.6); 7.5483 (1.7); 7.5425 (1.9); 7.5275 (2.0); 7.5217 (2.3); 7.4808 (4.4); 7.4763 (4.5); 7.4430 (3.8); 7.4372 (3.4); 7.3022 (3.0); 7.2813 (2.6); 6.2538 (4.5); 6.2492 (4.4); 4.0085 (4.9); 3.7729 (1.2); 3.7548 (3.9); 3.7368 (4.0); 3.7188 (1.2); 3.3349 (19.2); 2.8955 (6.0); 2.7368 (5.0); 2.7362 (5.0); 2.5296 (0.6); 2.5248 (0.9); 2.5163 (9.4); 2.5118 (18.8); 2.5072 (24.6); 2.5026 (17.9); 2.4982 (8.7); 2.4432 (16.0); 1.2355 (0.9); 1.1303 (4.6); 1.1123 (10.0); 1.0943 (4.5); −0.0002 (0.4)

I-352: ¹H-NMR (400.2 MHz, d₆-DMSO):

δ=8.5449 (11.1); 8.5396 (11.1); 8.3175 (0.4); 7.9579 (0.8); 7.8300 (8.8); 7.6811 (4.8); 7.6618 (7.0); 7.6578 (6.3); 7.6305 (0.4); 7.5680 (0.4); 7.5553 (2.6); 7.5463 (12.7); 7.5421 (14.7); 7.5361 (6.2); 7.5227 (6.0); 7.5165 (6.5); 7.5149 (6.6); 7.5099 (6.2); 7.5029 (5.5); 7.4970 (14.3); 7.4950 (16.0); 7.4872 (15.1); 7.4841 (14.9); 7.4814 (9.6); 7.4679 (2.5); 7.4646 (2.9); 7.4417 (0.7); 7.4319 (3.5); 7.4231 (2.8); 7.4187 (2.8); 7.4130 (4.6); 7.4050 (3.2); 7.3991 (3.4); 7.3910 (2.8); 7.3802 (0.4); 7.3300 (0.6); 7.3189 (0.6); 7.2997 (9.0); 7.2815 (5.9); 6.2670 (15.2); 6.2626 (15.0); 4.2020 (0.7); 4.1007 (1.4); 4.0298 (1.0); 4.0123 (2.1); 3.9950 (4.0); 3.9786 (5.1); 3.9621 (3.8); 3.9457 (1.6); 3.9294 (0.4); 3.3474 (101.2); 2.8958 (6.3); 2.7381 (5.3); 2.7372 (5.3); 2.7164 (0.6); 2.7003 (0.4); 2.6781 (0.4); 2.5944 (0.4); 2.5775 (0.6); 2.5315 (1.4); 2.5266 (2.2); 2.5182 (25.9); 2.5137 (51.2); 2.5091 (66.6); 2.5045 (48.2); 2.5000 (23.2); 2.3360 (0.4); 1.3405 (0.4); 1.3018 (0.9); 1.2595 (1.6); 1.2361 (5.4); 1.0930 (2.1); 1.0510 (1.9); 0.8835 (0.5); 0.8692 (0.8); 0.8523 (1.5); 0.8348 (0.8); −0.0002 (1.4)

I-353: ¹H-NMR (400.2 MHz, d₆-DMSO):

δ=8.4965 (7.1); 8.4913 (7.1); 7.9577 (0.6); 7.7358 (5.9); 7.6671 (3.1); 7.6479 (4.6); 7.6439 (4.2); 7.5612 (1.4); 7.5479 (1.8); 7.5419 (3.6); 7.5285 (4.1); 7.5213 (6.0); 7.5164 (4.4); 7.5083 (4.0); 7.5043 (6.4); 7.4990 (8.8); 7.4949 (15.2); 7.4904 (13.0); 7.4811 (4.5); 7.4776 (4.6); 7.4708 (1.5); 7.4620 (1.7); 7.4585 (1.7); 7.4167 (2.2); 7.4120 (1.9); 7.3981 (3.7); 7.3938 (3.5); 7.3805 (2.2); 7.3760 (2.1); 7.3201 (5.1); 7.3019 (3.4); 7.2990 (3.2); 6.2936 (9.9); 6.2890 (9.8); 4.1064 (16.0); 3.3452 (57.0); 3.2797 (43.7); 2.8956 (4.3); 2.7377 (3.7); 2.5313 (0.8); 2.5179 (15.1); 2.5136 (29.3); 2.5090 (37.9); 2.5045 (27.7); 2.5001 (13.6); 1.2363 (1.3); 0.8528 (0.3); −0.0002 (0.8)

I-354: ¹H-NMR (400.2 MHz, d₆-DMSO):

δ=8.5101 (5.8); 8.5051 (5.7); 7.9581 (0.4); 7.7609 (5.2); 7.6664 (2.7); 7.6472 (4.0); 7.6435 (3.6); 7.5683 (0.4); 7.5586 (1.4); 7.5453 (1.9); 7.5392 (4.0); 7.5335 (7.7); 7.5291 (9.0); 7.5199 (4.4); 7.5182 (4.4); 7.5112 (6.4); 7.5064 (7.4); 7.4989 (4.2); 7.4903 (3.4); 7.4853 (5.0); 7.4816 (3.9); 7.4712 (1.5); 7.4661 (2.0); 7.4623 (1.6); 7.4191 (1.9); 7.4147 (1.7); 7.4005 (3.4); 7.3965 (3.1); 7.3826 (1.9); 7.3785 (1.7); 7.3299 (0.5); 7.3096 (4.3); 7.2912 (3.0); 6.2906 (7.2); 6.2863 (7.0); 4.0954 (9.9); 3.5896 (2.0); 3.5716 (6.2); 3.5536 (6.2); 3.5356 (2.1); 3.3463 (24.1); 2.8957 (2.3); 2.7381 (2.0); 2.5313 (0.7); 2.5177 (15.4); 2.5136 (29.0); 2.5091 (36.7); 2.5045 (27.1); 2.5003 (13.6); 1.2362 (1.1); 1.0094 (7.7); 0.9914 (16.0); 0.9733 (7.5); −0.0002 (0.8)

I-355: ¹H-NMR (400.2 MHz, d₆-DMSO):

δ=8.5322 (6.8); 8.5272 (6.8); 7.9584 (0.8); 7.7810 (6.1); 7.7707 (1.8); 7.7665 (1.4); 7.7565 (1.5); 7.7523 (1.6); 7.7472 (2.7); 7.7433 (2.8); 7.7334 (2.5); 7.7294 (2.5); 7.7106 (2.5); 7.6930 (2.4); 7.6851 (2.7); 7.6673 (2.5); 7.6620 (1.4); 7.6441 (1.3); 7.5181 (0.8); 7.5136 (1.5); 7.4984 (8.9); 7.4948 (9.7); 7.4878 (11.0); 7.4831 (12.8); 7.4784 (5.0); 7.4626 (1.4); 7.4591 (1.5); 7.4190 (2.2); 7.4134 (1.8); 7.4002 (3.5); 7.3952 (3.1); 7.3835 (2.3); 7.3782 (2.1); 7.3199 (5.6); 7.3019 (3.5); 7.2995 (3.2); 6.2837 (10.6); 6.2837 (10.5); 4.1025 (16.0); 3.3443 (47.8); 3.2798 (45.8); 2.8972 (5.2); 2.7390 (4.4); 2.5324 (0.8); 2.5190 (15.4); 2.5146 (30.2); 2.5100 (39.1); 2.5055 (28.4); 2.5011 (13.9); 1.2350 (1.2); −0.0002 (0.8)

I-356: ¹H-NMR (400.2 MHz, d₆-DMSO):
δ=8.5542 (16.0); 8.0458 (0.5); 8.0391 (3.3); 8.0345 (2.3); 8.0284 (2.0); 8.0239 (2.5); 8.0212 (2.6); 8.0148 (3.9); 8.0065 (0.6); 7.9573 (0.3); 7.9479 (0.5); 7.9389 (3.0); 7.9331 (2.5); 7.9304 (2.4); 7.9252 (2.2); 7.9191 (3.0); 7.9150 (4.3); 7.9077 (0.7); 7.8159 (0.8); 7.8103 (1.8); 7.7986 (5.2); 7.7931 (8.8); 7.7836 (9.3); 7.7740 (7.1); 7.7690 (4.2); 7.7570 (1.3); 7.7517 (0.6); 7.5014 (7.9); 7.4974 (7.9); 7.4753 (0.8); 7.4676 (8.2); 7.4652 (9.0); 7.4555 (9.6); 7.4520 (6.0); 7.4360 (0.7); 7.4327 (0.9); 7.4279 (0.6); 7.4184 (2.5); 7.4088 (1.9); 7.4061 (2.0); 7.3997 (3.2); 7.3908 (2.1); 7.3864 (2.4); 7.3775 (1.8); 7.2991 (5.9); 7.2809 (3.7); 6.2315 (10.8); 6.2271 (10.7); 4.2733 (1.6); 4.1184 (0.9); 4.1021 (2.4); 4.0857 (3.2); 4.0693 (2.4); 4.0529 (0.9); 3.3395 (31.1); 2.8952 (1.8); 2.7380 (1.5); 2.7369 (1.5); 2.5311 (0.9); 2.5264 (1.4); 2.5178 (15.6); 2.5133 (31.2); 2.5087 (40.8); 2.5041 (29.4); 2.4995 (14.2); 1.3021 (0.5); 1.2590 (0.9); 1.2360 (2.2); 1.1526 (2.2); 1.1384 (2.2); 0.8521 (0.4); −0.0002 (0.9)

I-357: ¹H-NMR (400.2 MHz, d₆-DMSO):
δ=8.5077 (10.8); 8.0422 (0.6); 8.0361 (2.6); 8.0313 (1.8); 8.0244 (1.8); 8.0215 (2.0); 8.0184 (2.1); 8.0118 (3.1); 8.0037 (0.5); 7.9569 (0.4); 7.9420 (0.4); 7.9337 (2.6); 7.9274 (2.0); 7.9242 (2.0); 7.9203 (1.8); 7.9138 (2.5); 7.9093 (3.7); 7.9025 (0.7); 7.8126 (0.7); 7.8068 (1.4); 7.7953 (4.5); 7.7904 (6.4); 7.7808 (7.1); 7.7711 (4.7); 7.7667 (3.5); 7.7549 (1.0); 7.7494 (0.5); 7.6496 (1.4); 7.6344 (1.4); 7.6294 (2.5); 7.6229 (1.0); 7.6197 (1.2); 7.6165 (1.1); 7.6084 (1.1); 7.6023 (1.9); 7.5744 (1.2); 7.5669 (1.4); 7.5573 (1.2); 7.5516 (1.4); 7.5491 (1.3); 7.5419 (0.4); 7.5380 (0.5); 7.5350 (0.5); 7.5306 (0.6); 7.5280 (0.4); 7.4947 (0.9); 7.4900 (1.4); 7.4703 (7.1); 7.4562 (3.9); 7.4526 (3.8); 7.4372 (1.5); 7.4334 (1.6); 7.4112 (7.0); 7.4069 (7.1); 7.3945 (3.4); 7.3897 (3.0); 7.3774 (2.0); 7.3724 (1.8); 7.3294 (4.6); 7.3115 (2.8); 7.3086 (2.5); 6.2678 (6.7); 6.2633 (6.5); 4.3744 (0.4); 4.3118 (16.0); 3.6866 (0.5); 3.4078 (27.3); 3.3417 (13.2); 2.8939 (2.2); 2.7365 (1.8); 2.5301 (0.8); 2.5252 (1.3); 2.5167 (15.0); 2.5123 (29.4); 2.5077 (38.2); 2.5032 (27.7); 2.4987 (13.5); 1.2372 (1.2); −0.0002 (0.8)

I-358: ¹H-NMR (400.2 MHz, d₆-DMSO):
δ=8.5029 (10.1); 8.0422 (0.4); 8.0358 (2.2); 8.0310 (1.5); 8.0245 (1.4); 8.0209 (1.7); 8.0180 (1.7); 8.0114 (2.6); 8.0033 (0.5); 7.9395 (0.3); 7.9311 (2.1); 7.9249 (1.7); 7.9219 (1.6); 7.9175 (1.4); 7.9112 (2.0); 7.9068 (3.0); 7.8999 (0.5); 7.8130 (0.5); 7.8073 (1.1); 7.7958 (3.5); 7.7907 (5.4); 7.7811 (5.9); 7.7715 (4.1); 7.7668 (2.8); 7.7550 (0.8); 7.7496 (0.4); 7.4991 (0.7); 7.4947 (1.2); 7.4798 (4.2); 7.4763 (6.0); 7.4647 (6.8); 7.4601 (9.3); 7.4568 (3.6); 7.4409 (1.2); 7.4372 (1.2); 7.4131 (1.6); 7.4079 (1.4); 7.3945 (2.5); 7.3897 (2.3); 7.3772 (1.5); 7.3723 (1.4); 7.3122 (3.5); 7.2941 (2.4); 7.2913 (2.2); 6.2579 (6.6); 6.2534 (6.6); 4.2859 (9.4); 3.6950 (2.0); 3.6770 (6.4); 3.6589 (6.5); 3.6409 (2.1); 3.3399 (15.2); 2.8948 (1.3); 2.7373 (1.1); 2.5307 (0.6); 2.5259 (0.9); 2.5173 (10.8); 2.5129 (21.6); 2.5083 (28.2); 2.5038 (20.6); 2.4993 (10.1); 1.2366 (0.9); 1.2255 (0.3); 1.2071 (0.4); 1.0668 (7.6); 1.0488 (16.0); 1.0307 (7.4); −0.0002 (0.6)

I-359: ¹H-NMR (400.2 MHz, d₆-DMSO):
δ=8.4969 (8.0); 8.4917 (7.0); 7.9569 (0.9); 7.7828 (6.4); 7.6875 (3.6); 7.6685 (5.0); 7.6640 (4.1); 7.6482 (0.5); 7.6344 (0.5); 7.6295 (0.7); 7.5921 (9.0); 7.5876 (8.1); 7.5702 (1.8); 7.5569 (2.7); 7.5511 (4.4); 7.5372 (6.0); 7.5344 (6.2); 7.5295 (4.7); 7.5178 (3.8); 7.5077 (3.6); 7.5038 (3.3); 7.4884 (1.5); 7.4845 (1.1); 7.4613 (3.3); 7.4578 (1.9); 7.4424 (4.6); 7.4236 (3.5); 7.4202 (3.1); 7.3527 (5.0); 7.3457 (6.6); 7.3428 (6.6); 7.3361 (6.5); 7.3267 (4.6); 7.3183 (3.5); 7.2202 (10.6); 7.2149 (16.0); 7.2064 (15.1); 7.1987 (15.3); 6.8692 (6.5); 6.8598 (6.6); 6.8563 (5.8); 6.8525 (5.3); 6.8458 (4.3); 6.3238 (9.4); 6.3193 (8.3); 4.9545 (16.0); 4.2017 (0.4); 3.9370 (15.9); 3.3490 (61.4); 2.9027 (1.0); 2.8942 (5.7); 2.7452 (1.0); 2.7370 (5.0); 2.6768 (0.4); 2.5167 (36.3); 2.5124 (52.3); 2.5079 (58.5); 2.5033 (40.0); 2.4990 (18.7); 2.3346 (0.4); 1.2363 (2.0); 0.8522 (0.5); −0.0002 (1.0)

I-360: ¹H-NMR (300.2 MHz, CDCl3):
δ=8.7042 (1.8); 8.6974 (1.8); 8.1146 (1.1); 8.1109 (1.2); 8.0882 (1.2); 8.0850 (1.3); 7.8064 (1.2); 7.7998 (1.6); 7.7954 (1.2); 7.7266 (0.5); 7.7222 (0.5); 7.7011 (1.1); 7.6991 (1.1); 7.6970 (1.1); 7.6755 (0.8); 7.6708 (0.7); 7.6425 (0.7); 7.6402 (0.8); 7.6381 (0.8); 7.6174 (1.2); 7.6154 (1.2); 7.6133 (1.1); 7.5927 (0.7); 7.5879 (0.6); 7.5815 (1.9); 7.5742 (2.4); 7.5660 (3.2); 7.5523 (1.5); 7.5248 (0.5); 7.5197 (0.9); 7.5040 (0.9); 7.4854 (0.9); 7.4764 (0.6); 7.4637 (0.5); 7.4549 (0.4); 7.3120 (3.0); 7.3057 (3.1); 7.2985 (3.2); 7.2817 (1.1); 7.2792 (1.2); 7.2569 (1.0); 7.2543 (1.0); 5.8663 (1.8); 5.8631 (1.9); 5.8603 (1.8); 3.1658 (16.0); 2.8180 (0.4); 2.0386 (15.0); 0.0325 (3.2)

NMR-Peak Lists for Compounds of Formula (VI)

VI-01: ¹H-NMR (300.2 MHz, CDCl3):
δ=8.7927 (0.6); 8.7840 (0.6); 8.1230 (0.4); 7.9224 (0.4); 7.9153 (0.5); 7.9086 (0.4); 7.8698 (0.3); 7.8462 (0.4); 7.4680 (1.0); 7.4613 (1.4); 7.4505 (1.1); 7.4468 (1.2); 7.4374 (0.4); 7.4216 (0.3); 7.2987 (1.0); 1.6847 (0.6); 1.4152 (16.0); 0.0387 (0.9)

VI-02: ¹H-NMR (300.2 MHz, CDCl3):
δ=8.7883 (1.3); 8.7793 (1.3); 8.0783 (0.5); 8.0756 (0.6); 8.0488 (1.3); 7.9384 (0.9); 7.9297 (0.9); 7.8600 (0.5); 7.8571 (0.6); 7.8338 (0.7); 7.7333 (0.5); 7.7293 (0.4); 7.7073 (0.7); 7.7018 (0.7); 7.5999 (0.3); 7.5824 (0.6); 7.5771 (0.6); 7.5558 (0.6); 7.5494 (0.6); 7.5446 (0.6); 7.5392 (0.6); 7.5213 (0.4); 7.5178 (0.6); 7.5135 (0.5); 7.4395 (0.6); 7.4344 (0.7); 7.4278 (1.0); 7.4261 (1.0); 7.4200 (1.7); 7.4165 (1.7); 7.2998 (2.0); 6.9862 (0.4); 6.9778 (0.4); 6.9673 (0.4); 6.9613 (0.5); 6.9590 (0.5); 6.9519 (0.4); 6.9437 (0.4); 6.9341 (0.4); 1.4773 (1.9); 1.4191 (28.6); 1.3873 (0.3); 1.3134 (4.7); 1.3015 (16.0); 1.2837 (1.3); 0.0409 (2.0)

VI-03: ¹H-NMR (300.2 MHz, D2O):
δ=6.3774 (0.5); 6.3702 (0.6); 5.5333 (0.4); 5.2736 (0.4); 5.2698 (0.4); 5.1512 (0.5); 5.1223 (0.4); 4.9681 (0.4); 4.9124 (0.4); 4.9072 (0.3); 4.7585 (5.3); 4.7325 (0.4); 2.7974 (0.7); 1.9889 (1.5); −0.8222 (0.9); −1.2636 (16.0); −2.5037 (4.8)

NMR-Peak Lists for Compounds of Formula (XX)

XX-01: ¹H-NMR (300.1 MHz, d₆-DMSO):
δ=8.3658 (0.5); 7.9043 (0.7); 7.8776 (0.8); 7.7787 (0.9); 7.7546 (0.9); 7.6734 (0.6); 7.6687 (0.6); 7.6503 (1.0); 7.6462 (0.9); 7.6227 (0.5); 7.6178 (0.5); 7.5731 (0.9); 7.5332 (0.6); 7.5099 (0.7); 7.4826 (0.4); 7.4488 (0.6); 7.4257 (0.5); 7.4218 (0.5); 7.4080 (0.8); 7.4026 (0.9); 7.3815 (0.4); 6.6918 (0.4); 3.3084 (35.5); 2.5122 (12.8); 2.5062 (25.6); 2.5002 (34.2); 2.4942 (23.4); 2.4884 (10.6); 1.3567 (16.0); 0.0108 (0.9); 0.0000 (22.3); −0.0111 (0.6)

XX-02: ¹H-NMR (300.1 MHz, d₆-DMSO):
δ=12.9368 (0.3); 8.3271 (0.7); 7.9263 (1.4); 7.8985 (1.7); 7.8147 (1.4); 7.7901 (2.4); 7.7022 (0.9); 7.6978 (0.9); 7.6790 (1.4); 7.6745 (1.8); 7.6650 (1.2); 7.6510 (1.3); 7.6462 (1.7); 7.6376 (0.5); 7.6179 (0.9); 7.5950 (0.7); 7.5642 (1.4); 7.5377 (1.6); 7.5142 (0.7); 7.4610 (0.9); 7.4567 (1.4); 7.4293 (1.6); 7.4027 (0.6); 7.3974 (0.7); 6.7684 (0.7); 3.3284 (5.8); 2.5136 (7.0); 2.5078 (13.8);

2.5019 (18.2); 2.4960 (12.6); 2.0755 (0.4); 1.3570 (16.0); 0.0107 (0.4); −0.0001 (10.9); −0.0112 (0.4)

XX-03: $^1$H-NMR (300.1 MHz, $d_6$-DMSO):

δ=8.2718 (0.8); 7.9354 (1.6); 7.9081 (2.0); 7.8690 (1.4); 7.8224 (1.2); 7.7961 (1.4); 7.7456 (0.5); 7.7158 (1.9); 7.7111 (1.6); 7.6919 (2.6); 7.6882 (2.6); 7.6645 (1.6); 7.6597 (1.5); 7.5715 (1.2); 7.5479 (1.7); 7.5245 (0.8); 7.4900 (1.0); 7.4857 (0.9); 7.4583 (1.7); 7.4316 (0.7); 7.4265 (0.7); 6.7781 (0.6); 3.3319 (10.9); 3.1671 (0.7); 2.5139 (9.0); 2.5082 (18.1); 2.5024 (24.0); 2.4966 (16.8); 1.3670 (16.0); 0.0108 (0.5); −0.0001 (13.7); −0.0111 (0.5)

XX-04: $^1$H-NMR (300.1 MHz, $d_6$-DMSO):

δ=8.3123 (0.9); 8.1347 (0.4); 7.9110 (1.1); 7.8831 (1.4); 7.8070 (1.1); 7.7818 (1.6); 7.7594 (0.7); 7.6875 (1.4); 7.6830 (1.4); 7.6645 (1.2); 7.6598 (1.4); 7.6368 (1.2); 7.6320 (0.9); 7.6160 (0.9); 7.5867 (0.5); 7.5464 (0.9); 7.5432 (0.9); 7.5191 (1.6); 7.4923 (1.5); 7.4668 (0.6); 7.4624 (0.6); 7.3516 (1.2); 7.3477 (1.2); 7.3255 (0.9); 7.3215 (0.9); 7.2636 (0.5); 6.3490 (2.1); 6.3431 (2.0); 4.8940 (1.4); 4.6631 (0.9); 3.3232 (25.0); 3.2999 (0.6); 2.5131 (12.9); 2.5073 (25.5); 2.5014 (33.6); 2.4954 (23.0); 2.4899 (10.5); 1.6531 (4.6); 1.3784 (16.0); 0.0109 (1.0); 0.0000 (27.2); −0.0111 (0.9)

XX-05: $^1$H-NMR (300.1 MHz, $d_6$-DMSO):

δ=8.2768 (0.8); 8.2694 (0.8); 7.9182 (0.8); 7.8900 (0.9); 7.7928 (0.7); 7.7674 (1.2); 7.7415 (0.7); 7.6973 (0.9); 7.6922 (0.9); 7.6871 (0.7); 7.6759 (0.7); 7.6691 (1.2); 7.6637 (1.3); 7.6586 (1.2); 7.6517 (1.5); 7.6413 (1.0); 7.6361 (0.7); 7.6255 (0.5); 7.6197 (0.4); 7.5522 (0.6); 7.5487 (0.6); 7.5255 (0.9); 7.5159 (0.5); 7.5110 (0.4); 7.5024 (0.4); 7.4986 (0.5); 7.4895 (0.8); 7.4848 (0.8); 7.4653 (0.6); 7.4607 (0.6); 7.4381 (1.0); 7.4330 (1.0); 7.4118 (0.5); 7.4067 (0.4); 6.7715 (0.8); 3.7979 (0.5); 3.3229 (4.3); 3.1895 (0.8); 2.5135 (2.0); 2.5076 (4.0); 2.5016 (5.4); 2.4956 (3.7); 2.4897 (1.7); 1.3633 (16.0); 1.3017 (0.3); 1.2746 (0.7); −0.0001 (3.7)

XX-06: $^1$H-NMR (300.1 MHz, $d_6$-DMSO):

δ=9.4489 (1.8); 8.4797 (0.7); 7.9435 (1.0); 7.9153 (1.3); 7.8919 (0.6); 7.8598 (1.0); 7.8323 (1.0); 7.7474 (1.4); 7.7188 (1.4); 7.7139 (1.6); 7.6958 (1.1); 7.6907 (1.7); 7.6677 (0.9); 7.6628 (1.2); 7.6349 (1.4); 7.5966 (1.0); 7.5901 (0.8); 7.5753 (1.3); 7.5684 (1.0); 7.5522 (1.1); 7.5417 (0.4); 7.5292 (0.4); 7.0467 (2.1); 7.0399 (2.0); 5.0009 (0.3); 3.3145 (55.8); 2.5128 (9.8); 2.5068 (19.5); 2.5008 (26.0); 2.4948 (17.6); 2.4889 (7.9); 1.2956 (16.0); 0.0109 (0.6); 0.0000 (18.0); −0.0111 (0.6)

XX-07: $^1$H-NMR (300.1 MHz, $d_6$-DMSO):

δ=8.4800 (0.5); 7.9431 (0.6); 7.9154 (0.9); 7.8904 (0.4); 7.8525 (0.6); 7.8271 (0.6); 7.7108 (0.4); 7.7060 (0.4); 7.6876 (0.7); 7.6829 (0.9); 7.6597 (0.8); 7.6551 (0.7); 7.6125 (0.4); 7.6007 (0.5); 7.5720 (0.6); 7.5676 (0.5); 7.5444 (0.7); 7.5210 (0.4); 7.5173 (0.4); 7.5087 (0.9); 7.5035 (1.5); 7.4910 (1.3); 7.4882 (1.4); 7.4746 (1.3); 7.4689 (1.2); 6.2625 (1.0); 6.2573 (1.0); 4.2596 (0.5); 3.3174 (16.0); 2.5130 (5.5); 2.5071 (10.7); 2.5011 (14.1); 2.4951 (9.5); 2.4893 (4.2); 1.3131 (9.9); 0.7780 (16.0); 0.0108 (0.4); −0.0001 (10.2); −0.1035 (8.0)

XX-08: $^1$H-NMR (300.1 MHz, $d_6$-DMSO):

δ=8.3977 (0.6); 7.9565 (1.6); 7.9287 (2.0); 7.8693 (1.6); 7.8427 (1.6); 7.7274 (0.9); 7.7230 (1.2); 7.7043 (1.6); 7.6999 (2.1); 7.6953 (1.7); 7.6763 (1.8); 7.6724 (1.7); 7.6481 (0.8); 7.6085 (0.6); 7.5859 (1.6); 7.5827 (1.6); 7.5592 (1.8); 7.5359 (0.9); 7.5325 (0.8); 7.5234 (1.1); 7.5192 (1.0); 7.4918 (1.7); 7.4648 (1.7); 7.4599 (0.8); 6.2966 (0.6); 3.3274 (18.9); 2.5135 (12.0); 2.5077 (23.8); 2.5018 (31.3); 2.4959 (21.5); 1.3406 (16.0); 0.0108 (0.7); −0.0001 (19.1); −0.0111 (0.6)

XX-09: $^1$H-NMR (300.1 MHz, $d_6$-DMSO):

δ=8.3188 (0.6); 7.9526 (1.4); 7.9245 (1.8); 7.8654 (1.7); 7.8398 (1.7); 7.7295 (0.9); 7.7250 (0.9); 7.7070 (1.8); 7.7021 (1.8); 7.6893 (1.0); 7.6790 (1.5); 7.6741 (1.2); 7.6627 (0.8); 7.6434 (0.6); 7.5845 (1.2); 7.5607 (1.6); 7.5374 (0.8); 7.5344 (0.8); 7.5179 (1.0); 7.4866 (1.6); 7.4596 (0.7); 7.4545 (0.8); 6.2904 (0.6); 3.3262 (24.9); 2.5131 (18.3); 2.5075 (35.9); 2.5016 (47.4); 2.4959 (33.2); 1.3460 (16.0); 0.7298 (5.1); 0.0107 (1.3); −0.0002 (31.0); −0.0111 (1.2); −0.1498 (1.7); −0.1982 (0.9)

XX-10: $^1$H-NMR (300.1 MHz, $d_6$-DMSO):

δ=8.4433 (0.6); 7.9503 (1.9); 7.9222 (3.6); 7.8619 (1.4); 7.8354 (1.5); 7.8121 (0.6); 7.7552 (0.7); 7.7277 (2.3); 7.7065 (2.9); 7.7015 (2.9); 7.6789 (2.0); 7.5889 (2.1); 7.5627 (2.5); 7.5471 (1.8); 7.5429 (1.7); 7.5156 (2.2); 7.4877 (1.0); 7.4839 (0.9); 7.1101 (1.0); 3.3278 (9.0); 2.5140 (9.9); 2.5082 (19.3); 2.5023 (25.2); 2.4964 (17.3); 2.4909 (7.8); 1.3128 (16.0); 1.2731 (3.6); 1.2377 (0.3); 0.0108 (0.6); −0.0001 (15.7); −0.0112 (0.5)

XX-11: $^1$H-NMR (300.1 MHz, $d_6$-DMSO):

δ=8.4007 (0.3); 7.9538 (1.3); 7.9260 (1.7); 7.8611 (0.9); 7.8357 (1.0); 7.7238 (0.6); 7.6983 (1.2); 7.6734 (0.7); 7.6071 (0.8); 7.5807 (1.8); 7.5550 (2.2); 7.5297 (1.0); 7.4058 (0.8); 7.3745 (1.2); 7.3495 (0.5); 7.3427 (0.6); 6.1906 (0.9); 3.3483 (0.6); 2.5077 (13.4); 2.5021 (17.2); 2.4967 (12.2); 2.0759 (1.2); 1.3409 (16.0); 0.0001 (9.5)

XX-12: $^1$H-NMR (300.1 MHz, $d_6$-DMSO):

δ=8.5197 (0.5); 7.9463 (0.8); 7.9166 (1.2); 7.8981 (0.7); 7.8504 (0.8); 7.8258 (1.0); 7.7082 (0.5); 7.7038 (0.5); 7.6808 (1.0); 7.6576 (0.8); 7.6336 (0.7); 7.6153 (0.5); 7.6042 (0.6); 7.5965 (0.6); 7.5855 (0.8); 7.5690 (1.0); 7.5598 (0.6); 7.5424 (1.4); 7.5267 (2.9); 7.5169 (1.8); 7.5084 (0.8); 7.5031 (0.7); 7.4370 (1.5); 7.4325 (1.5); 6.2602 (1.7); 6.2550 (1.7); 5.2087 (0.4); 5.1918 (0.9); 5.1738 (0.5); 4.0838 (0.8); 3.3127 (38.2); 2.5126 (9.8); 2.5067 (19.7); 2.5007 (26.3); 2.4947 (18.0); 2.4889 (8.2); 1.3102 (16.0); 0.0110 (0.5); 0.0000 (16.8); −0.0110 (0.6)

NMR-Peak Lists for Compounds of Formula (IXa)

IXa-01: $^1$H-NMR (499.9 MHz, CDCl3):

δ=7.5907 (3.1); 7.5870 (3.0); 7.5247 (1.9); 7.5085 (2.3); 7.3444 (0.8); 7.3327 (0.9); 7.3278 (1.6); 7.3162 (1.6); 7.3114 (0.9); 7.2998 (0.8); 7.2640 (1.7); 7.1778 (1.2); 7.1759 (1.2); 7.1607 (2.0); 7.1590 (2.0); 7.1438 (1.0); 7.1420 (0.9); 6.3403 (3.6); 6.3365 (3.4); 3.7153 (16.0); 1.7065 (1.5); −0.0002 (1.7)

IXa-02: $^1$H-NMR (400.1 MHz, $d_6$-DMSO):

δ=7.6816 (4.0); 7.6616 (5.1); 7.6063 (6.6); 7.6024 (6.6); 7.5531 (1.7); 7.5378 (2.0); 7.5324 (3.4); 7.5171 (3.4); 7.5122 (2.3); 7.4967 (2.0); 7.4573 (2.7); 7.4551 (2.8); 7.4342 (4.3); 7.4139 (1.8); 7.4119 (1.8); 6.3070 (7.7); 6.3025 (7.6); 4.0437 (0.9); 4.0357 (0.5); 4.0273 (2.2); 4.0109 (2.9); 3.9945 (2.2); 3.9782 (0.9); 3.3539 (1.4); 2.5124 (0.8); 2.5082 (1.1); 2.5041 (0.8); 1.9849 (0.6); 1.3806 (16.0); 1.3642 (15.7); 1.2987 (15.5); 1.2822 (15.3); 1.1702 (0.4); −0.0135 (0.9)

IXa-03: $^1$H-NMR (400.1 MHz, $d_6$-DMSO):

δ=7.6428 (0.5); 7.6227 (0.7); 7.5520 (1.2); 7.5478 (1.3); 7.5127 (0.5); 7.4970 (0.4); 7.4935 (0.4); 7.4171 (0.3); 7.3957 (0.5); 6.2056 (1.0); 3.3136 (0.6); 2.5127 (0.6); 2.5083 (0.8); 2.5039 (0.6); 1.4084 (16.0); 0.0055 (0.4)

IXa-04: $^1$H-NMR (499.9 MHz, CDCl3):

δ=7.6255 (5.5); 7.6218 (5.8); 7.5227 (3.4); 7.5066 (4.0); 7.3456 (1.6); 7.3339 (1.7); 7.3291 (2.9); 7.3174 (2.9); 7.3127 (1.7); 7.3010 (1.5); 7.2633 (4.2); 7.1745 (2.0); 7.1725 (2.1); 7.1576 (3.5); 7.1556 (3.8); 7.1408 (1.6); 7.1388 (1.7); 6.2998 (6.2); 6.2961 (6.4); 4.0191 (0.3); 4.0045 (1.0); 3.9906 (1.6); 3.9768 (2.9); 3.9624 (3.7);

3.9478 (3.8); 3.9333 (3.2); 3.9195 (1.6); 3.9057 (1.1); 3.8912 (0.4); 1.6677 (1.8); 1.3784 (8.1); 1.3638 (16.0); 1.3493 (7.9); −0.0002 (4.2)

IXa-05: $^1$H-NMR (300.2 MHz, CDCl3):

δ=10.0728 (0.4); 7.6972 (14.2); 7.6909 (14.4); 7.5813 (0.4); 7.5616 (4.6); 7.5585 (7.4); 7.5554 (4.7); 7.5347 (6.2); 7.5316 (9.9); 7.5285 (6.4); 7.5001 (0.6); 7.4442 (0.3); 7.4222 (0.7); 7.4153 (0.7); 7.4048 (0.8); 7.3935 (4.4); 7.3742 (5.1); 7.3660 (7.9); 7.3467 (8.0); 7.3388 (5.0); 7.3194 (5.2); 7.3118 (2.1); 7.2996 (35.4); 7.2934 (4.8); 7.2843 (4.7); 7.2785 (3.3); 7.2639 (12.7); 7.2586 (7.2); 7.2453 (8.7); 7.2400 (17.6); 7.2354 (13.6); 7.2294 (8.2); 7.2240 (3.3); 7.2147 (5.1); 7.1975 (6.1); 7.1939 (6.3); 7.1693 (8.7); 7.1657 (8.7); 7.1476 (1.4); 7.1412 (4.2); 7.1376 (3.9); 7.1237 (0.8); 7.1095 (0.4); 7.1013 (0.4); 7.0794 (10.6); 7.0731 (11.0); 7.0530 (9.3); 7.0484 (7.7); 6.3561 (15.9); 6.3498 (16.0); 6.0518 (0.5); 4.4687 (0.5); 4.4455 (1.0); 4.4220 (0.6); 4.3068 (0.4); 4.2885 (0.5); 4.2658 (0.4); 4.2515 (1.5); 4.2282 (1.8); 4.2225 (1.8); 4.2061 (4.2); 4.1989 (2.3); 4.1838 (4.4); 4.1758 (5.2); 4.1541 (8.4); 4.1305 (5.7); 4.1248 (5.2); 4.1090 (2.0); 4.1010 (5.0); 4.0841 (2.3); 4.0805 (2.1); 4.0556 (1.9); 3.2859 (0.5); 3.2618 (1.1); 3.2372 (0.9); 3.2270 (0.5); 3.2049 (0.8); 3.1821 (5.4); 3.1767 (5.9); 3.1599 (5.4); 3.1527 (10.0); 3.1304 (5.1); 3.1225 (4.7); 3.1013 (0.8); 3.0776 (0.5); 3.0278 (0.4); 2.0857 (1.8); 1.6310 (0.8); 1.3730 (0.4); 1.3482 (0.9); 1.3416 (0.9); 1.3236 (2.0); 1.3084 (5.6); 1.3005 (5.2); 1.2764 (1.0); 0.9452 (2.0); 0.9234 (6.4); 0.9000 (2.4); 0.0522 (1.2); 0.0414 (36.4); 0.0304 (1.5)

NMR-Peak Lists for Compounds of Formula (IXb)

IXb-01: $^1$H-NMR (300.1 MHz, d$_6$-DMSO):

δ=7.7035 (3.2); 7.6991 (4.4); 7.6932 (3.0); 7.6743 (16.0); 7.6684 (14.6); 7.5954 (2.1); 7.5757 (2.5); 7.5674 (5.4); 7.5476 (5.6); 7.5421 (6.1); 7.5396 (6.0); 7.5328 (5.2); 7.5218 (4.3); 7.5091 (5.4); 7.5035 (5.5); 7.4809 (1.9); 7.4753 (1.3); 6.5396 (1.0); 6.4309 (9.6); 6.4251 (9.4); 5.2729 (5.5); 5.2550 (7.9); 5.2532 (8.1); 5.2355 (5.8); 4.3932 (2.8); 4.3758 (2.8); 4.3475 (5.6); 4.3301 (5.5); 4.2598 (5.3); 4.2401 (5.2); 4.2144 (2.7); 4.1941 (2.6); 3.3278 (178.0); 3.3045 (2.1); 2.7335 (0.8); 2.7276 (1.0); 2.7217 (0.8); 2.5134 (65.2); 2.5076 (128.8); 2.5016 (170.4); 2.4958 (117.2); 2.4902 (53.5); 2.4428 (0.4); 2.2778 (0.8); 2.2717 (1.0); 0.1949 (0.4); 0.0108 (3.8); −0.0001 (108.2); −0.0112 (3.6); −0.1986 (0.4)

IXb-02: $^1$H-NMR (300.1 MHz, d$_6$-DMSO):

δ=7.7005 (0.5); 7.6953 (0.4); 7.6894 (1.0); 7.6836 (1.0); 7.6790 (0.6); 7.6750 (0.6); 7.6700 (0.4); 7.5683 (0.4); 7.5488 (0.5); 7.5424 (0.4); 7.5318 (0.4); 7.5258 (0.5); 7.5228 (0.4); 7.5014 (0.5); 7.4963 (0.5); 6.4809 (0.9); 6.4751 (0.9); 4.6240 (0.5); 4.5810 (1.0); 4.5054 (0.9); 4.4622 (0.4); 3.3288 (3.8); 2.5141 (1.6); 2.5083 (3.2); 2.5024 (4.2); 2.4966 (2.9); 0.7547 (1.1); 0.7412 (1.2); 0.7319 (16.0); 0.0003 (2.9); −0.0995 (0.3); −0.1294 (5.2); −0.1380 (0.5); −0.1468 (0.6); −0.1586 (5.2)

IXb-03: $^1$H-NMR (300.1 MHz, d$_6$-DMSO):

δ=7.9828 (3.0); 7.9763 (3.1); 7.6996 (1.2); 7.6945 (0.8); 7.6744 (1.7); 7.6124 (0.5); 7.5926 (0.7); 7.5845 (1.3); 7.5647 (1.4); 7.5590 (1.4); 7.5540 (1.4); 7.5476 (1.3); 7.5386 (1.1); 7.5231 (1.4); 7.5181 (1.4); 7.4950 (0.5); 7.4898 (0.4); 7.2002 (3.2); 7.1937 (3.1); 3.7436 (16.0); 3.4360 (0.4); 3.3348 (0.9); 2.5112 (1.4); 2.5057 (1.8); 2.5000 (1.3); −0.0001 (0.8)

IXb-04: $^1$H-NMR (300.1 MHz, d$_6$-DMSO):

δ=7.7758 (1.1); 7.7701 (1.1); 7.2752 (0.3); 7.2696 (0.5); 7.2480 (0.5); 6.7601 (0.7); 6.7324 (0.6); 6.5929 (0.4); 6.5897 (0.3); 6.5611 (0.6); 6.5413 (1.2); 6.5355 (1.2); 5.1493 (1.5); 4.5854 (2.6); 3.4301 (1.0); 2.6088 (0.8); 2.6034 (1.0); 0.9046 (0.4); 0.8773 (16.0); 0.1014 (0.5); 0.0001 (6.2)

Biological Data

Example A

In Vivo Preventive Test on Botrytis cinerea (Grey Mould)

Solvent: 5% by volume of Dimethyl sulfoxide
10% by volume of Acetone
Emulsifier: 1 μl of Tween® 80 per mg of active ingredient The compounds to be tested were made soluble and homogenized in a mixture of Dimethyl sulfoxide/Acetone/Tween® 80 and then diluted in water to the desired concentration.

The young plants of gherkin were treated by spraying the compounds to be tested prepared as described above. Control plants were treated only with an aqueous solution of Acetone/Dimethyl sulfoxide/Tween® 80.

After 24 hours, the plants were contaminated by spraying the leaves with an aqueous suspension of Botrytis cinerea spores. The contaminated gherkin plants were incubated for 4 to 5 days at 17° C. and at 90% relative humidity.

The test was evaluated 4 to 5 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: I-020; I-026; I-031; I-056; I-059; I-072; I-083; I-090; I-099; I-106; I-146; I-159; I-218; I-282; I-292; I-301; I-322.

In this test the following compounds according to the invention showed efficacy between 80% and 89% at a concentration of 500 ppm of active ingredient: I-008; I-076; I-081; I-108; I-118; I-128; I-173; I-203.

In this test the following compounds according to the invention showed efficacy between 90% and 100% at a concentration of 500 ppm of active ingredient: I-009; I-010; I-022; I-024; I-038; I-050; I-051; I-057; I-058; I-060; I-065; I-066; I-070; I-071; I-080; I-082; I-084; I-087; I-088; I-091; I-092; I-093; I-096; I-097; I-100; I-104; I-105; I-107; I-117; I-122; I-124; I-125; I-129; I-135; I-143; I-144; I-147; I-148; I-149; I-150; I-151; I-153; I-160; I-178; I-180; I-184; I-206; I-220; I-224; I-226; I-228; I-229; I-230; I-252; I-277; I-279; I-287; I-288; I-289; I-290; I-291; I-293; I-294; I-295; I-296; I-299; I-302; I-304; I-306; I-307; I-310; I-311; I-312; I-321; I-324; I-325; I-326; I-327.

Example B

In Vivo Preventive Test on Septoria tritici (Leaf Spot on Wheat)

Solvent: 5% by volume of Dimethyl sulfoxide
10% by volume of Acetone
Emulsifier: 1 μl of Tween® 80 per mg of active ingredient The compounds to be tested were made soluble and homogenized in a mixture of Dimethyl sulfoxide/Acetone/Tween® 80 and then diluted in water to the desired concentration.

The young plants of wheat were treated by spraying the compounds to be tested prepared as described above. Control plants were treated only with an aqueous solution of Acetone/Dimethyl sulfoxide/Tween® 80.

After 24 hours, the plants were contaminated by spraying the leaves with an aqueous suspension of *Septoria tritici* spores. The contaminated wheat plants were incubated for 72 hours at 18° C. and at 100% relative humidity and then for 21 days at 20° C. and at 90% relative humidity.

The test was evaluated 24 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: I-030; I-041; I-050; I-076; I-303; I-306; I-312; I-324.

In this test the following compounds according to the invention showed efficacy between 80% and 89% at a concentration of 500 ppm of active ingredient: I-013; I-014; I-023; I-051; I-056; I-149.

In this test the following compounds according to the invention showed efficacy between 90% and 100% at a concentration of 500 ppm of active ingredient: I-018; I-144; I-304.

Example C

In Vivo Preventive Test on *Sphaerotheca fuliginea* (Powdery Mildew on Cucurbits)

Solvent: 5% by volume of Dimethyl sulfoxide
  10% by volume of Acetone
Emulsifier: 1 µl of Tween® 80 per mg of active ingredient The compounds to be tested were made soluble and homogenized in a mixture of Dimethyl sulfoxide/Acetone/Tween® 80 and then diluted in water to the desired concentration.

The young plants of gherkin were treated by spraying the compounds to be tested prepared as described above. Control plants were treated only with an aqueous solution of Acetone/Dimethyl sulfoxide/Tween® 80.

After 24 hours, the plants were contaminated by spraying the leaves with an aqueous suspension of *Sphaerotheca fuliginea* spores. The contaminated gherkin plants were incubated for 8 days at 20° C. and at 70-80% relative humidity.

The test was evaluated 15 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: I-051; I-070; I-163; I-178; I-290; I-326.

In this test the following compounds according to the invention showed efficacy between 80% and 89% at a concentration of 500 ppm of active ingredient: I-060; I-069; I-117; I-118.

In this test the following compounds according to the invention showed efficacy between 90% and 100% at a concentration of 500 ppm of active ingredient: I-050; I-129; I-242; I-243; I-270; I-277; I-289; I-294; I-307; I-310; I-311; I-312; I-320; I-321; I-324; I-325; I-327.

Example D

*Leptnosphaeria nodorum* In Vitro Cell Test

Solvent: DMSO
Culture medium: 14.6 g anhydrous D-glucose (VWR), 7.1 g Mycological Peptone (Oxoid), 1.4 g granulated Yeast Extract (Merck), QSP 1 liter
Inoculum: spore suspension The compounds to be tested were solubilized in DMSO and the solution used to prepare the required range of concentrations. The final concentration of DMSO used in the assay was ≤1%.

A spore suspension of *L. nodorum* was prepared and diluted to the desired spore density.

The compounds were evaluated for their ability to inhibit spore germination and mycelium growth in liquid culture assay. The compounds were added in the desired concentration to the culture medium with spores. After 6 days incubation, fungi-toxicity of compounds was determined by spectrometric measurement of mycelium growth. Inhibition of fungal growth was determined by comparing the absorbance values in wells containing the compound to be tested with the absorbance in control wells without compound to be tested.

In this test the following compounds according to the invention showed efficacy between 70% and 79% at a concentration of 20 ppm of active ingredient: I-011; I-022; I-035; I-041; I-052; I-064; I-085; I-127; I-131; I-138; I-152; I-168; I-188; I-200; I-202; I-209; I-212; I-219; I-221; I-237; I-256.

In this test the following compounds according to the invention showed efficacy between 80% and 89% at a concentration of 20 ppm of active ingredient: I-005; I-027; I-032; I-033; I-043; I-044; I-045; I-047; I-056; I-060; I-065; I-069; I-075; I-078; I-087; I-095; I-100; I-103; I-106; I-117; I-118; I-119; I-121; I-122; I-123; I-130; I-132; I-136; I-143; I-145; I-146; I-151; I-153; I-154; I-162; I-164; I-165; I-173; I-175; I-177; I-182; I-183; I-185; I-198; I-201; I-216; I-217; I-220; I-231; I-257; I-285; I-295; I-303; I-310; I-323.

In this test the following compounds according to the invention showed efficacy between 90% and 100% at a concentration of 20 ppm of active ingredient: I-001; I-002; I-003; I-004; I-006; I-007; I-008; I-009; I-010; I-013; I-014; I-015; I-017; I-018; I-019; I-020; I-021; I-023; I-024; I-025; I-026; I-028; I-029; I-030; I-031; I-034; I-036; I-037; I-038; I-039; I-040; I-042; I-048; I-050; I-051; I-053; I-057; I-058; I-059; I-061; I-066; I-070; I-071; I-072; I-076; I-079; I-080; I-081; I-082; I-083; I-084; I-086; I-089; I-090; I-096; I-097; I-098; I-099; I-101; I-102; I-104; I-105; I-107; I-108; I-124; I-125; I-128; I-129; I-135; I-144; I-147; I-148; I-149; I-150; I-155; I-156; I-157; I-158; I-159; I-160; I-161; I-163; I-166; I-169; I-170; I-171; I-172; I-178; I-179; I-180; I-184; I-186; I-187; I-190; I-195; I-197; I-206; I-207; I-208; I-213; I-214; I-215; I-222; I-223; I-224; I-225; I-226; I-227; I-228; I-229; I-230; I-252; I-281; I-287; I-288; I-289; I-290; I-291; I-292; I-293; I-294; I-296; I-297; I-298; I-299; I-300; I-301; I-302; I-304; I-305; I-306; I-307; I-308; I-312; I-320; I-321; I-322; I-324; I-325; I-326; I-327.

Example E

*Pyricularia oryzae* In Vitro Cell Test

Solvent: DMSO

Culture medium: 14.6 g anhydrous D-glucose (VWR), 7.1 g Mycological Peptone (Oxoid), 1.4 g granulated Yeast Extract (Merck), QSP 1 liter Inoculum: spore suspension The compounds to be tested were solubilized in DMSO and the solution used to prepare the required range of concentrations. The final concentration of DMSO used in the assay was ≤1%.

A spore suspension of *P. oryzae* was prepared and diluted to the desired spore density.

The compounds were evaluated for their ability to inhibit spore germination and mycelium growth in liquid to culture assay. The compounds were added in the desired concentration to the culture medium with spores. After 5 days incubation, fungi-toxicity of compounds was determined by spectrometric measurement of mycelium growth. Inhibition of fungal growth was determined by comparing the absorbance values in wells containing the compound to be tested with the absorbance in control wells without compound to be tested.

In this test the following compounds according to the invention showed efficacy between 70% and 79% at a concentration of 20 ppm of active ingredient: I-015; I-061; I-065; I-086; I-089; I-090; I-104; I-138; I-152; I-159; I-168; I-180; I-323.

In this test the following compounds according to the invention showed efficacy between 80% and 89% at a concentration of 20 ppm of active ingredient: I-005; I-016; I-032; I-046; I-049; I-053; I-054; I-055; I-056; I-072; I-080; I-082; I-084; I-098; I-123; I-127; I-131; I-132; I-136; I-157; I-158; I-160; I-162; I-171; I-175; I-190; I-206; I-211; I-212; I-222; I-227; I-248; I-253; I-295; I-299; I-326.

In this test the following compounds according to the invention showed efficacy between 90% and 100% at a concentration of 20 ppm of active ingredient: I-001; I-002; I-003; I-004; I-006; I-007; I-008; I-009; I-010; I-013; I-014; I-017; I-018; I-019; I-020; I-021; I-022; I-023; I-024; I-025; I-026; I-027; I-028; I-030; I-031; I-033; I-034; I-035; I-036; I-037; I-038; I-039; I-040; I-041; I-042; I-043; I-044; I-045; I-047; I-048; I-050; I-051; I-057; I-058; I-059; I-060; I-066; I-070; I-071; I-076; I-077; I-079; I-081; I-083; I-096; I-097; I-099; I-101; I-102; I-105; I-107; I-117; I-118; I-119; I-121; I-122; I-124; I-125; I-128; I-143; I-144; I-145; I-146; I-147; I-148; I-149; I-150; I-154; I-155; I-156; I-161; I-164; I-165; I-166; I-167; I-169; I-170; I-172; I-173; I-179; I-182; I-184; I-186; I-187; I-195; I-197; I-201; I-202; I-207; I-208; I-216; I-217; I-219; I-224; I-225; I-226; I-228; I-229; I-230; I-233; I-237; I-246; I-252; I-255; I-256; I-257; I-281; I-285; I-287; I-288; I-289; I-290; I-291; I-292; I-293; I-294; I-296; I-297; I-298; I-300; I-301; I-302; I-303; I-304; I-305; I-306; I-307; I-308; I-312; I-320; I-321; I-322; I-324; I-325; I-327.

Example F

*Colletotrichum lindemuthianum* In Vitro Cell Test

Solvent: DMSO

Culture medium: 14.6 g anhydrous D-glucose (VWR), 7.1 g Mycological Peptone (Oxoid), 1.4 g granulated Yeast Extract (Merck), QSP 1 liter Inoculum: spores suspension The compounds to be tested were solubilized in DMSO and the solution used to prepare the required range of concentrations. The final concentration of DMSO used in the assay was ≤1%.

A spore suspension of *C. lindemuthianum* was prepared and diluted to the desired spore density.

The compounds to be tested were evaluated for their ability to inhibit spores germination and mycelium to growth in liquid culture assay. The compounds were added in the desired concentration to the culture medium with spores. After 6 days incubation, fungi-toxicity of compounds was determined by spectrometric measurement of mycelium growth. Inhibition of fungal growth was determined by comparing the absorbance values in wells containing the compound to be tested with the absorbance in control wells without compound to be tested.

In this test the following compounds according to the invention showed efficacy between 70% and 79% at a concentration of 20 ppm of active ingredient: I-068; I-078; I-120; I-131; I-161; I-169; I-177; I-253; I-255; I-259; I-260; I-300; I-321.

In this test the following compounds according to the invention showed efficacy between 80% and 89% at a concentration of 20 ppm of active ingredient: I-064; I-066; I-070; I-076; I-079; I-089; I-095; I-101; I-118; I-123; I-132; I-139; I-158; I-160; I-164; I-191; I-198; I-202; I-206; I-219; I-228; I-230; I-233; I-237; I-246; I-262; I-292; I-294; I-298; I-303; I-311; I-320.

In this test the following compounds according to the invention showed efficacy between 90% and 100% at a concentration of 20 ppm of active ingredient: I-050; I-051; I-065; I-071; I-072; I-074; I-080; I-081; I-082; I-083; I-084; I-090; I-096; I-097; I-098; I-099; I-100; I-102; I-103; I-104; I-105; I-106; I-107; I-108; I-117; I-119; I-121; I-122; I-124; I-125; I-127; I-128; I-129; I-143; I-144; I-145; I-146; I-147; I-148; I-149; I-150; I-151; I-152; I-153; I-154; I-155; I-156; I-157; I-159; I-162; I-163; I-165; I-166; I-170; I-175; I-178; I-179; I-182; I-184; I-187; I-195; I-197; I-200; I-201; I-203; I-207; I-208; I-211; I-212; I-215; I-216; I-217; I-223; I-224; I-225; I-226; I-227; I-229; I-252; I-256; I-257; I-287; I-288; I-289; I-290; I-291; I-293; I-296; I-297; I-299; I-301; I-302; I-304; I-306; I-307; I-308; I-312; I-322; I-323; I-324; I-325; I-326; I-327.

Example G

In Vivo Preventive Test on *Venturia* Test (Apples)

| | | |
|---|---|---|
| Solvent: | 24.5 | parts by weight of acetone |
| | 24.5 | parts by weight of dimethylacetamide |
| Emulsifier: | 1 | part by weight of alkylaryl polyglycol ether |

To produce a suitable preparation of active compound, 1 part by weight of the compound to be tested was mixed with the stated amounts of solvent and emulsifier, and the concentrate was diluted with water to the desired concentration.

To test for preventive activity, young plants were sprayed with the preparation of the compound to be tested at the stated rate of application. After the spray coating had dried on, the plants were inoculated with an aqueous conidia suspension of the causal agent of apple scab (*Venturia inaequalis*) and then remained for 1 day in an incubation cabinet at approximately 20° C. and a relative atmospheric humidity of 100%.

The plants were then placed in a greenhouse at approximately 21° C. and a relative atmospheric humidity of approximately 90%.

The test was evaluated 10 days after the inoculation. 0% means an efficacy which corresponds to that of the untreated control, while an efficacy of 100% means that no disease is observed.

In this test the following compounds according to the invention showed efficacy between 70% and 79% at a concentration of 250 ppm of active ingredient: I-060.

In this test the following compounds according to the invention showed efficacy between 90% and 100% at a concentration of 250 ppm of active ingredient: I-024; I-050.

Example H

Comparative Data—In Vivo Preventive Test on *Botrytis cinerea* (Grey Mould)

The compounds to be tested were prepared by homogenization in a mixture of acetone/Dimethyl sulfoxide/Tween®, and then diluted with water to obtain the desired active material concentration.

The young plants of gherkin were treated by spraying the compound prepared as described above. Control plants were treated only with an aqueous solution of acetone/Dimethyl sulfoxide/Tween®.

After 24 hours, the plants were contaminated by spraying the leaves with an aqueous suspension of *Botrytis cinerea* spores. The contaminated gherkin plants were incubated for 4 to 5 days at 17° C. and at 90% relative humidity.

The test was evaluated 4 to 5 days after the inoculation. 0% means an efficacy which corresponds to that of the control plants while an efficacy of 100% means that no disease was observed.

In this test, compound I-066 and I-027 were shown to exhibit better efficacy than structurally related compounds (L=O) prepared in accordance with the teaching of WO 2013/058256.

| Test compounds | Rate of application of active compound in ppm | Efficacy in % |
|---|---|---|
| Prepared in accordance with the teaching of WO 2013/058256: | | |
| 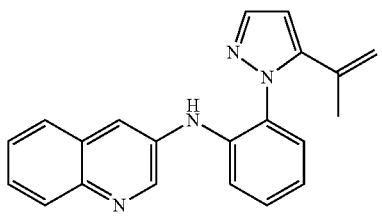 | 500 | 20 |
| 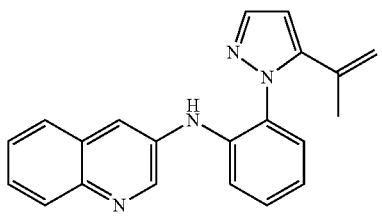 | 500 | 68 |
| According to the invention: | | |
| Ex. I-066 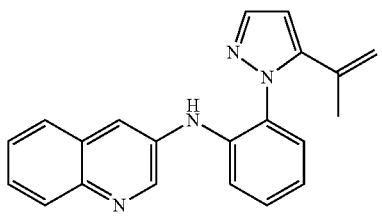 | 500 | 98 |

-continued

| Test compounds | | Rate of application of active compound in ppm | Efficacy in % |
|---|---|---|---|
| Ex. I-067 | 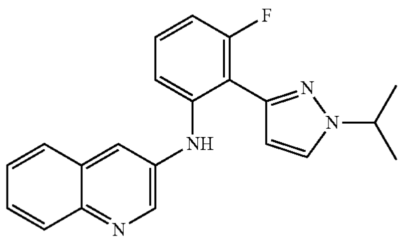 [SMILES: CC(C)n1ccc(-c2c(F)cccc2Nc2cnc3ccccc3c2)n1]  | 500 | 95 |

Example I

Comparative Data—*Leptnosphaeria nodorum* In Vitro Cell Test

Solvent: DMSO

Culture medium: 14.6 g anhydrous D-glucose (VWR), 7.1 g Mycological Peptone (Oxoid), 1.4 g granulated Yeast Extract (Merck), QSP 1 liter Inoculum: spore suspension The compounds to be tested were solubilized in DMSO and the solution used to prepare the required range of concentrations. The final concentration of DMSO used in the assay was ≤1%.

A spore suspension of *L. nodorum* was prepared and diluted to the desired spore density.

The tested compounds were evaluated for their ability to inhibit spore germination and mycelium growth to in liquid culture assay. The compounds were added in the desired concentration to the culture medium with spores. After 6 days incubation, fungi-toxicity of compounds was determined by spectrometric measurement of mycelium growth. Inhibition of fungal growth was determined by comparing the absorbance values in wells containing the fungicides with the absorbance in control wells without fungicides.

In this test, compound I-066 was shown to exhibit better efficacy than structurally related compound (L=O) prepared in accordance with the teaching of WO 2013/058256.

| Test compound | | Rate of application of active compound in ppm | Efficacy in % |
|---|---|---|---|
| | Prepared in accordance with the teaching of WO 2013/058256: | | |
| | 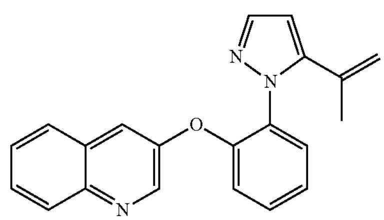 [SMILES: C=C(C)c1ccnn1-c1ccccc1Oc1cnc2ccccc2c1]  | 4 | 64 |
| | According to the invention: | | |
| Ex. I-066 | 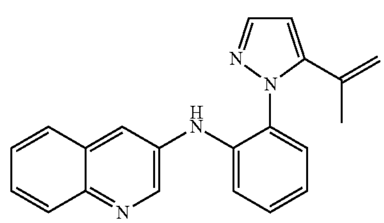 [SMILES: C=C(C)c1ccnn1-c1ccccc1Nc1cnc2ccccc2c1]  | 4 | 94 |

Example J

Comparative Data—*Ustilago avenae* In Vitro Cell Test

Solvent: DMSO
Culture medium: 14.6 g anhydrous D-glucose (VWR), 7.1 g Mycological Peptone (Oxoid), 1.4 g granulated Yeast Extract (Merck), QSP 1 liter
Inoculum: spore suspension The tested compounds were solubilized in DMSO and the solution used to prepare the required range of concentrations. The final concentration of DMSO used in the assay was ≤1%.

Inoculum was prepared from a pre-culture of *U. avenae* grown in liquid medium and diluted to the desired to optical density (OD).

The tested compounds were evaluated for their ability to inhibit mycelium growth in liquid culture assay. The compounds were added in the desired concentrations to culture medium containing the spore suspension. After 4 days of incubation, the fungicidal efficacy of compounds was determined by spectrometric measurement of mycelium growth. Inhibition of fungal growth was determined by comparing the absorbance values in wells containing the fungicides with the absorbance in control wells without fungicides.

In this test, compound I-066 was shown to exhibit better efficacy than structurally related compound (L=O) prepared in accordance with the teaching of WO 2013/058256.

Example K

Comparative Data—In Vivo Preventive Test on *Colletotrichum lindemuthianum* (Antrachnose on Bean)

The compounds to be tested were prepared by homogenization in a mixture of acetone/Dimethyl sulfoxide/Tween®, and then diluted with water to obtain the desired active material concentration.

The young plants of bean were treated by spraying the compounds to be tested prepared as described above. Control plants were treated only with an aqueous solution of acetone/Dimethyl sulfoxide/Tween®.

After 24 hours, the plants were contaminated by spraying the leaves with an aqueous suspension of *Colletotrichum lindemuthianum* spores. The contaminated bean plants were incubated for 24 hours at 20° C. and at 100% relative humidity and then for 5 days at 20° C. and at 90% relative humidity.

The test was evaluated 6 days after the inoculation. 0% means an efficacy which corresponds to that of the control plants while an efficacy of 100% means that no disease was observed.

In this test, compound I-027 was shown to exhibit better efficacy than structurally related compound (L=O) prepared in accordance with the teaching of WO 2013/058256.

| Test compound | Rate of application of active compound in ppm | Efficacy in % |
|---|---|---|
| Prepared in accordance with the teaching of WO 2013/058256: | | |
| 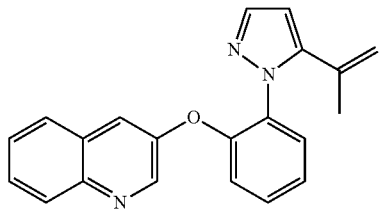 | 20 | 1 |
| According to the invention: | | |
| Ex. I-066 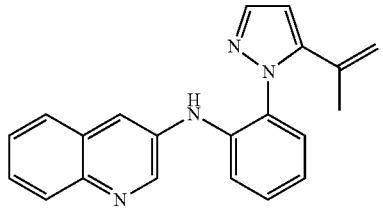 [SMILES: C=C(C)c1ccnn1-c1ccccc1Nc1cnc2ccccc2c1] | 20 | 63 |

| Active compound | Rate of application of active compound in ppm | Efficacy in % |
|---|---|---|
| Prepared in accordance with the teaching of WO 2013/058256: | 500 | 0 |
| According to the invention:<br>Ex. I-027 | 500 | 65 |

Example L

Comparative Data—*Septoria tritici* In Vitro Cell Test

Solvent: DMSO Culture medium: 14.6 g anhydrous D-glucose (VWR), 7.1 g Bacteriological Peptone (Oxoid), 1.4 g granulated Yeast Extract (Merck), QSP 1 liter Inoculum: spore suspension The compounds to be tested were solubilized in DMSO and the solution used to prepare the required range of concentrations. The final concentration of DMSO used in the assay was ≤1%.

A spore suspension of *S. tritici* was prepared and diluted to the desired spore density.

The tested compounds were evaluated for their ability to inhibit spore germination and mycelium growth in liquid culture assay. The compounds were added in the desired concentration to the culture medium to with spores. After 7 days incubation, fungi-toxicity of compounds was determined by spectrometric measurement of mycelium growth. Inhibition of fungal growth was determined by comparing the absorbance values in wells containing the tested compound with the absorbance in control wells without tested compound.

In this test, compound I-063 was shown to exhibit better efficacy than structurally related compound (L=O) prepared in accordance with the teaching of WO 2013/058256.

| Active compound | Rate of application of active compound in ppm | Efficacy in % |
|---|---|---|
| Prepared in accordance with the teaching of WO 2013/058256: | 4 | 0 |

| Active compound | Rate of application of active compound in ppm | Efficacy in % |
|---|---|---|
| According to the invention: | | |
| Ex. I-063 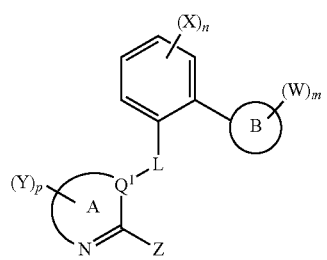 | 4 | 96 |
The invention claimed is:
1. A compound of formula (I)
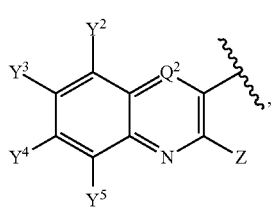
wherein
A is
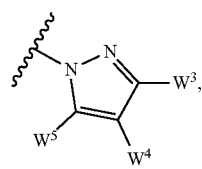
wherein:
$Q^2$ is $CY^1$ or N;
$Y^1$, $Y^2$, $Y^3$, $Y^4$ and $Y^5$ are independently a hydrogen atom or Y and
B is selected from the group consisting of:
B¹
B²
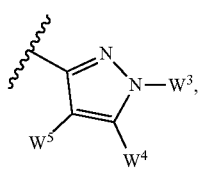
B³
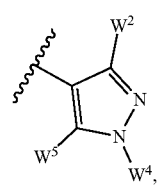
B⁴
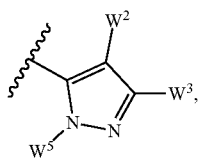
B⁵
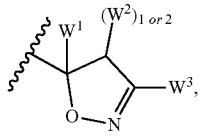
B⁶
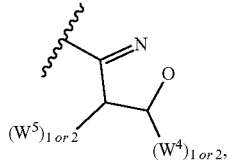
B⁷
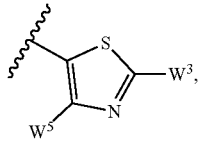

-continued

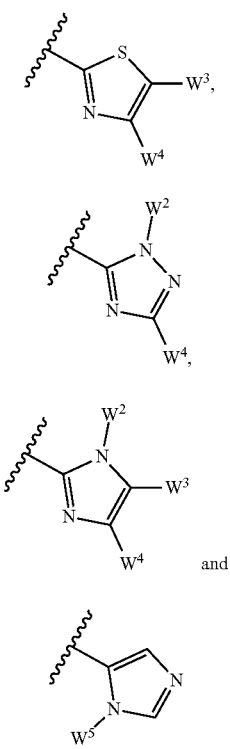

wherein $W^1$, $W^2$, $W^3$, $W^4$ and $W^5$ are independently a hydrogen atom or W;
$Q^1$ is C;
Z is selected from the group consisting of hydrogen atom, $C_1$-$C_8$-alkyl, and $C_1$-$C_8$-halogenoalkyl comprising up to 9 halogen atoms that can be the same or different;
m is 0, 1, 2, 3 or 4;
n is 0, 1, 2, 3 or 4;
p is 0, 1, 2, 3, 4 or 5;
L is $NR^3$ or $CR^1R^2$, wherein
  $R^1$ and $R^2$ are independently selected from the group consisting of hydrogen atom and halogen atom,
  $R^3$ is selected from the group consisting of hydrogen atom and $C_1$-$C_8$-alkyl;
W is independently selected from the group consisting of halogen atom, $C_1$-$C_8$-alkyl, $C_1$-$C_8$-halogenoalkyl comprising up to 9 halogen atoms that can be the same or different, hydroxy-$C_1$-$C_8$-alkyl, $C_2$-$C_8$-alkenyl, $C_3$-$C_7$-cycloalkyl, aryl, aryl-$C_1$-$C_8$-alkyl, $C_1$-$C_8$-alkoxycarbonyl, and tri($C_1$-$C_8$-alkyl)silyloxy-$C_1$-$C_8$-alkyl,
wherein said aryl and the aryl moiety of the aryl-$C_1$-$C_8$-alkyl group may be substituted with one or more halogen atom that may be the same or different;
X is independently selected from the group consisting of halogen atom, $C_1$-$C_8$-alkyl, and $C_1$-$C_8$-halogenoalkoxy comprising up to 9 halogen atoms that can be the same or different;
Y is independently selected from the group consisting of halogen atom, hydroxyl, $C_1$-$C_8$-alkyl, and $C_1$-$C_8$-halogenoalkyl comprising up to 9 halogen atoms that can be the same or different;
as well as a salt, N-oxide, metal complex, metalloid complex and/or optically active isomer or geometric isomer thereof.

2. The compound according to claim 1 wherein L is $NR^3$.

3. The compound according to claim 1 wherein Z is selected from the group consisting of hydrogen atom, $C_1$-$C_6$-alkyl, and $C_1$-$C_6$-halogenoalkyl comprising up to 9 halogen atoms that can be the same or different.

4. The compound according to claim 1 wherein Y is independently selected from the group consisting of halogen atom, hydroxyl, $C_1$-$C_6$-alkyl and $C_1$-$C_6$-halogenoalkyl comprising up to 9 halogen atoms that can be the same or different.

5. The compound according to claim 1 wherein W is selected from the group consisting of halogen atom, $C_1$-$C_6$-alkyl, $C_1$-$C_6$-halogenoalkyl comprising up to 9 halogen atoms that can be the same or different, hydroxy-$C_1$-$C_6$-alkyl, $C_2$-$C_6$-alkenyl, $C_1$-$C_6$-alkoxycarbonyl, $C_3$-$C_7$-cycloalkyl, aryl, aryl-$C_1$-$C_6$-alkyl (wherein said aryl may be substituted with one or more halogen atoms), and tri($C_1$-$C_6$-alkyl)silyloxy-$C_1$-$C_6$-alkyl.

6. The compound according to claim 1 wherein X is independently selected from the group consisting of halogen atom, $C_1$-$C_6$-alkyl, and $C_1$-$C_6$-halogenoalkoxy comprising up to 9 halogen atoms that can be the same or different.

7. A composition comprising one or more compounds of formula (I) according to claim 1 and at least one agriculturally suitable auxiliary.

8. A method for controlling unwanted phytopathogenic fungi, the method comprising applying one or more compounds of formula (I) according to claim 1 or a composition thereof to the fungi and/or to one or more plants, plant parts, seeds, fruits or to soil in which the plants grow.

9. A process for preparation of a compound of formula (I) according to claim 1, the process comprising reacting a compound of formula (II) with a compound of formula (III)

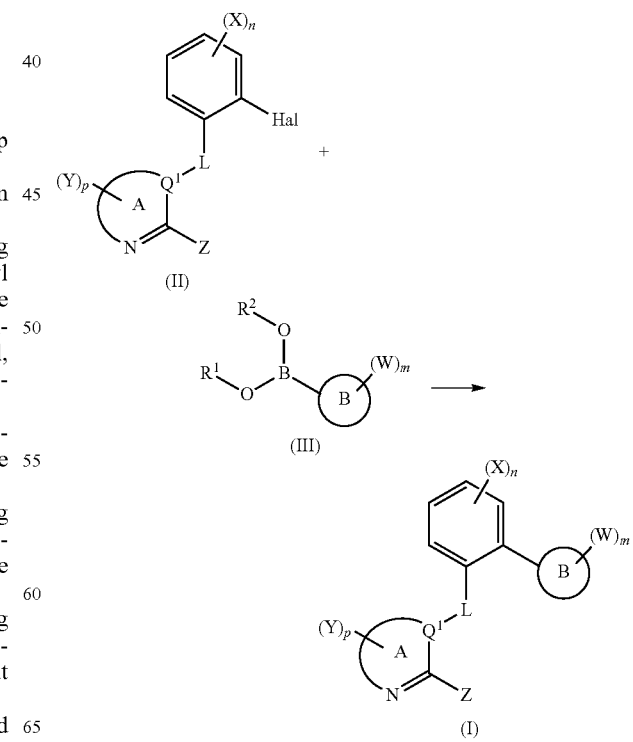

wherein
Hal is Cl, Br or I;
R$^1$ and R$^2$ are independently hydrogen or a substituted or non-substituted C$_1$-C$_8$-alkyl, or
R$^1$ and R$^2$ groups form together with the oxygen atom to which they are respectively attached a 5- or 6-membered ring.

10. A process for preparation of a compound of formula (I) according to claim 1, the method comprising reacting a compound of formula (VI) with a compound of formula (VII):

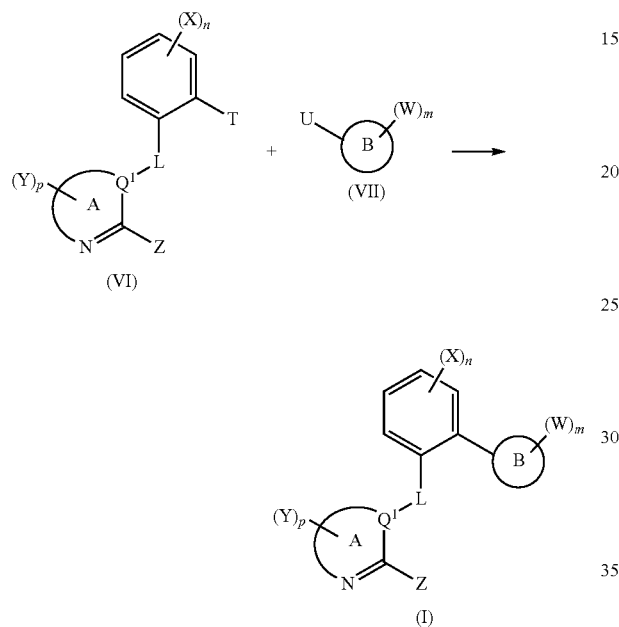

wherein
T is a boron derivative;
U is a chloro, bromo, iodo, a mesyl group, a tosyl group or a triflyl group.

11. A compound of formula (VI) and/or a salt thereof

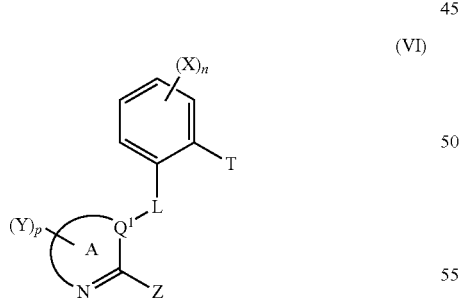

wherein:
T represents a boron derivative;
wherein
A is

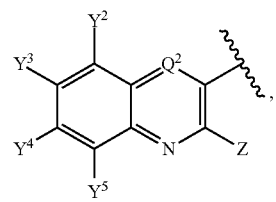

wherein:
Q$^2$ is CY$^1$ or N;
Y$^1$, Y$^2$, Y$^3$, Y$^4$ and Y$^5$ are independently a hydrogen atom or Y;
Q$^1$ is C;
Z is selected from the group consisting of hydrogen atom, C$_1$-C$_8$-alkyl, and C$_1$-C$_8$-halogenoalkyl comprising up to 9 halogen atoms that can be the same or different;
n is 0, 1, 2, 3 or 4;
p is 0, 1, 2, 3, 4 or 5;
L is NR$^3$ or CR$^1$R$^2$, wherein
R$^1$ and R$^2$ are independently selected from the group consisting of hydrogen atom and halogen atom,
R$^3$ is selected from the group consisting of hydrogen atom and C$_1$-C$_8$-alkyl;
X is independently selected from the group consisting of halogen atom, C$_1$-C$_8$-alkyl, and C$_1$-C$_8$-halogenoalkoxy comprising up to 9 halogen atoms that can be the same or different;
Y is independently selected from the group consisting of halogen atom, hydroxyl, C$_1$-C$_8$-alkyl, and C$_1$-C$_8$-halogenoalkyl comprising up to 9 halogen atoms that can be the same or different.

12. A compound of formula (IXa) and/or a salt thereof

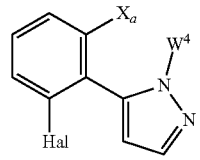

wherein:
W$^4$ is a C$_1$-C$_8$-alkyl, a C$_1$-C$_8$-halogenoalkyl comprising up to 9 halogen atoms that can be the same or different, a C$_2$-C$_8$-alkenyl, a C$_3$-C$_8$-cycloalkyl, or an aryl;
Hal represents Br or I; and
X$_a$ represents F, Cl, Br or I.

* * * * *